US007122536B2

(12) United States Patent
Sikorski et al.

(10) Patent No.: US 7,122,536 B2
(45) Date of Patent: *Oct. 17, 2006

(54) (R)-CHIRAL HALOGENATED SUBSTITUTED FUSED HETEROCYCLIC AMINO COMPOUNDS USEFUL FOR INHIBITING CHOLESTEROL ESTER TRANSFER PROTEIN ACTIVITY

(75) Inventors: James A. Sikorski, Des Peres, MO (US); Richard C. Durley, Chesterfield, MO (US); Margaret L. Grapperhaus, Troy, IL (US); Mark A. Massa, Ballwin, MO (US); Emily J. Reinhard, Chesterfield, MO (US); Yvette M. Fobian, Labadie, MO (US); Michael B. Tollefson, O'Fallon, MO (US); Lijuan Wang, Wildwood, MO (US); Brian S. Hickory, Wildwood, MO (US); Monica B. Norton, Saint Louis, MO (US); William F. Vernier, Saint Louis, MO (US); Deborah A. Mischke, Defiance, MO (US); Michele A. Promo, Chesterfield, MO (US); Ashton T. Hamme, St. Louis, MO (US); Dale P. Spangler, Deerfield, IL (US); Melvin L. Rueppel, St. Louis, MO (US)

(73) Assignee: Pfizer Inc., New York, NY (US)

( * ) Notice: Subject to any disclaimer, the term of this patent is extended or adjusted under 35 U.S.C. 154(b) by 148 days.

This patent is subject to a terminal disclaimer.

(21) Appl. No.: 10/929,013

(22) Filed: Aug. 27, 2004

(65) Prior Publication Data

US 2005/0043294 A1     Feb. 24, 2005

Related U.S. Application Data

(62) Division of application No. 10/017,290, filed on Dec. 12, 2001, now Pat. No. 6,803,388, which is a division of application No. 09/401,915, filed on Sep. 23, 1999, now abandoned.

(51) Int. Cl.
*A61K 31/33* (2006.01)
*A61K 31/557* (2006.01)
*A61K 31/535* (2006.01)

(52) U.S. Cl. .............. 514/183; 514/211.09; 514/230.5; 540/468; 540/552; 544/105

(58) Field of Classification Search ............... 540/468, 540/552; 544/105; 514/183, 211.09, 230.5
See application file for complete search history.

(56) References Cited

U.S. PATENT DOCUMENTS

| 2,700,686 | A | 1/1955 | Dickey et al. ............ 260/633 |
| 3,334,017 | A | 8/1967 | Biel ........................... 167/65 |
| 3,359,316 | A | 12/1967 | Biel ........................ 260/570.8 |
| 3,534,100 | A | 10/1970 | Bollag et al. .............. 260/569 |
| 5,306,718 | A | 4/1994 | Lauffer et al. ........... 514/230.8 |
| 5,932,587 | A | 8/1999 | Schmeck et al. ........... 514/278 |
| 6,063,788 | A | 5/2000 | Brandes et al. ............ 514/290 |
| 6,069,148 | A | 5/2000 | Schmidt et al. ............ 514/277 |
| 6,127,383 | A | 10/2000 | Schmidt et al. ............ 514/312 |
| 6,448,295 | B1 | 9/2002 | Sikorski et al. ............ 514/654 |
| 6,451,823 | B1 | 9/2002 | Sikorski et al. ............ 514/351 |
| 6,451,830 | B1 | 9/2002 | Sikorski et al. ............ 514/378 |
| 6,455,519 | B1 | 9/2002 | Sikorski et al. ........ 514/211.09 |
| 6,458,803 | B1 | 10/2002 | Sikorski et al. ............ 514/311 |
| 6,458,852 | B1 | 10/2002 | Sikorski et al. ............ 514/658 |
| 6,462,092 | B1 | 10/2002 | Sikorski et al. ............ 514/655 |
| 6,476,057 | B1 | 11/2002 | Sikorski et al. ............ 514/351 |
| 6,476,075 | B1 | 11/2002 | Sikorski et al. ............ 514/574 |
| 6,479,552 | B1 | 11/2002 | Sikorski et al. ............ 514/649 |
| 6,482,862 | B1 | 11/2002 | Sikorski et al. ............ 514/654 |
| 6,521,607 | B1 | 2/2003 | Sikorski et al. ............ 514/150 |
| 6,544,974 | B1 | 4/2003 | Sikorski et al. ............ 514/183 |
| 6,583,183 | B1 | 6/2003 | Sikorski et al. ............ 514/654 |
| 6,586,433 | B1 | 7/2003 | Sikorski et al. ............ 514/242 |
| 6,605,624 | B1 | 8/2003 | Lee et al. .................. 514/332 |
| 6,677,341 | B1 | 1/2004 | Sikorski et al. ............ 514/245 |
| 6,677,353 | B1 | 1/2004 | Sikorski et al. ............ 514/311 |
| 6,677,375 | B1 | 1/2004 | Sikorski et al. ............ 514/574 |
| 6,677,379 | B1 | 1/2004 | Sikorski et al. ............ 514/649 |
| 6,677,380 | B1 | 1/2004 | Sikorski et al. ............ 514/649 |
| 6,677,382 | B1 | 1/2004 | Sikorski et al. ............ 514/658 |
| 6,683,099 | B1 | 1/2004 | Sikorski et al. ............ 514/351 |
| 6,683,113 | B1 | 1/2004 | Sikorski et al. ............ 514/649 |
| 6,696,435 | B1 * | 2/2004 | Sikorski et al. ........ 514/211.09 |

(Continued)

FOREIGN PATENT DOCUMENTS

CH            441366          1/1968

(Continued)

OTHER PUBLICATIONS

Barter, P. J., et al. *High density lipoproteins and coronary heart disease*, Atherosclerosis, vol. 121, pp. 1-12 (1996).

(Continued)

*Primary Examiner*—Peter O'Sullivan
(74) *Attorney, Agent, or Firm*—Gregg C. Benson; Lisa A. Samuels

(57) ABSTRACT

The invention relates to substituted aryl and heteroaryl (R)-Chiral Halogenated 1-Substitutedamino-(n+1)-Alkanol compounds useful as inhibitors of cholesteryl ester transfer protein (CETP; plasma lipid transfer protein-I) and compounds, compositions and methods for treating atherosclerosis and other coronary artery diseases. Novel high yield, stereoselective processes for the preparation of the chiral substituted alkanol compounds from chiral and achiral intermediates are described.

34 Claims, No Drawings

U.S. PATENT DOCUMENTS

| | | | |
|---|---|---|---|
| 6,696,472 B1 | 2/2004 | Sikorski et al. | 514/351 |
| 6,699,898 B1 | 3/2004 | Sikorski et al. | 514/378 |
| 6,710,089 B1 | 3/2004 | Sikorski et al. | 514/654 |
| 6,723,752 B1 | 4/2004 | Sikorski et al. | 514/649 |
| 6,723,753 B1 | 4/2004 | Sikorski et al. | 514/649 |
| 6,765,023 B1 | 7/2004 | Sikorski et al. | 514/655 |
| 6,787,570 B1 | 9/2004 | Sikorski et al. | 514/645 |
| 6,794,396 B1 | 9/2004 | Sikorski et al. | 514/333 |
| 6,803,388 B1 | 10/2004 | Sikorski et al. | 514/658 |

FOREIGN PATENT DOCUMENTS

| | | |
|---|---|---|
| DE | 19627430 | 1/1998 |
| EP | 0442172 | 8/1991 |
| EP | 0314435 | 9/1993 |
| EP | 0801060 | 10/1997 |
| EP | 0796846 | 7/2000 |
| EP | 0818197 | 11/2003 |
| EP | 0818448 | 11/2003 |
| GB | 2305665 | 4/1997 |
| JP | 5320117 | 12/1993 |
| JP | 10287662 | 10/1998 |
| WO | WO9001874 | 3/1990 |
| WO | WO9002113 | 3/1990 |
| WO | WO9738973 | 10/1997 |
| WO | WO9839299 | 9/1998 |

OTHER PUBLICATIONS

Tall, A. R., *Plasma cholesteryl ester transfer protein*, Journal of Lipid Research, vol. 34, pp. 1255-1274 (1993).
McCarthy, P. A., et al., *New Approaches to Atherosclerosis: An Overview*, Medicinal Research Reviews, vol. 13, No. 2, pp. 139-159, (1993).
Sirtori, C. R., *New Targets for Lipid Lowering and Atherosclerosis Prevention*, Pharmac. Ther., vol. 67, No. 3, pp. 433-447 (1995).
Swenson, T. L., et al., *Mechanism of Cholesteryl Ester Transfer Protein Inhibition by a Neutralizing Monoclonal Antibody and Mapping of the Monoclonal Antibody Epitope*, Journal of Biological Chemistry, vol. 264, No. 24, pp. 14318-14326, (1989).
Son, Y. C., et a., *Purification and Characterization of Human Plasma Proteins that Inhibit Lipid Transfer Activities*, Biochimica et Biophysica Acta, vol. 795, pp. 473-480, (1984).
Morton, R. E., et al., *Regulation of lipid transfer between lipoproteins by an endogenous plasma protein: selective inhibition among lipoprotein classes*, Journal of Lipid Research, vol. 35, pp. 836-847, (1994).
Tollefson, J. H., et al., *Regulation of plasma lipid transfer by the high-density lipoproteins*, American Physiological Society, pp. E894-E902, (1988).
Cho, Kyung-Hyun, et al., *A peptide from hog plasma that inhibits human cholesteryl ester transfer protein*, Biochimica et Biophysica Acta, vol. 1391, pp. 133-144 (1998).
Hegde, V. R., et al. *A depsipeptide fungal metabolite inhibitor of cholesteryl ester transfer protein*, Biorganic & Medicinal Chemistry Letters, vol. 8, pp. 1277-1280, (1998).
Barrett, A. G. M., et al., *Total Synthesis and Stereochemical Assignment of the Quinquecyclopropane-Containing Cholesteryl Ester Transfer Protein Inhibitor U-106305*, J. Am. Chem. Soc., vol. 118, pp. 7863-7864 (1996).
Kuo, M. S., et al., *Discovery, Isolation, Structure Elucidation, and Biosynthesis of U-106305, a Cholesteryl Ester Transfer Protein Inhibitor from UC 11136*, J. Am. Chem. Soc., vol. 117, pp. 10629-10634, (1995).
Pietzonka, T., et al., *Phosphonate-containing Analogs of Cholesteryl Ester as Novel Inhibitors of Cholesteryl Ester Transfer Protein*, Bioorganic & Medicinal Chemistry Letters, vol. 6, No. 16, pp. 1951-9154 (1996).
Coval, S. J., et al., *Wiedendiol-A and -B Cholesteryl Ester Transfer Protein Inhibitors from the Marin Sponge Xestospongia Wiedenmayeri*, Bioorganic & Medicinal Chemistry Letters, vol. 5, No. 6, pp. 605-610 (1995).
Lee, J. C., et al., *A Cholesteryl Ester Transfer Protein Inhibitor from an Insect-associated Fungus*, The Journal of Antibiotics, vol. 49, No. 7, pp. 693-696, (1996).
Busch, S. J., et al., *Cholesteryl Ester Analogs Inhibit Cholesteryl Ester but not Triglyceride Transfer Catalyzed by the Plasma Cholesteryl Ester-Triglyceride Transfer Protein*, Lipids, vol. 25, No. 4, pp. 216-220 (1990).
Connolly, D. T., et al., *Inactivation of Cholesteryl Ester Transfer Protein by Cysteine Modification*, Biochemical & Biophysical Research Communications, vol. 223, pp. 42-47 (1996).
Xia, Y., et al., *Substituted 1,3,5-Triazines as Cholesteryl Ester Transfer Protein Inhibitors*, Bioorganic & Medicinal Chemistry Letters, vol. 6, No. 7, pp. 919-922 (1996).
Bisgaier, C. L., et al.; *Cholesteryl Ester Transfer Protein Inhibition by PD 140195*, Lipids, vol. 29, No. 12, pp. 811-818, (1994).
Wagaw, S., et al., *The Synthesis of Aminopyridines: A Method Employing Palladium-Catalyzed Carbon-Nitrogen Bond Formation*, J. Org. Chem., vol. 61, pp. 7240-7241, (1996).
Wolfe, J. P., et al., *An Improved Catalyst System for Aromatic Carbon-Nitrogen Bond Formation: The Possible Involvement of Bis(Phosphine) Palladium Complexes as Key Intermediates*, J. Am. Chem. Soc., vol. 118, pp. 7215-7216, (1996).
Wolfe, J. P., et al., *Improved Functional Group Compatibility in the Palladium-Catalyzed Amination of Aryl Bromides*, Tetrahedron Letters, vol. 38, No. 36, pp. 6359-6362 (1997).
Marcoux, J. F., et al. *A General Copper-Catalyzed Synthesis of Diaryl Ethers*, J. Am. Chem. Soc., vol. 119, pp. 10539-10540, (1997).
Sheradsky, T., et al., *Studies on the Preparation of N-Alkyl-O-phenylhydroxylamines*, J. Chem. Soc. Perkin Trans., vol. 12, pp. 2781-2781, (1980).
Stembach, D. D., et al. *Reduction of O-Acyl Oximes*, Tetrahedron Letters, vol. 22, No. 35, pp. 3331-3334, (1981).
Ramachandran, P. V., et al., *Chiral Synthesis via Organoboranes. 40. Selective Reductions. 55. A Simple One-Pot Synthesis of the Enantiomers of (Trifluoromethyl)oxirane. A General Synthesis in High Optical Purities of α-Trifluoromethyl Secondary Alcohols via the Ring-Cleavage Reactions of the Epoxide*, J. Org. Chem., vol. 60, pp. 41-46, (1995).
McBee, E. T., et al., *The Preparation and Properties of 3,3,3-Trifluoro-1,2-epoxypropane*, J. Am. Chem. Soc., vol. 74, pp. 3022-3023 (1952).
DesMarteau, D. D., et al., *The first fluoroalkylation of amino acids and peptides in water utilizing the novel iodonium salt $(CF_3SO_2)_2NI(Ph)CH_2CF_3$*, Chem. Commun., pp. 2241-2242 (1998).
*Reagents for Organic Synthesis*, Feiser & Feiser, vol. 1, copyright 1967, John Wiley & Sons, Inc.
*Vogel's Textbook of Practical Organic Chemistry*, Fifth Edition, copyright 1989, John Wiley & Sons, Inc., pp. 902-905.
*The Systematic Identification of Organic Compounds: A Laboratory Manual*, Shriner/Fuson/Curtin, Fifth Edition, copyright 1956 and 1964, John Wiley & Sons, Inc.
English Language abstract for JP 50320117, 1993.
English Language abstract for JP 10287662, 1998.
English Language abstract for WO 90/02113, 1990.
*English Language Equivalent to CH 441366, 1968.
** English Language Equivalent to EP 0818197, 2003.
*** English Language Equivalent to DE 19627430, 1998.
**** English Language Equivalent to EP 0796846, 2000.
***** English Language Equivalent to EP 0818448, 2003.
****** English Language Equivalent to WO 90/01874, 1990.
*House's Modern Synthetic Reactions*, W. A. Benjamin, Inc., pp. 163-215, 1965.
*March's Advanced Organic Chemistry*, 4th Edition, John Wiley & Sons, pp. 293-412 and pp. 649-658.
Bonin, P. D., et al., *A peptide inhibitor of cholesteryl ester transfer protein identified by screening a beteriophage display library*, J. Peptide Res., vol. 51, pp. 216-225, (1998).
*House's Modern Synthetic Reactions*, W. A. Benjamin, Inc., Chapter 7, pp. 353-421, 1972.
Vanhessche, K. P. M., et al., *Catalytic Asymmetric Synthesis of New Halogenated Chiral Synthons*, Chem. Eur. J., vol. 3, No. 4, pp. 517-522, (1997).
U.S. Appl. No. 10/326,035 (our reference: PC31137).

* cited by examiner

(R)-CHIRAL HALOGENATED SUBSTITUTED FUSED HETEROCYCLIC AMINO COMPOUNDS USEFUL FOR INHIBITING CHOLESTEROL ESTER TRANSFER PROTEIN ACTIVITY

CROSS REFERENCE TO RELATED APPLICATIONS

This application claims the benefit of priority from U.S. application Ser. No. 10/017,290, filed Dec. 12, 2001, now U.S. Pat. No. 6,803,388, which clams priority from U.S. application Ser. No. 09/401,915, filed Sep. 23, 1999, now abandoned, both of which are incorporated in their entireties for all purposes.

FIELD OF THE INVENTION

This invention is in the field of treating cardiovascular disease, and specifically relates to compounds, compositions, methods for treating atherosclerosis and other coronary artery disease, and methods for making compounds of this invention. More particularly, the invention relates to (R)-chiral halogenated 1-substitutedamino-(n+1)-alkanol compounds that inhibit cholesteryl ester transfer protein (CETP), also known as plasma lipid transfer protein-I.

BACKGROUND OF THE INVENTION

Numerous studies have demonstrated that a low plasma concentration of high density lipoprotein (HDL) cholesterol is a powerful risk factor for the development of atherosclerosis (Barter and Rye, *Atherosclerosis*, 121, 1–12 (1996)). HDL is one of the major classes of lipoproteins that function in the transport of lipids through the blood. The major lipids found associated with HDL include cholesterol, cholesteryl ester, triglycerides, phospholipids and fatty acids. The other classes of lipoproteins found in the blood are low density lipoprotein (LDL) and very low density lipoprotein (VLDL). Since low levels of HDL cholesterol increase the risk of atherosclerosis, methods for elevating plasma HDL cholesterol would be therapeutically beneficial for the treatment of atherosclerosis and other diseases associated with accumulation of lipid in the blood vessels. These diseases include, but are not limited to, coronary heart disease, peripheral vascular disease, and stroke.

*Atherosclerosis* underlies most coronary artery disease (CAD), a major cause of morbidity and mortality in modem society. High LDL cholesterol (above 180 mg/dl) and low HDL cholesterol (below 35 mg/dl) have been shown to be important contributors to the development of atherosclerosis. Other diseases, such as peripheral vascular disease, stroke, and hypercholesterolaemia are negatively affected by adverse HDL/LDL ratios. Inhibition of CETP by the subject compounds is shown to effectively modify plasma HDL/LDL ratios, and to check the progress and/or formation of these diseases.

CETP is a plasma protein that facilitates the movement of cholesteryl esters and triglycerides between the various lipoproteins in the blood (Tall, *J. Lipid Res.*, 34, 1255–74 (1993)). The movement of cholesteryl ester from HDL to LDL by CETP has the effect of lowering HDL cholesterol. It therefore follows that inhibition of CETP should lead to elevation of plasma HDL cholesterol and lowering of plasma LDL cholesterol, thereby providing a therapeutically beneficial plasma lipid profile (McCarthy, *Medicinal Res. Revs.*, 13, 139–59 (1993); Sitori, *Pharmac. Ther.*, 67,443–47 (1995)). This exact phenomenon was first demonstrated by Swenson et al., (*J. Biol. Chem.*, 264, 14318 (1989)) with the use of a monoclonal antibody that specifically inhibited CETP. In rabbits, the antibody caused an elevation of the plasma HDL cholesterol and a decrease in LDL cholesterol. Son et al. (*Biochim. Biophys. Acta* 795, 743–480 (1984)), Morton et al. (*J. Lipid Res.* 35, 836–847 (1994)) and Tollefson et al. (*Am. J. Physiol.*, 255, (Endocrinol. Metab. 18, E894–E902 (1988))) describe proteins from human plasma that inhibit CETP. U.S. Pat. No. 5,519,001, issued to Kushwaha et al., describes a 36 amino acid peptide derived from baboon apo C-1 that inhibits CETP activity. Cho et al. (*Biochim. Biophys. Acta* 1391, 133–144 (1998)) describe a peptide from hog plasma that inhibits human CETP. Bonin et al. (*J. Peptide Res.*, 51, 216–225 (1998)) disclose a decapeptide inhibitor of CETP. A depsipeptide fungal metabolite is disclosed as a CETP inhibitor by Hedge et al. in *Bioorg. Med. Chem. Lett.*, 8, 1277–80 (1998).

There have been several reports of non-peptidic compounds that act as CETP inhibitors. Barrett et al. (*J. Am. Chem. Soc.*, 188, 7863–63 (1996)) and Kuo et al. (*J. Am. Chem. Soc.*, 117, 10629–34 (1995)) describe cyclopropane-containing CETP inhibitors. Pietzonka et al. (*Bioorg. Med. Chem. Lett*, 6, 1951–54 (1996)) describe phosphonate-containing analogs of cholesteryl ester as CETP inhibitors. Coval et al. (*Bioorg. Med. Chem. Lett.*, 5, 605–610 (1995)) describe Wiedendiol-A and -B, and related sesquiterpene compounds as CETP inhibitors. Japanese Patent Application No. 10287662-A describes polycyclic, non-amine containing, polyhydroxylic natural compounds possessing CETP inhibition properties. Lee et al. (*J. Antibiotics*, 49, 693–96 (1996)) describe CETP inhibitors derived from an insect fungus. Busch et al. (*Lipids*, 25, 216–220, (1990)) describe cholesteryl acetyl bromide as a CETP inhibitor. Morton and Zilversmit (*J. Lipid Res.*, 35, 836–47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.* 223, 42–47 (1996)) describe other cysteine modification reagents as CETP inhibitors. Xia et al. describe 1,3,5-triazines as CETP inhibitors (Bioorg. Med. Chem. Lett., 6, 919–22 (1996)). Bisgaier et al. (*Lipids*, 29, 811–8 (1994)) describe 4-phenyl-5-tridecyl-4H-1,2,4-triazole-thiol as a CETP inhibitor. Oomura et al. disclose non-peptidic tetracyclic and hexacyclic phenols as CETP inhibitors in Japanese Patent Application No. 10287662.

Some substituted heteroalkylamine compounds are known. In European Patent Application No. 796846, Schmidt et al. describe 2-aryl-substituted pyridines as cholesteryl ester transfer protein inhibitors useful as cardiovascular agents. One substitutent at C3 of the pyridine ring can be an hydroxyalkyl group. In European Patent Application No. 801060, Dow and Wright describe heterocyclic derivatives substituted with an aldehyde addition product of an alkylamine to afford 1-hydroxy-1-amines. These are reported to be β3-adrenergic receptor agonists useful for treating diabetes and other disorders. In Great Britain Patent Application No. 2305665, Fisher et al. disclose 3-agonist secondary amino alcohol substituted pyridine derivatives useful for treating several disorders including cholesterol levels and artheroscrotic diseases. In European Patent Application No. 818448, Schmidt et al. describe tetrahydroquinoline derivatives as cholesteryl ester transfer protein inhibitors. European Patent Application No. 818197, Schmek et al. describe pyridines with fused heterocycles as cholesteryl ester transfer protein inhibitors. Brandes et al. in German Patent Application No. 19627430 describe bicyclic condensed pyridine derivatives as cholesteryl ester transfer protein inhibitors. In WO Patent Application No. 09839299, Muller-Gliemann et al. describe quinoline derivatives as cholesteryl ester transfer protein inhibitors. U.S. Pat. No. 2,700,686, issued to Dickey and Towne, describes N-(2-haloalkyl-2-hydroxyethyl)amines in which the amine is further substituted with either 1 to 2 aliphatic groups or one aromatic group and one aliphatic group. U.S. Pat. No. 2,700,686 further describes a process to prepare the N-(2-haloalkyl-2-hydroxyethyl)amines by reacting halogenated-1,2-epoxyalkanes with the corresponding aliphatic amines and N-alkylanilines and their use as dye intermediates.

SUMMARY OF THE INVENTION

The present invention provides chiral compounds that can be used to inhibit cholesteryl ester transfer protein (CETP) activity and that have the general structure:

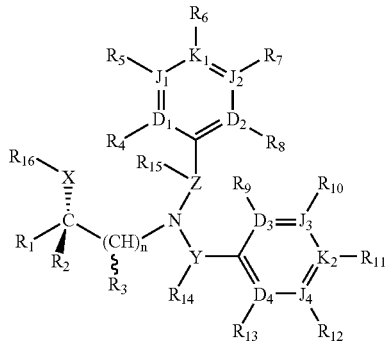

In another aspect, the present invention includes pharmaceutical compositions comprising a pharmaceutically effective amount of the chiral compounds of this invention and a pharmaceutically acceptable carrier.

In another aspect, this invention relates to methods of using these chiral inhibitors as therapeutic agents in humans to inhibit cholesteryl ester transfer protein (CETP) activity, thereby decreasing the concentrations of low density lipoprotein (LDL) and raising the level of high density lipoprotein (HDL), resulting in a therapeutically beneficial plasma lipid profile. The compounds and methods of this invention can also be used to treat dyslipidemia (hypoalphalipoproteinemia), hyperlipoproteinaemia (chylomicronemia and hyperapobetalipoproteinemia), peripheral vascular disease, hypercholesterolaemia, atherosclerosis, coronary artery disease and other CETP-mediated disorders. The compounds can also be used in prophylactic treatment of subjects who are at risk of developing such disorders. The compounds can be used to lower the risk of atherosclerosis. The compounds of this invention would be also useful in prevention of cerebral vascular accident (CVA) or stroke. Besides being useful for human treatment, these compounds are also useful for veterinary treatment of companion animals, exotic animals and farm animals such as primates, rabbits, pigs, horses, and the like.

DESCRIPTION OF THE INVENTION

The present invention relates to a class of compounds comprising (R)-chiral halogenated 1-substitutedamino-(n+1)-alkanols which are beneficial in the therapeutic and prophylactic treatment of coronary artery disease as given in Formula I-H (also referred to herein as generic polycyclic aryl and heteroaryl (R)-chiral halogenated 1-substitutedamino-(n+1)-alkanols):

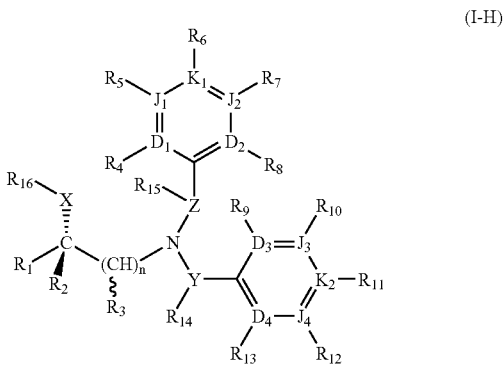

or a pharmaceutically-acceptable salt thereof, wherein;

n is an integer selected from 1 through 4;

X is oxy;

$R_1$ is selected from the group consisting of haloalkyl, haloalkenyl, haloalkoxymethyl, and haloalkenyloxymethyl with the proviso that $R_1$ has a higher Cahn-Ingold-Prelog stereochemical system ranking than both $R_2$ and $(CHR_3)_n$—N(A)Q wherein A is Formula (II) and Q is Formula (III);

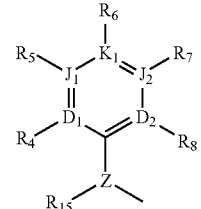

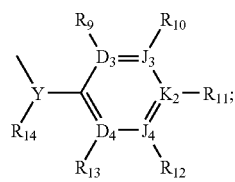

$R_{16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, dialkoxyphosphonoalkyl, trialkylsilyl, and a spacer selected from the group consisting of a covalent single bond and a linear spacer moiety having a chain length of 1 to 4 atoms linked to the point of bonding of any aromatic substituent selected from the group consisting of $R_4$, $R_8$, $R_9$, $R_{13}$, $R_{14}$, and $R_{15}$ to form a heterocyclyl ring having from 5 through 10 contiguous members;

$D_1$, $D_2$, $J_1$, $J_2$ and $K_1$ are independently selected from the group consisting of C, N, O, S and covalent bond with the provisos that no more than one of $D_1$, $D_2$, $J_1$, $J_2$ and $K_1$ can be a covalent bond, no more than one of $D_1$, $D_2$, $J_1$, $J_2$ and $K_1$ can be O, no more than one of $D_1$, $D_2$, $J_1$, $J_2$ and $K_1$ can be S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ can be N;

$D_3$, $D_4$, $J_3$, $J_4$ and $K_2$ are independently selected from the group consisting of C, N, O, S and covalent bond with the provisos that no more than one can be a covalent bond, no more than one of $D_3$, $D_4$, $J_3$, $J_4$ and $K_2$ can be O, no more than one of $D_3$, $D_4$, $J_3$, $J_4$ and $K_2$ can be S, no more than two of $D_3$, $D_4$, $J_3$, $J_4$ and $K_2$ can be O and S, one of $D_3$, $D_4$, $J_3$, $J_4$ and $K_2$ must be a covalent bond when two of $D_3$, $D_4$, $J_3$, $J_4$ and $K_2$ are O and S, and no more than four of $D_3$, $D_4$, $J_3$, $J_4$ and $K_2$ can be N;

$R_2$ is hydrido;

$R_2$ can be selected from the group consisting of hydroxyalkyl, alkyl, alkenyl, alkynyl, aryl, aralkyl, aralkoxyalkyl, aryloxyalkyl, alkoxyalkyl, heteroaryloxyalkyl, alkenyloxyalkyl, cycloalkyl, cycloalkylalkyl, cycloalkylalkenyl, cycloalkenyl, cycloalkenylalkyl, haloalkyl, haloalkenyl, halocycloalkyl, haloalkoxy, haloalkoxyalkyl, haloalkenyloxyalkyl, halocycloalkoxy, halocycloalkoxyalkyl, halocycloalkenyloxyalkyl, heteroaryl, heteroarylalkyl, heteroarylthioalkyl, perhaloaryl, perhaloaralkyl, perhaloaralkyl, heteroaralkylthioalkyl, monocarboalkoxyalkyl, dicarboalkoxyalkyl, monocyanoalkyl, dicyanoalkyl, carboalkoxycyanoalkyl, alkylsulfinylalkyl, alkylsulfonylalkyl, arylsulfinylalkyl, arylsulfonylalkyl, cycloalkylsulfinylalkyl, cycloalkylsufonylalkyl, heteroarylsulfonylalkyl, heteroarylsulfinylalkyl, aralkylsulfonylalkyl, carboxy, carboxyalkyl, carboalkoxy, carboxamide, carboxamidoalkyl, carboaralkoxy, dicyanoalkyl, carboalkoxycyanoalkyl, dialkoxyphosphonoalkyl, and diaralkoxyphosphonoalkyl with the proviso that $R_2$ has a lower Cahn-Ingold-Prelog system ranking than both $R_1$ and $(CHR_3)_n$—N(A)Q;

$R_3$ is selected from the group consisting of hydrido, hydroxy, halo, cyano, aryloxy, hydroxyalkyl, amino, alkylamino, dialkylamino, acyl, acylamido, alkoxy, alkyl, alkenyl, alkynyl, aryl, aralkyl, aryloxyalkyl, alkoxyalkyl, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, haloalkyl, haloalkenyl, haloalkoxy, haloalkoxyalkyl, haloalkenyloxyalkyl, alkylthioalkyl, arylthioalkyl, cycloalkyl, cycloalkylalkyl, cycloalkylalkenyl, cycloalkenyl, cycloalkenylalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, arylsulfinylalkyl, arylsulfonylalkyl, cycloalkylsulfinylalkyl, cycloalkylsufonylalkyl, heteroarylsulfonylalkyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphonoalkyl, and diaralkoxyphosphonoalkyl with the provisos that $(CHR_3)_n$—N(A)Q has a lower Cahn-Ingold-Prelog stereochemical system ranking than $R_1$ and a higher Cahn-Ingold-Prelog stereochemical system ranking than $R_2$;

Y is selected from a group consisting of a covalent single bond, $(C(R_{14})_2)_q$ wherein q is an integer selected from 1 through 2 and $(CH(R_{14}))_g$—W—$(CH(R_{14}))_p$ wherein g and p are integers independently selected from 0 through 1;

$R_{14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_9$ and $R_{13}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_4$ and $R_8$ to form a heterocyclyl having from 5 through 8 contiguous members with the proviso that, when Y is a covalent bond, an $R_{14}$ substituent is not attached to Y;

$R_{14}$ and $R_{15}$ can be taken together to form a spacer selected from a moiety having a chain length of 2 to 5 atoms to form a heterocyclyl ring having from 5 through 8 contiguous members;

$R_{14}$ and $R_{14}$, when bonded to the different atoms, can be taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{14}$ and $R_{14}$, when bonded to the same atom can be taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

W is selected from the group consisting of O, C(O), C(S), C(O)N($R_{14}$), C(S)N($R_{14}$), ($R_{14}$)NC(O), ($R_{14}$)NC(S), S, S(O), S(O)$_2$, S(O)$_2$N($R_{14}$), ($R_{14}$)NS(O)$_2$, and N($R_{14}$) with the proviso that $R_{14}$ is selected from other than halo and cyano;

Z is independently selected from a group consisting of a covalent single bond, $(C(R_{15})_2)_q$ wherein q is an integer selected from 1 through 2, $(CH(R_{15}))_j$—W—$(CH(R_{15}))_k$ wherein j and k are integers independently selected from 0 through 1 with the proviso that, when Z is a covalent single bond, an $R_{15}$ substituent is not attached to Z;

$R_{15}$ is independently selected, when Z is $(C(R_{15})_2)_q$ wherein q is an integer selected from 1 through 2, from the group consisting of hydrido, hydroxy, halo, cyano, aryloxy, amino, alkylamino, dialkylamino, hydroxyalkyl, acyl, aroyl, heteroarpyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_4$ and $R_8$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_9$ and $R_{13}$ to form a heterocyclyl having from 5 through 8 contiguous members;

$R_{15}$ and $R_{15}$, when bonded to the different atoms, can be taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{15}$ and $R_{15}$, when bonded to the same atom, can be taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{15}$ is independently selected, when Z is $(CH(R_{15}))_j$—W—$(CH(R_{15}))_k$ wherein j and k are integers independently selected from 0 through 1, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroaralkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_4$ and $R_8$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_9$ and $R_{13}$ to form a heterocyclyl ring having from 5 through 8 contiguous members;

$R_4$, $R_5$, $R_6$, $R_7$, $R_8$, $R_9$, $R_{10}$, $R_{11}$, $R_{12}$, and $R_{13}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkyl, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkoxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyalkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_4$, $R_5$, $R_6$, $R_7$, and $R_8$ present, that there are one to five non-hydrido ring substituents $R_9$, $R_{10}$, $R_{11}$, $R_{12}$, and $R_{13}$ present, and $R_4$, $R_5$, $R_6$, $R_7$, $R_8$, $R_9$, $R_{10}$, $R_{11}$, $R_{12}$, and $R_{13}$ are each independently selected to maintain the tetravalent nature of carbon, trivalent nature of nitrogen, the divalent nature of sulfur, and the divalent nature of oxygen;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ can be independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_4$ and $R_5$, $R_5$ and $R_6$, $R_6$ and $R_7$, and $R_7$ and $R_8$, can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time;

$R_4$ and $R_9$, $R_4$ and $R_{13}$, $R_8$ and $R_9$, and $R_8$ and $R_{13}$ can be independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_4$ and $R_9$, $R_4$ and $R_{13}$, $R_8$ and $R_9$, and $R_8$ and $R_{13}$ can be used at the sane time;

$R_5$ and $R_{10}$, $R_5$ and $R_{12}$, $R_7$ and $R_{10}$, and $R_7$ and $R_{12}$ can be independently selected to form a spacer pair wherein said spacer pair is taken together to form a linear moiety wherein said linear moiety forms a C8 to C13 heterocyclyl ring having from 8 through 13 contiguous members with the proviso that no more than one of the group consisting of spacer pairs $R_5$ and $R_{10}$, $R_5$ and $R_{12}$, $R_7$ and $R_{10}$, and $R_7$ and $R_{12}$ can be used at the same time.

In a another embodiment of compounds of Formula I-H, $D_1$, $D_2$, $J_1$, $J_2$ and $K_1$ are each carbon with the proviso that at least one of $D_3$, $D_4$, $J_3$, $J_4$ and $K_2$ is selected from the group consisting of O, S, and N, wherein $D_3$, $D_4$, $J_3$, $J_4$ and $K_2$ are independently selected from the group consisting of C, N, O, S and covalent bond with the provisos that no more than one of $D_3$, $D_4$, $J_3$, $J_4$ and $K_2$ can be a covalent bond, no more than one of $D_3$, $D_4$, $J_3$, $J_4$ and $K_2$ can be O, no more than one of $D_3$, $D_4$, $J_3$, $J_4$ and $K_2$ can be S, one of $D_3$, $D_4$, $J_3$, $J_4$ and $K_2$ must be a covalent bond when two of $D_3$, $D_4$, $J_3$, $J_4$ and $K_2$ are O and S, and no more than four of D3, $D_4$, $J_3$, $J_4$ and $K_2$ can be N;

$D_1$, $D_2$, $J_1$, $J_2$ and $K_1$ can be selected from the group consisting of C, O, S, N and covalent bond with the provisos that $D_3$, $D_4$, $J_3$, $J_4$ and $K_2$ are each carbon and at least one of $D_1$, $D_2$, $J_1$, $J_2$ and $K_1$ is selected from the group consisting of O, S, and N wherein, when $D_1$, $D_2$, $J_1$, $J_2$ and $K_1$ are selected from the group consisting of C, O, S, covalent bond, and N, no more than one of $D_1$, $D_2$, $J_1$, $J_2$ and $K_1$ can be a covalent bond, no more than one of $D_1$, $D_2$, $J_1$, $J_2$ and $K_1$ can be O, no more than one of $D_1$, $D_2$, $J_1$, $J_2$ and $K_1$ can be S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ can be N;

n is an integer selected from 1 through 4;

X is oxy;

$R_{16}$ is selected from the group consisting of hydrido, acyl, aroyl, and trialkylsilyl;

$R_1$ is selected from the group consisting of haloalkyl, haloalkenyl, haloalkoxymethyl, and haloalkenyloxymethyl with the proviso that $R_1$ has a higher Cahn-Ingold-Prelog stereochemical system ranking than both $R_2$ and $(CHR_3)_n$—N(A)Q wherein A is Formula (II) and Q is Formula (III);

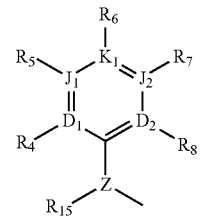

(II)

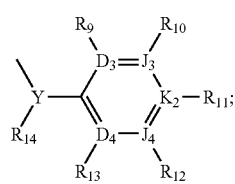

(III)

$R_2$ is hydrido;

$R_2$ can be selected from the group consisting of aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl with the proviso that $R_2$ has a lower Cahn-Ingold-Prelog system ranking than both $R_1$ and $(CHR_3)_n$—N(A)Q;

$R_3$ is selected from the group consisting of hydrido, hydroxy, cyano, aryl, aralkyl, acyl, alkoxy, alky, alkenyl, alkoxyalkl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl with the provisos that $(CHR_3)_n$—N(A)Q has a lower Cahn-Ingold-Prelog stereochemical system ranking than $R_1$ and a higher Cahn-Ingold-Prelog stereochemical system ranking than $R_2$;

Y is selected from the group consisting of covalent single bond and $(C(R_{14})_2)_q$ wherein q is an integer selected from 1 through 2;

$R_{14}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 1;

W is oxy;

$R_{15}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$ and $R_{12}$ are independently selected from the group consisting of hydrido, carboxy, heteroaralkylthio, heteroarylsulfonyl, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, lower alkylamino, alkylthio, arylamino, aralkylamino, arylthio, arylthioalkyl, alkylsulfonyl, alkylsulfonamido, monoarylamidosulfonyl, arylsulfonyl, heteroarylthio, heterocyclylsulfonyl, heterocyclylthio, alkanoyl, alkenoyl, aroyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyalkyl, aryl, aryloxy, aralkoxy, saturated heterocyclyl, heteroaryl, heteroaryloxy, heteroaryloxyalkyl, heteroaralkyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ spacer pairs can be independently selected from the group consisting of alkylene, alkenylene, alkylenedioxy, aralkylene, diacyl, haloalkylene, and aryloxylene with the provisos that no more than one of the group consisting of spacer pairs $R_4$ and $R_5$, $R_5$ and $R_6$, $R_6$ and $R_7$, and $R_7$ and $R_8$ can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In an even more specific embodiment of compounds Formula I-H, $D_1$, $D_2$, $J_1$, $J_2$ and $K_1$ are each carbon;

$D_3$, $D_4$, $J_3$, $J_4$ and $K_2$ are independently selected from the group consisting of C, N, O, S and covalent bond with the provisos that at least one of $D_3$, $D_4$, $J_3$, $J_4$ and $K_2$ is selected from the group consisting of O, S, and N, wherein no more than one of $D_3$, $D_4$, $J_3$, $J_4$ and $K_2$ can be a covalent bond, no more than one of $D_3$, $D_4$, $J_3$, $J_4$ and $K_2$ can be O, no more than one of $D_3$, $D_4$, $J_3$, $J_4$ and $K_2$ can be S, one of $D_3$, $D_4$, $J_3$, $J_4$ and $K_2$ must be a covalent bond when two of $D_3$, $D_4$, $J_3$, $J_4$ and $K_2$ are O and S, and no more than four of $D_3$, $D_4$, $J_3$, $J_4$ and $K_2$ can be N;

n is an integer selected from 1 to 3;

X is oxy;

$R_1$ is selected from the group consisting of trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, and heptafluoropropyl;

$R_{16}$ is selected from the group consisting of acetyl, benzoyl, dimethyl tert-butylsilyl, hydrido, and trimethylsilyl;

$R_2$ is hydrido;

$R_2$ can be selected from the group consisting of hydrido, methyl, ethyl, propyl, butyl, isopropyl, isobutyl, vinyl, phenyl, 4-trifluoromethylphenyl, 1,1,2,2-tetrafluoroethoxymethyl, chloromethyl, trifluoromethoxymethyl, fluoromethyl, difluoromethyl, 2,2,3,3,3-pentafluoropropyl, and pentafluorophenoxymethyl with the proviso that $R_2$ has a lower Cahn-Ingold-Prelog system ranking than both $R_1$ and $(CHR_3)_n$—N(A)Q;

$R_3$ is selected from the group consisting of hydrido, hydroxy, cyano, acetyl, methoxy, ethoxy, methyl, ethyl, propyl, vinyl, phenyl, methoxymethyl, 4-trifluoromethylphenyl, trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, heptafluoropropyl, pentafluorophenyl, and pentafluorophenoxymethyl with the provisos that $(CHR_3)_n$—N(A)Q has a lower Cahn-Ingold-Prelog stereochemical system ranking than $R_1$ and a higher Cahn-Ingold-Prelog stereochemical system ranking than $R_2$.

In another even more specific embodiment of compounds Formula I-H,

D3, $D_4$, $J_3$, $J_4$ and $K_2$ are each carbon;

$D_1$, $D_2$, $J_1$, $J_2$ and $K_1$ are independently selected from the group consisting of C, N, O, S and covalent bond with the provisos that at least one of $D_1$, $D_2$, $J_1$, $J_2$ and $K_1$ is selected from the group consisting of O, S, and N, wherein no more than one of $D_1$, $D_2$, $J_1$, $J_2$ and $K_1$ can be a covalent bond, no more than one of $D_1$, $D_2$, $J_1$, $J_2$ and $K_1$ can be O, no more than one of $D_1$, $D_2$, $J_1$, $J_2$ and $K_1$ can be S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ can be N;

n is an integer selected from 1 to 3;

X is oxy;

$R_1$ is selected from the group consisting of trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, and heptafluoropropyl;

$R_{16}$ is selected from the group consisting of acetyl, benzoyl, dimethyl tert-butylsilyl, hydrido, and trimethylsilyl;

$R_2$ is hydrido;

$R_2$ can be selected from the group consisting of hydrido, methyl, ethyl, propyl, butyl, isopropyl, isobutyl, vinyl, phenyl, 4-trifluoromethylphenyl, 1,1,2,2-tetrafluoroethoxymethyl, chloromethyl, trifluoromethoxymethyl, fluoromethyl, difluoromethyl, 2,2,3,3,3-pentafluoropropyl, and pentafluorophenoxymethyl with the proviso that $R_2$ has a lower Cahn-lngold-Prelog system ranking than both $R_1$ and $(CHR_3)_n$—N(A)Q;

$R_3$ is selected from the group consisting of hydrido, hydroxy, cyano, acetyl, methoxy, ethoxy, methyl, ethyl, propyl, vinyl, phenyl, methoxymethyl, 4-trifluoromethylphenyl, trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3, 3,3-pentafluoropropyl, heptafluoropropyl, pentafluorophenyl, and pentafluorophenoxymethyl with the provisos that $(CHR_3)_n$—N(A)Q has a lower Cahn-Ingold-Prelog stereochemical system ranking than $R_1$ and a higher Cahn-Ingold-Prelog stereochemical system ranking than $R_2$.

In a preferred embodiment of compounds of Formula I-H, the compounds correspond to the Formula I-C (also referred to herein as phenyl (R)-chiral halogenated 1-substitutedamino-(n+1)-alkanols):

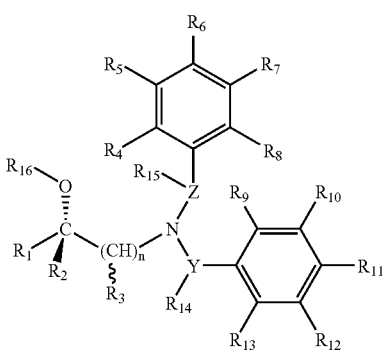

(I-C)

or a pharmacuetically acceptable salt thereof, wherein;

n is an integer selected from 1 through 4;

$R_{16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_4$, $R_8$, $R_9$, and $R_{13}$ to form a heterocyclyl ring having from 5 through 10 contiguous members with the proviso that said linear spacer moiety is other than covalent single bond when $R_2$ is alkyl;

$R_1$ is selected from the group consisting of haloalkyl, haloalkenyl, haloalkoxymethyl, and haloalkenyloxymethyl with the proviso that $R_1$ has a higher Cahn-Ingold-Prelog stereochemical system ranking than both $R_2$ and $(CHR_3)_n$—N(Ap)Qp wherein Ap is Formula (II-P) and Qp is Formula (III-P);

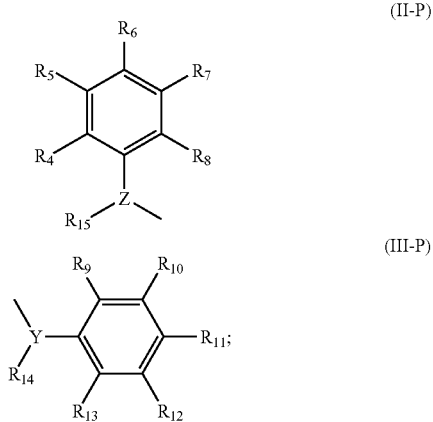

$R_2$ is hydrido;

$R_2$ can be selected from the group consisting of aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl with the proviso that $R_2$ has a lower Cahn-Ingold-Prelog system ranking than both $R_1$ and $(CHR_3)_n$—N(Ap)Qp;

$R_3$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl with the provisos that $(CHR_3)_n$—N(Ap)Qp has a lower Cahn-Ingold-Prelog stereochemical system ranking than $R_1$ and a higher Cahn-Ingold-Prelog stereochemical system ranking than $R_2$;

Y is selected from the group consisting of covalent single bond and $(C(R_{14})_2)_q$ wherein q is an integer selected from 1 through 2;

$R_{14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 1;

W is selected from the group consisting of O, C(O), C(S), $C(O)N(R_{14})$, $C(S)N(R_{14})$, $(R_{14})NC(O)$, $(R_{14})NC(S)$, S, S(O), $S(O)_2$, $S(O)_2N(R_{14})$, $(R_{14})NS(O)_2$, and $N(R_{14})$ with the proviso that $R_{14}$ is other than cyano;

$R_{15}$ is selected from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, heteroaralkyl, arylalkenyl, heteroarylalkenyl, carboxyalkyl, carboalkoxy, alkoxycarboxamindo, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ can be independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_4$ and $R_5$, $R_5$ and $R_6$, $R_6$ and $R_7$, and $R_7$ and $R_8$, can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In a preferred embodiment of compounds of Formula I-C, n is an integer selected from 1 through 4;

$R_{16}$ is selected from the group consisting of hydrido, acyl, aroyl, and trialkylsilyl;

$R_1$ is selected from the group consisting of haloalkyl, haloalkenyl, haloalkoxymethyl, and haloalkenyloxymethyl with the proviso that $R_1$ has a higher Cahn-Ingold-Prelog stereochemical system ranking than both $R_2$ and $(CHR_3)_n$—N(Ap)Qp wherein Ap is Formula (II-P) and Qp is Formula (III-P);

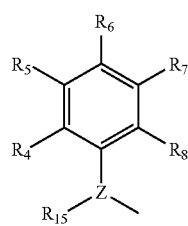

(II-P)

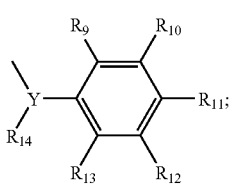

(III-P)

$R_2$ is hydrido;

$R_2$ can be selected from the group consisting of aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl with the proviso that $R_2$ has a lower Cahn-Ingold-Prelog system ranking than both $R_1$ and $(CHR_3)_n$—N(AP)Qp;

$R_3$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl with the provisos that $(CHR_3)_n$—N(Ap)Qp has a lower Cahn-Ingold-Prelog stereochemical system ranking than $R_1$ and a higher Cahn-Ingold-Prelog stereochemical system ranking than $R_2$;

Y is selected from the group consisting of covalent single bond and $(C(R_{14})_2)_q$ wherein q is an integer selected from 1 through 2;

$R_{14}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 1;

W is oxy;

$R_{15}$ is selected from the group consisting of hydrido, cyano, hydroxyalkyl, acyl, alkoxy, alkyl, alkenyl, alkoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of hydrido, carboxy, heteroaralkylthio, heteroarylsulfonyl, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, lower alkylamino, alkylthio, arylamino, aralkylamino, arylthio, arylthioalkyl, alkylsulfonyl, alkylsulfonamido, monoarylamidosulfonyl, arylsulfonyl, heteroarylthio, heterocyclylsulfonyl, heterocyclylthio, alkanoyl, alkenoyl, aroyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyalkyl, aryl, aralkyl, aryloxy, aralkoxy, saturated heterocyclyl, heteroaryl, heteroaryloxy, heteroaryloxyalkyl, arylalkyl, heteroarylalkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ spacer pairs can be independently selected from the group consisting of alkylene, alkenylene, alkylenedioxy, aralkylene, diacyl, haloalkylene, and aryloxylene with the provisos that no more than one of the group consisting of spacer pairs $R_4$ and $R_5$, $R_5$ and $R_6$, $R_6$ and $R_7$, and $R_7$ and $R_8$ can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In a more preferred embodiment of compounds of Formula I-C, n is an integer selected from 1 through 2;

$R_1$ is selected from the group consisting of haloalkyl and haloalkoxymethyl with the proviso that $R_1$ has a higher Cahn-Ingold-Prelog stereochemical system ranking than both $R_2$ and $(CHR_3)_n$—$N(Ap)Qp$ wherein Ap is Formula (II-P) and Qp is Formula (III-P);

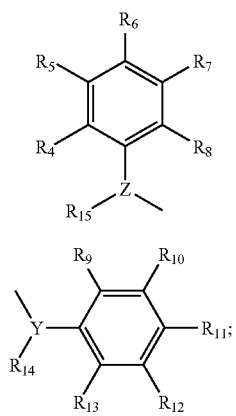

$R_{16}$ is hydrido;

$R_2$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl, and heteroaryl with the proviso that $R_2$ has a lower Cahn-Ingold-Prelog system ranking than both $R_1$ and $(CHR_3)_n$—$N(Ap)Qp$;

$R_3$ is selected from the group consisting of hydrido, aryl, alkyl, alkenyl, haloalkyl, and haloalkoxyalkyl with the provisos that $(CHR_3)_n$—$N(Ap)Qp$ has a lower Cahn-Ingold-Prelog stereochemical system ranking than $R_1$ and a higher Cahn-Ingold-Prelog stereochemical system ranking than $R_2$;

Y is selected from the group consisting of a covalent single bond and alkylene;

Z is selected from the group consisting of a covalent single bond and alkylene;

$R_{14}$ is selected from the group consisting of hydrido, alkyl, and haloalkyl;

$R_{15}$ is selected from the group consisting of hydrido, alkyl, and haloalkyl;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl.

In an even more preferred embodiment of compounds of Formula I-C, n is the integer 1;

$R_{16}$ is hydrido;

$R_1$ is haloalkyl with the proviso that $R_1$ has a higher Cahn-Ingold-Prelog stereochemical system ranking than both $R_2$ and $(CHR_3)_n$—$N(Ap)Qp$ wherein Ap is Formula (II-P) and Qp is Formula (III-P);

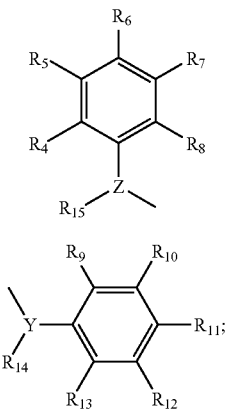

$R_2$ is hydrido;

$R_2$ can be selected from the group consisting of alkyl, haloalkyl, aryl, and haloalkoxy with the proviso that $R_2$ has a lower Cahn-Ingold-Prelog system ranking than both $R_1$ and $(CHR_3)_n$—$N(Ap)Qp$;

$R_3$ is selected from the group consisting of hydrido, alkyl, and haloalkyl with the provisos that $(CHR_3)_n$—$N(Ap)Qp$ has a lower-Cahn-Ingold-Prelog stereochemical system ranking than $R_1$ and a higher Cahn-Ingold-Prelog stereochemical system ranking than $R_2$;

Y is alkylene;

Z is covalent single bond;

$R_{14}$ is hydrido;

$R_4$, $R_8$, $R_9$, and $R_{13}$ are independently selected from the group consisting of hydrido and halo;

$R_5$, $R_6$, $R_7$, $R_{10}$, $R_{11}$ and $R_{12}$ are independently selected from the group consisting of hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, and heteroaryloxyalkyl.

In an embodiment of compounds of Formula I-C, n is an integer selected from 1 to 3;

$R_1$ is selected from the group consisting of trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, and heptafluoropropyl with the proviso that $R_1$ has a higher Cahn-Ingold-Prelog stereochemical system ranking than both $R_2$ and $(CHR_3)_n$—$N(Ap)Qp$ wherein Ap is Formula (II-P) and Qp is Formula (III-P);

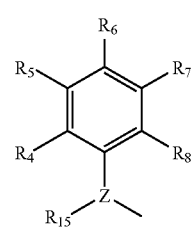

-continued

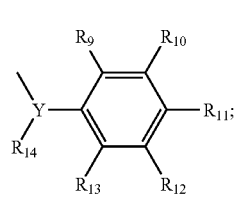
(III-P)

R₁₆ is selected from the group consisting of acetyl, benzoyl, dimethyl tert-butylsilyl, hydrido, and trimethylsilyl;

R₂ is hydrido;

R₂ can be selected from the group consisting of methyl, ethyl, propyl, butyl, isopropyl, isobutyl, vinyl, phenyl, 4-trifluoromethylphenyl, 1,1,2,2-tetrfluoroethoxymethyl, chloromethyl, trifluoromethoxymethyl, fluoromethyl, difluoromethyl, 2,2,3,3,3-pentafluoropropyl, and and pentafluorophenoxymethyl with the proviso that R₂ has a lower Cahn-Ingold-Prelog system ranking than both R₁ and (CHR₃)ₙ—N(Ap)Qp;

R₃ is selected from the group consisting of hydrido, hydroxy, cyano, acetyl, methoxy, ethoxy, methyl, ethyl, propyl, vinyl, phenyl, methoxymethyl, 4-trifluoromethylphenyl, trifluoromethyl, 1,1,2,2-tetrafluoroethoxymethyl, trifluoromethoxymethyl, chloromethyl, fluoromethyl, difluoromethyl, chlorodifluoromethyl, pentafluoroethyl, 2,2,3,3,3-pentafluoropropyl, heptafluoropropyl, pentafluorophenyl, and pentafluorophenoxymethyl with the provisos that (CHR₃)ₙ—N(Ap)Qp has a lower Cahn-Ingold-Prelog stereochemical system ranking than R₁ and a higher Cahn-Ingold-Prelog stereochemical system ranking than R₂.

In a preferred embodiment of compounds of Formula I-C, compounds have the Formula I-CP:

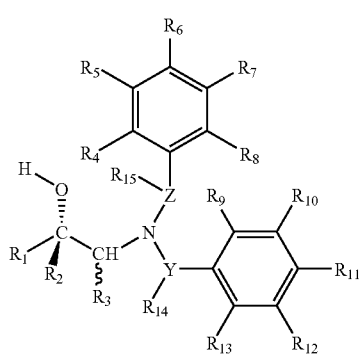
(I-CP)

or a phamaceutically acceptable salt thereof, wherein;

R₁ is selected from the group consisting of trifluoromethyl, 1,1,2,2-tetrafluoroethoxymethyl, trifluoromethoxymethyl, difluoromethyl, chlorodifluoromethyl, and pentafluoroethyl with the proviso that R₁ has a higher Cahn-Ingold-Prelog stereochemical system ranking than both R₂ and (CHR₃)ₙ—N(Ap)Qp wherein Ap is Formula (II-P) and Qp is Formula (II-P);

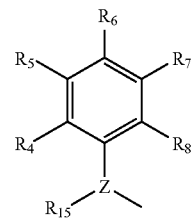
(II-P)

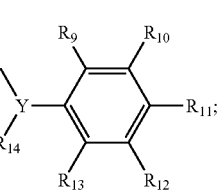
(III-P)

R₂ is hydrido;

R₂ can be selected from the group consisting of methyl, ethyl, propyl, butyl, vinyl, phenyl, 4-trifluoromethylphenyl, 1,1,2,2-tetrafluoroethoxymethyl, trifluoromethoxymethyl, difluoromethyl, and 2,2,3,3,3-pentafluoropropyl with the proviso that R₂ has a lower Cahn-Ingold-Prelog system ranking than both R₁ and (CHR₃)ₙ—N(Ap)Qp;

R₃ is selected from the group consisting of hydrido, phenyl, 4trifluoromethylphenyl, methyl, ethyl, vinyl, methoxymethyl, trifluoromethyl, trifluoromethoxymethyl, difluoromethyl, chlorodifluoromethyl, and pentafluoroethyl with the provisos that (CHR₃)ₙ—N(Ap)Qp has a lower Cahn-Ingold-Prelog stereochemical system ranking than R₁ and a higher Cahn-Ingold-Prelog stereochemical system ranking than R₂.

In a even more preferred embodiment of compounds of Formula I-CP,

R₁ is selected from the group consisting of trifluoromethyl, 1,1,2,2-tetrafluoroethoxymethyl, trifluoromethoxymethyl, difluoromethyl, chlorodifluoromethyl, and pentafluoroethyl with the proviso that R₁ has a higher Cahn-Ingold-Prelog stereochemical system ranking than both R₂ and (CHR₃)ₙ—N(Ap)Qp wherein Ap is Formula (II-P) and Qp is Formula (III-P);

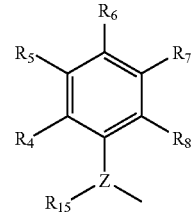
(II-P)

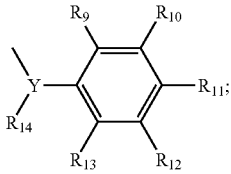
(III-P)

R₂ is hydrido;

R₂ can be selected from the group consisting of methyl, ethyl, phenyl, 4-trifluoromethylphenyl, trifluoromethoxymethyl, 1,1,2,2-tetrafluoroethoxymethyl, difluoromethyl, and 2,2,3,3,3-pentafluoropropyl with the proviso that $R_2$ has a lower Cahn-Ingold-Prelog system ranking than both $R_1$ and $(CHR_3)_n$—$N(Ap)Qp$;

$R_3$ is selected from the group consisting of hydrido, phenyl, 4-trifluoromethylphenyl, methyl, trifluoromethyl, difluoromethyl, and chlorodifluoromethyl with the provisos that $(CHR_3)_n$—$N(Ap)Qp$ has a lower Cahn-Ingold-Prelog stereochemical system ranking than $R_1$ and a higher Cahn-Ingold-Prelog stereochemical system ranking than $R_2$.

In a most preferred embodiment of compounds of Formula I-CP, $R_1$ is selected from the group consisting of trifluoromethyl, chlorodifluoromethyl, and pentafluoroethyl with the proviso that $R_1$ has a higher Cahn-Ingold-Prelog stereochemical system ranking than both $R_2$ and $(CHR_3)_n$—$N(Ap)Qp$ wherein Ap is Formula (II-P) and Qp is Formula (III-P);

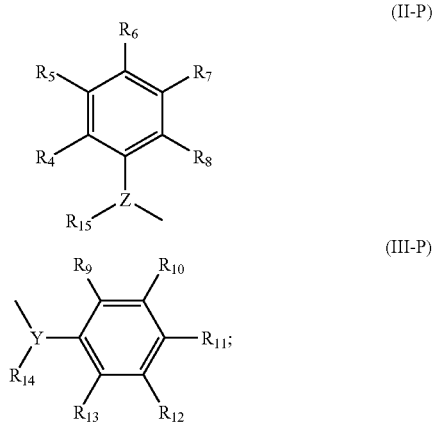

$R_2$ is hydrido;

$R_2$ can be phenyl with the proviso that $R_2$ has a lower Cahn-Ingold-Prelog system ranking than both $R_1$ and $(CHR_3)_n$—$N(Ap)Qp$;

$R_3$ is selected from the group consisting of hydrido, methyl, trifluoromethyl, and difluoromethyl with the provisos that $(CHR_3)_n$—$N(Ap)Qp$ has a lower Cahn-Ingold-Prelog stereochemical system ranking than $R_1$ and a higher Cahn-Ingold-Prelog stereochemical system ranking than $R_2$.

In another embodiment of compounds of Formulas I-H or I-C, the compounds correspond to the Cyclo I-H Formulas:

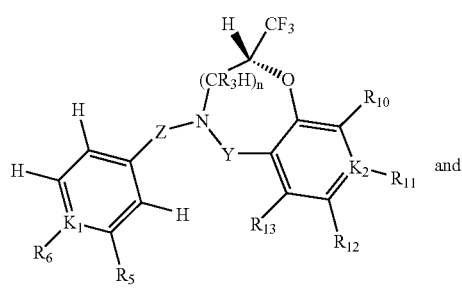

Cyclo I-H

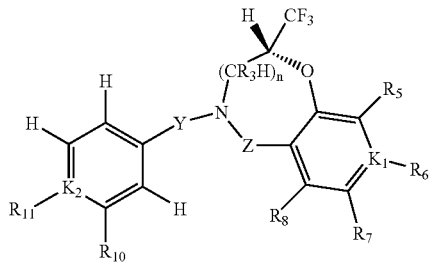

Cyclo I-H wherein:

$K_1$ and $K_2$ are independently selected from the group consisting of C and N;

n is an integer selected from 1 through 3;

$R_1$ is selected from the group consisting of haloalkyl, haloalkenyl, haloalkoxymethyl, and haloalkenyloxymethyl with the proviso that $R_1$ has a higher Cahn-Ingold-Prelog stereochemical system ranking than both $R_2$ and $(CHR_3)_n$—$N(Apch)Qph$ wherein Apch is Formula (II-PCH) and Qph is Formula (III-PH);

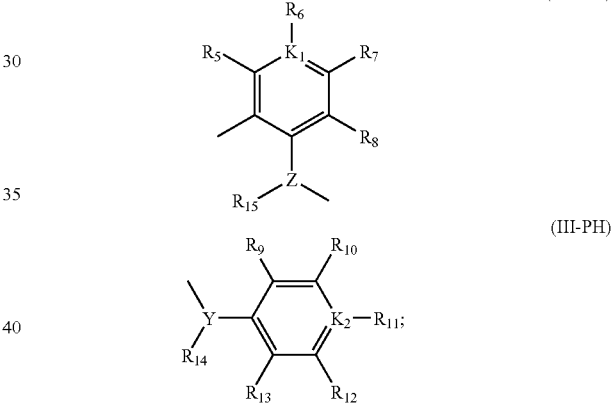

$R_2$ is hydrido;

$R_2$ is selected from the group consisting of aryl, aralkyl, alkyl, alkenyl, alkoxyalkyl, alkenyloxyalkyl, haloalkyl, haloalkenyl, halocycloalkyl, haloalkoxy, haloalkoxyalkyl, haloalkenyloxyalkyl, halocycloalkoxy, perhaloaryl, perhaloaralkyl, perhaloaryloxyalkyl, heteroaryl, heteroarylalkyl, dicyanoalkyl, and carboalkoxycyanoalkyl with the proviso that $R_2$ has a lower Cahn-Ingold-Prelog system ranking than both $R_1$ and $(CHR_3)_n$—$N(Apch)Qph$;

$R_3$ is selected from the group consisting of hydrido, hydroxy, halo, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboalkoxycyanoalkyl, carboxamide, and carboxamidoalkyl with the provisos that $(CHR_3)_n$—$N(Apch)Qph$ has a lower Cahn-Ingold-Prelog stereochemical system ranking than $R_1$ and a higher Cahn-Ingold-Prelog stereochemical system ranking than $R_2$;

Y is selected from the group consisting of a covalent single bond and $(C(R_{14})_2)_q$ wherein q is an integer selected from 1 through 2;

$R_{14}$ is consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 1;

W is selected from the group consisting of O, C(O), S, S(O), and $S(O)_2$;

$R_{15}$ is selected from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl,haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl arnidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, heteroaralkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl;

$R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ can be independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_5$ and $R_6$, $R_6$ and $R_7$, and $R_7$ and $R_8$, can be used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ can be used at the same time.

In an embodiment of compounds of Formula Cyclo I-H,
n is the integer 1;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl with the proviso that $R_1$ has a higher Cahn-Ingold-Prelog stereochemical system ranking than both $R_2$ and $(CHR_3)_n$—N(Apch)Qph wherein Apch is Formula (II-PCH) and Qph is Formula (III-PH);

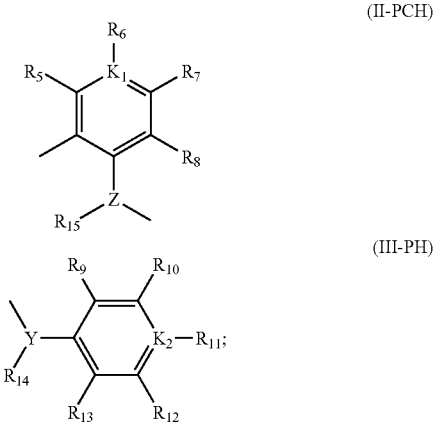

$R_2$ is hydrido;

$R_2$ is selected from the group consisting of phenyl, 4-trifluoromethylphenyl, vinyl, 1,1,2,2-tetrafluoroethoxymethyl, trifluoromethoxymethyl, difluoromethyl, and 2,2,3,3,3-pentafluoropropyl with the proviso that $R_2$ has a lower Cahn-Ingold-Prelog system ranking than both $R_1$ and $(CHR_3)_n$—N(Apch)Qph;

$R_3$ is selected from the group consisting of hydrido, methyl, ethyl, vinyl, phenyl, 4-trifluoromethylphenyl, methoxymethyl, trifluoromethyl, trifluoromethoxymethyl, difluoromethyl, chlorodifluoromethyl, and pentafluoroethyl with the provisos that $(CHR_3)_n$—N(Apch)Qph has a lower Cahn-Ingold-Prelog stereochemical system ranking than $R_1$ and a higher Cahn-Ingold-Prelog stereochemical system ranking than $R_2$.

In another embodiment of compounds of Formula Cyclo I-H,
n is the integer 1;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is hydrido;

$R_3$ is selected from the group consisting of hydrido, methyl, ethyl, vinyl, phenyl, 4-trifluoromethylphenyl, methoxymethyl, trifluoromethyl, trifluoromethoxymethyl, difluoromethyl, chlorodifluoromethyl, and pentafluoroethyl with the provisos that $(CHR_3)_n$—N(Apch)Qph has a lower Cahn- Ingold-Prelog stereochemical system ranking than $R_1$ and a higher Cahn-Ingold-Prelog stereochemical system ranking than $R_2$.

In a preferred embodiment of compounds of Formulas I-H, I-C, I-CP, and Cyclo I-H, Y is selected from the group consisting of methylene, ethylene, and ethylidene;

Z is covalent single bond;

$R_4$, $R_8$, $R_9$, and $R_{13}$ are independently selected from the group consisting of hydrido and fluoro with the proviso that there is no $R_4$, $R_8$, $R_9$, or $R_{13}$ when the embodiment is a compound of Formula Cyclo I-H;

$R_5$ and $R_{10}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy,tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_6$ and $R_{11}$ are independently selected from the group consisting of chloro, fluoro, hydrido, pentafluoroethyl, 1,1,2,2-tetrafluoroethoxy, trifluoromethyl, and trifluoromethoxy;

$R_7$ and $R_{12}$ are independently selected from the group consisting of hydrido, fluoro, and trifluoromethyl.

In an even more preferred embodiment of compounds of Formulas I-H, I-C, I-CP, and Cyclo I-H, Y is methylene;

Z is covalent single bond;

$R_4$, $R_8$, $R_9$, and $R_{13}$ are independently selected from the group consisting of hydrido and fluoro with the proviso that there is no $R_4$, $R_8$, $R_9$, or $R_{13}$ when the embodiment is a compound of Formula Cyclo I-H;

$R_5$ and $R_{10}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 3-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenxyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl,tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difludromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrido, pentafluoroethyl, 1,1,2,2-tetrafluoroethoxy, and trifluoromethyl;

$R_7$ and $R_{12}$ are independently selected from the group consisting of hydrido, fluoro, and trifluoromethyl.

In a most preferred embodiment of compounds of Formulas I-H, I-C, I-CP, and Cyclo I-H, Y is methylene;

Z is covalent single bond;

$R_4$, $R_8$, $R_9$, and $R_{13}$ are independently selected from the group consisting of hydrido and fluoro with the proviso that there is no $R_4$, $R_8$, $R_9$, or $R_{13}$ when the embodiment is a compound of Formula Cyclo I-H;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, isobutyl, isopropoxy, pentafluoroethyl, trifluoromethoxy, trifluoromethyl, and trifluoromethylthio;

$R_6$ and $R_{11}$ are independently selected from the group consisting of fluoro and hydrido;

$R_7$ and $R_{12}$ are independently selected from the group consisting of hydrido and fluoro.

DEFINITIONS

The use of generic terms in the description of the compounds are herein defined for clarity.

Standard single letter elemental symbols are used to represent specific types of atoms unless otherwise defined. The symbol "C" represents a carbon atom.

The symbol "O" represents an oxygen atom. The symbol "N" represents a nitrogen atom. The symbol "P" represents a phosphorus atom. The symbol "S" represents a sulfur atom. The symbol "H" represents a hydrogen atom. Double letter elemental symbols are used as defined for the elements of the periodical table (i.e., Cl represents chlorine, Se represents selenium, etc.).

As utilized herein, the term "alkyl", either alone or within other terms such as "haloalkyl" and "alkylthio", means an acyclic alkyl radical containing from 1 to about 10, preferably from 1 to about 8 carbon atoms and more preferably 1 to about 6 carbon atoms. Said alkyl radicals may be optionally substituted with groups as defined below. Examples of such radicals include methyl, ethyl, chloroethyl, hydroxyethyl, n-propyl, oxopropyl, isopropyl, n-butyl, cyanobutyl, isobutyl, sec-butyl, tert-butyl, pentyl, aminopentyl, isoamyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 2 to about 8 carbon atoms and more preferably 2 to about 6 carbon atoms. Said alkenyl radicals may be optionally substituted with groups as defined below. Examples of suitable alkenyl radicals include propenyl, 2-chloropropenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical (=CH—), or two hydrido radicals may be attached to a carbon atom to form a "methylene" (—CH$_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are mono-hydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, ethylidene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene ($CH_2$=C), 1,2-vinylidene (—CH=CH—), and 1,4-butadienyl (—CH=CH—CH=CH—).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "lower haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydoxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "lower haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "lower alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloalkoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "lower alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated, partially saturated and unsaturated heteroatom-containing ring-shaped radicals having from 5 through ring members selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents as defined below. Preferred heterocyclic radicals include five to twelve membered fused or unfused radicals. Non-limiting examples of heterocyclic radicals include pyrrolyl, pyridinyl, pyridyloxy, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, tetraazolyl, and the like.

The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalkylsulfonyl radicals attached to an alkyl radical, where alkyl is defined as above. The term "aminosulfonyl" denotes an amino radical attached to a sulfonyl radical.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above.

The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "lower cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different-halo radicals. More-preferred-halocycloalkyl-radicals are "lower halocycloalkyl" radicals having three to about eight carbon atoms.

Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals.

The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radical attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "lower alkylthio" radicals having one to six carbon atoms. An example of "lower alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The terms alkylamino denotes "monoalkylamino" and "dialkylamino" containing one or two alkyl radicals, respectively, attached to an amino radical.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamnino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "arylsulfinyl" embraces radicals containing an aryl radical, as defined above, attached to a divalent S(=O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent S(=O) atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. Examples of such radicals include benzyloxy, 1-phenylethoxy, 3-trifluoromethoxybenzyloxy, 3-trifluoromethylbenzyloxy, 3,5-difluorobenyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "lower heteroaralkoxy" radicals having heteroaryl radicals attached to lower alkoxy radical as described above.

The term "haloheteroaryloxyalkyl" embraces heteroaryloxyalkyl radicals, as defined above, wherein one to four halo radicals are attached to an heteroaryloxy group.

The term "heteroarylamino" embraces heterocyclyl radicals, as defined above, attached to an amino group. Examples of such radicals include pyridylamino.

The term "heteroarylaminoalkyl" embraces heteroarylamino radicals, as defined above, attached to an alkyl group. Examples of such radicals include pyridylmethylamino.

The term "heteroaryloxy" embraces heterocyclyl radicals, as defined above, attached to an oxy group. Examples of such radicals include 2-thiophenyloxy, 2-pyrimidyloxy, 2-pyridyloxy, 3-pyridyloxy, and 4-pyridyloxy.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl. The term "alkoxyalkyl" embraces alkoxy radicals, as defined above, attached to an alkyl group. Examples of such radicals include methoxymethyl.

The term "carbonyl" denotes a carbon radical having two of the four covalent bonds shared with an oxygen atom. The-term "carboxy" embraces a hydroxyl radical, as defined above, attached to one of two unshared bonds in a carbonyl group. The term "carboxamide" embraces amino, monoalkylamino, dialkylamino, monocycloalkylamino, alkylcycloalkylamino, and dicycloalkylamino radicals, attached to one of two unshared bonds in a carbonyl group. The term "carboxamidoalkyl" embraces carboxamide radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutanoyl. The term "diacyl", alone or in combination, means having two or more carbonyl or thionocarbonyl groups bonded to a radical selected from, for example, alkylene, alkenylene, alkynylene, haloalkylene, alkoxyalkylene, aryl, heterocyclyl, heteroaryl, aralkyl, cycloalkyl, cycloalkylalkyl, and cycloalkenyl. Examples of "diacyl" are phthaloyl, malonyl, succinyl, adipoyl, and the like.

The term "benzylidenyl" radical denotes substituted and unsubstituted benzyl groups having attachment points for two covalent bonds. One attachment point is through the methylene of the benzyl group with the other attachment point through an ortho carbon of the phenyl ring. The methylene group is designated for attached to the lowest numbered position. Examples include the base compound benzylidene of structure:

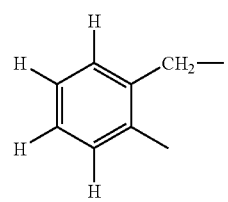

The term "phenoxylidenyl" radical denotes substituted and unsubstituted phenoxy groups having attachment points for two covalent bonds. One attachment point is through the oxy of the phenoxy group with the other attachment point through an ortho carbon of the phenyl ring. The oxy group is designated for attached to the lowest numbered position. Examples include the base compound phenoxylidene of structure:

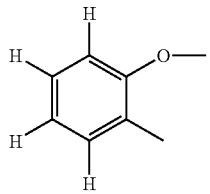

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

Said "alkyl", "alkenyl", "alkynyl", "alkanoyl", "alkylene", "alkenylene", "benzylidenyl", "phenoxylidenyl", "hydroxyalkyl", "haloalkyl", "haloalkylene", "haloalkenyl", "alkoxy", "alkenyloxy", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylalkyl", "alkylsulfinyl", "alkylsulfinylalkyl", "haloalkylsulfinylalkyl", "aralkyl", "heteroaralkyl", "perhaloaralkyl", "aralkylsulfonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxy", "cycloalkoxyalkyl", "cycloalkylalkoxy", "cycloalkenyloxy", "cycloalkenyloxyalkyl", "cycloalkylenedioxy", "halocycloalkoxy", "halocycloalkoxyalkyl", "halocycloalkenyloxy", "halocycloalkenyloxyalkyl", "alkylthio", "haloalkylthio", "alkylsulfinyl", "amino", "oxy", "thio", "alkylamino", "arylamino", "aralkylamino", "arylsulfinyl", "arylsulfinylalkyl", "arylsulfonyl", "arylsulfonylalkyl", "heteroarylsulfinyl", "heteroarylsulfinylalkyl", "heteroarylsulfonyl", "heteroarylsulfonylalkyl", "heteroarylamino", "heteroarylaminoalkyl", "heteroaryloxy", "heteroaryloxyalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl" and "diacyl" groups defined above may optionally have 1 to 5 non-hydrido substituents such as perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxyphosphonoalkyl.

The term "spacer" can include a covalent bond and a linear moiety having a backbone of 1 to 7 continous atoms. The spacer may have 1 to 7 atoms of a univalent or multi-valent chain. Univalent chains may be constituted by a radical selected from =C(H)—, =C(R$_{17}$)—, —O—, —S—, —S(O)—, —S(O)$_2$—, —NH—, —N(R$_{17}$)—, —N=, —CH(OH)—, =C(OH)—, —CH(OR$_{17}$)—, =C(OR$_{17}$)—, and —C(O)— wherein R$_{17}$ is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: lower alkylene, lower alkenyl, —O—, —O—CH$_2$—, —S—CH$_2$—, —CH$_2$CH$_2$—, ethenyl, —CH=CH(OH)—, —OCH$_2$O—, —O(CH$_2$)$_2$O—, —NHCH$_2$—, —OCH(R$_{17}$)O—, —O(CH$_2$CHR$_{17}$)O—, —OCF$_2$O—, —O(CF$_2$)$_2$O—, —S—, —S(O)—, —S(O)$_2$—, —N(H)—, —N(H)O—, —N(R$_{17}$)O—, —N(R$_{17}$)—, —C(O)—, —C(O)NH—, —C(O)NR$_{17}$—, —N=, —OCH$_2$—, —SCH$_2$—, S(O) CH$_2$—, —CH$_2$C(O)—, —CH(OH)—, =C(OH)—, —CH (OR$_{17}$)—, =C(OR$_{17}$)—, S(O)$_2$CH$_2$—, and —NR$_{17}$CH$_2$— and many other radicals defined above or generally known or ascertained by one of skill-in-the art. Side chains may include substituents such as 1 to 5 non-hydrido substituents such as perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Chiral compounds of the present invention have a hydroxyl group substitutent on a chiral carbon of the alkanol and propanol compounds of the present invention specifically in the R-stereoisomeric configuration based on the Cahn-Ingold-Prelog convention for stereoisomeric carbon atoms. The R-stereoisomeric configuration compounds of the present invention may optionally have one or more additional chiral carbons present in each compound. The R-stereoisomeric configuration compounds of the present invention can exist in tautomeric, geometric, and other stereoisomeric forms. The present invention having a hydroxyl group substitutent on a chiral carbon of the alkanol and propanol compounds in the R-stereoisomeric configuration contemplates all such forms of said invented compounds, including cis- and trans-geometric isomers, E- and Z-geometric isomers, diastereomers, and other mixtures thereof, as falling within the scope of the invention. Pharmaceutically acceptable sales of such tautomeric, geometric or stereoisomeric forms are also included within the invention. The standard definitions for the Cahn-Ingold-Prelog convention and stereochemical system can be found in Pure Applied Chemistry, 1976, Vol. 45, pages 15–30 and Cahn et al., Angewandte Chemie International Edition English, 1966, Vol. 5, pages 385–415.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters in addition to said hydroxyl group substitutent on a chiral carbon of the alkanol and propanol compounds in the R-stereoisomeric configuration and are meant to include R, S, and mixtures of R and S forms for each additional stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto " and "enol" tautomeric forms. Said amide carbonyl groups may be both oxo (C=O) and thiono (C=S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The following general synthetic sequences are useful in making the present invention. Abbreviations used in the schemes are as follows: "AA" represents amino acids, "BINAP" represents 2,2'-bis(diphenylphosphino)-1,1'-binaphthyl, "Boc" represents tert-butyloxycarbonyl, "BOP" represents benzotriazol-1-yl-oxy-tris-(dimethylamino), "bu" represents butyl, "dba" represents dibenzylideneacetone, "DCC" represents 1,3-dicyclohexylcarbodiimide, "DIBAlH" represents diisobutylaluminum hydride, "DIPEA" represents diisopropylethylamine, "DMF" represents dimethylformamide, "DMSO" represents dimethylsulfoxide, "Fmoc" represents 9-fluorenylmethoxycarbonyl, "LDA" represents lithium diisopropylamide, "PHTH" represents a phthaloyl group, "pnZ" represents 4-nitrobenzyloxycarbonyl, "PTC" represents a phase transfer catalyst, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, and "Z" represents benzyloxycarbonyl.

The present invention comprises a pharmaceutical composition comprising a therapeutically-effective amount of a compound of Formulas I-H, I-HP, I-C, I-CP, I-HPC, Cyclo I-H, Cyclo I-C, and Cyclo I-CP in association with at least one pharmaceutically-acceptable carrier, adjuvant or diluent.

The present invention also comprises a treatment and prophylaxis of coronary artery disease and other CETP-mediated disorders in a subject, comprising administering to the subject having such disorder a therapeutically-effective amount of a compound of Formula I-H:

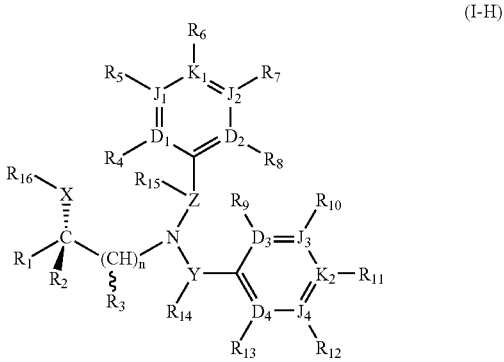

(I-H)

or a pharmaceutically-acceptable salt thereof, wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, X, Y, and Z are as defined above for the compounds of Formula I-H.

As a further embodiment, compounds of the present invention of Formulas I-H, I-HP, I-C, I-CP, I-HPC, Cyclo I-H, Cyclo I-C, and Cyclo I-CP or a pharmaceutically-acceptable salt thereof as defined above comprise a treatment and prophylaxis of coronary artery disease and other CETP-mediated disorders in a subject, comprising administering to the subject having such disorder a therapeutically-effective amount of compounds I-H, I-HP, I-C, I-CP, I-HPC, Cyclo I-H, Cyclo I-C, and Cyclo I-CP of the present invention or a pharmaceutically-acceptable salt thereof.

Compounds of Formulas I-H, I-HP, I-C, I-CP, I-HPC, Cyclo I-H, Cyclo I-C, and Cyclo I-CP are capable of inhibiting activity of cholesteryl ester transfer protein (CETP), and thus could be used in the manufacture of a medicament, a method for the prophylactic or therapeutic treatment of diseases mediated by CETP, such as peripheral vascular disease, hyperlipidaemia, hypercholesterolemia, and other diseases attributable to either high LDL and low HDL or a combination of both, or a procedure to study the mechanism of action of the cholesteryl ester transfer protein (CETP) to enable the design of better inhibitors. The compounds of Formula I-H would be also useful in prevention of cerebral vascular accident (CVA) or stroke.

Also included in the family of compounds of Formula I-H, I-HP, I-C, I-CP, I-HPC, Cyclo I-H, Cyclo I-C, and Cyclo I-CP are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula I-H may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, aralphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula V-H include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound of Formula I-H by reacting, for example, the appropriate acid or base with the compound of Formula I-H.

Also embraced within this invention is a class of pharmaceutical compositions comprising the active compounds of Formula I-H in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient If the active agent is absorbed through the skin, a controlled and predetermined flow of the active agent is administered to the recipient In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glyco, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The present invention further comprises a process for the preparation of (R)-chiral compounds of Formulas I-H, I-HP, I-C, I-CP, I-HPC, Cyclo I-H, Cyclo I-C, and Cyclo I-CP by reacting suitable secondary amines with (R)-chiral forms of alcohols, epoxides, and cyclic sulfate esters.

The present invention also comprises a process for the preparation of (R)-chiral compounds of Formulas I-H, I-HP, I-C, I-CP, I-HPC, Cyclo I-H, Cyclo I-C, and Cyclo I-CP by reacting a suitable secondary amine with a substantially stoichiometric amount of a (R)-chiral epoxide in the presence of a transition metal-based salt.

The present invention also comprises a process for the preparation of (R)-chiral precursor compounds useful in the preparation of compounds of Formulas I-H, I-HP, I-C, I-CP, I-HPC, Cyclo I-H, Cyclo I-C, and Cyclo I-CP by reacting a suitable primary amine with a substantially stoichiometric amount of a (R)-chiral epoxide with or without the presence of an added transition metal-based compound.

All mentioned references are incorporated by reference as if here written.

Although this invention has been described with respect to specific embodiments, the details of these embodiments are not to be construed as limitations.

GENARAL SYNTHETIC PROCEDURES

The compounds of the present invention can be synthesized, for example, according to the following procedures of Schemes 1 through 58 below, wherein the substituents are as defined for Formulas I-H, I-HP, I-C, I-CP, I-HPC, Cyclo I-H, Cyclo I-C, and Cyclo I-CP above except where further noted.

Synthetic Schemes 1 and 2 shows the preparation of compounds of formula XII ("Generic Secondary Amines") which are intermediates in the preparation of the compounds of the present invention corresponding to Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") wherein A and Q are independently aryl and heteroaryl. Schemes 1 and 2, taken together, prepare 1-substitutedamino-2-alkanols of the present invention by addition of a halogenated, oxygen containing precursor to a secondary amine to introduce an oxy containing alkyl group wherein the two groups making up the secondary amine both are made up of aromatic groups or both groups contain aromatic rings wherein said aromatic rings maybe 0 to 2 aryl rings and 0 to 2 heteroaryl rings.

The "Generic Imine" corresponding to Formula XII can be prepared through dehydration techniques generally known in the art and the preferred technique depending on the nature of "Generic Amine-I" of Formula X by reacting it with the "Generic Carbonyl Compound" of Formula XI. For example, when Z is a covalent bond, methylene, methine substituted with another subsitutent, ethylene, or another subsiduent as defined in Formula I-H, the two reactants (X and XI) react by refluxing them in an aprotic solvent, such as hexane, toluene, cyclohexane, benzene, and the like, using a Dean-Stark type trap to remove water. After about 2–8 hours or until the removal of water is complete, the aprotic solvent is removed in vacuo to yield the "Generic Imine" of Formula XII. Alternately, when Z is an oxygen, the "Generic Imine" is an oxime derivative. Oxime type "Generic Imine" compounds are readily prepared from the corresponding O-substituted hydroxylamine and the appropriate aldehyde or ketone type "Generic Carbonyl Compound". Suitable procedures are described by Shriner, Fuson, and Curtin in The Systematic Indentification of Organic Compounds, 5th Edition, John Wiley & Sons and by Fieser and Fieser in Reagents for Organic Synthesis, Volume 1, John Wiley & Sons, which are incorporated herein by reference. Alternately, when Z is a nitrogen, the "Generic Imine" is a hydrazone derivative. Hydrazone type "Generic Imine" compounds are readily prepared from the corresponding hydrazine and the appropriate aldehyde or ketone type "Generic Carbonyl Compound". Suitable procedures for forming the hydrazone imines are also described by Shriner, Fuson, and Curtin in The Systematic Indentification of Organic Compounds, 5th Edition, John Wiley & Sons, and by Fieser and Fieser in Reagents of Organic Synthesis, Volume 1, John Wiley & Sons, which are incorporated herein by reference.

Scheme 1 shows the preparation of "Generic Imine" compounds in which the amine functionality is bonded to Z; Z is bonded to A; and Y is bonded to Q. One of skill in the art will recognize that A and Q as defined can be structurally interchanged to prepare "Generic Imine" compounds with similar, identical or different structures.

The "Generic Secondary Amines" of Formula XIII can be prepared from the corresponding "Generic Imine" of Formula XII in several ways.

For example, in one synthetic scheme (Reduction Method-1), which is preferred when Z is a nitrogen, the "Generic Imine" hydrazone of Formula XII is partially or completely dissolved in lower alkanols such as ethanol or like solvent containing sufficient organic acid such as acetic acid or mineral acid such as HCl or sulfuric acid to neutralize the hydrazone as described in WO Patent Application No. 9738973, Swiss Patent CH 441366 and U.S. Pat. Nos. 3,359,316 and 3,334,017, which are incorporated herein by reference. The resulting mixture is then hydrogenated at 0–100° C., more preferrably 20–50° C., and most preferrably between 20–30° C. and pressures of 10–200 psi hydrogen or more preferrably between 50–70 psi hydrogen in the presence of a noble metal catalyst such as $PtO_2$. The mixture is cooled, and a base such as sodium carbonate or sodium hydroxide added until the solution is neutral to just alkaline (pH 6–8).

Isolation of the desired product can be accomplished, for example, by removing the ethanol, adding water, and extracting the aqueous-organic mixture twice with a solvent, such as diethyl ether or methylene chloride, that is immiscible with water. The combined solvent extract is washed with saturated brine, dried with a drying agent such as anhydrous magnesium sulfate, and concentrated in vacuo to yield the "Generic Secondary Amines" hydrazine of Formula XIII. If needed the "Generic Secondary Amines" hydrazine can be further purified by crystallization, distillation at reduced pressure, or liquid chromatography.

In another synthetic scheme (Reduction Method-2), which is preferred when Z is-a single bond or carbon, the "Generic Imine" of Formula XII is slurried in a lower alcohol such as ethanol, methanol or like solvent at 0–10° C. and solid sodium borohydride is added in batches over 5–10 minutes at 0–10° C. with stirring. The reaction mixture is stirred below 10° C. for 30–90 minutes and then is warmed gradually to 15–30° C. After about 1–10 hours, the mixture is cooled and acid is added until the aqueous layer was just acidic (pH 5–7).

Isolation of the desired product can be accomplished, for example, by extracting the aqueous layer twice with a solvent, such as diethyl ether or methylene chloride, that is immiscible with water. The combined solvent extract is washed with saturated brine, dried with a drying agent such as anhydrous MgSO4, and concentrated in vacuo to yield the "Generic Secondary Amines" amine, aniline, or amine of Formula XIII. If needed the "Generic Secondary Amines" amine, aniline, or amine derivative can be further purified by crystallization, distillation at reduced pressure, or liquid chromatography.

In yet another synthetic scheme (Reduction Method-3), which is preferred when Z is an oxygen, the "Generic Imine" oxime of Formula XII is slurried in a lower alcohol solvent such methanol or like solvent at 0–10° C. and acidified to a pH less than 4. Solid sodium cyanoborohydride is added in batches over 30–90 minutes at 0–20° C. with stirring and addition of a suitable organic or mineral acid to keep the pH at or below 4. The reaction mixture is stirred and warmed gradually to about 20–25° C. After about 1–10 hours, the mixture is cooled and base added until the mixture was just slightly alkaline.

Isolation of the desired product can be accomplished, for example, by removing the methanol or other low boiling solvent in vacuo. The residue is slurried with water and aqueous-organic mixture is extracted twice with a solvent, such as diethyl ether or methylene chloride, that is immiscible with water. The combined solvent extract is washed with saturated brine, dried with a drying agent such as anhydrous $MgSO_4$, and concentrated in vacuo to yield the "Generic Secondary Amines" hydroxylamine of Formula XIII. If needed the "Generic Secondary Amines" hydroxylamine can be further purified by crystallization, distillation at reduced pressure, or liquid chromatography.

The "Generic Secondary Amines" of Formula XIII can also be prepared, according to Scheme 1 by two alkylation procedures based on the nucleophilic substitution of bromides by amines. In one procedure, "Generic Amine-1" of Formula X is reacted with "Generic Bromide-1" of Formula XXI. In another alkylation procedure, "Generic Amine-2" of Formula XXII is reacted together with "Generic Bromide-2" of Formula XXIII.

In one synthetic alkylation scheme (Alkylation Method-1), a "Generic Amine-1" of Formula X is reacted with a "Generic Bromide-2" of Formula XXIII as described in Vogel's Textbook of Practical Organic Chemistry, Fifth Edition, 1989, pages 902 to 905 and references cited therein all of which are incorporated herein by reference. In this procedure, the "Generic Amine-1" is placed in a reaction vessel equipped with a reflux condenser with the capability to either cool or heat the vessel as dictated by the reaction. A suitable "Generic Amine-1" will be selected from primary amine and primary aromatic amine classes of compounds. Cooling may be needed and used should the reaction prove strongly exothermic. Heating may be needed and used to drive the reaction to completion. A suitable solvent may also be used to dissolve the "Generic Amine-1". Suitable solvents are hydrocarbons such as toluene, hexane, xylene, and cyclohexane, ethers, amides such as dimethylformamide, esters such as ethyl acetate, ketones such as acetone, and nitriles such as acetonitrile or mixtures of two or more of these solvents. A suitable base is also added to the reaction vessel. Suitable bases include cesium carbonate, calcium carbonate, sodium carbonate and sodium bicarbonate. The base will normally be added in at least a stoichmetric quantity compared to the "Generic Amine-1" so as to neutralize liberated acid as it forms.

The "Generic Bromide-1" of Formula XXI is then added to the reaction vessel in portions so as to minimize the rate of heat evolution and minimize the concentration of the "Generic Bromide-1". The "Generic Bromide-1" will be selected from primary and secondary organic alkyl and substituted alkyl halide compounds. The halide will preferably be a bromide although iodides and chlorides may also be generally used. One of skill in the art will also be able to readily select and utilize organic alkyl and substituted alkyl compounds containing readily displaceable primary and secondary groups such as tosylates, mesylates, triflates, and the like. Alternately, the halides can be generally prepared from the corresponding alcohols by reaction with, for example, concentrated hydrohalic acids such as HBr or by reaction with phosphorus trihalides such as $PBr_3$ as described in Fieser and Fieser in Reagents for Organic Synthesis, Volume 1, John Wiley & Sons, which are incorporated herein by reference. The appropriate alcohols can be converted to tosylates, mesylates, and triflates using procedures described below.

Addition of the "Generic Bromide-1" is carried out over a period of a few minutes to several hours at temperatures between 0 and 150° C. Preferrably, the addition will take 30–120 minutes at a temperature of 0 to 50° C. The reaction can be stirred until completion. Completion can be monitored, for example, spectroscopically using nuclear magnetic resonance or chromatographically using thin layer, liquid, or gas chromatographic procedures. If the reaction does not proceed to completion, the reactants may be heated until completion is obtained and verified.

Isolation of the desired product can be accomplished, for example, when a water immiscible solvent was used for the reaction, by adding water to the finished reaction. Additional base such as sodium carbonate can be added to ensure the reaction is basic (pH of 9 to 11). The organic layer containing the "Generic Secondary Amine" is washed with saturated brine, dried with a drying agent such as anhydrous $MgSO_4$, and concentrated in vacuo to yield the "Generic Secondary Amine" amine, aniline, or amine of Formula XIII. If needed the "Generic Secondary Amine" amine, aniline, or amine derivative can be further purified by crystallization, distillation at reduced pressure, or liquid chromatography.

In a second synthetic alkylation scheme (Alkylation Method-2), a "Generic Amine-2" of Formula XXII is reacted with a "Generic Bromide-2" of Formula XXIII in a method employing palladium catalyzed carbon-nitrogen bond formation. Suitable procedures for this conversion are described in Wagaw and Buchwald, J. Org. Chem. (1996), 61, 7240–7241, Wolfe, Wagaw and Buchwald, J. Am. Chem. Soc. (1996), 118,7215–7216, and Wolfe and Buchwald, Tetrahedron Letters (1997), 38(36), 6359–6362 and references cited therein all of which are incorporated herein by reference. The preferred "Generic Bromide-2" of Formula XXIII are generally aryl bromides, aryl triflates, and heteroaryl bromides.

The "Generic Amine-1" and "Generic Amine-2" amines, hydroxylamines, and hydrazines, the "Generic Carbonyl Compound" aldehydes, ketones, hydrazones, and oximes, and "Generic Bromide-1" and "Generic Bromide-2" halides, tosylates, mesylates, triflates, and precursor alcohols required to prepare the "Generic Secondary Amine" compounds are available from commercial sources, can be prepared by one skilled in the art from published procedures, and/or can be obtained using specific procedures shown in Schemes 42,43, and 44. Commercial sources include but are not limited to Aldrich Chemical, TCI-America, Lancaster-Synthesis, Oakwood Products, Acros Organics, and Maybridge Chemical. Disclosed procedures for "Generic Amine" amines, hydroxylamines, and hydrazines include Sheradsky and Nov, J. Chem. Soc., Perkin Trans. 1 (1980), (12), 2781–6; Marcoux, Doye, and Buchwald, J. Am. Chem. Soc. (1997), 119, 1053–9; Sternbach and Jamison, Tetrahedron Lett. (1981), 22(35), 33314; U.S. Pat. No. 5,306,718; EP No. 314435; WO No. 9001874; WO No. 9002113; JP No. 05320117; WO No. 9738973; Swiss Patent No. CH 441366; U.S. Pat. Nos. 3,359,316 and 3,334,017; and references cited therein which are incorporated herein by reference. Representative specific "Generic Secondary Amine" of Formula XIII compounds useful for the preparation of compounds of the present invention are listed in Tables 3, 4, and 5.

TABLE 3

Structure of "Secondary Phenyl Amine" Reagents.

(XIIIA)

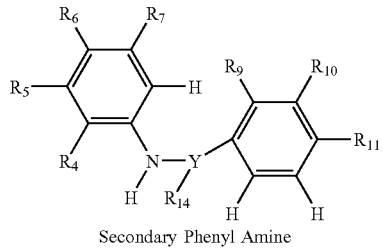

Secondary Phenyl Amine

| Reagent Number | $R_4$ | $R_5$ | $R_6$ | $R_7$ | $R_9$ | $R_{10}$ | $R_{11}$ | Y | $R_{14}$ |
|---|---|---|---|---|---|---|---|---|---|
| 1N | H | phenoxy | H | H | H | $OCF_2CF_2H$ | H | CH | H |
| 2N | H | $OCF_3$ | H | H | H | $OCF_2CF_2H$ | H | CH | H |
| 3N | F | H | H | F | H | $OCF_2CF_2H$ | H | CH | H |
| 4N | H | F | H | H | H | $OCF_2CF_2H$ | H | CH | H |
| 5N | H | phenoxy | H | H | H | $OCF_3$ | H | CH | H |
| 6N | H | $OCF_3$ | H | H | H | $OCF_3$ | H | CH | H |
| 7N | H | H | phenyl | H | H | $OCF_3$ | H | CH | H |
| 8N | H | phenyl | H | H | H | $OCF_3$ | H | CH | H |

TABLE 3-continued

Structure of "Secondary Phenyl Amine" Reagents.

(XIIIA)

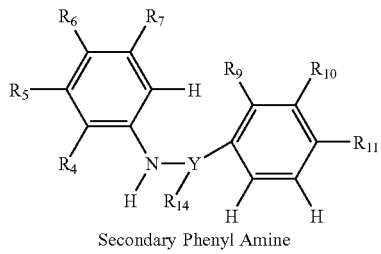

Secondary Phenyl Amine

| Reagent Number | $R_4$ | $R_5$ | $R_6$ | $R_7$ | $R_9$ | $R_{10}$ | $R_{11}$ | Y | $R_{14}$ |
|---|---|---|---|---|---|---|---|---|---|
| 9N | H | H | H | H | H | $OCF_3$ | H | CH | H |
| 10N | H | Br | H | H | H | $OCF_3$ | H | CH | H |
| 11N | H | $CF_3$ | F | H | H | $CF_3$ | H | CH | H |
| 12N | H | $CH_3$ | H | H | H | $CF_3$ | H | CH | H |
| 13N | H | $CF_3$ | H | H | H | $CF_3$ | H | CH | H |
| 14N | H | $CH_3$ | H | H | H | $OCF_3$ | H | CH | H |
| 15N | H | F | F | H | H | $OCF_3$ | H | CH | H |
| 16N | H | Br | H | H | H | $CF_3$ | H | CH | H |
| 17N | H | $CF_3$ | F | H | H | $OCF_3$ | H | CH | H |
| 18N | H | F | H | H | H | $OCF_3$ | H | CH | H |
| 19N | H | Cl | H | H | H | $OCF_3$ | H | CH | H |
| 20N | H | F | H | H | H | $CF_3$ | H | CH | H |
| 21N | H | F | F | H | H | $CF_3$ | H | CH | H |
| 22N | H | Cl | H | H | H | $CF_3$ | H | CH | H |
| 23N | H | F | H | H | H | phenoxy | H | CH | H |
| 24N | H | $CF_3$ | Cl | H | H | $CH_3$ | H | CH | H |
| 25N | H | $CF_3$ | F | H | H | $CH_3$ | H | CH | H |
| 26N | H | H | H | H | H | $CF_3$ | H | CH | H |
| 27N | F | F | H | H | H | $CF_3$ | H | CH | H |
| 28N | H | H | $OCH_3$ | H | H | $CF_3$ | H | CH | H |
| 29N | H | F | F | H | H | $CH_3$ | H | CH | H |
| 30N | H | $OCH_3$ | H | H | H | $CH_3$ | H | CH | H |
| 31N | H | H | $CH_3$ | H | H | H | H | CH | H |
| 32N | H | Cl | H | H | H | H | H | CH | H |
| 33N | H | F | H | H | H | F | H | CH | H |
| 34N | H | H | $OCH_3$ | H | H | $CH_3$ | H | CH | H |
| 35N | H | H | H | H | H | H | H | CH | H |
| 36N | H | H | $CH_3$ | H | H | $CH_3$ | H | CH | H |
| 37N | H | H | Cl | H | H | H | H | CH | H |
| 38N | H | F | H | H | H | 3-$CF_3$-phenoxy | H | CH | H |
| 39N | H | F | H | H | H | 4-$CH_3$O-phenoxy | H | CH | H |
| 40N | H | F | H | H | H | 4-Cl-phenoxy | H | CH | H |
| 41N | H | F | H | H | H | H | H | CH | H |
| 42N | H | F | H | H | H | $CH_3$ | H | CH | H |
| 43N | H | F | H | F | H | $CH_3$ | H | CH | H |
| 44N | F | F | H | H | H | $CH_3$ | H | CH | H |
| 45N | H | Cl | H | H | H | $CH_3$ | H | CH | H |
| 46N | H | $CH_3$ | H | H | H | $CH_3$ | H | CH | H |
| 48N | H | H | $CH_3$ | H | H | $CF_3$ | H | CH | H |
| 51N | H | H | $CH_3$ | H | H | F | H | CH | H |
| 52N | H | $CF_3$ | H | H | H | F | H | CH | H |
| 53N | H | $CF_3$ | H | H | H | $CH_3$ | H | CH | H |
| 54N | H | $OCH_3$ | H | H | H | $CF_3$ | H | CH | H |
| 56N | H | H | $CH_3$ | H | H | $CF_3$ | H | CH | H |
| 57N | H | phenoxy | H | H | H | H | $OCF_3$ | CH | H |
| 58N | H | H | H | H | H | H | $OCF_3$ | CH | H |
| 59N | H | $OCF_3$ | H | H | H | H | $OCF_3$ | CH | H |
| 60N | H | $CF_3$ | F | H | H | H | $CF_3$ | CH | H |
| 61N | H | H | $OCH_3$ | H | H | H | $CF_3$ | CH | H |
| 62N | H | $CH_3$ | H | H | H | H | $CF_3$ | CH | H |
| 63N | H | Cl | H | H | H | H | $CF_3$ | CH | H |
| 64N | H | $CF_3$ | H | H | H | H | $OCF_3$ | CH | H |
| 65N | H | F | H | H | H | H | $OCF_3$ | CH | H |
| 66N | H | F | H | F | H | H | $OCF_3$ | CH | H |
| 67N | H | Br | H | H | H | H | $OCF_3$ | CH | H |
| 68N | H | Cl | H | H | H | H | $OCF_3$ | CH | H |
| 69N | H | F | F | H | H | H | $OCF_3$ | CH | H |
| 70N | H | F | H | H | H | H | phenyl | CH | H |
| 71N | H | $CH_3$ | H | H | H | H | $OCF_3$ | CH | H |
| 72N | H | F | F | H | H | H | $CF_3$ | CH | H |

TABLE 3-continued

Structure of "Secondary Phenyl Amine" Reagents.

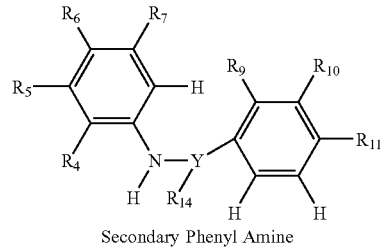

Secondary Phenyl Amine (XIIIA)

| Reagent Number | $R_4$ | $R_5$ | $R_6$ | $R_7$ | $R_9$ | $R_{10}$ | $R_{11}$ | Y | $R_{14}$ |
|---|---|---|---|---|---|---|---|---|---|
| 73N | H | Cl | H | H | H | H | $CH_3$ | CH | H |
| 74N | H | $OCH_3$ | H | H | H | H | $CH_3$ | CH | H |
| 75N | H | F | H | H | H | H | $CH_3$ | CH | H |
| 76N | F | F | H | H | H | H | $OCF_3$ | CH | H |
| 78N | H | H | $OCH_3$ | H | H | H | $CH_3$ | CH | H |
| 79N | H | H | $CH_3$ | H | H | H | $CH_3$ | CH | H |
| 80N | H | $CH_3$ | H | H | H | H | $CH_3$ | CH | H |
| 82N | H | F | F | H | H | H | $CH_3$ | CH | H |
| 83N | H | F | H | F | H | H | $CH_3$ | CH | H |
| 84N | F | F | H | H | H | H | $CH_3$ | CH | H |
| 85N | F | $CF_3$ | H | H | H | H | $CH_3$ | CH | H |
| 86N | H | H | $CH_3$ | H | H | H | $CF_3$ | CH | H |
| 88N | H | $CF_3$ | H | H | H | H | $CH_3$ | CH | H |
| 90N | H | H | $CF_3$ | H | H | H | $CH_3$ | CH | H |
| 92N | H | $CF_3$ | F | H | H | H | $CH_3$ | CH | H |

TABLE 4

Structure of "Secondary Phenyl Amine" Reagents
(Z is covalent bond; there is no $R_{15}$ substituent; $R_4$ and $R_{13}$ equal H).

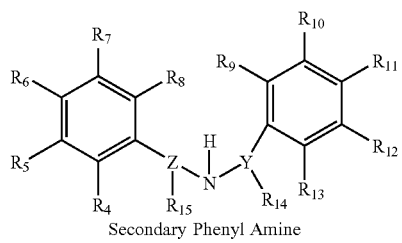

Secondary Phenyl Amine (XIII-A)

| Rgnt. No. | $R_5$ | $R_6$ | $R_7$ | $R_8$ | Y | $R_{14}$ | $R_9$ | $R_{10}$ | $R_{11}$ | $R_{12}$ | Spacer | Spacer Bond Points |
|---|---|---|---|---|---|---|---|---|---|---|---|---|
| 93N | Br | H | H | | CH | H | | H | H | $OCF_3$ | —O— | $R_8 + R_9$ |
| 94N | $OCF_3$ | H | H | | CH | H | | H | H | $OCF_3$ | — | $R_8 + R_9$ |
| 95N | Br | H | H | | C | | H | $OCF_3$ | H | H | =CH— | $R_8 + R_{14}$ |
| 96N | OH | OH | H | H | CH | H | H | $C_6H_5O$ | H | H | none | none |
| 97N | $C_6H_5O$ | H | H | H | CH | H | H | OH | OH | H | none | none |
| 98N | 3-pyridyl | H | H | H | CH | H | H | $CF_3$ | H | H | none | none |
| 99N | $SO_2N(CH_3)_2$ | H | H | H | CH | H | H | $OCF_3$ | H | H | none | none |
| 100N | $SO_2CH_3$ | H | H | H | CH | H | H | $OCF_3$ | H | H | none | none |
| 101N | $C_6H_5O$ | H | H | H | CH | H | H | $C_6H_5O$ | H | H | none | none |
| 102N | $CF_3O$ | H | H | H | CH | H | H | $C_6H_5O$ | H | H | none | none |
| 103N | $C_6H_5$ | H | H | H | CH | H | H | $C_6H_5O$ | H | H | none | none |
| 104N | H | $C_6H_5$ | H | H | CH | H | H | $C_6H_5O$ | H | H | none | none |
| 105N | $C_6H_5O$ | H | H | H | CH | H | H | 4-Cl-$C_6H_4O$ | H | H | none | none |
| 106N | $CF_3O$ | H | H | H | CH | H | H | 4-Cl-$C_6H_4O$ | H | H | none | none |
| 107N | $C_6H_5O$ | H | H | H | CH | H | H | 3,4-Cl-$C_6H_3O$ | H | H | none | none |
| 108N | $CF_3O$ | H | H | H | CH | H | H | 3,4-Cl-$C_6H_3O$ | H | H | none | none |
| 109N | $CF_3O$ | H | H | H | CH | H | H | 3,5-Cl-$C_6H_3O$ | H | H | none | none |
| 110N | $CF_3O$ | H | H | H | CH | H | H | 3-$CH_3O$-$C_6H_4O$ | H | H | none | none |

TABLE 4-continued

| | | | | | | | | | | | | |
|---|---|---|---|---|---|---|---|---|---|---|---|---|
| 111N | CF$_3$O | H | H | H | CH | H | H | H | 3-CH$_3$O-C$_6$H$_4$O | H | none | none |
| 112N | CF$_3$O | H | H | H | CH | H | H | 3-CF$_3$-C$_6$H$_4$O | H | H | none | none |
| 113N | CF$_3$O | H | H | H | CH | H | H | C$_6$H$_5$-CH$_2$O | H | H | none | none |
| 114N | CF$_3$O | H | H | H | CH | H | H | C$_6$H$_5$-CH$_2$O | CH$_3$O | H | none | none |
| 115N | CF$_3$O | H | H | H | CH | H | H | C$_6$H$_5$-CH$_2$O | C$_6$H$_5$-CH$_2$O | H | none | none |
| 116N | CF$_3$O | H | H | H | CH | H | H | ethoxy | H | H | none | none |
| 117N | CF$_3$O | H | H | H | CH | H | H | CH$_3$CO$_2$ | H | H | none | none |
| 118N | CF$_3$O | H | H | H | CH | H | H | HOCH$_2$-CH$_2$O | H | H | none | none |
| 119N | CF$_3$O | H | H | H | CH | H | H | ![epoxide structure] | H | H | none | none |
| 120N | CF$_3$O | H | H | H | CH | H | H | R$_{10}$ + R$_{11}$ = OCH$_2$O | H | none | none |
| 121N | CF$_3$O | H | H | H | CH | H | H | R$_{10}$ + R$_{11}$ = OCH$_2$CH$_2$O | H | none | none |
| 122N | CF$_3$O | H | H | H | CH | H | H | CH$_3$O | CH$_3$O | H | none | none |
| 123N | CF$_3$O | H | H | H | CH | H | H | ethoxy | CH$_3$O | H | none | none |
| 124N | CF$_3$O | H | H | H | CH | H | H | ethoxy | ethoxy | H | none | none |
| 125N | CF$_3$O | H | H | H | CH | H | H | CH$_3$CO$_2$ | CH$_3$CO$_2$ | H | none | none |
| 126N | CF$_3$O | H | H | H | CH | H | H | CH$_3$O | CH$_3$CO$_2$ | H | none | none |
| 127N | CF$_3$O | H | H | H | CH | H | H | n-butoxy | H | H | none | none |
| 128N | CF$_3$O | H | H | H | CH | H | H | CH$_3$O | H | H | none | none |
| 129N | CF$_3$O | H | H | H | CH | H | H | H | CH$_3$O | H | none | none |
| 130N | CH$_3$O | H | H | H | CH | H | H | Ch$_3$O | H | H | none | none |
| 131N | CH$_3$O | H | H | H | CH | H | H | H | CF$_3$O | H | none | none |
| 132N | CF$_3$O | H | H | H | CH | H | H | H | ethoxy | H | none | none |
| 133N | CF$_3$O | H | H | H | CH | H | H | H | n-propoxy | H | none | none |
| 134N | C$_6$H$_5$-CH$_2$O | H | H | H | CH | H | H | CF$_3$O | H | H | none | none |
| 135N | C$_6$H$_5$-CH$_2$O | H | H | H | CH | H | H | C$_6$H$_5$O | H | H | none | none |
| 136N | ethoxy | H | H | H | CH | H | H | CF$_3$O | H | H | none | none |
| 137N | R$_5$ + R$_6$ = OCH$_2$O | H | H | CH | H | H | CF$_3$O | H | H | none | none |
| 138N | R$_5$ + R$_6$ = OCH$_2$O | H | H | CH | H | H | C$_6$H$_5$O | H | H | none | none |
| 139N | R$_5$ + R$_6$ = OCH$_2$CH$_2$O | H | H | CH | H | H | CF$_3$O | H | H | none | none |
| 140N | CH$_3$O | CH$_3$O | H | H | CH | H | H | CF$_3$O | H | H | none | none |
| 141N | R$_5$ + R$_6$ = OCH$_2$CH$_2$CH$_2$O | H | H | CH | H | H | CF$_3$O | H | H | none | none |
| 142N | cyclopentoxy | CH$_3$O | H | H | CH | H | H | CF$_3$O | H | H | none | none |
| 143N | H | C$_6$H$_5$O | H | H | CH | H | H | CF$_3$O | H | H | none | none |
| 144N | CH$_3$O | CH$_3$O | CH$_3$O | H | CH | H | H | CF$_3$O | H | H | none | none |
| 145N | H | CF$_3$O | H | H | CH | H | H | CF$_3$O | H | H | none | none |
| 146N | H | Benzyl | H | H | CH | H | H | CF$_3$O | H | H | none | none |
| 147N | C$_6$H$_5$O | H | H | H | CH | H | H | R$_{10}$ + R$_{11}$ = OCH$_2$CH$_2$O | H | none | none |
| 148N | H | CF$_3$O | H | H | CH | H | H | CF$_3$ | H | H | none | none |
| 149N | C$_6$H$_5$O | H | H | H | CH | H | H | CF$_3$ | H | H | none | none |
| 150N | C$_6$H$_5$ | H | H | H | CH | H | H | CF$_3$ | H | H | none | none |
| 151N | H | C$_6$H$_5$ | H | H | CH | H | H | CF$_3$ | H | H | none | none |
| 152N | CN | H | H | H | CH | H | H | CF$_3$ | H | H | none | none |
| 153N | H | OCF$_3$ | H | H | CH | H | H | CF$_3$ | H | H | none | none |
| 154N | OCF$_3$ | H | H | H | CH | H | H | H | CF$_3$ | H | none | none |
| 155N | C$_6$H$_5$O | H | H | H | CH | H | H | H | CF$_3$ | H | none | none |
| 156N | C$_6$H$_5$ | H | H | H | CH | H | H | H | CF$_3$ | H | none | none |
| 157N | H | C$_6$H$_5$ | H | H | CH | H | H | H | CF$_3$ | H | none | none |
| 158N | CN | H | H | H | CH | H | H | H | CF$_3$ | H | none | none |
| 159N | OCF$_3$ | H | H | H | CH | H | H | H | CF$_3$ | H | none | none |
| 160N | CF$_3$ | H | H | H | CH | H | H | H | C$_6$H$_5$ | H | none | none |
| 161N | CF$_3$ | H | H | H | CH | H | H | 3-CF$_3$-C$_6$H$_5$O | H | H | none | none |
| 162N | CF$_3$ | H | H | H | CH | H | H | C$_6$H$_5$O | H | H | none | none |
| 163N | CF$_3$ | H | H | H | CH | H | H | CF$_3$O | H | H | none | none |
| 164N | H | CF$_3$ | H | H | CH | H | H | H | C$_6$H$_5$ | H | none | none |
| 165N | H | CF$_3$ | H | H | CH | H | H | 3-CF$_3$-C$_6$H$_5$O | H | H | none | none |
| 166N | H | CF$_3$ | H | H | CH | H | H | CF$_3$O | H | H | none | none |
| 167N | H | CF$_3$ | H | H | CH | H | H | C$_6$H$_5$O | H | H | none | none |
| 168N | CF$_3$ | H | CF$_3$ | H | CH | H | H | CF$_3$O | H | H | none | none |
| 169N | CF$_3$ | H | CF$_3$ | H | CH | H | H | C$_6$H$_5$O | H | H | none | none |
| 170N | CF$_3$O | H | H | H | CH | H | H | CF$_3$ | H | CF$_3$ | none | none |
| 171N | C$_6$H$_5$O | H | H | H | CH | H | H | CF$_3$ | H | CF$_3$ | none | none |
| 172N | H | C$_6$H$_5$O | H | H | CH | H | H | C$_6$H$_5$O | H | H | none | none |
| 173N | H | CF$_3$O | H | H | CH | H | H | CF$_3$O | H | H | none | none |
| 174N | H | CF$_3$O | H | H | CH | H | H | H | C$_6$H$_5$O | H | none | none |
| 175N | C$_6$H$_5$O | H | H | H | CH | H | H | H | C$_6$H$_5$O | H | none | none |
| 176N | H | C$_6$H$_5$O | H | H | CH | H | H | H | OCF$_3$ | H | none | none |
| 177N | H | C$_6$H$_5$O | H | H | CH | H | H | H | C$_6$H$_5$O | H | none | none |
| 178N | C$_6$H$_5$O | H | H | H | CH | H | H | H | CN | H | none | none |

TABLE 4-continued

| | | | | | | | | | | | |
|---|---|---|---|---|---|---|---|---|---|---|---|
| 179N | $C_6H_5O$ | H | H | H | CH | H | H | CN | H | H | none | none |
| 180N | $C_6H_5O$ | H | H | H | CH | H | H | $NO_2$ | H | H | none | none |
| 181N | $C_6H_5O$ | H | H | H | CH | H | H | H | $NO_2$ | H | none | none |
| 182N | $C_6H_5O$ | H | H | H | CH | H | H | H | $SO_2CH_3$ | H | none | none |
| 183N | $C_6H_5O$ | H | H | H | CH | H | H | H | 2-$NO_2$-4-Cl-$C_6H_3O$ | H | none | none |
| 184N | $C_6H_5O$ | H | H | H | CH | H | H | 4-Cl-$C_6H_4O$ | H | H | none | none |
| 185N | $C_6H_5O$ | H | H | H | CH | H | H | 3,4-Cl-$C_6H_3O$ | H | H | none | none |
| 186N | $C_6H_5O$ | H | H | H | CH | H | H | 3-$CF_3$-$C_6H_3O$ | H | H | none | none |
| 187N | $C_6H_5O$ | H | H | H | CH | H | H | 3,5-Cl-$C_6H_3O$ | H | H | none | none |
| 188N | $C_6H_5O$ | H | H | H | CH | H | H | H | $CH_3O$ | H | none | none |
| 189N | $C_6H_5O$ | H | H | H | CH | H | H | H | $CO_2CH_3$ | H | none | none |
| 190N | $C_6H_5O$ | H | H | H | CH | H | H | 3-$CH_3O$-$C_6H_5O$ | H | H | none | none |
| 191N | $C_6H_5O$ | H | H | H | CH | H | H | 4-$CH_3O$-$C_6H_5O$ | H | H | none | none |
| 193N | $C_6H_5O$ | H | H | H | CH | H | H | $CO_2CH_3$ | H | H | none | none |
| 194N | CN | H | H | H | CH | H | H | $OCF_3$ | H | H | none | none |
| 195N | $NO_2$ | H | H | H | CH | H | H | $OCF_3$ | H | H | none | none |
| 196N | H | CN | H | H | CH | H | H | $OCF_3$ | H | H | none | none |
| 197N | H | $NO_2$ | H | H | CH | H | H | $OCF_3$ | H | H | none | none |
| 198N | $SO_2CH_3$ | H | H | H | CH | H | H | $OCF_3$ | H | H | none | none |
| 199N | H | $SO_2CH_3$ | H | H | CH | H | H | $OCF_3$ | H | H | none | none |
| 200N | H | 4-F-$C_6H_5$-$SO_2$ | H | H | CH | H | H | $OCF_3$ | H | H | none | none |
| 201N | $SO_2N(CH_3)_2$ | H | H | H | CH | H | H | $OCF_3$ | H | H | none | none |
| 202N | H | $SO_2N(CH_3)_2$ | H | H | CH | H | H | $OCF_3$ | H | H | none | none |
| 203N | H | $CONH_2$ | H | H | CH | H | H | $OCF_3$ | H | H | none | none |
| 204N | H | CONH-$C_6H_5$ | H | H | CH | H | H | $OCF_3$ | H | H | none | none |
| 205N | H | $CO_2CH_3$ | H | H | CH | H | H | $OCF_3$ | H | H | none | none |
| 206N | H | $CO_2C_4H_9$ | H | H | CH | H | H | $OCF_3$ | H | H | none | none |
| 207N | H | 4-Cl-$C_6H_5$ | H | H | CH | H | H | $C_6H_5O$ | H | H | none | none |
| 208N | H | 4-$CF_3O$-$C_6H_5$ | H | H | CH | H | H | $CF_3O$ | H | H | none | none |
| 209N | 4-F-$C_6H_4O$ | H | H | H | CH | H | H | $CF_3O$ | H | H | none | none |
| 210N | $C_6F_5O$ | H | H | H | CH | H | H | $CF_3O$ | H | H | none | none |
| 211N | H | 4-F-$C_6H_5$ | H | H | CH | H | H | $CF_3O$ | H | H | none | none |
| 212N | H | 4-CN-$C_6H_5$ | H | H | CH | H | H | $CF_3O$ | H | H | none | none |
| 213N | H | 4-$C_6H_5$-$C_6H_5$ | H | H | CH | H | H | $CF_3O$ | H | H | none | none |
| 214N | $C_6H_5O$ | H | H | H | CH | $CH_3$ | H | $CF_3O$ | H | H | none | none |
| 215N | $C_6H_5O$ | H | H | H | CH | $CH_3$ | H | $NO_2$ | H | H | none | none |
| 216N | $C_6H_5O$ | H | H | H | CH | $CH_3$ | H | H | CN | H | none | none |
| 217N | $C_6H_5O$ | H | H | H | CH | 3-$CF_3$-$C_6H_5$ | H | $CF_3$ | H | H | none | none |
| 218N | $C_6H_5O$ | H | H | H | CH | $C_6H_5$ | H | H | $C_6H_5$ | H | none | none |
| 219N | $C_6H_5O$ | H | H | H | CH | $C_6H_5$ | H | $CF_3$ | H | H | none | none |
| 220N | $C_6H_5O$ | H | H | H | CH | $CH_3$ | H | F | H | H | none | none |
| 221N | $C_6H_5O$ | H | H | H | CH | $CF_3$ | H | H | H | H | none | none |
| 222N | bond to -O- of $R_6$ aryl group 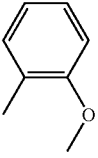 | | H | H | CH | H | H | $CF_3O$ | H | H | none | none |
| 223N | to $CH_2$ of $R_6$ aryl group 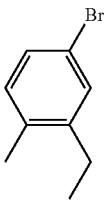 | | H | H | CH | H | H | $CF_3O$ | H | H | none | none |
| 224N | $C_6H_5O$ | H | H | H | CH | H | H | $OCF_2CF_2H$ | H | H | none | none |
| 225N | 4-Cl-$C_6H_5O$ | H | H | H | CH | H | H | $OCF_2CF_2H$ | H | H | none | none |
| 226N | 4-F-$C_6H_5O$ | H | H | H | CH | H | H | $OCF_2CF_2H$ | H | H | none | none |
| 227N | 3,4-Cl-$C_6H_5O$ | H | H | H | CH | H | H | $OCF_2CF_2H$ | H | H | none | none |

TABLE 4-continued

| | | | | | | | | | | | | |
|---|---|---|---|---|---|---|---|---|---|---|---|---|
| 228N | H | $C_6H_5$ | H | H | CH | H | H | $OCF_2CF_2H$ | H | H | none | none |
| 229N | H | 4-Cl-$C_6H_5$ | H | H | CH | H | H | $OCF_2CF_2H$ | H | H | none | none |
| 230N | H | 4-F-$C_6H_5$ | H | H | CH | H | H | $OCF_2CF_2H$ | H | H | none | none |
| 231N | H | 4-Br-$C_6H_5$ | H | H | CH | H | H | $OCF_2CF_2H$ | H | H | none | none |
| 232N | 4-Br-$C_6H_5O$ | H | H | H | CH | H | H | $OCF_2CF_2H$ | H | H | none | none |
| 233N | $C_6H_5O$ | H | H | H | CH | H | H | $OCF_2CF_3$ | H | H | none | none |
| 234N | 4-Cl-$C_6H_5O$ | H | H | H | CH | H | H | $OCF_2CF_3$ | H | H | none | none |
| 235N | 4-F-$C_6H_5O$ | H | H | H | CH | H | H | $OCF_2CF_3$ | H | H | none | none |
| 236N | 3,4-Cl-$C_6H_5O$ | H | H | H | CH | H | H | $OCF_2CF_3$ | H | H | none | none |
| 237N | H | $C_6H_5$ | H | H | CH | H | H | $OCF_2CF_3$ | H | H | none | none |
| 238N | H | 4-Cl-$C_6H_5$ | H | H | CH | H | H | $OCF_2CF_3$ | H | H | none | none |
| 239N | H | 4-F-$C_6H_5$ | H | H | CH | H | H | $OCF_2CF_3$ | H | H | none | none |
| 240N | H | 4-Br-$C_6H_5$ | H | H | CH | H | H | $OCF_2CF_3$ | H | H | none | none |
| 241N | 4-Br-$C_6H_5O$ | H | H | H | CH | H | H | $OCF_2CF_3$ | H | H | none | none |
| 242N | $C_6H_5O$ | H | H | H | CH | H | H | $OCCl_2CCl_2H$ | H | H | none | none |
| 243N | 4-Cl-$C_6H_5O$ | H | H | H | CH | H | H | $OCCl_2CCl_2H$ | H | H | none | none |
| 244N | 4-F-$C_6H_5O$ | H | H | H | CH | H | H | $OCCl_2CCl_2H$ | H | H | none | none |
| 245N | 3,4-Cl-$C_6H_5O$ | H | H | H | CH | H | H | $OCCl_2CCl_2H$ | H | H | none | none |
| 246N | H | $C_6H_5$ | H | H | CH | H | H | $OCCl_2CCl_2H$ | H | H | none | none |
| 247N | H | 4-Cl-$C_6H_5$ | H | H | CH | H | H | $OCCl_2CCl_2H$ | H | H | none | none |
| 248N | H | 4-F-$C_6H_5$ | H | H | CH | H | H | $OCCl_2CCl_2H$ | H | H | none | none |
| 249N | H | 4-Br-$C_6H_5$ | H | H | CH | H | H | $OCCl_2CCl_2H$ | H | H | none | none |
| 250N | 4-Br-$C_6H_5O$ | H | H | H | CH | H | H | $OCCl_2CCl_2H$ | H | H | none | none |
| 251N | $C_6H_5O$ | H | H | H | CH | H | H | $OCCl_2CCl_3$ | H | H | none | none |
| 252N | 4-Cl-$C_6H_5O$ | H | H | H | CH | H | H | $OCCl_2CCl_3$ | H | H | none | none |
| 253N | 4-F-$C_6H_5O$ | H | H | H | CH | H | H | $OCCl_2CCl_3$ | H | H | none | none |
| 254N | 3,4-Cl-$C_6H_5O$ | H | H | H | CH | H | H | $OCCl_2CCl_3$ | H | H | none | none |
| 255N | H | $C_6H_5$ | H | H | CH | H | H | $OCCl_2CCl_3$ | H | H | none | none |
| 256N | H | 4-Cl-$C_6H_5$ | H | H | CH | H | H | $OCCl_2CCl_3$ | H | H | none | none |
| 257N | H | 4-F-$C_6H_5$ | H | H | CH | H | H | $OCCl_2CCl_3$ | H | H | none | none |
| 258N | H | 4-Br-$C_6H_5$ | H | H | CH | H | H | $OCCl_2CCl_3$ | H | H | none | none |
| 259N | 4-Br-$C_6H_5O$ | H | H | H | CH | H | H | $OCCl_2CCl_3$ | H | H | none | none |
| 260N | $C_6H_5O$ | H | H | H | CH | H | H | $OCCl_2CF_3$ | H | H | none | none |
| 261N | 4-Cl-$C_6H_5O$ | H | H | H | CH | H | H | $OCCl_2CF_3$ | H | H | none | none |
| 262N | 4-F-$C_6H_5O$ | H | H | H | CH | H | H | $OCCl_2CF_3$ | H | H | none | none |
| 263N | 3,4-Cl-$C_6H_5O$ | H | H | H | CH | H | H | $OCCl_2CF_3$ | H | H | none | none |
| 264N | H | $C_6H_5$ | H | H | CH | H | H | $OCCl_2CF_3$ | H | H | none | none |
| 265N | H | 4-Cl-$C_6H_5$ | H | H | CH | H | H | $OCCl_2CF_3$ | H | H | none | none |
| 266N | H | 4-F-$C_6H_5$ | H | H | CH | H | H | $OCCl_2CF_3$ | H | H | none | none |
| 267N | H | 4-Br-$C_6H_5$ | H | H | CH | H | H | $OCCl_2CF_3$ | H | H | none | none |
| 268N | 4-Br-$C_6H_5O$ | H | H | H | CH | H | H | $OCCl_2CF_3$ | H | H | none | none |
| 269N | $C_6H_5O$ | H | H | H | CH | H | H | $OCF_2CCl_3$ | H | H | none | none |
| 270N | 4-Cl-$C_6H_5O$ | H | H | H | CH | H | H | $OCF_2CCl_3$ | H | H | none | none |
| 271N | 4-F-$C_6H_5O$ | H | H | H | CH | H | H | $OCF_2CCl_3$ | H | H | none | none |
| 272N | 3,4-Cl-$C_6H_5O$ | H | H | H | CH | H | H | $OCF_2CCl_3$ | H | H | none | none |
| 273N | H | $C_6H_5$ | H | H | CH | H | H | $OCF_2CCl_3$ | H | H | none | none |
| 274N | H | 4-Cl-$C_6H_5$ | H | H | CH | H | H | $OCF_2CCl_3$ | H | H | none | none |
| 275N | H | 4-F-$C_6H_5$ | H | H | CH | H | H | $OCF_2CCl_3$ | H | H | none | none |
| 276N | H | 4-Br-$C_6H_5$ | H | H | CH | H | H | $OCF_2CCl_3$ | H | H | none | none |
| 277N | 4-Br-$C_6H_5O$ | H | H | H | CH | H | H | $OCF_2CCl_3$ | H | H | none | none |
| 278N | $C_6H_5O$ | H | H | H | CH | H | H | $OCF_2CF_2H$ | $OCF_2CF_2H$ | H | none | none |
| 279N | 4-Cl-$C_6H_5O$ | H | H | H | CH | H | H | $OCF_2CF_2H$ | $OCF_2CF_2H$ | H | none | none |
| 280N | 4-F-$C_6H_5O$ | H | H | H | CH | H | H | $OCF_2CF_2H$ | $OCF_2CF_2H$ | H | none | none |
| 281N | 3,4-Cl-$C_6H_5O$ | H | H | H | CH | H | H | $OCF_2CF_2H$ | $OCF_2CF_2H$ | H | none | none |
| 282N | H | $C_6H_5$ | H | H | CH | H | H | $OCF_2CF_2H$ | $OCF_2CF_2H$ | H | none | none |
| 283N | H | 4-Cl-$C_6H_5$ | H | H | CH | H | H | $OCF_2CF_2H$ | $OCF_2CF_2H$ | H | none | none |
| 284N | H | 4-F-$C_6H_5$ | H | H | CH | H | H | $OCF_2CF_2H$ | $OCF_2CF_2H$ | H | none | none |
| 285N | H | 4-Br-$C_6H_5$ | H | H | CH | H | H | $OCF_2CF_2H$ | $OCF_2CF_2H$ | H | none | none |
| 286N | 4-Br-$C_6H_5O$ | H | H | H | CH | H | H | $OCF_2CF_2H$ | $OCF_2CF_2H$ | H | none | none |
| 287N | $C_6H_5O$ | H | H | H | CH | H | H | $OCF_3$ | $OCF_3$ | H | none | none |
| 288N | 4-Cl-$C_6H_5O$ | H | H | H | CH | H | H | $OCF_3$ | $OCF_3$ | H | none | none |
| 289N | 4-F-$C_6H_5O$ | H | H | H | CH | H | H | $OCF_3$ | $OCF_3$ | H | none | none |
| 290N | 3,4-Cl-$C_6H_5O$ | H | H | H | CH | H | H | $OCF_3$ | $OCF_3$ | H | none | none |
| 291N | H | $C_6H_5$ | H | H | CH | H | H | $OCF_3$ | $OCF_3$ | H | none | none |
| 292N | H | 4-Cl-$C_6H_5$ | H | H | CH | H | H | $OCF_3$ | $OCF_3$ | H | none | none |
| 293N | H | 4-F-$C_6H_5$ | H | H | CH | H | H | $OCF_3$ | $OCF_3$ | H | none | none |
| 294N | H | 4-Br-$C_6H_5$ | H | H | CH | H | H | $OCF_3$ | $OCF_3$ | H | none | none |
| 295N | 4-Br-$C_6H_5O$ | H | H | H | CH | H | H | $OCF_3$ | $OCF_3$ | H | none | none |
| 296N | $C_6H_5O$ | H | H | H | CH | H | H | $OCF_2H$ | $OCF_2H$ | H | none | none |
| 297N | 4-Cl-$C_6H_5O$ | H | H | H | CH | H | H | $OCF_2H$ | $OCF_2H$ | H | none | none |
| 298N | 4-F-$C_6H_5O$ | H | H | H | CH | H | H | $OCF_2H$ | $OCF_2H$ | H | none | none |

TABLE 4-continued

| | | | | | | | | | | | | |
|---|---|---|---|---|---|---|---|---|---|---|---|---|
| 299N | 3,4-Cl-C$_6$H$_5$O | H | H | H | CH | H | H | OCF$_2$H | OCF$_2$H | H | none | none |
| 300N | H | C$_6$H$_5$ | H | H | CH | H | H | OCF$_2$H | OCF$_2$H | H | none | none |
| 301N | H | 4-Cl-C$_6$H$_5$ | H | H | CH | H | H | OCF$_2$H | OCF$_2$H | H | none | none |
| 302N | H | 4-F-C$_6$H$_5$ | H | H | CH | H | H | OCF$_2$H | OCF$_2$H | H | none | none |
| 303N | H | 4-Br-C$_6$H$_5$ | H | H | CH | H | H | OCF$_2$H | OCF$_2$H | H | none | none |
| 304N | 4-Br-C$_6$H$_5$O | H | H | H | CH | H | H | OCF$_2$H | OCF$_2$H | H | none | none |
| 305N | C$_6$H$_5$O | H | H | H | CH | H | H | R$_{10}$ + R$_{11}$ = OCF$_2$CF$_2$O | | H | none | none |
| 306N | 4-Cl-C$_6$H$_5$O | H | H | H | CH | H | H | R$_{10}$ + R$_{11}$ = OCF$_2$CF$_2$O | | H | none | none |
| 307N | 4-F-C$_6$H$_5$O | H | H | H | CH | H | H | R$_{10}$ + R$_{11}$ = OCF$_2$CF$_2$O | | H | none | none |
| 308N | 3,4-Cl-C$_6$H$_5$O | H | H | H | CH | H | H | R$_{10}$ + R$_{11}$ = OCF$_2$CF$_2$O | | H | none | none |
| 309N | H | C$_6$H$_5$ | H | H | CH | H | H | R$_{10}$ + R$_{11}$ = OCF$_2$CF$_2$O | | H | none | none |
| 310N | H | 4-Cl-C$_6$H$_5$ | H | H | CH | H | H | R$_{10}$ + R$_{11}$ = OCF$_2$CF$_2$O | | H | none | none |
| 311N | H | 4-F-C$_6$H$_5$ | H | H | CH | H | H | R$_{10}$ + R$_{11}$ = OCF$_2$CF$_2$O | | H | none | none |
| 312N | H | 4-Br-C$_6$H$_5$ | H | H | CH | H | H | R$_{10}$ + R$_{11}$ = OCF$_2$CF$_2$O | | H | none | none |
| 313N | 4-Br-C$_6$H$_5$O | H | H | H | CH | H | H | R$_{10}$ + R$_{11}$ = OCF$_2$CF$_2$O | | H | none | none |
| 314N | C$_6$H$_5$O | H | H | H | CH | H | H | R$_{10}$ + R$_{11}$ = OCCl$_2$CCl$_2$O | | H | none | none |
| 315N | 4-Cl-C$_6$H$_5$O | H | H | H | CH | H | H | R$_{10}$ + R$_{11}$ = OCCl$_2$CCl$_2$O | | H | none | none |
| 316N | 4-F-C$_6$H$_5$O | H | H | H | CH | H | H | R$_{10}$ + R$_{11}$ = OCCl$_2$CCl$_2$O | | H | none | none |
| 317N | 3,4-Cl-C$_6$H$_5$O | H | H | H | CH | H | H | R$_{10}$ + R$_{11}$ = OCCl$_2$CCl$_2$O | | H | none | none |
| 318N | H | C$_6$H$_5$ | H | H | CH | H | H | R$_{10}$ + R$_{11}$ = OCCl$_2$CCl$_2$O | | H | none | none |
| 319N | H | 4-Cl-C$_6$H$_5$ | H | H | CH | H | H | R$_{10}$ + R$_{11}$ = OCCl$_2$CCl$_2$O | | H | none | none |
| 320N | H | 4-F-C$_6$H$_5$ | H | H | CH | H | H | R$_{10}$ + R$_{11}$ = OCCl$_2$CCl$_2$O | | H | none | none |
| 321N | H | 4-Br-C$_6$H$_5$ | H | H | CH | H | H | R$_{10}$ + R$_{11}$ = OCCl$_2$CCl$_2$O | | H | none | none |
| 322N | 4-Br-C$_6$H$_5$O | H | H | H | CH | H | H | R$_{10}$ + R$_{11}$ = OCCl$_2$CCl$_2$O | | H | none | none |
| 323N | H | H | H | H | CH | H | H | OH | H | H | none | none |
| 324N | H | H | H | H | CH | H | H | OH | OH | H | none | none |
| 325N | H | H | H | H | CH | H | H | H | OH | H | none | none |
| 326N | H | H | H | H | CH | H | H | OCH$_2$CF$_3$ | H | H | none | none |
| 327N | H | H | H | H | CH | H | H | H | OCH$_2$CF$_3$ | H | none | none |
| 328N | H | H | H | H | CH | H | H | OCH$_2$CF$_2$CF$_3$ | H | H | none | none |
| 329N | H | H | H | H | CH | H | H | OCH$_2$CF$_2$CF$_3$ | H | H | none | none |
| 330N | H | H | H | H | CH | H | H | OCH(CF$_3$)$_3$ | H | H | none | none |
| 331N | H | 4-F-C$_6$H$_5$O | H | H | CH | H | H | H | H | H | none | none |
| 332N | 4-F-C$_6$H$_5$O | H | H | H | CH | H | H | H | H | H | none | none |
| 333N | H | cyclo-hexoxy | H | H | CH | H | H | H | H | H | none | none |
| 334N | cyclo-hexoxy | H | H | H | CH | H | H | H | H | H | none | none |
| 335N | H | C(CH$_3$)$_3$ | H | H | CH | H | H | H | H | H | none | none |
| 336N | F | H | H | H | CH | H | H | 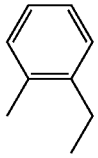 | bond to indicated phenyl carbon of R$_{10}$ subst. | H | none | none |

TABLE 5

Structure of "Secondary Phenyl Amine" Reagents (Y and Z each equal CH; R$_7$, R$_8$, R$_{12}$, R$_{13}$, R$_{14}$, and R$_{15}$ each equal H).

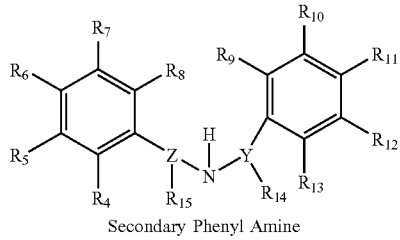

Secondary Phenyl Amine (XIII-A)

| Reagent Number | R$_4$ | R$_5$ | R$_6$ | R$_9$ | R$_{10}$ | R$_{11}$ |
|---|---|---|---|---|---|---|
| 1DB | H | OCF$_3$ | H | H | OCF$_3$ | H |
| 2DB | H | Cl | H | H | H | CF$_3$ |
| 3DB | H | Br | H | H | OCF$_3$ | H |
| 4DB | H | Cl | H | H | OCF$_3$ | H |
| 5DB | H | Cl | H | H | CF$_3$ | H |
| 6DB | H | H | Cl | H | CF$_3$ | H |
| 7DB | H | F | H | H | OCF$_3$ | H |
| 8DB | H | H | Cl | H | H | CF$_3$ |

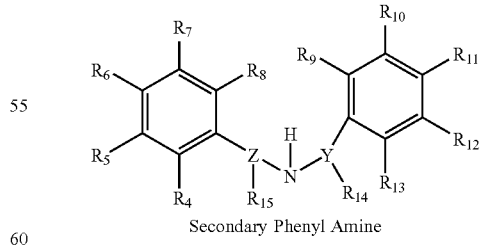

TABLE 5-continued

Structure of "Secondary Phenyl Amine"Reagents (Y and Z each equal CH; $R_7$, $R_8$, $R_{12}$, $R_{13}$, $R_{14}$, and $R_{15}$ each equal H).

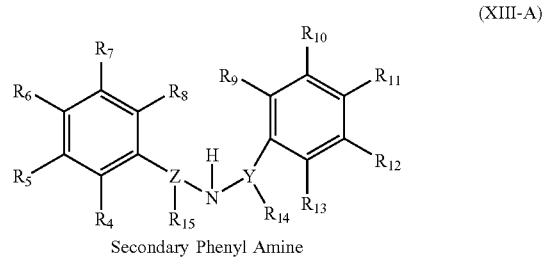

Secondary Phenyl Amine

| Reagent Number | $R_4$ | $R_5$ | $R_6$ | $R_9$ | $R_{10}$ | $R_{11}$ |
|---|---|---|---|---|---|---|
| 9DB | H | F | H | H | H | $CF_3$ |
| 10DB | H | H | F | H | H | $CF_3$ |
| 11DB | F | H | H | H | H | $CF_3$ |
| 12DB | H | Cl | H | $CF_3$ | H | H |
| 13DB | H | H | Cl | $CF_3$ | H | H |
| 14DB | Cl | H | H | $CF_3$ | H | H |
| 15DB | H | F | H | $CH_3$ | H | H |
| 16DB | H | H | F | H | H | $CH_3$ |
| 17DB | H | F | H | H | $CH_3$ | H |
| 18DB | F | H | H | $CH_3$ | H | H |
| 19DB | H | H | F | H | $CH_3$ | H |
| 20DB | F | H | H | H | H | $CH_3$ |
| 21DB | F | H | H | H | $CF_3$ | H |
| 22DB | Cl | H | H | H | $CF_3$ | H |
| 23DB | H | F | H | $CF_3$ | H | H |
| 24DB | H | H | F | $CF_3$ | H | H |
| 25DB | H | F | H | H | $CF_3$ | H |
| 26DB | H | H | F | H | $CF_3$ | H |
| 27DB | H | $OCF_3$ | H | H | H | $OCF_3$ |

As summarized in the general Scheme 1 and specific descriptions above, Schemes 3, 4, 9, and 10 illustrate the principles of Scheme 1 for the preparation of specifically substituted "Secondary Heteroaryl Amines" (XIIIA–H) having 0 to 2 aryl groups and 0 to 2 aromatic heterocyclyl groups and "Secondary Phenyl Amines" (XIII-A) having two aryl groups.

Synthetic Scheme 2 shows the preparation of the class of compounds of the present invention corresponding to Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") wherein A and Q are independently aryl and heteroaryl.

Derivatives of "Generic Polycyclic Aryl and Heteroaryl (R)-Chiral Halogenated 1-Substitutedamino-(n+1)-alkanols", "Generic Polycyclic Aryl and Heteroaryl (R)-Chiral Halogenated 1-Substitutedamino-2-propanols", "Polycyclic Aryl-Heteroaryl (R)-Chiral Halogenated 1-Substitutedamino-2-propanols", "Polycyclic Phenyl (R)-Chiral Halogenated 1-Substitutedamino-(n+1)-Alkanols", and "Polycyclic Phenyl (R)-Chiral Halogenated 1-Substitutedamino-2-Propanols", wherein A and Q are independently aryl and heteroaryl, in which the hetero atom (—O—) is attached to an alkyl group removed from the amine by three or more carbons are readily prepared by anion chemistry using Method B of Scheme 2. The anion of "Generic Secondary Amine" amines, hydroxylamines, and hydrazines of Formula XIII are readily formed by dissolving the specific amine, hydroxylamine, or hydrazine in an aprotic solvent, such as tetrahydrofuran, toluene, ether, dimethylformamide, and dimethylformamide, under anhydrous conditions. The solution is cooled to a temperature between −78 and 0° C., preferably between −78 and −60° C. and the anion formed by the addition of at least one equivalent of a strong, aprotic, non-nucleophillic base such as NaH or n-butyllithium under an inert atmosphere for each acidic group present Maintaining the temperature between −78 and 0° C., preferably between −78 and −60° C., with suitable cooling, an appropriate alkyl halide, alkyl benzenesulfonate such as a alkyl tosylate, alkyl mesylate, alkyl triflate or similar alkylating reagent of the general structure:

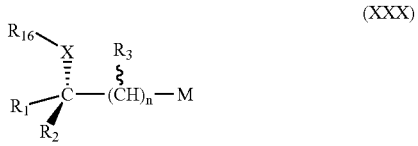

(XXX)

where M is a readily displaceable group such as chloride, bromide, iodide, tosylate, triflate, and mesylate, X is oxy, and XXX is a chiral reagent in the indicated (R)-configuration. After allowing the reaction mixture to warm to room temperature, the reaction product is added to water, neutralized if necessary, and extracted with a water-immiscible solvent such as diethyl ether or methylene chloride. The combined aprotic solvent extract is washed with saturated brine, dried over drying agent such as anhydrous MgSO4 and concentrated in vacuo to yield crude Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols"), wherein A and Q are independently aryl and heteroaryl. This material is purified, for example, by eluting through silica gel with 5–40% of a medium polar solvent such as ethyl acetate in a non-polar solvent such as hexanes to yield Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)Chiral Halogenated 1-Substitutedamino-2-Propanols"). Products are tested for purity by HPLC. If necessary, Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") compounds are purified by additional chromatography or recrystallization. Products are structurally confirmed by low and high resolution mass spectrometry and NMR. Examples of specific compounds prepared are summarized in Tables 6 and 7.

Compounds of Formula (XXX), which can be used to prepare the "Polycyclic Phenyl (R)-Chiral Halogenated 1-Substitutedamino-(n+1)-Alkanol" compounds of Tables 6 and 7, are given in Table 2. Reagents 1a and 2a in Table 2 are prepared from the corresponding alcohols. (R)-Chiral alcohol precursors to 1a, 2a, and similar alcohols that can be envisioned by one of inventive skill can be obtained from the corresponding racemic mixture of the R-enatiomer and S-enantiomer by separation procedures using preparative gas chromatography and high pressure liquid chromatography using chiral chromatographic columns. The tosylates of chiral alcohols and racemic mixtures are readily obtained by reacting the corresponding alcohol with tosyl chloride using procedures found in House's Modern Synthetic Reactions, Chapter 7, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons, which are incorporated herein by reference.

TABLE 6

Structure of Phenyl (R)-Chiral Halogenated 1-Substitutedamino-(n+1)-Alkanols
(Y is CH; $R_8$, $R_9$, $R_{12}$, $R_{13}$, and $R_{14}$ are each H; Z is covalent bond and $R_{15}$ is absent).

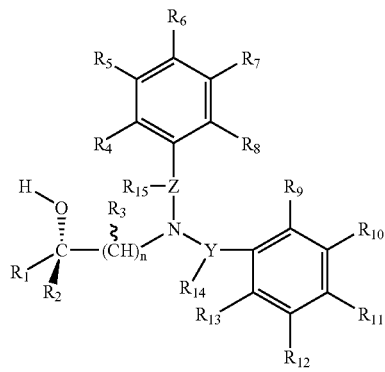

Inhibitor Number
Column 1 + Column 2

| Reagent | Reagent | $R_1$ | n | $R_2$ | $R_3$ | $R_4$ | $R_5$ | $R_6$ | $R_7$ | $R_{10}$ | $R_{11}$ |
|---|---|---|---|---|---|---|---|---|---|---|---|
| 1A | 1N | $CF_3$ | 3 | H | H | H | $C_6H_5O$ | H | H | $OCF_2CF_2H$ | H |
| 1A | 2N | $CF_3$ | 3 | H | H | H | $OCF_3$ | H | H | $OCF_2CF_2H$ | H |
| 1A | 3N | $CF_3$ | 3 | H | H | F | H | H | F | $OCF_2CF_2H$ | H |
| 1A | 4N | $CF_3$ | 3 | H | H | H | F | H | H | $OCF_3$ | H |
| 1A | 5N | $CF_3$ | 3 | H | H | H | $C_6H_5O$ | H | H | $OCF_3$ | H |
| 1A | 6N | $CF_3$ | 3 | H | H | H | $OCF_3$ | H | H | $OCF_3$ | H |
| 1A | 7N | $CF_3$ | 3 | H | H | H | H | phenyl | H | $OCF_3$ | H |
| 1A | 8N | $CF_3$ | 3 | H | H | H | phenyl | H | H | $OCF_3$ | H |
| 1A | 9N | $CF_3$ | 3 | H | H | H | H | H | H | $OCF_3$ | H |
| 1A | 10N | $CF_3$ | 3 | H | H | H | Br | H | H | $OCF_3$ | H |
| 1A | 11N | $CF_3$ | 3 | H | H | H | $CF_3$ | F | H | $CF_3$ | H |
| 1A | 12N | $CF_3$ | 3 | H | H | H | $CH_3$ | H | H | $CF_3$ | H |
| 1A | 13N | $CF_3$ | 3 | H | H | H | $CF_3$ | H | H | $CF_3$ | H |
| 1A | 14N | $CF_3$ | 3 | H | H | H | $CH_3$ | H | H | $OCF_3$ | H |
| 1A | 15N | $CF_3$ | 3 | H | H | H | F | F | H | $OCF_3$ | H |
| 1A | 16N | $CF_3$ | 3 | H | H | H | Br | H | H | $CF_3$ | H |
| 1A | 17N | $CF_3$ | 3 | H | H | H | $CF_3$ | F | H | $OCF_3$ | H |
| 1A | 18N | $CF_3$ | 3 | H | H | H | F | H | H | $OCF_3$ | H |
| 1A | 19N | $CF_3$ | 3 | H | H | H | Cl | H | H | $OCF_3$ | H |
| 1A | 20N | $CF_3$ | 3 | H | H | H | F | H | H | $CF_3$ | H |
| 1A | 21N | $CF_3$ | 3 | H | H | H | F | F | H | $CF_3$ | H |
| 1A | 22N | $CF_3$ | 3 | H | H | H | Cl | H | H | $CF_3$ | H |
| 1A | 23N | $CF_3$ | 3 | H | H | H | F | H | H | phenoxy | H |
| 1A | 24N | $CF_3$ | 3 | H | H | H | $CF_3$ | Cl | H | $CH_3$ | H |
| 1A | 25N | $CF_3$ | 3 | H | H | H | $CF_3$ | F | H | $CH_3$ | H |
| 1A | 26N | $CF_3$ | 3 | H | H | H | H | H | H | $CF_3$ | H |
| 1A | 27N | $CF_3$ | 3 | H | H | F | F | H | H | $CF_3$ | H |
| 1A | 28N | $CF_3$ | 3 | H | H | H | H | $OCH_3$ | H | $CF_3$ | H |
| 1A | 29N | $CF_3$ | 3 | H | H | H | F | F | H | $CH_3$ | H |
| 1A | 30N | $CF_3$ | 3 | H | H | H | $OCH_3$ | H | H | $CH_3$ | H |
| 1A | 31N | $CF_3$ | 3 | H | H | H | H | $CH_3$ | H | H | H |
| 1A | 32N | $CF_3$ | 3 | H | H | H | Cl | H | H | H | H |
| 1A | 33N | $CF_3$ | 3 | H | H | H | F | H | H | F | H |
| 1A | 34N | $CF_3$ | 3 | H | H | H | H | $OCH_3$ | H | $CH_3$ | H |
| 1A | 35N | $CF_3$ | 3 | H | H | H | H | H | H | H | H |

TABLE 6-continued

Structure of Phenyl (R)-Chiral Halogenated 1-Substitutedamino-(n+1)-Alkanols
(Y is CH; $R_8$, $R_9$, $R_{12}$, $R_{13}$, and $R_{14}$ are each H; Z is covalent bond and $R_{15}$ is absent).

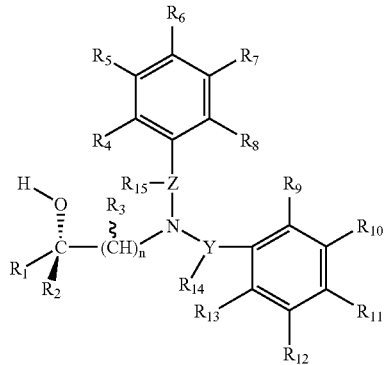

Inhibitor Number
Column 1 + Column 2

| Reagent | Reagent | $R_1$ | n | $R_2$ | $R_3$ | $R_4$ | $R_5$ | $R_6$ | $R_7$ | $R_{10}$ | $R_{11}$ |
|---|---|---|---|---|---|---|---|---|---|---|---|
| 1A | 36N | $CF_3$ | 3 | H | H | H | H | $CH_3$ | H | $CH_3$ | H |
| 1A | 37N | $CF_3$ | 3 | H | H | H | H | Cl | H | H | H |
| 1A | 38N | $CF_3$ | 3 | H | H | H | F | H | H | 3-$CF_3$- | H |
| 1A | 39N | $CF_3$ | 3 | H | H | H | F | H | H | 4-$CH_3$O-phenoxy | H |
| 1A | 40N | $CF_3$ | 3 | H | H | H | F | H | H | 4-Cl-phenoxy | H |
| 1A | 41N | $CF_3$ | 3 | H | H | H | F | H | H | H | H |
| 1A | 42N | $CF_3$ | 3 | H | H | H | F | H | H | $CH_3$ | H |
| 1A | 43N | $CF_3$ | 3 | H | H | H | F | H | F | $CH_3$ | H |
| 1A | 44N | $CF_3$ | 3 | H | H | F | F | H | H | $CH_3$ | H |
| 1A | 45N | $CF_3$ | 3 | H | H | H | Cl | H | H | $CH_3$ | H |
| 1A | 46N | $CF_3$ | 3 | H | H | H | $CH_3$ | H | H | $CH_3$ | H |
| 1A | 48N | $CF_3$ | 3 | H | H | H | H | $CH_3$ | H | $CF_3$ | H |
| 1A | 51N | $CF_3$ | 3 | H | H | H | H | $CH_3$ | H | F | H |
| 1A | 52N | $CF_3$ | 3 | H | H | H | $CF_3$ | H | H | F | H |
| 1A | 53N | $CF_3$ | 3 | H | H | H | $CF_3$ | H | H | $CH_3$ | H |
| 1A | 54N | $CF_3$ | 3 | H | H | H | $OCH_3$ | H | H | $CF_3$ | H |
| 1A | 56N | $CF_3$ | 3 | H | H | H | H | $CH_3$ | H | $CF_3$ | H |
| 1A | 57N | $CF_3$ | 3 | H | H | H | $C_6H_5O$ | H | H | H | $OCF_3$ |
| 1A | 58N | $CF_3$ | 3 | H | H | H | H | H | H | H | $OCF_3$ |
| 1A | 59N | $CF_3$ | 3 | H | H | H | $OCH_3$ | H | H | H | $OCF_3$ |
| 1A | 60N | $CF_3$ | 3 | H | H | H | $CF_3$ | F | H | H | $OCF_3$ |
| 1A | 61N | $CF_3$ | 3 | H | H | H | H | $OCH_3$ | H | H | $OCF_3$ |
| 1A | 62N | $CF_3$ | 3 | H | H | H | $CH_3$ | H | H | H | $OCF_3$ |
| 1A | 63N | $CF_3$ | 3 | H | H | H | Cl | H | H | H | $OCF_3$ |
| 1A | 64N | $CF_3$ | 3 | H | H | H | $CF_3$ | H | H | H | $OCF_3$ |
| 1A | 65N | $CF_3$ | 3 | H | H | H | F | H | H | H | $OCF_3$ |
| 1A | 66N | $CF_3$ | 3 | H | H | H | F | H | F | H | $OCF_3$ |
| 1A | 67N | $CF_3$ | 3 | H | H | H | Br | H | H | H | $OCF_3$ |
| 1A | 68N | $CF_3$ | 3 | H | H | H | Cl | H | H | H | $OCF_3$ |
| 1A | 69N | $CF_3$ | 3 | H | H | H | F | F | H | H | $OCF_3$ |
| 1A | 70N | $CF_3$ | 3 | H | H | H | F | H | H | H | phenyl |
| 1A | 71N | $CF_3$ | 3 | H | H | H | $CH_3$ | H | H | H | $OCF_3$ |
| 1A | 72N | $CF_3$ | 3 | H | H | H | F | F | H | H | $CF_3$ |
| 1A | 73N | $CF_3$ | 3 | H | H | H | Cl | H | H | H | $CH_3$ |
| 1A | 74N | $CF_3$ | 3 | H | H | H | $OCH_3$ | H | H | H | $CH_3$ |
| 1A | 75N | $CF_3$ | 3 | H | H | H | F | H | H | H | $CH_3$ |
| 1A | 76N | $CF_3$ | 3 | H | H | F | F | H | H | H | $OCF_3$ |
| 1A | 78N | $CF_3$ | 3 | H | H | H | H | $OCH_3$ | H | H | $CH_3$ |
| 1A | 79N | $CF_3$ | 3 | H | H | H | H | $CH_3$ | H | H | $CH_3$ |
| 1A | 80N | $CF_3$ | 3 | H | H | H | $CH_3$ | H | H | H | $CH_3$ |
| 1A | 82N | $CF_3$ | 3 | H | H | H | F | F | H | H | $CH_3$ |
| 1A | 83N | $CF_3$ | 3 | H | H | H | F | H | F | H | $CH_3$ |
| 1A | 84N | $CF_3$ | 3 | H | H | F | F | H | H | H | $CH_3$ |
| 1A | 85N | $CF_3$ | 3 | H | H | F | $CF_3$ | H | H | H | $CH_3$ |
| 1A | 86N | $CF_3$ | 3 | H | H | H | H | $CH_3$ | H | H | $CH_3$ |
| 1A | 88N | $CF_3$ | 3 | H | H | H | $CF_3$ | H | H | H | $CH_3$ |
| 1A | 90N | $CF_3$ | 3 | H | H | H | H | $CF_3$ | H | H | $CH_3$ |
| 1A | 92N | $CF_3$ | 3 | H | H | H | $CF_3$ | F | H | H | $CH_3$ |

TABLE 7

Structure of Phenyl (R)-Chiral Halogenated 1-Substitutedamino-(n+1)-Alkanols
(Y and Z are each CH; $R_8$, $R_9$, $R_{12}$, $R_{13}$, $R_{14}$ and $R_{15}$ are each H).

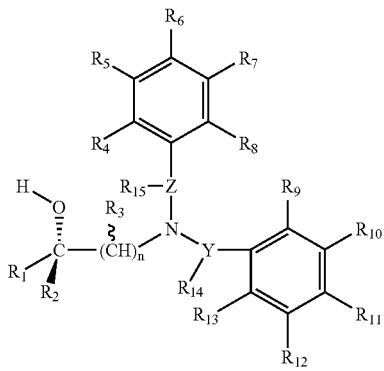

Inhibitor Number
Column 1 + Column 2

| Reagent | Reagent | $R_1$ | n | $R_2$ | $R_3$ | $R_4$ | $R_5$ | $R_6$ | $R_9$ | $R_{10}$ | $R_{11}$ |
|---|---|---|---|---|---|---|---|---|---|---|---|
| 1A | 1DB  | $CF_3$ | 3 | H | H | H | $OCF_3$ | H | H | $OCF_3$ | H |
| 1A | 2DB  | $CF_3$ | 3 | H | H | H | Cl | H | H | H | $CF_3$ |
| 1A | 3DB  | $CF_3$ | 3 | H | H | H | Br | H | H | $OCF_3$ | H |
| 1A | 4DB  | $CF_3$ | 3 | H | H | H | Cl | H | H | $OCF_3$ | H |
| 1A | 5DB  | $CF_3$ | 3 | H | H | H | Cl | H | H | $CF_3$ | H |
| 1A | 6DB  | $CF_3$ | 3 | H | H | H | H | Cl | H | $CF_3$ | H |
| 1A | 7DB  | $CF_3$ | 3 | H | H | H | F | H | H | $OCF_3$ | H |
| 1A | 8DB  | $CF_3$ | 3 | H | H | H | H | Cl | H | H | $CF_3$ |
| 1A | 9DB  | $CF_3$ | 3 | H | H | H | F | H | H | H | $CF_3$ |
| 1A | 10DB | $CF_3$ | 3 | H | H | H | H | F | H | H | $CF_3$ |
| 1A | 11DB | $CF_3$ | 3 | H | H | F | H | H | H | H | $CF_3$ |
| 1A | 12DB | $CF_3$ | 3 | H | H | H | Cl | H | $CF_3$ | H | H |
| 1A | 13DB | $CF_3$ | 3 | H | H | H | H | Cl | $CF_3$ | H | H |
| 1A | 14DB | $CF_3$ | 3 | H | H | Cl | H | H | $CF_3$ | H | H |
| 1A | 15DB | $CF_3$ | 3 | H | H | H | F | H | $CH_3$ | H | H |
| 1A | 16DB | $CF_3$ | 3 | H | H | H | H | F | H | H | $CH_3$ |
| 1A | 17DB | $CF_3$ | 3 | H | H | H | F | H | H | $CH_3$ | H |
| 1A | 18DB | $CF_3$ | 3 | H | H | F | H | H | $CH_3$ | H | H |
| 1A | 19DB | $CF_3$ | 3 | H | H | H | H | F | H | $CH_3$ | H |
| 1A | 20DB | $CF_3$ | 3 | H | H | F | H | H | H | H | $CH_3$ |
| 1A | 21DB | $CF_3$ | 3 | H | H | F | H | H | H | $CF_3$ | H |
| 1A | 22DB | $CF_3$ | 3 | H | H | Cl | H | H | H | $CF_3$ | H |
| 1A | 23DB | $CF_3$ | 3 | H | H | H | F | H | $CF_3$ | H | H |
| 1A | 24DB | $CF_3$ | 3 | H | H | H | H | F | $CF_3$ | H | H |
| 1A | 25DB | $CF_3$ | 3 | H | H | H | F | H | H | $CF_3$ | H |
| 1A | 26DB | $CF_3$ | 3 | H | H | H | H | F | H | $CF_3$ | H |
| 1A | 27DB | $CF_3$ | 3 | H | H | H | $OCF_3$ | H | H | H | $OCF_3$ |

Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") compounds can also be prepared using Method B of Scheme 2 through the use of racemic (XXX) as described followed by preparative separation of the R-enantiomer from the S-enatiomer using chiral chromatographic procedures such as preparative gas chromatography and high pressure liquid chromatography using readily available chiral chromatographic columns and procedures.

A preferred procedure for Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-CP ("Polycyclic Phenyl (R)-Chiral Halogenated 1-Substitutedamino-2-Propanols") compounds is the novel inventive Method A of Scheme 2. (R)-Chiral oxirane reagents useful in Method A are exemplified, but not limited to those in Table 1. Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-CP ("Polycyclic Phenyl (R)-Chiral Halogenated 1-Substitutedamino-2-Propanols") compounds are prepared by reacting "Generic Secondary Amine" amines, hydroxylamines, and hydrazines of Formula XIII with (R)-chiral oxiranes of the type listed in Table 1 and represented by the general structure:

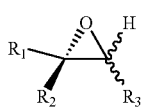

(XX)

Oxiranes having a specific stereochemical arrangement of $R_1$, $R_2$ and $R_3$ can be prepared using chiral procedures such as those published in 1995 by Ramachandran, Gong, and Brown in the Journal of Organic Chemistry, Vol. 60, pages 41 to 46; cited references also detail alternate procedures to prepare chiral and achiral epoxides, which are incorporated herein by reference. For example, the specific preparation of R-(+)-1,1,1-trifluoro-2,3-epoxypropane,

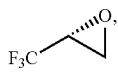

using a procedure adopted from H. C. Brown et al. (J. Org. Chem. 60, 41–46, (1995)), is accomplished as described in Example 4. Many of the epoxides summarized in Table 1 can be prepared in the (R)-configuration using procedures analogous to that given above for R-(+)-1,1,1-trifluoro-2,3-epoxypropane.

In some cases, achiral oxiranes of (XX) can be prepared from the corresponding alkenes by reaction of epoxidation reagents such as meta-chloroperbenzoic acid (MCPBA) and similar type reagents readily selectable by a person of skill-in-the-art with alkenes. Fieser and Fieser in Reagents for Organic Synthesis, John Wiley & Sons provides, along with cited references, numerous suitable epoxidation reagents and reaction conditions, which are incorporated herein by reference. These achiral oxiranes can be reacted in an identical manner to that described for (R)-chiral oxiranes with "Generic Secondary Amine" amines, hydroxylamines, and hydrazines of Formula XIII to afford racemic compounds structurally identical to those of Formula I-HP, Formula I-HPC, and Formula I-C but with the corresponding (S) chiral configuration present in an equivalent amount Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-CP ("Polycyclic Phenyl (R)-Chiral Halogenated 1-Substitutedamino-2-Propanols") compounds can be obtained by preparative chiral chromatography of said racemic mixtures to obtain the (R)-chiral configuration of Formula I-HP, Formula I-HPC, and Formula I-CP substantially free of the (S)-chiral configuration enantiomer. Alternatively, achiral oxiranes may be separated by chiral preparative chromatography into their respective (R)-Chiral and (S)-Chiral enantiomers and the (R)-Chiral enantiomer reacted to afford Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-CP ("Polycyclic Phenyl (R)-Chiral Halogenated 1-Substitutedamino-2-Propanols") compounds.

A mixture of a "Generic Secondary Amine" amine, hydroxylamine, or hydrazine of Formula XIII and an excess of a halogenated oxirane of (R)-chiral configuration of Formula XX are stirred and heated to 40–90° C. for 5 to 48 hours in a tightly capped or contained reaction vessel. More preferably, a Lewis acid such as a transition metal-based salts (for example, ytterbium triflate, hafnium triflate, scandium triflate, neodynium triflate, gadolium triflate, and zirconium triflate) in methylene chloride, tetrahydrofuran, or, more preferably, acetonitrile is added to speed up the reaction to a total time of 4 to 18 hours, improve yields, to permit the reaction temperature to be reduced to 15–65° C., and to use a smaller excess of halogenated oxirane. When a Lewis acid is used, the reaction should be carried out under inert, anhydrous conditions using a blanket of dry nitrogen or argon gas. After cooling to room temperature and testing the reaction mixture for complete reaction by thin layer chromatography or high pressure liquid chromatography (hplc), the reaction product is added to water and extracted with a water immiscible solvent such as diethyl ether or methylene chloride. (Note: If the above analysis indicates that reaction is incomplete, heating should be resumed until complete with the optional addition of more of the oxirane). The combined aprotic solvent extract is washed with saturated brine, dried over drying agent such as anhydrous $MgSO_4$ and concentrated in vacuo to yield crude Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-C ("Polycyclic Phenyl (R)-Chiral Halogenated 1-Substitutedamino-2-Propanols") compounds. This material is purified by eluting through silica gel with 5–40% of a medium polar solvent such as ethyl acetate in a non-polar solvent such as hexanes to yield Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)Chiral Halogenated 1-Substitutedamino-2-Propanols"), and Formula I-C ("Polycyclic Phenyl (R)Chiral Halogenated 1-Substitutedamino-2-Propanols") compounds. Products are tested for purity by HPLC. If necessary, the Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-C ("Polycyclic Phenyl (R)-Chiral Halogenated 1-Substitutedamino-2-Propanols") compounds are purified by additional chromatography or recrystallization. Products are structurally confirmed by low and high resolution mass spectrometry and NMR. Examples of specific Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-C ("Polycyclic Phenyl (R)-Chiral Halogenated 1-Substitutedamino-2-Pro panols") compounds prepared are summarized in the Examples 1 through 44, and Example Tables 1 through 12.

TABLE 1

Structure of (R)-Chiral Oxirane Reagents.

(XX)

$$R_1 \diagdown \overset{O}{\underset{R_2}{\diagup}} \overset{H}{\underset{R_3}{\diagup}}$$

| Reagent Number | $R_1$ | $R_2$ | $R_3$ |
|---|---|---|---|
| 1 | $CF_3$ | H | H |
| 2 | $CCl_3$ | H | H |
| 3 | $CF_3$ | $CH_3$ | H |
| 4 | $CF_3CF_2$ | H | H |
| 5 | $CF_3CF_2CF_2$ | H | H |
| 6 | $CF_3OCF_2CF_2$ | H | H |
| 7 | $CF_3CH_2$ | H | H |
| 9 | $CF_3$ | H | $CF_3$ |
| 11 | $CF_3$ | $C_6H_5$ | H |
| 12 | $CCl_3$ | $C_6H_5$ | H |
| 13 | $CCl_3$ | Cyclopropyl | H |
| 14 | $CCl_3$ | $CH_3$ | H |
| 15 | $CCl_3$ | $(CH_3)_2CH$ | H |
| 16 | $CHCl_2$ | H | H |
| 18 | $CF_3$ | H | $CH_3$ |
| 27 | $CCl_3CH_2$ | H | H |
| 28 | $CBr_3CH_2$ | H | H |
| 29 | $CHBr_2CH_2$ | H | H |
| 30 | $CBrCl_2$ | H | H |
| 31 | $CClF_2$ | H | H |
| 32 | $CCl_2F$ | H | H |
| 33 | $CCl_3CCl_2$ | H | H |
| 43 | $FCH_2$ | H | H |
| 56 | $CBrF_2CClFCH_2$ | H | H |
| 57 | $HCF_2CF_2OCH_2$ | H | H |

TABLE 2

Structure and Source of Alcohol and Glycol Reagents.

(XXX)

$$R_{16} \diagdown \overset{X}{\underset{R_1}{\underset{|}{C}}} \overset{R_3}{\underset{R_2}{\diagup}} -(CH)_n - M$$

| Reagent Number | $R_1$ | n | M | $R_2$ | $R_3$ | X-$R_{16}$ | Source of Reagent |
|---|---|---|---|---|---|---|---|
| 1A | $CF_3$ | 3 | OTs | H | H | OH | Chiral separation and then tosylation of alcohol from Justus Liebigs Ann. Chem. (1969), 720, 81–97. |
| 2A | $CF_3CH_2CH_2$ | 3 | OTs | H | H | OH | Chiral separation and then tosylation of alcohol from Z. Naturforsch., B: Chem. Sci. (1997), 52 (3). 413–418 |

As summarized in the general Scheme 2 and specific descriptions above, Schemes 5, 6, 7, and 11 illustrate the principles of Scheme 2 for the preparation of specifically substituted Formula I-C ("Polycyclic Phenyl (R)-Chiral Halogenated 1-Substitutedamino-2-Propanols") having 2 aryl groups, Formula I-HP ("Generic Polycyclic Aryl and Heteroaryl (R)-Chiral Halogenated 1-Substitutedamino-2-propanols") having two aromatic substituents made up of 0 to 2 aryl groups and 0 to 2 aromatic heterocyclyl groups, and Formula I-HPC ("Polycyclic Aryl-Heteroaryl (R)-Chiral Halogenated 1-Substitutedamino-2-Propanols") having two aromatic substituents made up of 0 to 2 aryl groups and 0 to 2 aromatic heterocyclyl groups.

Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-C ("Polycyclic Phenyl (R)-Chiral Halogenated 1-Substitutedamino-2-Propanols") compounds can further be prepared in an alternate manner to procedures disclosed above and in Schemes 1 to 7 and 9 to 11. Schemes 45 to 50 detail such procedures to prepare aminopropanol compounds of the present invention by initial formation of an halogenated, oxygen containing primary alkylamine XVL ("Generic Substituted Alkylamine"). Said halogenated, oxygen containing primary alkylamine XVL, formed in Schemes 45 and 48, is itself converted to secondary amines, VLX-H ("Heteroaryl Alkyl Amine") and VLX ("Phenyl Alkyl Amine"), using procedures disclosed above. Primary alkylamine XVL is first reacted with an aldehydic or ketonic carbonyl compound, XI-AH ("Heteroaryl Carbonyl") and XI-A ("Phenyl Carbonyl") with azeotropic distillation to form imines, VL-H ("Heteroaryl Imine") and VL ("Phenyl Imine"). Said imines VL-H and VL are then reduced with or without prior isolation by Reduction Methods 1, 2 or 3 as disclosed above and in Schemes 1, 3, and 9 to yield secondary amines, VLX-H ("Heteroaryl Alkyl Amine) and VLX ("Phenyl Alkyl Amine"). Said secondary amine VLX-H can be converted according to Schemes 46 and 47 to give Formula I-HP ("Generic Polycyclic Aryl and Heteroaryl (R)-Chiral Halogenated 1-Substitutedamino-2-propanols") and Formula I-HPC ("Polycyclic Aryl-Heteroaryl (R)-Chiral Halogenated 1-Substitutedamino-2-Propanols") and Formula I-C ("Polycyclic Phenyl (R)-Chiral Halogenated 1-Substitutedamino-2-Propanols") compounds. Using Schemes 49 and 50, VLX can be converted to Formula I-C ("Polycyclic Phenyl (R)-Chiral Halogenated 1-Substitutedamino-2-Propanols") compounds. Compounds of this invention in which one aromatic substituent is aryl and the other aromatic substitutent is heteroaryl can be readily prepared by reacting VLX-H with an aralkyl bromide or aryl bromide instead of using an heteroaralkyl bromide or heteroaryl bromide as described in Schemes 46 and 47. Similarly, compounds of this invention in which one aromatic substituent is aryl and the other aromatic substitutent is heteroaryl can be readily prepared by reacting VLX with an heteroaryl bromide or heteroaralkyl bromide instead of using an aryl bromide or an aralkyl bromide as described in Schemes 49 and 50.

Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-C ("Polycyclic Phenyl (R)-Chiral Halogenated 1-Substitutedamino-2-Propanols") compounds can further be prepared in an alternate manner to procedures disclosed above and in Schemes 1 to 7, 9 to 11, and 45 to 50. Schemes 56, 57, and 58 detail alternate procedures to prepare (R)-Chiral Halogenated 1-Substitutedamino-2-propanols" compounds of the present invention by initial formation of an halogenated, oxygen containing secondary alkylamines VLX and VLXX ("Phenyl Alkylamines") and VLXX-O ("Phenyl Oxy Alkylamines"). Said secondary alkylamines VLX and VLXX ("Phenyl Alkylamines") and VLXX-O ("Phenyl Oxy Alkylamines") can be converted according to Schemes 56, 57, and 58 to Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-C ("Polycyclic Phenyl (R)-Chiral Halogenated 1-Substitutedamino-2-Propanols") compounds by reaction with appropriate aromatic halides such as aryl bromides and heteroaryl bromides as desired.

Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), and Formula I-C ("Polycyclic Phenyl (R)-Chiral Halogenated 1-Substitutedamino-2-Propanols") compounds can further be prepared in an alternate manner to procedures disclosed above and in Schemes 1 to 7, 9 through 11, 45 through 50, and 56 through 58. Another alternate procedure to prepare "(R)-Chiral Halogenated 1-Substitutedamino-2-propanols" compounds of the present invention can be achieved by reacting secondary amines of Formula XIIIA–H ("Secondary Heteroaryl Amines") and Formula XII-A ("Secondary Phenyl Amines") with certain cyclic sulfates. Cyclic sulfates useful in the preparation of "(R)-Chiral Halogenated 1-Substitutedamino-2-propanols" compounds of Formulas I-HP, I-HPC, and I-CP have a halogenated or haloalkoxy carbon adjacent to the cyclic sulfate. Some cyclic sulfates useful for the preparation of "(R)-Chiral Halogenated 1-Substitutedamino-2-propanols" compounds of Formulas I-HP, I-HPC, and I-CP have been described by K. P. M. Vanhessche and K. B. Sharpless in Chem. Eur. J, 1997, Vol. 3, No. 4, pages 517–522 and references cited therein. (2R)-(+)-3,3,3-Trifluoro-1,2-propanediol can be prepared as described in the reference cited immediately above from 3,3,3-trifluoropropene followed by separation from the predominating (2S)-(–)-3,3,3-trifluoro-1,2-propanediol. Alternatively, (2R)-(+)-3,3,3-Trifluoro-1,2-propanediol can be prepared by hydrolysis of (2R)-(+)-3,3,3-Trifluoro-2,3-epxoypropane analogous to the procedure described by described by McBee and Burton in J. Am. Chem. Soc., 1952, Vol. 74, page 3022. (2R)-(+)-3,3,3-Trifluoro-1,2-propanediol is converted by reaction with a slight excess of sulfuryl chloride in the presence of 2.5 molar equivalents of imidazole, methylene chloride solvent, and at a temperature of –20° C. to give the desired (4R)-(+) trriluoromethyl-2,2-dioxo-1,3,2-dioxathiolane. Reaction of other (R)-Chiral haloalkyl or haloalkoxyalkyl substituted 1,2-ethanediols can afford the corresponding (4R)-substituted-2,2-dioxo-1,3,2-dioxathiolanes. Reaction of (4R)-(+)-4-trifluoromethyl-2,2-1,3,2-dioxathiolane or another (4R)-substituted-2,2-dioxo-1,3,2-dioxathiolane with a secondary amine of Formula XIIIA–H ("Secondary Heteroaryl Amines") and Formula XIII-A ("Secondary Phenyl Amines") in an anhydrous polar, non-protic solvent such as tetrahydrofuran or acetonitrile at 25–60° C. until the reaction is complete can afford the mono-sulfate ester of a compound of Formulas I-HP, I-HPC, and I-CP. Removal of the solvent followed by addition of diethyl ether and excess 20% aqueous sulfuric acid can lead to a precipitant of the crude mono-sulfate ester of a compound of Formulas I-HP, I-HPC, and I-CP. This precipitant can be filtered, the solid can be washed with ether, it can be resuspended in aqueous 20% sulfuric acid, and can be heated to 80–95° C. to give an aqueous solution of the sulfate salt of crude a compound of Formulas I-HP, I-HPC, and I-CP. Neutralization of the aqueous solution, extraction with a water immiscible solvent such as diethyl ether or methylene chloride, drying the organic solvent over anhydrous magnesium sulfate, and removal of solvent can afford a compound of Formulas I-HP, I-HPC, and I-CP. Compounds of Formulas I-HP, I-HPC, and I-CP can be purified as described previously. By using a wide variety of (R)-Chiral diols, secondary amines of Formula XIIIA–H ("Secondary Heteroaryl Amines") and Formula XIII-A ("Secondary Phenyl Amines"), and reaction conditions described herein, a large variety of compounds of Formulas I-HP, I-HPC, and I-CP may be preparable.

Formula I-H ("Generic Polycyclic Aryl and Heteroaryl (R)-Chiral Halogenated 1-Substitutedamino-(n+1)-alkanols") and Formula I-C ("Polycyclic Phenyl (R)-Chiral Halogenated 1-Substitutedamino-(n+1)-Alkanols"), in which the halogenated hydroxy containing alkyl side chain has three carbons between the amine and hydroxy group, can be prepared in a manner similar to procedures disclosed above and in Schemes 45 to 50. Schemes 30 to 35 detail such procedures to prepare 1-amino-3-butanol compounds of the present invention by initial formation of an halogenated, oxygen containing primary alkylamine XL ("Generic Substituted Alkylamine"). Said halogenated, oxygen containing primary alkylamine XL, formed in Schemes 30 and 33, is itself converted to secondary amines, LX-H ("Heteroaryl Alkyl Amine") and LX ("Phenyl Alkyl Amine"), using procedures disclosed above. Primary alkylamine XL is first reacted with an aldehydic or ketonic carbonyl compound, XI-AH ("Heteroaryl Carbonyl") and XI-A ("Phenyl Carbonyl") with azeotropic distillation to form imines, L-H ("Heteroaryl Imine") and L ("Phenyl Imine"). Said imines L-H and L are then reduced with or without prior isolation by Reduction Methods 1, 2 or 3 as disclosed above and in Schemes 1, 3, and 9 to yield secondary amines, LX-H ("Heteroaryl Alkyl Amine) and LX ("Phenyl Alkyl Amine"). Said secondary amine LX-H can be converted according to Schemes 31 and 32 to Formula I-H ("Generic Polycyclic Aryl and Heteroaryl (R)-Chiral Halogenated 1-Substitutedamino-(n+1)-alkanols"). Using Schemes 34 and 35, LX can be converted to Formula I-C ("Polycyclic Phenyl (R)-Chiral Halogenated 1-Substitutedamino-(n+1)-Alkanols"). Compounds of this invention in which one aromatic substituent is aryl and the other aromatic substitutent is heteroaryl can be readily prepared by reacting LX-H with an aryl bromide instead of using an heteroaryl bromide as described in Schemes 31 and 32. Similarly, compounds of this invention in which one aromatic substituent is aryl and the other aromatic substitutent is heteroaryl can be readily prepared by reacting LX with an heteroaryl bromide instead of using an aryl bromide as described in Schemes 34 and 35.

Particularly useful procedures to prepare Formula I-H ("Generic Polycyclic Aryl and Heteroaryl (R)-Chiral Halogenated 1-Substitutedamino-(n+1)-alkanols"), (n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") compounds of the present invention in which the heteroaryl group is directly bonded is disclosed in Schemes 51 to 54. An halogenated, hydroxy containing primary alkylamine XVL ("Generic Substituted Alkylamine") formed in Schemes 45 and 48 is itself converted by reaction with LXXI-AH ("Heteroaryl Halide") to afford secondary amine VLXX-H ("Heteroaryl Secondary Amine") using procedures disclosed in Scheme 51 and above. VLXX-H is converted to Formula I-HP ("Generic Polycyclic Aryl and Heteroaryl (R)-Chiral Halogenated I-Substitutedamino-2-propanols"), Formula I-HPC ("Polycyclic Aryl-Heteroaryl (R)-Chiral Halogenated 1-Substitutedamino-2-Propanols"), and Formula I-CP ("Polycyclic Phenyl (R)-Chiral Halogenated 1-Substitutedamino-2-Propanols") compounds by alkylation chemistry with an aralkyl bromide or aralkyloxyalkyl bromide using either of two procedures disclosed in Scheme 52. Isolation and purification is effected as disclosed previously. An halogenated, hydroxy containing primary alkylamine XL ("Generic Substituted Alkylamine") formed in Schemes 30 and 33 is itself also converted by reaction with LXXI-AH ("Heteroaryl Halide") to afford secondary amine LXX-H ("Heteroaryl Secondary Amine) using procedures disclosed in Scheme 53 and above. LXX-H is converted to Formula I-H ("Generic Polycyclic Aryl and Heteroaryl (R)-Chiral Halogenated 1-Substitutedamino-(n+1)-alkanols") and Formula I-C ("Polycyclic Phenyl (R)-Chiral Halogenated 1-Substitutedamino-(n+1)-Alkanols") compounds by alkylation chemistry disclosed in Scheme 54 and previously and as given above with reference to Scheme 52. Isolation and purification of I-H and I-C are effected as disclosed previously.

Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated I-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") compounds can themselves serve as intermediates for conversion to additional compounds of this invention. Compounds of Formulas I-H, I-HP, I-C, I-CP, I-HPC and others of the present invention useful as intermediates include those in which the $R_7$ position substituent in Formulas I-H, I-HP, I-C, I-CP, and I-HPC is a bromo group, hydroxyl group, sulfhydryl group, bromomethyl or other bromoalkyl groups, nitro group, amino group, methoxycarbonyl or other alkoxy carbonyl groups, cyano group, or acyl group. Other preferred compounds of Formulas I-H, I-HP, I-C, I-CP, I-HPC and the present invention useful as intermediates include those in which the $R_{10}$ position substituent is a bromo group, hydroxyl group, sulfhydryl group, bromomethyl or other bromoalkyl groups, nitro group, amino group, methoxy carbonyl or other alkoxy carbonyl groups, cyano group, or acyl groups. Other compounds of Formulas I-H, I-HP, I-C, I-CP, I-HPC and the present invention useful as intermediates include those in which one or more of $R_6$, $R_7$, $R_{11}$, and $R_{12}$ substituents in Formula VII is a bromo group, hydroxyl group, sulfhydryl group, bromomethyl or other bromoalkyl groups, nitro group, amino group, methoxy carbonyl or other alkoxy carbonyl groups, cyano group, or acyl groups.

Scheme 8 discloses the conversion of a 3-bromo substituent at the $R_7$ position in Formula I-CP ("Polycyclic 3-Bromophenyl (R)-Chiral Halogenated 1-Substitutedamino-2-Propanols") compounds by reaction with a phenol to afford, after isolation and purification as described above for Schemes 2, 5, 6, 7, and 11, additional compounds of the present invention of Formula I-CP ("Polycyclic 3-Phenoxyphenyl (R)-Chiral Halogenated 1-Substitutedamino-2-Propanols").

Scheme 12 discloses the conversion of a 3-bromo substituent at the $R_7$ position in Formula I-HP and I-HPC ("Polycyclic 3-Bromophenyl amd 3-Bromoheteroaryl/Aryl-Heteroaryl (R)-Chiral Halogenated 1-Substitutedamino-2-Propanols") by reaction with a phenol or thiophenol to afford, after isolation and purification as described above for Schemes 2, 5, 6, 7, and 11, additional compounds of the present invention of Formula I-HP and I-HPC ("Polycyclic 3-Aryloxyaryl, 3-Heteroaryloxyaryl, 3-Heteroaryloxyheteroaryl, 3-Aryloxyheteroaryl 3-Arylthioaryl, 3-Heteroarylthioaryl, 3-Heteroarylthioheteroaryl, and 3-Arylthioheteroaryl Aryl amd Heteroaryl/Aryl-Heteroaryl (R)-Chiral Halogenated 1-Substitutedamino-2-Propanols").

Scheme 22 discloses the conversion of a 3-bromo substituent at the $R_7$ position in Formula I-CP ("Polycyclic 3-Bromophenyl (R)-Chiral Halogenated 1-Substitutedamino-2-Propanols") compounds by reaction with an aryl borinate or an aryl tin to afford, after isolation and purification as described above for Schemes 2, 5, 6, 7, and 11, additional compounds of the present invention of Formula I-CP ("Polycyclic 3-Arylphenyl (R)-Chiral Halogenated 1-Substitutedamino-2-Propanols").

Scheme 23 discloses the conversion of a 3-bromo substituent at the $R_7$ position in Formula I-CP ("Polycyclic 3-Bromophenyl (R)-Chiral Halogenated 1-Substitutedamino-2-Propanols") compounds by reaction with a primary or secondary amine to afford, after isolation and purification as described above for Schemes 2, 5, 6, 7, and 11, additional compounds of the present invention of Formula I-CP ("Polycyclic 3-$R_{22}$aminophenyl (R)-Chiral Halogenated 1-Substitutedamino-2-Propanols").

Scheme 40 discloses the conversion of a 3-bromo substituent at the $R_{10}$ position in Formula I-CP ("Polycyclic 3-Bromophenyl (R)-Chiral Halogenated 1-Substitutedamino-2-Propanols") compounds by reaction with an aryl borinate to afford, after isolation and purification as described above for Schemes 2, 5, 6, 7, and 11, additional compounds of the present invention of Formula I-CP ("Polycyclic 3-Arylphenyl (R)-Chiral Halogenated 1-Substitutedamino-2-Propanols").

Scheme 41 discloses the conversion of a 3-bromo substituent at the $R_{10}$ position in Formula I-CP ("Polycyclic 3-Bromophenyl (R)-Chiral Halogenated 1-Substitutedamino-2-Propanols") compounds by reaction with a heteroaryl dibutyl tin compound to afford, after isolation and purification as described above for Schemes 2, 5, 6, 7, and 11, additional compounds of the present invention of Formula I-CP ("Polycyclic 3-Heteroarylphenyl (R)-Chiral Halogenated 1-Substitutedamino-2-Propanols").

Scheme 21 discloses the conversion of a 3-bromomethyl substituent at the $R_7$ position in Formula I-CP ("Polycyclic 3-Bromomethylphenyl (R)-Chiral Halogenated 1-Substitutedamino-2-Propanols") by reaction with an aryl borinate to afford, after isolation and purification as described above for Schemes 2, 5, 6, 7, and 11, additional compounds of the present invention of Formula I-CP ("Polycyclic 3-Arylmethylphenyl (R)-Chiral Halogenated 1-Substitutedamino-2-Propanols").

Scheme 13 discloses the conversion of a 3-hydroxyl substituent at the $R_7$ position in Formula I-HP and I-HPC ("Polycyclic 3-Hydroxyphenyl amd 3-Hydroxyheteroaryl/Aryl-Heteroaryl (R)-Chiral Halogenated 1-Substitutedamino-2-Propanols") by reaction with an aryl bromide or heteroaryl bromide to afford, after isolation and purification as described above for Schemes 2, 5, 6, 7, and 11, additional compounds of the present invention of Formula I-HP and I-HPC ("Polycyclic 3-Aryloxyaryl, 3-Heteroaryloxyaryl, 3-Heteroaryloxyheteroaryl, and 3-Aryloxyheteroaryl Aryl-Heteroaryl (R)-Chiral Halogenated 1-Substitutedamino-2-Propanols").

Scheme 14 discloses the conversion of a 3-hydroxyl substituent at the $R_7$ position in Formula I-CP ("Polycyclic 3-Hyroxyphenyl (R)-Chiral Halogenated 1-Substitutedamino-2-Propanols") compounds by reaction with an aryl bromide to afford, after isolation and purification as described above for Schemes 2, 5, 6, 7, and 11, additional compounds of the present invention of Formula I-CP ("Polycyclic 3-Phenoxyphenyl (R)-Chiral Halogenated 1-Substitutedamino-2-Propanols").

Scheme 15 discloses the conversion of a 3-hydroxyl substituent at the $R_7$ position in Formula I-HP and I-HPC ("Polycyclic 3-Hydroxyphenyl amd 3-Hydroxyheteroaryl/Aryl-Heteroaryl (R)-Chiral Halogenated 1-Substitutedamino-2-Propanols") compounds by reaction with an aralkyl bromide or heteroaralkyl bromide to afford, after isolation and purification as described above for Schemes 2, 5, 6, 7, and 11, additional compounds of the present invention of Formula I-HP and I-HPC ("Polycyclic 3-Aralkyloxyaryl, 3-Heteroaralkyloxyaryl, 3-Heteroaralkyloxyheteroaryl, and 3-Aralkyloxyheteroaryl Aryl-Heteroaryl (R)-Chiral Halogenated 1-Substitutedamino-2-Propanols").

Scheme 16 discloses the conversion of a 3-hydroxyl substituent at the $R_7$ position in Formula I-CP ("Polycyclic 3-Hyroxyphenyl (R)-Chiral Halogenated 1-Substitutedamino-2-Propanols") compounds by reaction with an aralkyl bromide to afford, after isolation and purification as described above for Schemes 2, 5, 6, 7, and 11, additional compounds of the present invention of Formula I-CP ("Polycyclic3-Aralkyloxyaryl (R)-Chiral Halogenated 1-Substitutedamino-2-Propanols").

Scheme 20 discloses the conversion of a 3-hydroxyl substituent at the $R_7$ position in Formula I-CP ("Polycyclic 3-Hyroxyphenyl (R)-Chiral Halogenated 1-Substitutedamino-2-Propanols") compounds by reaction with an $R_{17}$-bromide to afford, after isolation and purification as described above for Schemes 2, 5, 6, 7, and 11, additional compounds of the present invention of Formula I-CP ("Polycyclic 3-$R_{17}$-oxyaryl (R)-Chiral Halogenated 1-Substitutedamino-2-Propanols").

Scheme 19 discloses the conversion of a 3-thio substituent at the $R_7$ position in Formula I-CP ("Polycyclic 3-thiophenyl (R)-Chiral Halogenated 1-Substitutedamino-2-Propanols") compounds by reaction with an $R_{17}$-bromide to afford, after isolation and purification as described above for Schemes 2, 5, 6, 7, and 11, additional compounds of the present invention of Formula I-CP ("Polycyclic 3-$R_{17}$thiaaryl (R)-Chiral Halogenated 1-Substitutedamino-2-Propanols"). "Polycyclic 3-$R_{17}$thiaaryl (R)-Chiral Halogenated 1-Substitutedamino-2-Propanols" can be oxidized to sulfonyl compounds of Formula I-CP ("Polycyclic 3-$R_{17}$sulfonylphenyl (R)-Chiral Halogenated 1-Substitutedamino-2-Propanols").

Scheme 24 discloses the conversion of a 3-nitro substituent at the $R_7$ position in Formula I-CP ("Polycyclic 3-Nitrophenyl (R)-Chiral Halogenated 1-Substitutedamino-2-Propanols") compounds by hydrogenation to afford, after isolation and purification as described above for Schemes 2, 5, 6, 7, and 11, additional compounds of the present invention of Formula I-CP ("Polycyclic 3-Aminophenyl (R)-Chiral Halogenated 1-Substitutedamino-2-Propanols"). "Polycyclic 3-Aminophenyl (R)-Chiral Halogenated 1-Substitutedamino-2-Propanols" can be acylated to acyl amide compounds of Formula I-CP ("Polycyclic 3-$R_{17}$-C(O)amidophenyl (R)-Chiral Halogenated 1-Substitutedamino-2-Propanols").

Schemes 25 and 26 disclose the conversion of a 3-amino substituent at the $R_7$ position in Formula I-CP ("Polycyclic 3-Aminophenyl (R)-Chiral Halogenated 1-Substitutedamino-2-Propanols") compounds by reaction with carbonyl compounds to afford, after isolation and purification as described above for Schemes 2, 5, 6, 7, and 11, additional compounds of the present invention of Formula I-CP ("Polycyclic 3-(Saturated Nitrogen Heterocycl-lyl)aryl (R)-Chiral Halogenated 1-Substitutedamino-2-Propanols" and ("Polycyclic 3-(Unsaturated Nitrogen Heterocycl-1yl)aryl (R)-Chiral Halogenated 1-Substitutedamino-2-Propanols", respectively).

Scheme 27 discloses the conversion of a 3-methoxycarbonyl substituent at the $R_7$ position in Formula I-CP ("Polycyclic 3-Carbomethoxyphenyl (R)-Chiral Halogenated 1-Substitutedamino-2-Propanols") compounds by reaction with amination reagents to afford, after isolation and purification as described above for Schemes 2, 5, 6, 7, and 11, additional compounds of the present invention of Formula I-CP ("Polycyclic 3-Carboxamidophenyl (R)-Chiral Halogenated 1-Substitutedamino-2-Propanols").

Scheme 28 discloses the conversion of a 3-cyano substituent at the $R_7$ position in Formula I-CP ("Polycyclic 3-Cyanophenyl (R)-Chiral Halogenated 1-Substitutedamino-2-Propanols") compounds by reaction with organometallic reagents to afford, after isolation and purification as described above for Schemes 2, 5, 6, 7, and 11, additional compounds of the present invention of Formula I-CP ("Polycyclic 3-Acylphenyl (R)-Chiral Halogenated 1-Substitutedamino-2-Propanols"). Said "Polycyclic 3-Acylphenyl (R)-Chiral Halogenated 1-Substitutedamino-2-Propanols", according to Scheme 29 can be reduced to hydroxyl compounds of Formula I-CP ("Polycyclic 3-hydroxysubstitutedmethylphenyl (R)-Chiral Halogenated 1-Substitutedamino-2-Propanols").

Scheme 36 discloses the conversion of a 3-methoxycarbonyl substituent at the $R_{10}$ position in Formula I-CP ("Polycyclic 3-Carbomethoxyphenyl (R)-Chiral Halogenated 1-Substitutedamino-2-Propanols") compounds by reaction with amination reagents to afford, after isolation and purification as described above for Schemes 2, 5, 6, 7, and 11, additional compounds of the present invention of Formula I-CP "Polycyclic 3-Carboxamdophenyl (R)-Chiral Halogenated 1-Substitutedamino-2-Propanols").

Scheme 37 discloses the conversion of a 3-methoxycarbonyl substituent at the $R_{10}$ position in Formula I-CP ("Polycyclic 3-Carbomethoxyphenyl (R)-Chiral Halogenated 1-Substitutedamino-2-Propanols") compounds by reaction with an organometallic reagent to afford, after isolation and purification as described above for Schemes 2, 5, 6, 7, and 11, additional compounds of the present invention of Formula I-CP "Polycyclic 3-(bis-$R_{20}$-hydroxymethyl)aryl (R)-Chiral Halogenated 1-Substitutedamino-2-Propanols").

Scheme 38 discloses the conversion of a 3-methoxycarbonyl substituent at the $R_{10}$ position in Formula I-CP ("Polycyclic 3-Carbomethoxyphenyl (R)-Chiral Halogenated 1-Substitutedamino-2-Propanols") compounds by reaction with lithium aluminum hydride to afford, after isolation and purification as described above for Schemes 2, 5, 6, 7, and 11, additional compounds of the present invention of Formula I-CP ("Polycyclic 3-Hydroxymethylphenyl (R)-Chiral Halogenated 1-Substitutedamino-2-Propanols").

Scheme 39 discloses the conversion of a 3-methoxycarbonyl substituent at the $R_{10}$ position in Formula I-CP ("Polycyclic 3-Carbomethoxyphenyl (R)-Chiral Halogenated 1-Substitutedamino-2-Propanols") compounds by reaction with an alkylation reagent to afford, after isolation and purification as described above for Schemes 2, 5, 6, 7, and 11, additional compounds of the present invention of Formula I-CP ("Polycyclic 3-(bis-$R_{21}$-hydroxymethyl)phenyl (R)-Chiral Halogenated 1-Substitutedamino-2-Propanols").

Scheme 55 discloses the conversion of a 3-methoxycarbonyl substituent at the $R_{10}$ position in Formula I-CP ("Polycyclic 3-Carbomethoxyphenyl (R)-Chiral Halogenated 1-Substitutedamino-2-Propanols") compounds by reaction intially with an amidation reagent and then an $R_{20}$-organometallic reagent to afford, after isolation and purification as described above for Schemes 2, 5, 6, 7, and 11, additional compounds of the present invention of Formula I-CP ("Polycyclic 3-($R_{20}$-carbonyl)phenyl (R)-Chiral Halogenated 1-Substitutedamino-2-Propanols").

Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated I-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") and other compounds of this invention posssessing hydroxyl, thiol, and amine functional groups can be converted to a wide variety derivatives. The hydroxyl group, wherein $R_{16}$ is a hydrogen and X is oxy, of compounds of Formulas I-H, I-HP, I-HPC, I-C, and I-CP can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. In like manner, compounds of Formulas I-H, I-HP, I-C, I-CP, I-HPC, Cyclo I-H, Cyclo I-C, and Cyclo I-CP that have at least one hydroxyl group present in the form of an alcohol or phenol can be acylated to its corresponding esters. Similarly, carbamic acid esters (urethans) can be obtained by reacting any hydroxyl group with isocyanates and carbamoyl chlorides. Sulfonate, phosphonate, and phosphate esters can be prepared using the corresponding acid chloride and similar reagents. Compounds of Formulas I-H, I-HP, I-C, I-CP, I-HPC, Cyclo I-H, Cyclo I-C, and Cyclo I-CP that have at least one thiol group present can be converted to the corresponding thioesters derivatives analogous to those of alcohols and phenols using the same reagents and comparable reaction conditions. Compounds of Formulas I-H, I-HP, I-C, I-CP, I-HPC, Cyclo I-H, Cyclo I-C, and Cyclo I-CP that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide. Suitable procedures and methods for preparing these derivatives can be found in House's Modern Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons. Reagents of a wide variety that can be used to derivatize hydroxyl, thiol, and amines of compounds of Formulas I-H, I-HP, I-C, I-CP, I-HPC, Cyclo I-H, Cyclo I-C, and Cyclo I-CP are available from commerical sources or the references cited above, which are incorporated herein by reference.

Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") and other compounds of this invention posssessing hydroxyl, thiol, and amine functional groups can be alkylated to a wide variety derivatives. The hydroxyl group, wherein $R_{16}$ is a hydrogen and X is oxy, of compounds of Formulas I-H, I-HP, I-C, I-CP, I-HPC, Cyclo I-H, Cyclo I-C, and Cyclo I-CP can be readily converted to ethers. Alkylation to form an ether is readily effected using a suitable alkylating reagent such as an alkyl bromide, alkyl iodide or alkyl sulfonate. The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents. In like manner, compounds of Formulas I-H, I-HP, I-C, I-CP, I-HPC, Cyclo I-H, Cyclo I-C, and Cyclo I-CP that have at least one hydroxyl group present in the form of an alcohol or phenol can be alkylated to their corresponding ethers. Compounds of Formulas I-H, I-HP, I-C, I-CP, I-HPC, Cyclo I-H, Cyclo I-C, and Cyclo I-CP that have at least one thiol group present can be converted to the corresponding thioether derivatives analogous to those of alcohols and phenols using the same reagents and comparable reaction conditions. Compounds of Formulas I-H, I-HP, I-C, I-CP, I-HPC, Cyclo I-H, Cyclo I-C, and Cyclo I-CP that have at least one primary, secondary or tertiary amine group present can be converted to the corresponding quaternary ammonium derivatives. Quaternary ammonium derivatives can be preparing using the approriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary, and three with a primary). With primary and secondary amines, two and one equivalents, respectively, of an acid scavenger are used concurrently. Tertiary amines can be prepared from the corresponding primary or secondary amine by reductive alkylation with aldehydes and ketones using reduction methods 1, 2, or 3 as shown in Scheme 3. Suitable procedures and methods for preparing these derivatives can be found in House's Modern Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formulas I-H, I-HP, I-C, I-CP, I-HPC, Cyclo I-H, Cyclo I-C, and Cyclo I-CP are available from commercial sources or the references cited above, which are incorporated herein by reference.

Formula I-H ("Generic Polycyclic Aryl and Heteroaryl (R)-Chiral Halogenated 1-Substitutedamino-(n+1)-alkanols"), Formula I-HP ("Generic Polycyclic Aryl and Heteroaryl (R)-Chiral Halogenated 1-Substitutedamino-2-propanols"), Formula I-HPC ("Polycyclic Aryl-Heteroaryl (R)-Chiral Halogenated 1-Substitutedamino-2-Propanols"), Formula I-C ("Polycyclic Phenyl (R)-Chiral Halogenated 1-Substitutedamino-(n+1)-Alkanols"), and Formula I-CP ("Polycyclic Phenyl (R)-Chiral Halogenated 1-Substitutedamino-2-Propanols") and certain other compounds of this invention can be converted, according to Schemes 17 and 18, to the corresponding cyclic derivatives represented by "Tricyclic tertiary-oxyalkylamines" and exemplified by Formulas Cyclo I-H ("Polycyclic Aryl and Heteroaryl (R)-Chiral Halogenated (N+1)-Cycloazaalkoxy"), Cyclo I-C ("Polycyclic Aryl Phenyl (R)-Chiral Halogenated (N+1)-Cycloazaalkoxy") and Cyclo I-CP ("Polycyclic Phenyl Phenyl (R)-Chiral Halogenated Cycloazaalkoxy"). The hydroxyl group, wherein $R_{16}$ is a hydrogen and X is oxy, of compounds of Formulas I-H, I-HP, I-C, I-CP, and I-HPC can be cyclized to corresponding cyclic ethers. Compounds suitable for cyclization will normally have at least one leaving group within 5 to 10 continuous atoms of the hydroxyl group wherein $R_{16}$ is a hydrogen and X is oxy. Most preferably the leaving group will be within 5 to 7 atoms of the hydroxyl group so as to form a 6 to 8 membered ring heteroatom containing ring. When the leaving group is part of an aromatic ring system, the leaving group will be preferably in an ortho position. Suitable leaving groups generally include halides, sulfates, sulfonates, trisubsituted amino, disubstituted sulfonium, diazonium, and like, and, in the case of aromatic systems, also includes nitro, alkoxy, aryloxy, heteroaryloxy, and alkylthio.

The cyclization reaction to form "Tricyclic tertiary-oxyalkylamines" of Formulas Cyclo I-H, Cyclo I-C and Cyclo I-CP can be accomplished by aromatic and aliphatic nucleophilic substitution reactions such as those disclosed in March's Advanced Organic Chemistry, 4th Edition, John Wiley & Sons, especially at pages 293–412 and 649–658 and the references cited therein, which are incorporated herein by reference. Hydroxyl containing suitably substituted compounds can be converted to a cyclic analog by heating a suitably substituted compound under anhydrous conditions in a suitable solvent, such as dimethylformamide, dimethylsulfoxide, N-methylpyrrolidone, tetraglyme, or hexamethylphosphoramide, in the presence of a suitable base such as potassium carbonate, cesium carbonate, sodium hydroxide, potassium tertiary-butoxide, or lithium diisopropylamide. Alternately, sodium amide in anhydrous ammonia solvent can be used. Temperatures in the range of −20° C. to 200° C. can be used for time periods of 30 minutes to more than 24 hours. The preferred temperature can be selected by standard synthetic chemical technique balancing maximum yield, maximum purity, cost, ease of isolation and operation, and time required. Isolation of the "Tricyclic tertiary-oxyalkylamines" can be effected as described above for other tertiary-oxyalkylamines. Representative "Tricyclic tertiary-oxyalkylamines" prepared using the methodology described above are included in Table 8.

The following examples are provided to illustrate the present invention and are not intended to limit the scope thereof. Those skilled in the art will readily understand that known variations of the conditions and processes of the following preparative procedures can be used to prepare these compounds.

TABLE 8

Structure of Substituted Tricyclictertiary-2-oxyalkylamines.

Cyclo I-H

| Y | Z | $R_5$ | $K_1$–$R_6$ | $R_{10}$ | $K_2$–$R_{11}$ | $R_{12}$ | $R_{13}$ |
|---|---|---|---|---|---|---|---|
| $CH_2$ | — | 4-chloro-3-ethylphenoxy | C-H | H | C-$CF_3$ | H | H |
| $CH_2$ | — | 4-chloro-3-ethylphenoxy | N | H | C-$CF_3$ | H | H |
| $CH_2$ | — | 4-chloro-3-ethylphenoxy | C-H | H | C-H | $CF_3$ | H |
| $CH_2$ | — | 4-chloro-3-ethylphenoxy | N | H | C-H | $CF_3$ | H |
| $CH_2$ | — | 4-chloro-3-ethylphenoxy | C-H | H | N | $CF_3$ | H |
| — | — | 4-chloro-3-ethylphenoxy | C-H | H | C-$CF_3$ | H | H |
| — | — | 4-chloro-3-ethylphenoxy | N | H | C-$CF_3$ | H | H |
| — | — | 4-chloro-3-ethylphenoxy | C-H | H | C-H | $CF_3$ | H |
| — | — | 4-chloro-3-ethylphenoxy | N | H | C-H | $CF_3$ | H |
| — | — | 4-chloro-3-ethylphenoxy | C-H | H | N | $CF_3$ | H |

Cyclo I-H

| Y | Z | $R_7$ | $K_1$–$R_6$ | $R_{10}$ | $K_2$–$R_{11}$ | $R_5$ | $R_8$ |
|---|---|---|---|---|---|---|---|
| $CH_2$ | — | 4-chloro-3-ethylphenoxy | C-H | $OCF_2CF_2H$ | C-H | H | H |
| $CH_2$ | — | 4-chloro-3-ethylphenoxy | N | $OCF_2CF_2H$ | C-H | H | H |
| $CH_2$ | — | 4-chloro-3-ethylphenoxy | C-H | $OCF_2CF_2H$ | N | H | H |
| $CH_2$ | — | phenoxy | C-H | $OCF_2CF_2H$ | C-H | H | H |
| $CH_2$ | — | phenoxy | N | $OCF_2CF_2H$ | C-H | H | H |
| $CH_2$ | — | phenoxy | C-H | $OCF_2CF_2H$ | N | H | H |
| $CH_2$ | — | 4-chloro-3-ethylphenoxy | C-H | $CF_2CF_3$ | C-H | H | H |
| $CH_2$ | — | 4-chloro-3-ethylphenoxy | N | $CF_2CF_3$ | C-H | H | H |
| $CH_2$ | — | 4-chloro-3-ethylphenoxy | C-H | $CF_2CF_3$ | N | H | H |
| $CH_2$ | — | phenoxy | C-H | $CF_2CF_3$ | C-H | H | H |
| $CH_2$ | — | phenoxy | N | $CF_2CF_3$ | C-H | H | H |
| $CH_2$ | — | phenoxy | C-H | $CF_2CF_3$ | N | H | H |
| $CH_2$ | — | 4-chloro-3-ethylphenoxy | C-H | $CF_3$ | C-H | H | H |
| $CH_2$ | — | 4-chloro-3-ethylphenoxy | N | $CF_3$ | C-H | H | H |

TABLE 8-continued

| | | | | | | | |
|---|---|---|---|---|---|---|---|
| CH$_2$ | — | 4-chloro-3-ethylphenoxy | C-H | CF$_3$ | N | H | H |
| CH$_2$ | — | phenoxy | C-H | CF$_3$ | C-H | H | H |
| CH$_2$ | — | phenoxy | N | CF$_3$ | C-H | H | H |
| CH$_2$ | — | phenoxy | C-H | CF$_3$ | N | H | H |
| CH$_2$ | — | 4-chloro-3-ethylphenoxy | C-H | OCF$_2$CF$_2$H | C-H | H | F |
| CH$_2$ | — | 4-chloro-3-ethylphenoxy | N | OCF$_2$CF$_2$H | C-H | H | F |
| CH$_2$ | — | 4-chloro-3-ethylphenoxy | C-H | OCF$_2$CF$_2$H | N | H | F |
| CH$_2$ | — | 4-chloro-3-ethylphenoxy | C-H | 2-furyl | C-H | H | H |
| CH$_2$ | — | 4-chloro-3-ethylphenoxy | N | 2-furyl | C-H | H | H |
| CH$_2$ | — | 4-chloro-3-ethylphenoxy | C-H | 2-furyl | N | H | H |
| CH$_2$ | — | 4-chloro-3-ethylphenoxy | C-H | SCF$_3$ | C-H | H | H |
| CH$_2$ | — | 4-chloro-3-ethylphenoxy | N | SCF$_3$ | C-H | H | H |
| CH$_2$ | — | 4-chloro-3-ethylphenoxy | C-H | SCF$_3$ | N | H | H |

Scheme 1

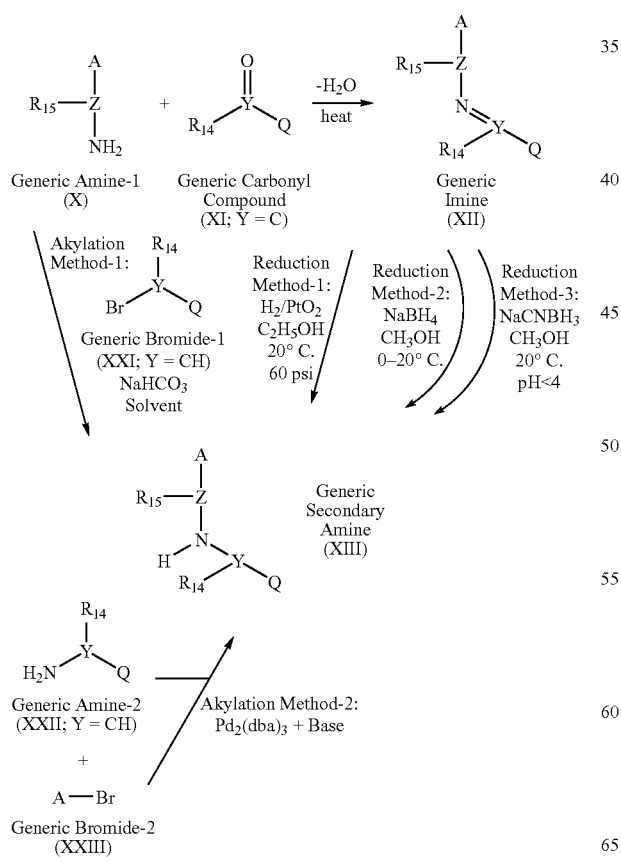

Scheme 2

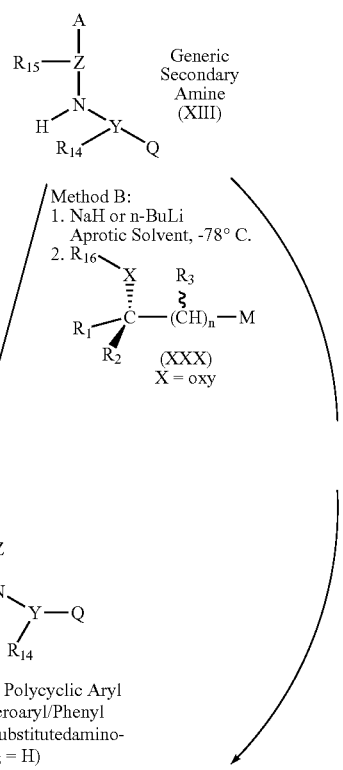

I-HP/I-HPC/I-CP: (Generic Polycyclic Aryl and Heteroaryl/Aryl-Heteroaryl/Phenyl (R)-Chiral Halogenated 1-Substitutedamino-2-Propanols; R$_{16}$ = H)

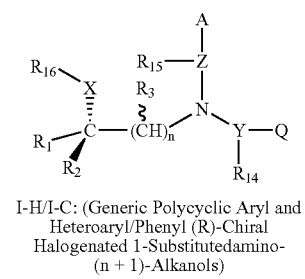

I-H/I-C: (Generic Polycyclic Aryl and Heteroaryl/Phenyl (R)-Chiral Halogenated 1-Substitutedamino-(n + 1)-Alkanols)

Scheme 3

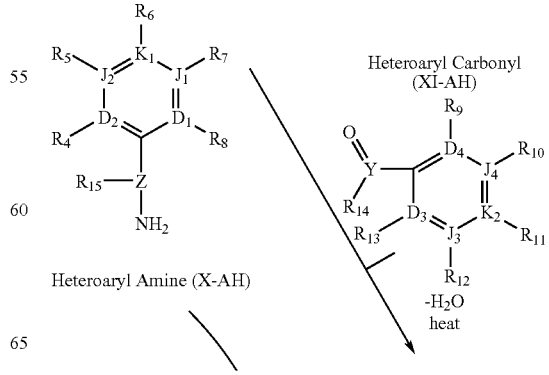

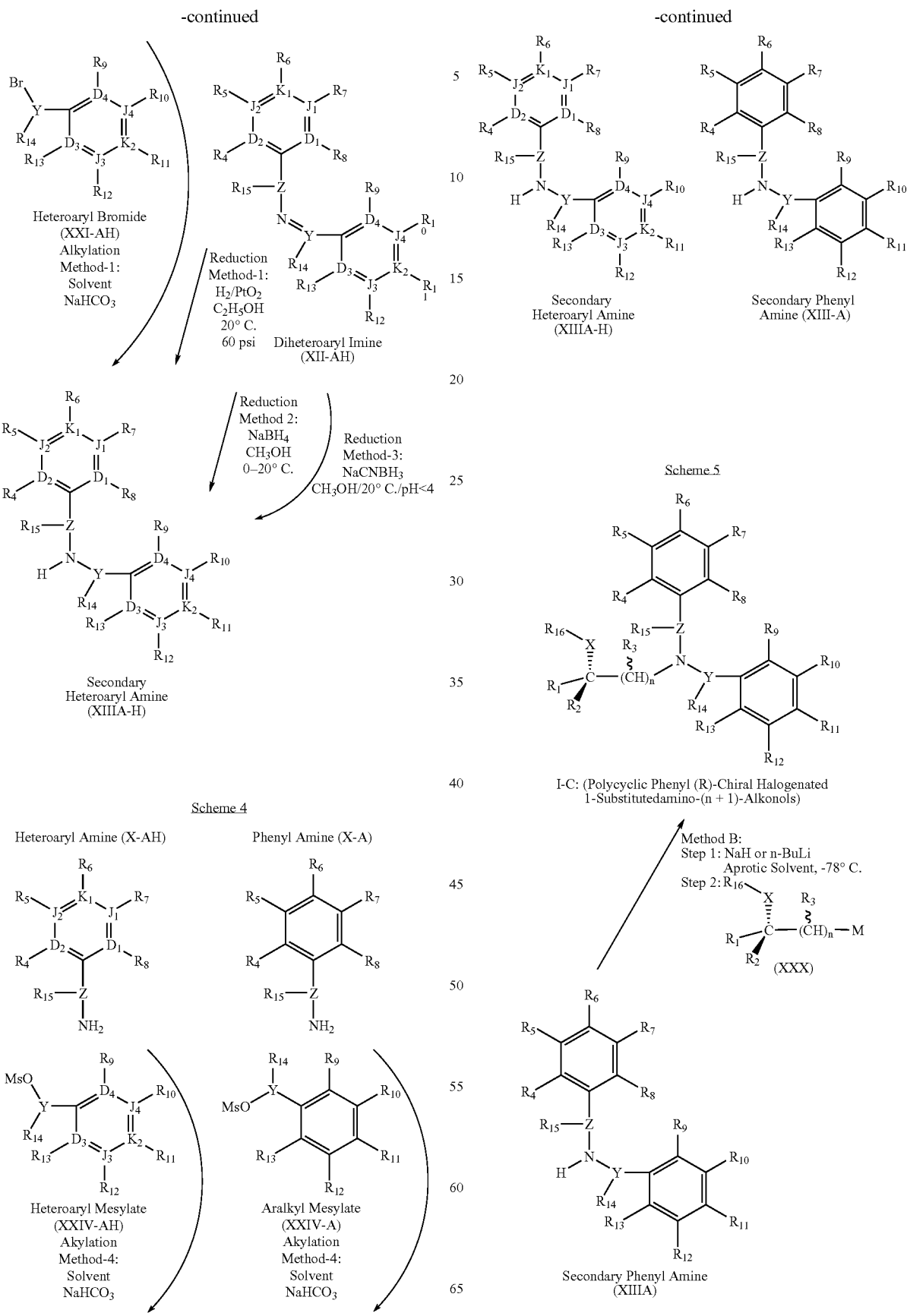

Scheme 6

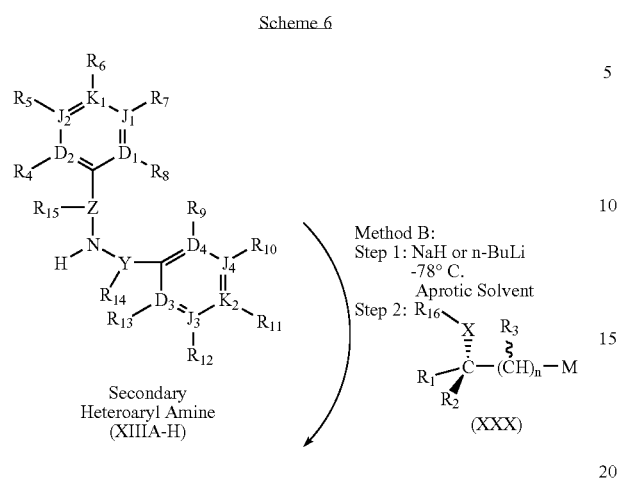

Secondary Heteroaryl Amine (XIIIA-H)

Method B:
Step 1: NaH or n-BuLi
-78° C.
Aprotic Solvent
Step 2: (XXX)

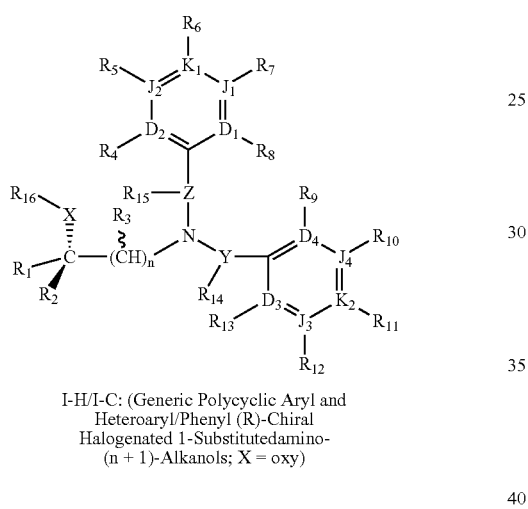

I-H/I-C: (Generic Polycyclic Aryl and Heteroaryl/Phenyl (R)-Chiral Halogenated 1-Substitutedamino-(n + 1)-Alkanols; X = oxy)

Scheme 7

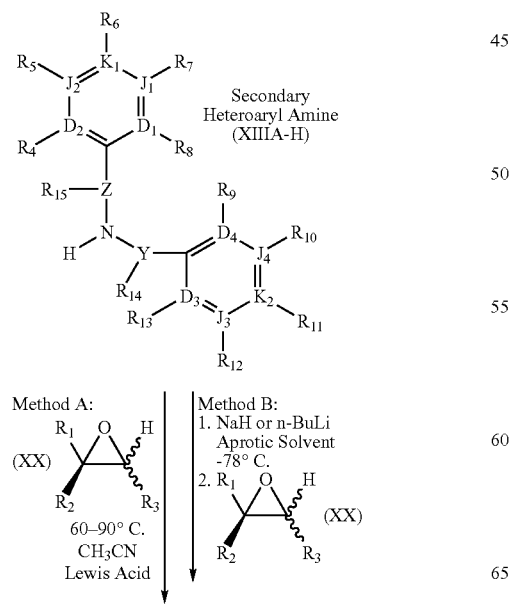

Secondary Heteroaryl Amine (XIIIA-H)

Method A:
(XX)

Method B:
1. NaH or n-BuLi
Aprotic Solvent
-78° C.
2. (XX)

60–90° C.
$CH_3CN$
Lewis Acid

-continued

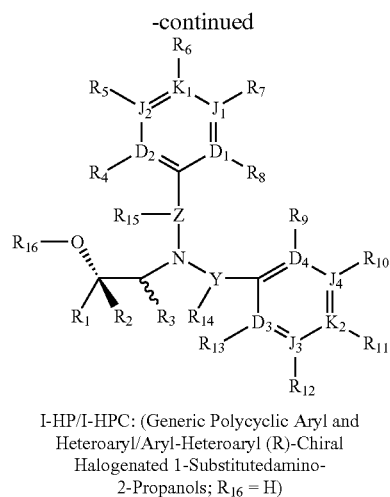

I-HP/I-HPC: (Generic Polycyclic Aryl and Heteroaryl/Aryl-Heteroaryl (R)-Chiral Halogenated 1-Substitutedamino-2-Propanols; $R_{16}$ = H)

Scheme 8

I-CP: (Polycyclic 3-Phenoxyphenyl (R)-Chiral Halogenated 1-Substitutedamino-2-Propanols; $R_{16}$ = H; X = oxy)

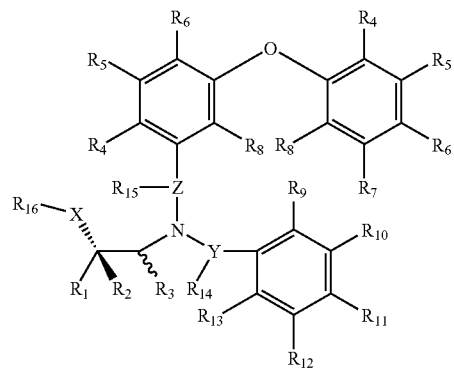

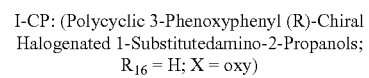

$Cu_2(triflate)_2$•Benzene
2 equivalents of a phenol
2.5 equiv. $Cs_2CO_3$
2.5 equiv. 1-Naphthoic Acid
4A Molecular Sieves
Dimethylacetamide/toluene
105° C./10–14 Days

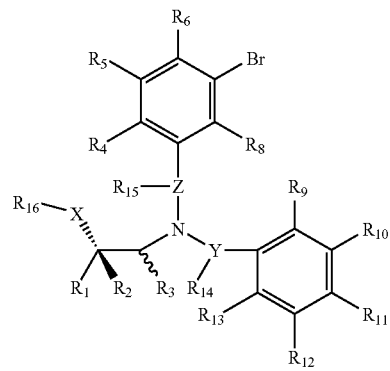

I-CP: (Polycyclic 3-Bromophenyl (R)-Chiral Halogenated 1-Substitutedamino-2-Propanols; $R_{16}$ = H; X = oxy)

Scheme 9
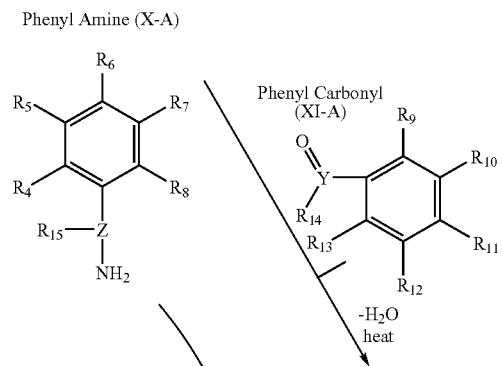
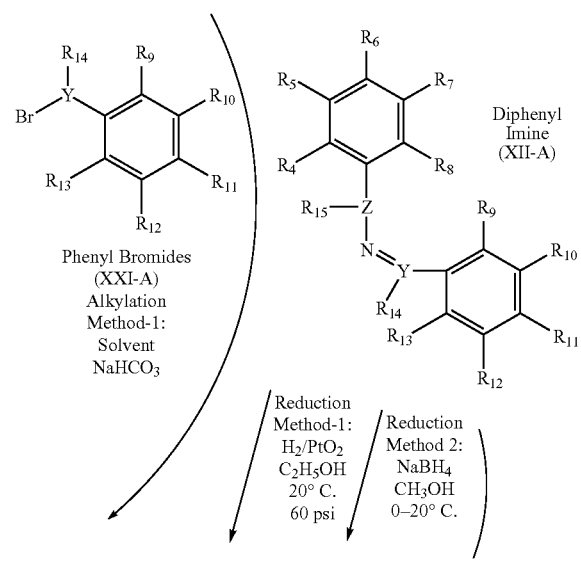
Scheme 10
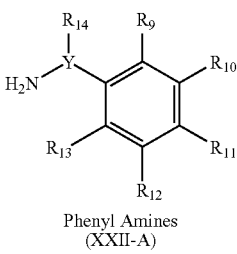 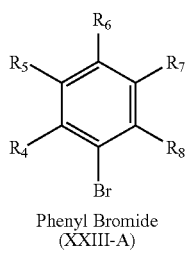
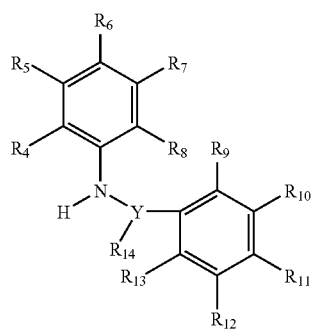
Scheme 11
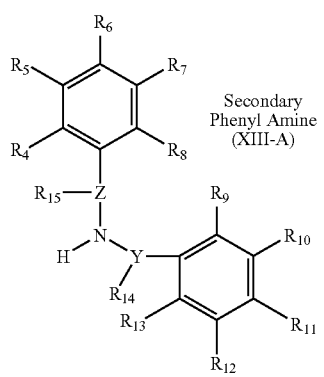

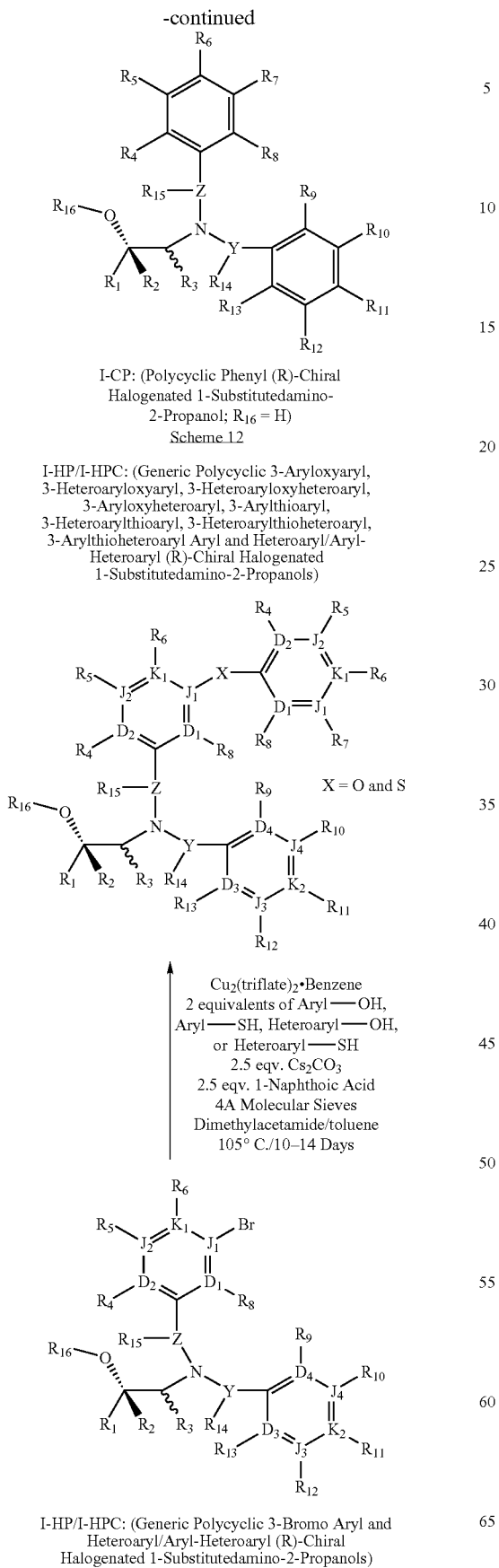

I-CP: (Polycyclic Phenyl (R)-Chiral Halogenated 1-Substitutedamino-2-Propanol; $R_{16}$ = H)

Scheme 12

I-HP/I-HPC: (Generic Polycyclic 3-Aryloxyaryl, 3-Heteroaryloxyaryl, 3-Heteroaryloxyheteroaryl, 3-Aryloxyheteroaryl, 3-Arylthioaryl, 3-Heteroarylthioaryl, 3-Heteroarylthioheteroaryl, 3-Arylthioheteroaryl Aryl and Heteroaryl/Aryl-Heteroaryl (R)-Chiral Halogenated 1-Substitutedamino-2-Propanols)

X = O and S

Cu$_2$(triflate)$_2$•Benzene
2 equivalents of Aryl—OH,
Aryl—SH, Heteroaryl—OH,
or Heteroaryl—SH
2.5 eqv. Cs$_2$CO$_3$
2.5 eqv. 1-Naphthoic Acid
4A Molecular Sieves
Dimethylacetamide/toluene
105° C./10–14 Days I-HP/I-HPC: (Generic Polycyclic 3-Bromo Aryl and Heteroaryl/Aryl-Heteroaryl (R)-Chiral Halogenated 1-Substitutedamino-2-Propanols)

Scheme 13

I-HP/I-HPC: (Generic Polycyclic 3-Aryloxyaryl, 3-Heteroaryloxyaryl3-Aryloxyheteroaryl or 3-Heteroaryloxyheteroaryl Aryl-Heteroaryl (R)-Chiral Halogenated 1-Substitutedamino-2-Propanols)

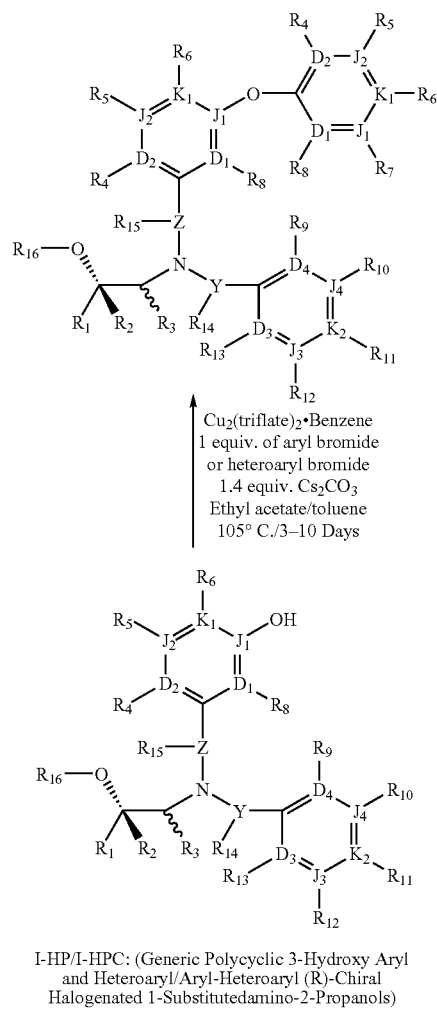

Cu$_2$(triflate)$_2$•Benzene
1 equiv. of aryl bromide
or heteroaryl bromide
1.4 equiv. Cs$_2$CO$_3$
Ethyl acetate/toluene
105° C./3–10 Days I-HP/I-HPC: (Generic Polycyclic 3-Hydroxy Aryl and Heteroaryl/Aryl-Heteroaryl (R)-Chiral Halogenated 1-Substitutedamino-2-Propanols)

Scheme 14

I-CP: (Generic Substituted Polycyclic 3-Phenoxyphenyl Aryl (R)-Chiral Halogenated 1-Substitutedamino-2-Propanols)

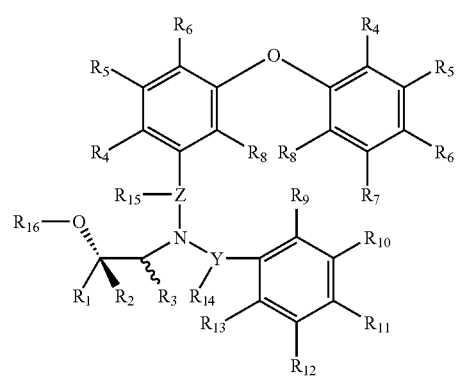

Scheme 16

I-CP: (Polycyclic 3-Aralkyloxyaryl Phenyl (R)-Chiral Halogenated 1-Substitutedamino-2-Propanols)

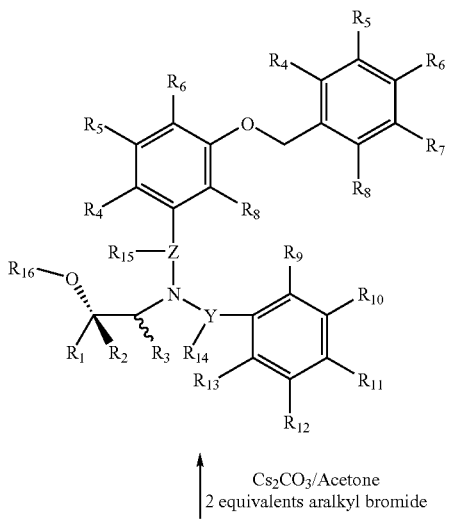

↑ Cs$_2$CO$_3$/Acetone
2 equivalents aralkyl bromide

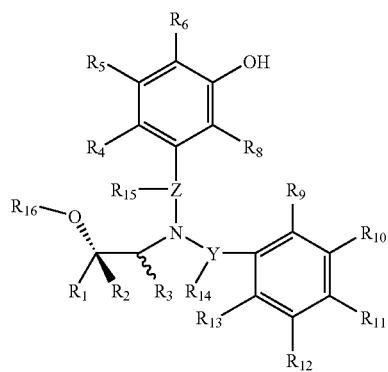

I-CP: (Polycyclic 3-Hydroxyphenyl Phenyl (R)-Chiral Halogenated 1-Substitutedamino-2-Propanols)

Scheme 17

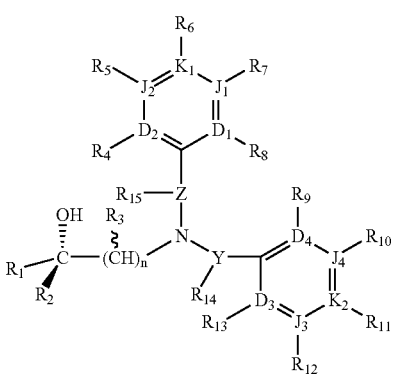

I-H/I-C: (Generic Polycyclic Aryl and Heteroaryl/Phenyl (R)-Chiral Halogenated 1-Substitutedamino- (n + 1)-Alkanols)

↘ LDA/DMF or NaNH$_2$/NH$_3$

---

-continued

↑ Cu$_2$(triflate)$_2$·Benzene
1 equiv. of aryl bromide or heteroaryl bromide
1.4 equiv. Cs$_2$CO$_3$
Ethyl acetate/toluene
105° C./3–10 Days

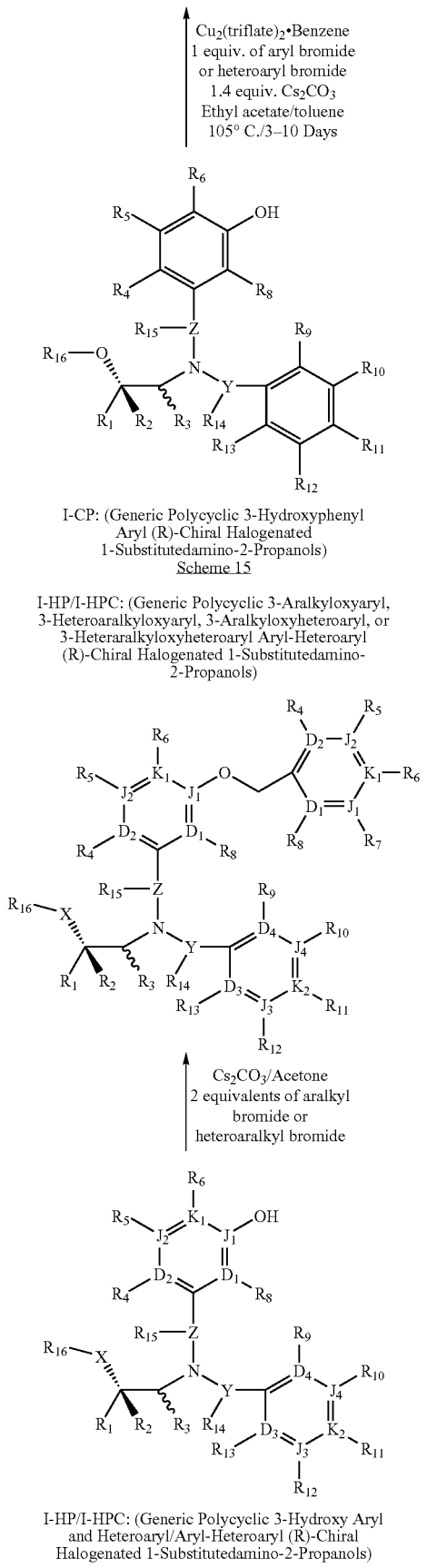

I-CP: (Generic Polycyclic 3-Hydroxyphenyl Aryl (R)-Chiral Halogenated 1-Substitutedamino-2-Propanols)

Scheme 15

I-HP/I-HPC: (Generic Polycyclic 3-Aralkyloxyaryl, 3-Heteroaralkyloxyaryl, 3-Aralkyloxyheteroaryl, or 3-Heteraralkyloxyheteroaryl Aryl-Heteroaryl (R)-Chiral Halogenated 1-Substitutedamino-2-Propanols)

↑ Cs$_2$CO$_3$/Acetone
2 equivalents of aralkyl bromide or heteroaralkyl bromide I-HP/I-HPC: (Generic Polycyclic 3-Hydroxy Aryl and Heteroaryl/Aryl-Heteroaryl (R)-Chiral Halogenated 1-Substitutedamino-2-Propanols)

-continued

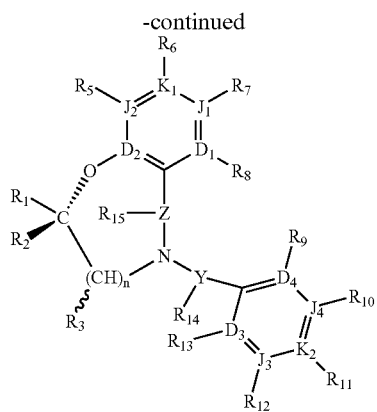

Cyclo I-H/Cyclo I-C: Polycyclic Aryl and
Heteroaryl/Phenyl (R)-Chiral Halogenated
(n + 1)-Cycloazaalkoxy)

Scheme 18

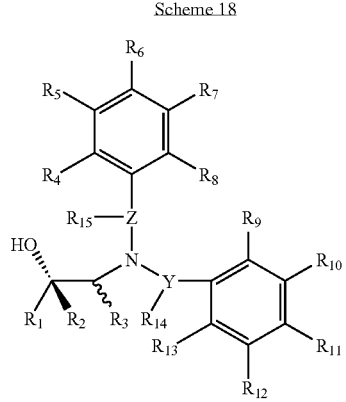

I-CP: (Generic Polycyclic Phenyl
Phenyl (R)-Chiral Halogenated
1-Substitutedamino-2-Propanols)

LDA/DMF
or
NaNH$_2$/NH$_3$

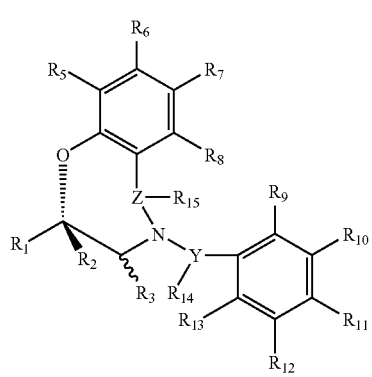

Cyclo I-CP: (Polycyclic Phenyl Phenyl
(R)-Chiral Halogenated
Cycloazaalkoxy)

Scheme 19

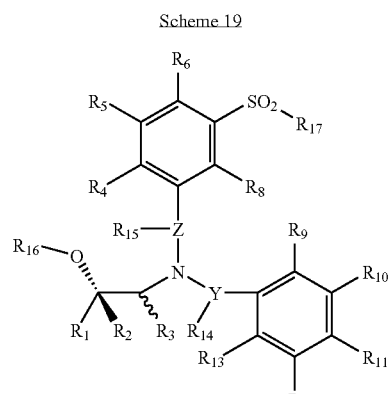

I-CP: (Polycyclic 3-R$_{17}$sulfonypheny
Phenyl (R)-Chiral
Halogenated 1-Substitutedamino-2-Propanols)

H$_2$O$_2$
TFA

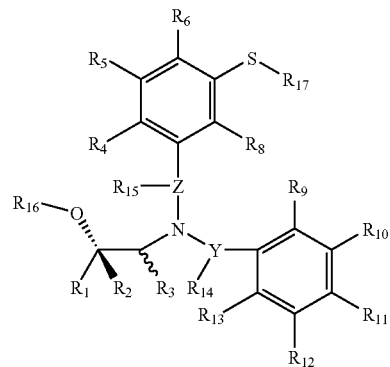

I-CP: (Polycyclic 3-R$_{17}$thiaphenyl
Phenyl (R)-Chiral Halogenated
1-Substitutedamino-2-Propanols)

R$_{17}$—Br
Cs$_2$CO$_3$
Acetone

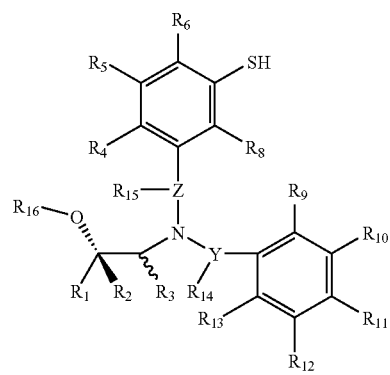

I-CP: (Polycyclic 3-Thiophenyl Phenyl (R)-Chiral
Halogenated 1-Substitutedamino-2-Propanols)

Scheme 20

I-CP: (Polycyclic 3-R$_{17}$-oxyphenyl Phenyl (R)-Chiral Halogenated 1-Substitutedamino-2-Propanols)

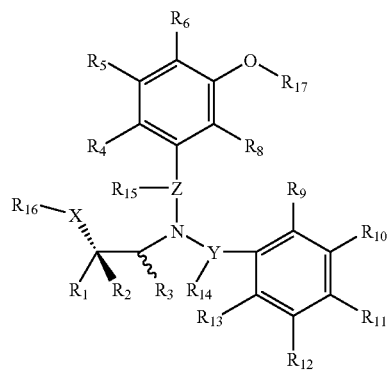

↑ Cs$_2$CO$_3$/Acetone
R$_{17}$—Br

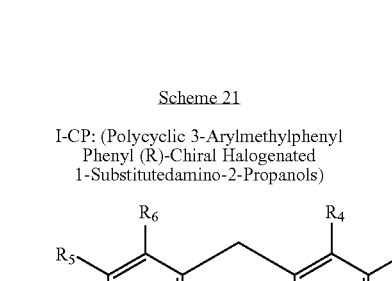

I-CP: (Polycyclic 3-Hydroxyphenyl Phenyl (R)-Chiral Halogenated 1-Substitutedamino-2-Propanols)

Scheme 21

I-CP: (Polycyclic 3-Arylmethylphenyl Phenyl (R)-Chiral Halogenated 1-Substitutedamino-2-Propanols)

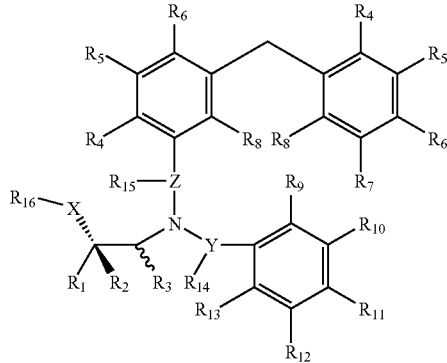

-continued

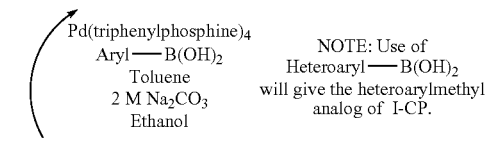

NOTE: Use of Heteroaryl—B(OH)$_2$ will give the heteroarylmethyl analog of I-CP.

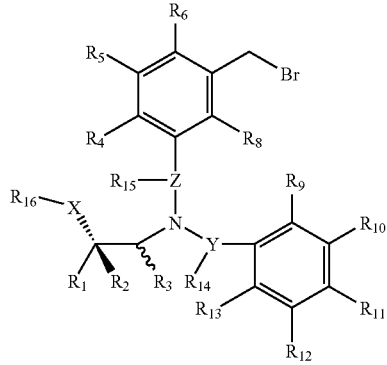

I-CP: (Polycyclic 3-Bromomethylphenyl Phenyl (R)-Chiral Halogenated 1-Substitutedamino-2-Propanols)

Scheme 22

I-CP: (Polycyclic 3-Arylphenyl Phenyl (R)-Chiral Halogenated 1-Substitutedamino-2-Propanols)

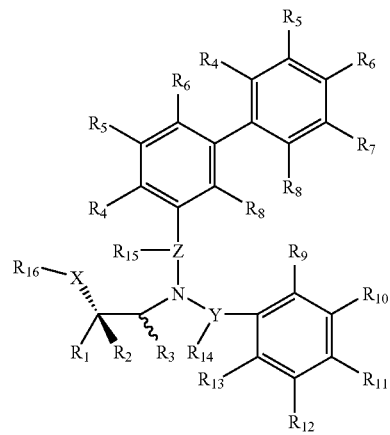

-continued

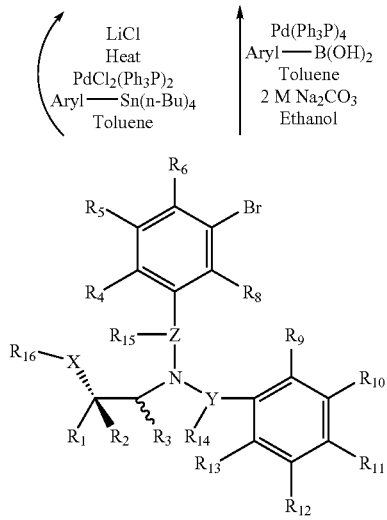

I-CP: (Polycyclic 3-Bromophenyl
Phenyl (R)-Chiral Halogenated
1-Substitutedamino-2-Propanols)
NOTE: Use of Heteroaryl—B(OH)$_2$
will give the heteroarylmethyl analog of I-CP.

Scheme 23

I-CP: (Polycyclic 3-R$_{22}$-aminophenyl Phenyl (R)-Chiral
Halogenated 1-Substitutedamino-2-Propanols)

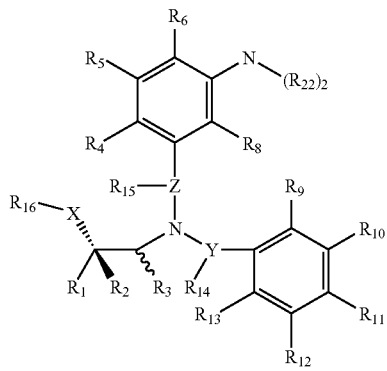

-continued $R_{22}$-primary or secondary amine
Pd(dba)$_3$/R-(+)-BINAP
2.5 equiv. Cs$_2$CO$_3$
Toluene/100° C./1–2 Days

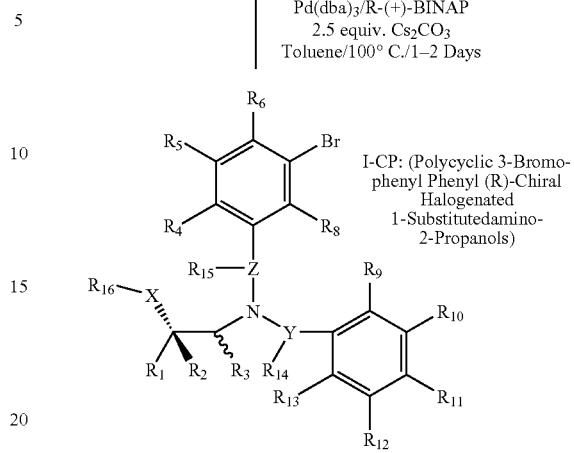

I-CP: (Polycyclic 3-Bromo-
phenyl Phenyl (R)-Chiral
Halogenated
1-Substitutedamino-
2-Propanols)

R$_{22}$ is selected independently from any one or two
of the following groups: hydrido, hydroxy, aryloxy,
alkyl, alkenyl, alkynyl, aryl, aralkyl,
alkoxyalkyl, aralkoxyalkyl, alkylsulfinylalkyl,
haloalkyl, haloalkenyl, halocycloalkyl,
halocycloalkoxy, halocycloalkoxyalkyl,
arylsulfinylalkyl, arylsulfonylalkyl, alkylamino
cycloalkylsulfinylalkyl, cycloalkylsufonylalkyl,
heteroarylsulfonylalkyl, heteroarylsulfinylalkyl,
aralkylsulfinylalkyl, aralkylsulfonylalkyl,
hydroxyalkyl, amino, alkoxy, alkylsulfonylalkyl,
aralkylthioalkyl, heteroaralkylthioalkyl,
heteroaryloxyalkyl, alkenyloxyalkyl, haloalkoxy,
haloalkoxyalkyl, haloalkenyloxyalkyl, heteroaryl,
halocycloalkenyloxyalkyl, heteroarylalkyl,
aryloxyalkyl, halocycloalkenyl, and heteroarylthioalkyl.

Scheme 24

I-CP: (Polycyclic 3-R$_{17}$—C(O) amidophenyl
Phenyl (R)-Chiral Halogenated
1-Sustitutedamino-2-Propanols; R$_{16}$ = H)

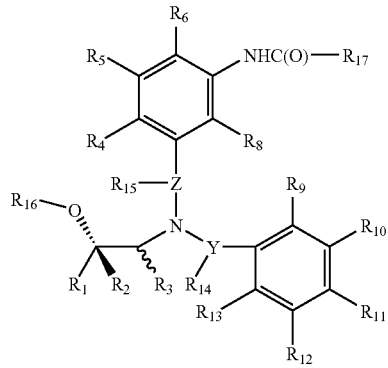

-continued

1. $R_{17}$—C(O)Cl
   Pyridine
   Toluene
2. TFA
   Water
   $NH_2$

I-CP: (Polycyclic 3-Aminophenyl Phenyl (R)-Chiral Halogenated 1-Substitutedamino-2-Propanols; $R_{16}$ = trialkylsilyl)

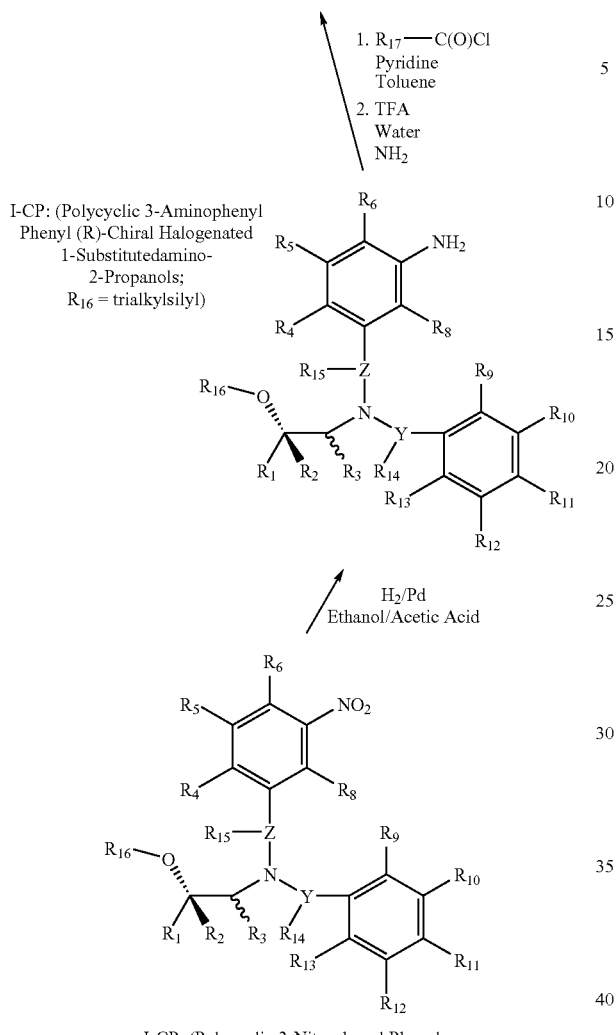

I-CP: (Polycyclic 3-Nitrophenyl Phenyl (R)-Chiral Halogenated 1-Substitutedamino-2-Propanols; $R_{16}$ = trialkylsilyl)

Scheme 25

I-CP: (Polycyclic 3-(Saturated nitrogen heterocycl-1-yl)phenyl Phenyl (R)-Chiral Halogenated 1-Substitutedamino-2-Propanols; $R_{16}$ = H)

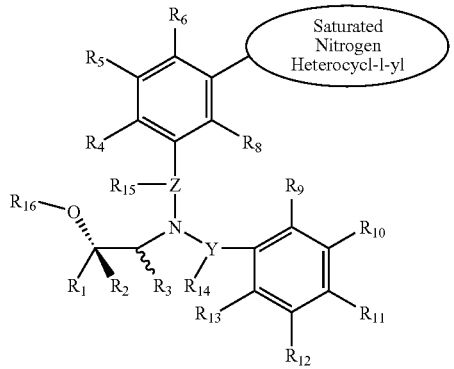

-continued

Acyclic, substituted gamma-oxo aldehydes and ketones
$H_2$/Pd
Ethanol/Acetic Acid

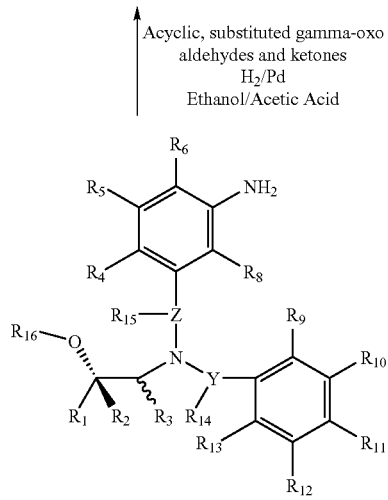

I-CP: (Polycyclic 3-Aminophenyl Phenyl (R)-Chiral Halogenated 1-Substitutedamino-2-Propanols; $R_{16}$ = H)

Scheme 26

I-CP: (Polycyclic 3-(Unsaturated nitrogen heterocycl-1-yl)phenyl Phenyl (R)-Chiral Halogenated 1-Substitutedamino-2-Propanols; $R_{16}$ = H)

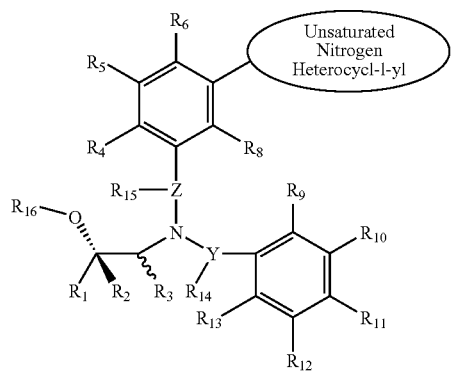

Acyclic, substituted 4-oxo carboxylic acid esters and 5-oxo carboxylic acid esters
Refluxing Acetic Acid

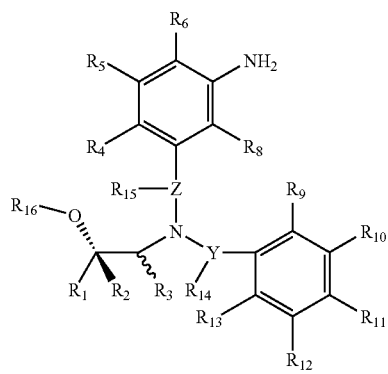

I-CP: (Polycyclic 3-Aminophenyl Phenyl (R)-Chiral Halogenated 1-Substitutedamino-2-Propanols; $R_{16}$ = H)

Scheme 27

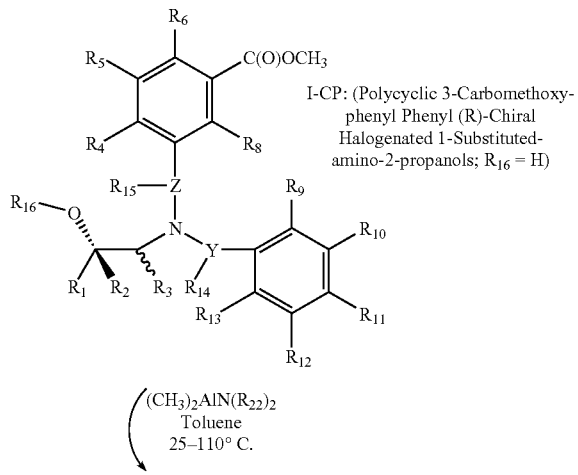

I-CP: (Polycyclic 3-Carbomethoxy-phenyl Phenyl (R)-Chiral Halogenated 1-Substituted-amino-2-propanols; $R_{16}$ = H)

$\begin{pmatrix} (CH_3)_2AlN(R_{22})_2 \\ \text{Toluene} \\ 25\text{–}110°\text{ C.} \end{pmatrix}$

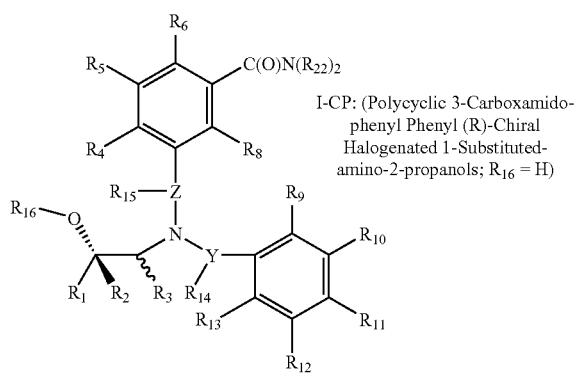

I-CP: (Polycyclic 3-Carboxamido-phenyl Phenyl (R)-Chiral Halogenated 1-Substituted-amino-2-propanols; $R_{16}$ = H)

$R_{22}$ is selected independently from any one or two of the following groups: hydrido, hydroxy, aryloxy, alkyl, alkenyl, alkynyl, aryl, aralkyl, aryloxyalkyl, alkoxyalkyl, aralkoxyalkyl, alkylsulfinylalkyl, haloalkyl, haloalkenyl, halocycloalkyl, halocycloalkoxy, halocycloalkoxyalkyl, heteroaryl, arylsulfinylalkyl, arylsulfonylalkyl, alkylamino cycloalkylsulfinylalkyl, cycloalkylsufonylalkyl, heteroarylsulfonylalkyl, heteroarylsulfinylalkyl, aralkylsulfinylalkyl, aralkylsulfonylalkyl, hydroxyalkyl, amino, alkoxy, alkylsulfonylalkyl, aralkylthioalkyl, heteroaralkylthioalkyl, heteroaryloxyalkyl, alkenyloxyalkyl, haloalkoxy, haloalkoxyalkyl, haloalkenyloxyalkyl, halocycloalkenyl, halocycloalkenyloxyalkyl, heteroarylalkyl, and heteroarylthioalkyl.

Scheme 28

I-CP: (Polycyclic 3-Cyanophenyl Phenyl (R)-Chiral Halogenated 1-Substitutedamino-2-Propanols; $R_{16}$ = H)

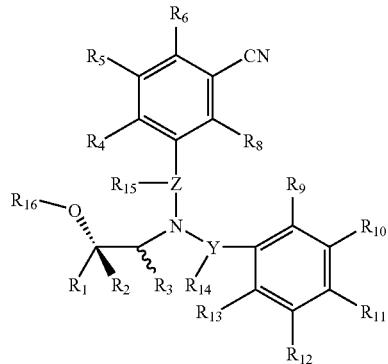

$\begin{pmatrix} \text{Method 1:} \\ 1.\ 2\text{–}5\ \text{equiv.} \\ R_{17}\text{—MgBr/ether} \\ 2.\ \text{HCl/H}_2\text{O} \end{pmatrix} \begin{pmatrix} \text{Method 2:} \\ 1.\ 2\ \text{equiv.}\ R_{17}\text{—Li} \\ \text{hydrocarbon solvent} \\ 2.\ \text{HCl/H}_2\text{O} \end{pmatrix}$

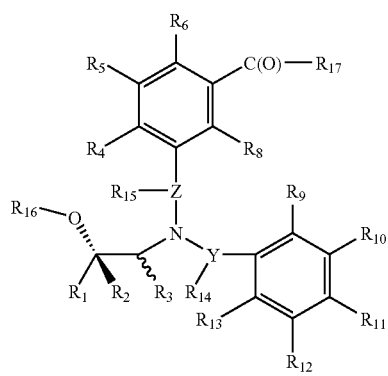

I-CP: (Polycyclic 3-Acylphenyl Phenyl (R)-Chiral Halogenated 1-Substitutedamino-2-Propanols; $R_{16}$ = H)
$R_{17}$ is selected from alkyl, alkenyl, alkynyl, aryl, aryloxyalkyl, aralkoxyalkyl, aralkylthioalkyl, heteroaryloxyalkyl, alkenyloxyalkyl, alkylthioalkyl, cycloalkyl, cycloalkylalkyl, cycloalkylalkenyl, heteroaryl, heteroarylalkyl, heteroarylthioalkyl, heteroaralkylthioalkyl, heteroaralkylthioalkyl, alkoxyalkyl, cycloalkenylalkyl, arylthioalkyl, aralkyl, and cycloalkenyl.

Scheme 29

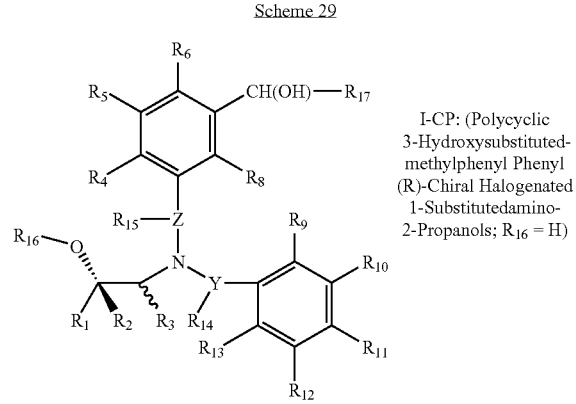

I-CP: (Polycyclic 3-Hydroxysubstituted-methylphenyl Phenyl (R)-Chiral Halogenated 1-Substitutedamino-2-Propanols; $R_{16}$ = H)

-continued

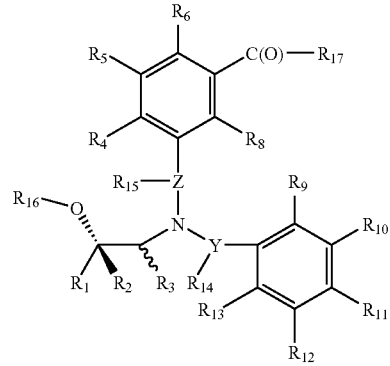

ICP: (Polycyclic 3-Acylphenyl Phenyl (R)-Chiral Halogenated 1-Substitutedamino-2-Propanols; $R_{16}$ = H)
$R_{17}$ is selected from alkyl, alkenyl, alkynyl, aryl, aryloxyalkyl, aralkoxyalkyl, aralkylthioalkyl, heteroaryloxyalkyl, alkenyloxyalkyl, alkylthioalkyl, cycloalkyl, cycloalkylalkyl, cycloalkylalkenyl, heteroaryl, heteroarylalkyl, heteroarylthioalkyl, aralkyl, heteroaralkylthioalkyl, heteroaralkylthioalkyl, alkoxyalkyl, cycloalkenylalkyl, arylthioalkyl, and cycloalkenyl.

Scheme 30

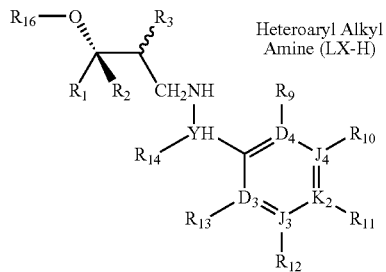

Heteroaryl Alkyl Amine (LX-H)

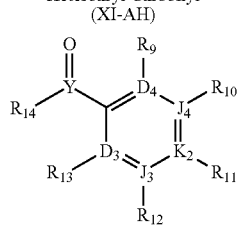

Heteroaryl Carbonyl (XI-AH)

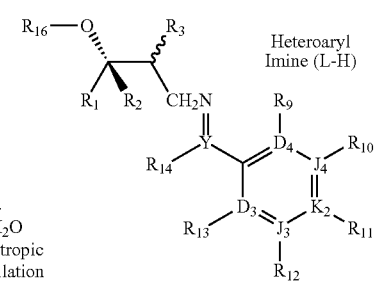

Heteroaryl Imine (L-H)

-continued

XL: (Generic Substituted Alkylamine)

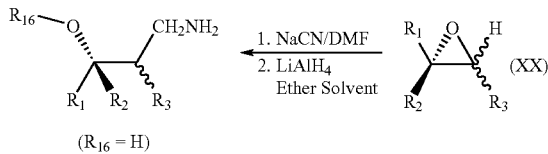

($R_{16}$ = H)

Scheme 31

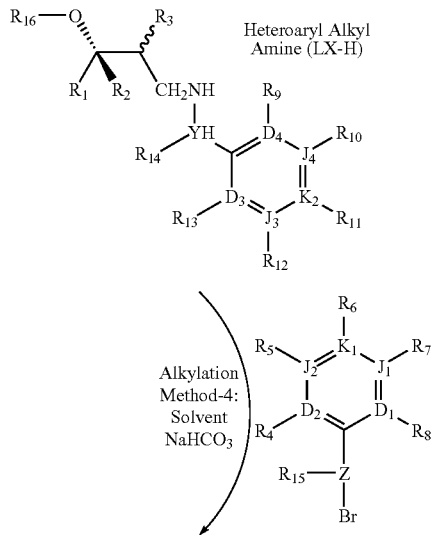

Heteroaryl Alkyl Amine (LX-H)

Alkylation Method-4: Solvent NaHCO$_3$

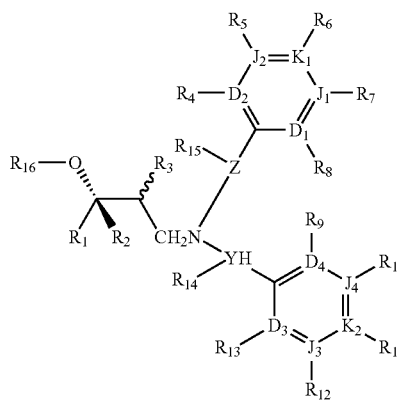

I-H: (Generic Polycyclic Aryl and Heteroaryl (R)-Chiral Halogenated 1-Substitutedamino-3-Butanols)

Scheme 32

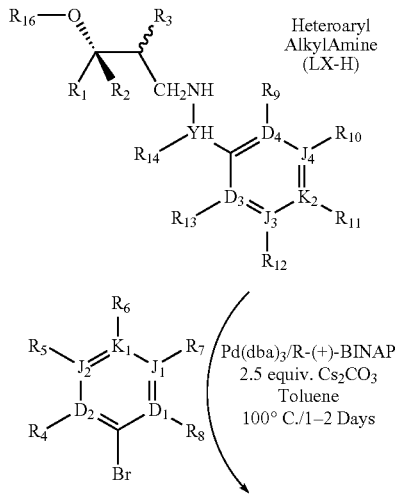

Heteroaryl AlkylAmine (LX-H)

Pd(dba)$_3$/R-(+)-BINAP
2.5 equiv. Cs$_2$CO$_3$
Toluene
100° C./1–2 Days

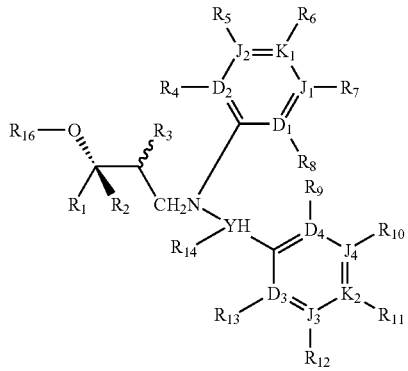

I-H: (Generic Polycyclic Aryl and Heteroaryl (R)-Chiral Halogenated 1-Substitutedamino-3-Butanols)

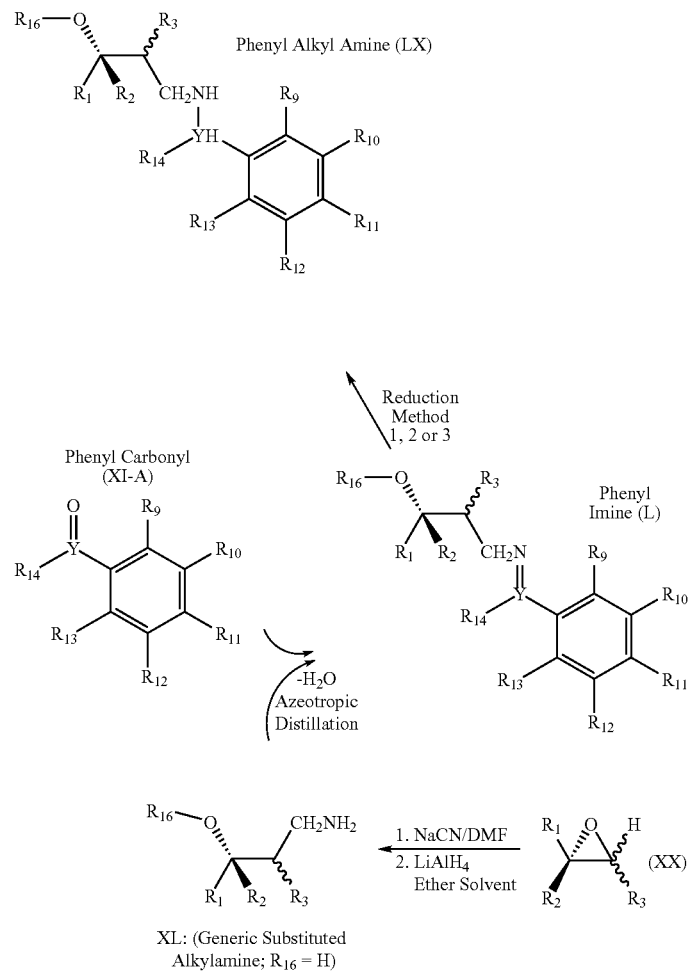
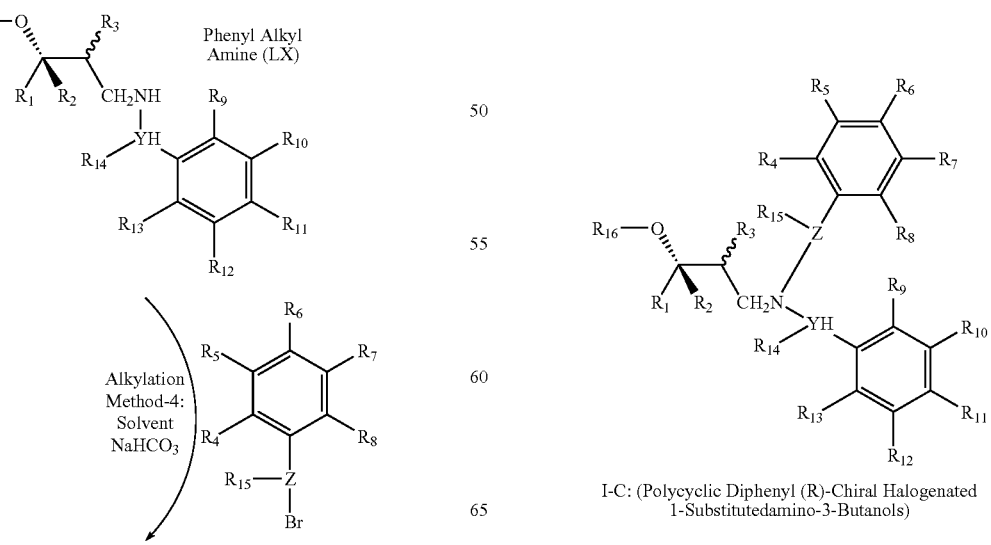

Scheme 35

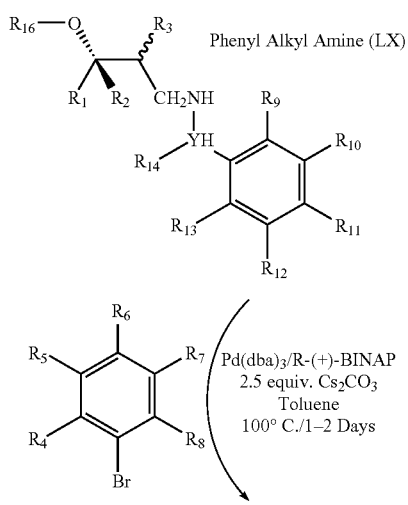

I-C: (Polycyclic Diphenyl (R)-Chiral Halogenated 1-Substitutedamino-3-Butanols)

Scheme 36

I-CP: (Polycyclic 3-Carbomethoxyaryl Phenyl (R)-Chiral Halogenated 1-Substitutedamino-2-Propanols; $R_{16}$ = H)

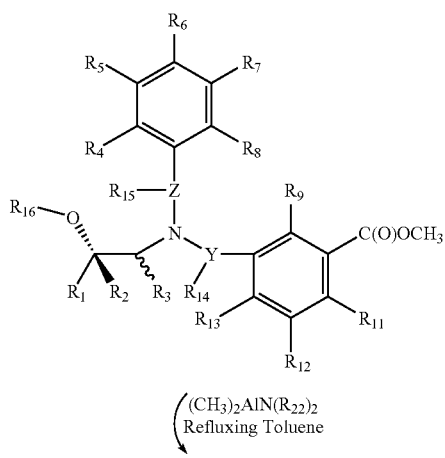

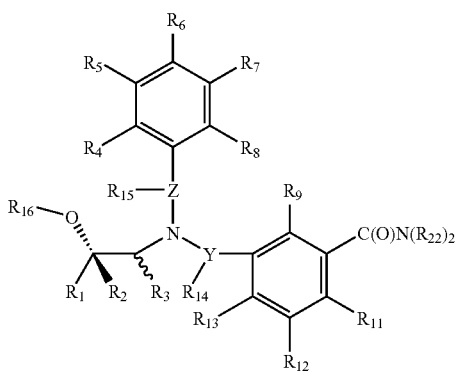

I-CP: (Polycyclic 3-Carboxamidoaryl Phenyl (R)-Chiral Halogenated 1-Substitutedamino-2-Propanols; $R_{16}$ = H)
NOTE: $R_{22}$ is as defined in Scheme 27

Scheme 37

I-CP: (Polycyclic 3-Carbomethoxyaryl Phenyl (R)-Chiral Halogenated 1-Substitutedamino-2-Propanols; $R_{16}$ = H)

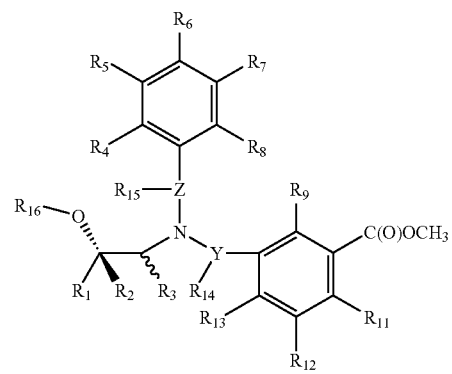

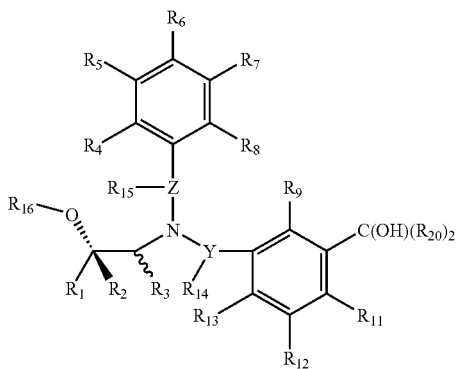

I-CP: (Polycyclic 3-(bis-$R_{20}$-hydroxymethyl)aryl Phenyl (R)-Chiral Halogenated 1-Substitutedamino-2-Propanols; $R_{16}$ = H)

$R_{20}$ is selected from alkyl, alkenyl, alkynyl, aryl, aryloxyalkyl, aralkoxyalkyl, aralkylthioalkyl, heteroaryloxyalkyl, alkenyloxyalkyl, alkylthioalkyl, heteroaryl, heteroarylalkyl, heteroarylthioalkyl, heteroaralkylthioalkyl, heteroaralkylthioalkyl, cycloalkenylalkyl, arylthioalkyl, aralkyl, alkoxyalkyl, and cycloalkenyl.

Scheme 38

I-CP: (Polycyclic 3-Carbomethoxyaryl Phenyl
(R)-Chiral Halogenated 1-Substitutedamino-
2-Propanols; $R_{16}$ = H)

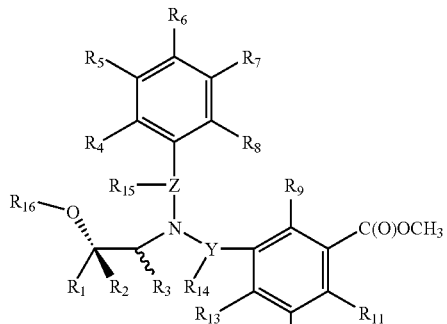

↓ THF
LiAlH₄

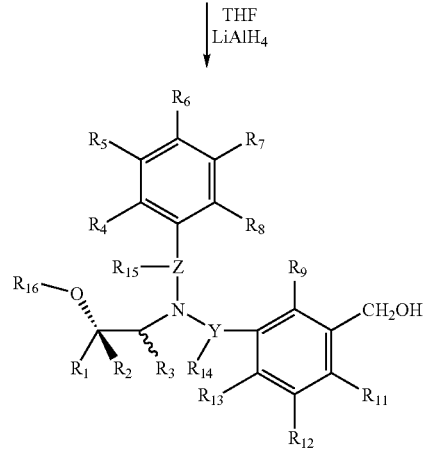

I-CP: (Polycyclic 3-Hydroxymethylaryl Phenyl
(R)-Chiral Halogenated 1-Substitutedamino-
2-Propanols; $R_{16}$ = H)

Scheme 39

I-CP: (Polycyclic 3-Carbomethoxyaryl Phenyl
(R)-Chiral Halogenated 1-Substitutedamino-
2-Propanols; $R_{16}$ = H)

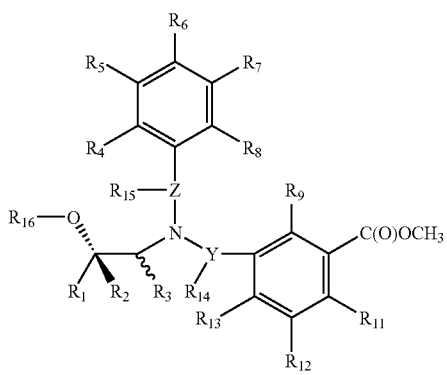

↓ TBAF
excess $R_{21}$—TMS
refluxing toluene

-continued

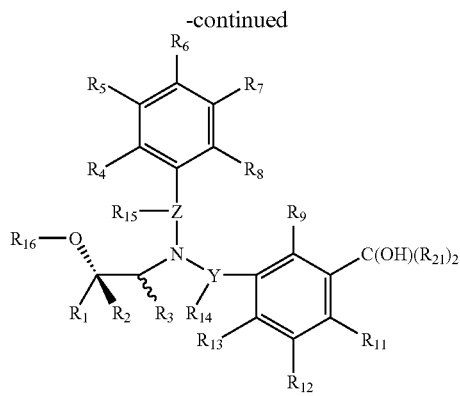

I-CP: (Polycyclic 3-(bis-$R_{21}$-hydroxymethyl)aryl
Phenyl (R)-Chiral Halogenated 1-Substitutedamino-
2-Propanols; $R_{16}$ = H)
$R_{21}$ is selected from perfluoroalkyl, perfluoroalkenyl,
perfluorocycloalkyl, perfluorocycloalkylalkyl,
perfluoroaralkyl, perfluoroalkoxyalkyl,

Scheme 40

I-CP: (Polycyclic 3-Arylaryl Phenyl
(R)-Chiral Halogenated 1-Substitutedamino-
2-Propanols; $R_{16}$ = H)

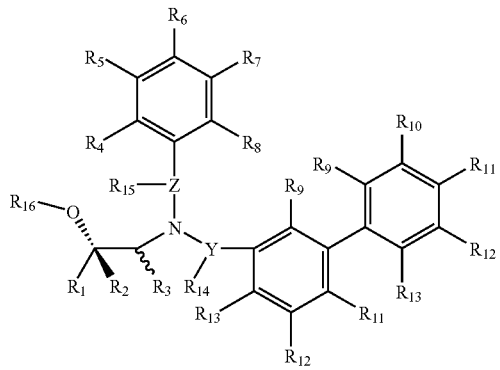

↑ Pd(triphenylphosphine)₄
Aryl—B(OH)₂
K₂CO₃, toluene, DMF

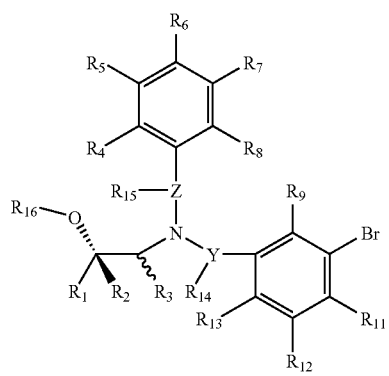

I-CP: (Polycyclic 3-Bromoaryl Phenyl
(R)-Chiral Halogenated 1-Substitutedamino-
2-Propanols; $R_{16}$ = H)

Scheme 41

I-CP: (Polycyclic 3-Heteroarylaryl Phenyl
(R)-Chiral Halogenated 1-Substitutedamino-
2-Propanols; $R_{16}$ = H)

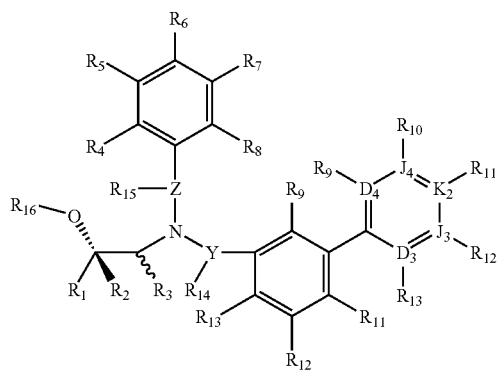

↑ Pd(triphenylphosphine)$_2$Cl$_2$
  Heteroaryl—SnBu$_3$
  Dioxane

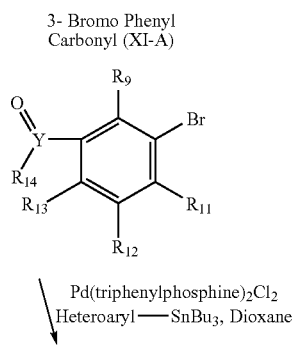

I-CP: (Polycyclic 3-Bromoaryl Phenyl
(R)-Chiral Halogenated 1-Substitutedamino-
2-Propanols; $R_{16}$ = H)

-continued

3-Heteroaryl Phenyl Carbonyl (XI-A)

↓ NaB(OAc)$_3$H
  Acetic Acid
  ClCH$_2$CH$_2$Cl

Phenyl Amine (X-A)

Secondary Phenyl Amine (XIII-A)

Scheme 42

3- Bromo Phenyl Carbonyl (XI-A)

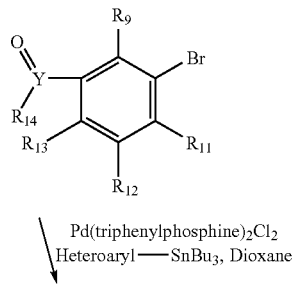

↓ Pd(triphenylphosphine)$_2$Cl$_2$
  Heteroaryl—SnBu$_3$, Dioxane

Scheme 43

3- Bromo Phenyl Carbonyl (XI-A)

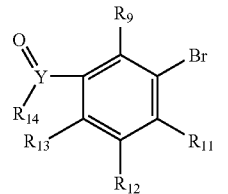

↓ Pd(triphenylphosphine)$_4$
  Heteroaryl—Br, THF, ZnCl$_2$

-continued

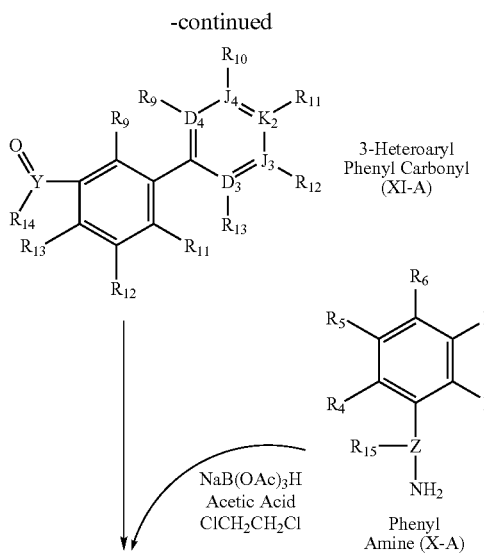
3-Heteroaryl Phenyl Carbonyl (XI-A)

NaB(OAc)₃H
Acetic Acid
ClCH₂CH₂Cl

Phenyl Amine (X-A)

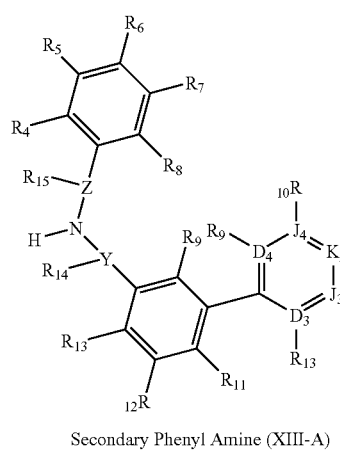
Secondary Phenyl Amine (XIII-A)

Scheme 44

3- B(OH)₂ Phenyl Carbonyl (XI-A)

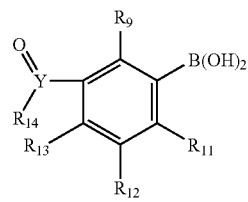

Pd(triphenylphosphine)₄
Heteroaryl—Br or Aryl—Br, K₂CO₃,
Toluene, DMF

-continued

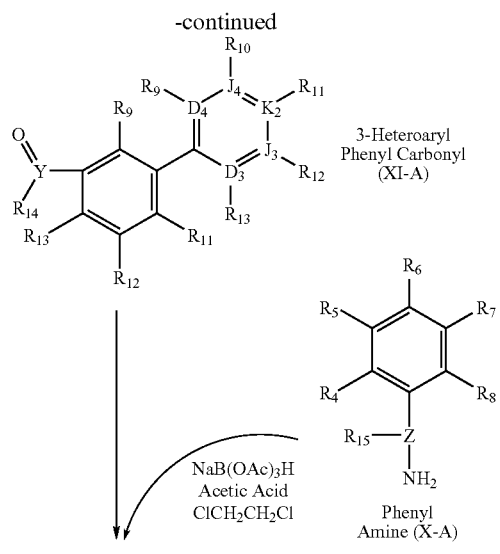
3-Heteroaryl Phenyl Carbonyl (XI-A)

NaB(OAc)₃H
Acetic Acid
ClCH₂CH₂Cl

Phenyl Amine (X-A)

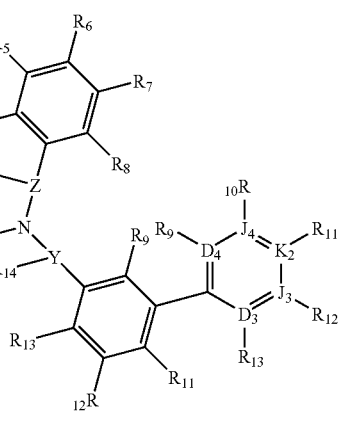
Secondary Phenyl Amine (XIII-A)

Scheme 45

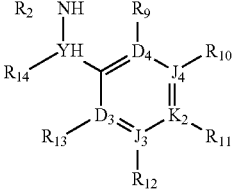
Heteroaryl Alkyl Amine (VLX-H)

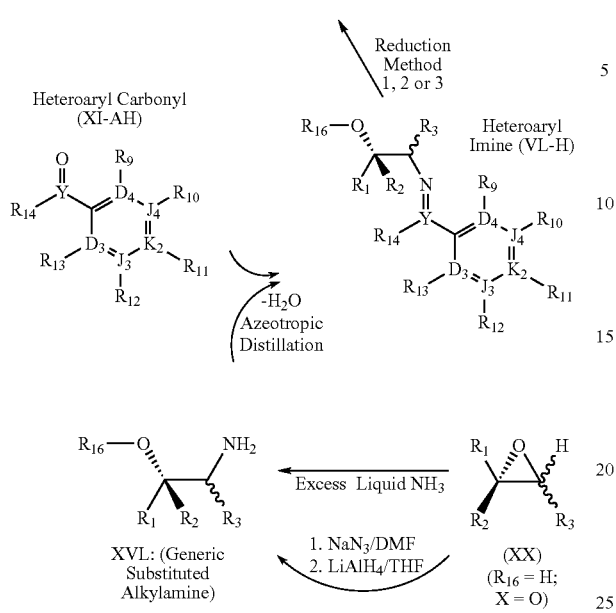
Scheme 46
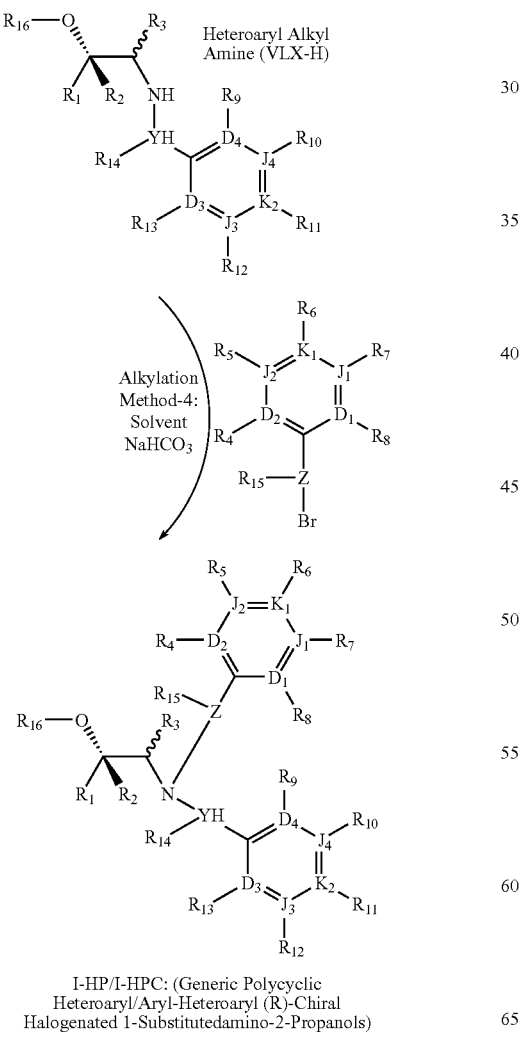
I-HP/I-HPC: (Generic Polycyclic Heteroaryl/Aryl-Heteroaryl (R)-Chiral Halogenated 1-Substitutedamino-2-Propanols)
Scheme 47
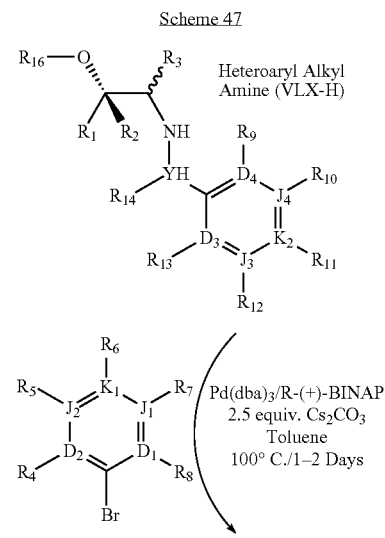
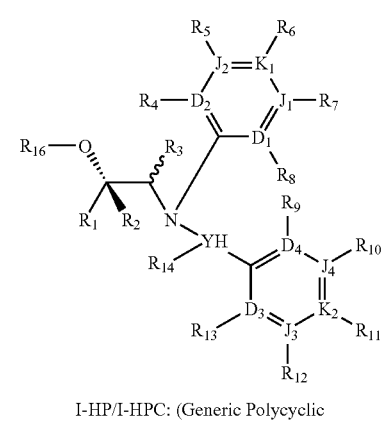
I-HP/I-HPC: (Generic Polycyclic Heteroaryl/Aryl-Heteroaryl (R)-Chiral Halogenated 1-Substitutedamino-2-Propanols)
Scheme 48
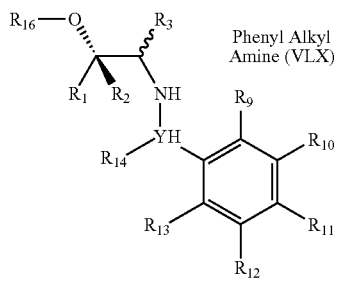

-continued

Phenyl Carbonyl (XI-A)

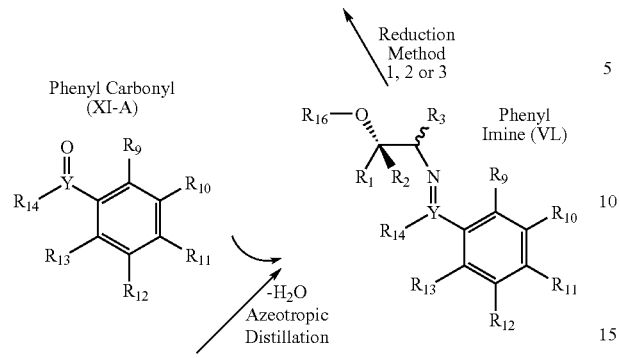

Reduction Method 1, 2 or 3

Phenyl Imine (VL)

−H$_2$O Azeotropic Distillation

XVL: (Generic Substituted Alkylamine)

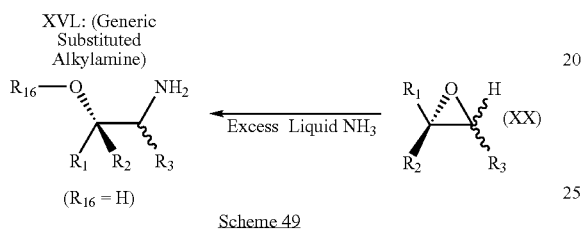

Excess Liquid NH$_3$ (R$_{16}$ = H)

Scheme 49

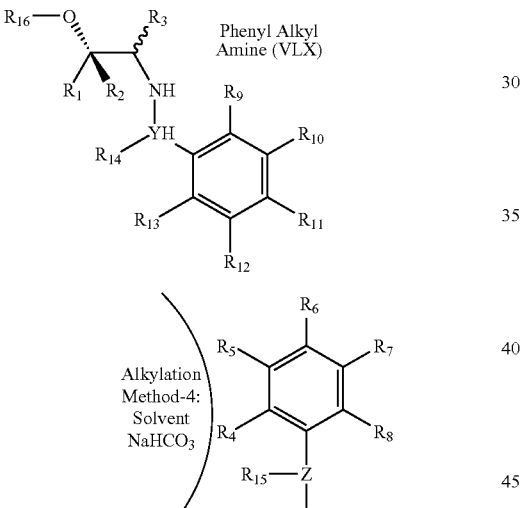

Phenyl Alkyl Amine (VLX)

Alkylation Method-4: Solvent NaHCO$_3$

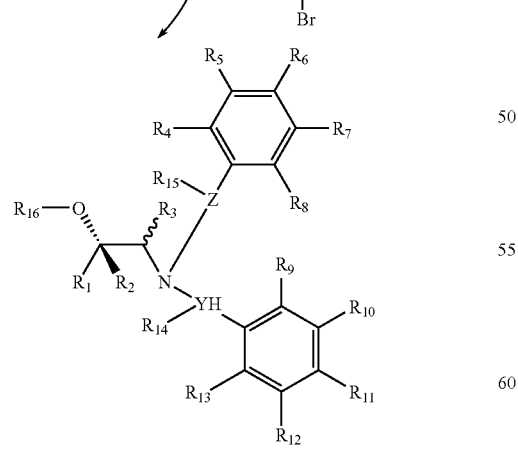

I-CP: (Polycyclic Diphenyl (R)-Chiral Halogenated 1-Substitutedamino-2-Propanols; R$_{16}$ = H)

Scheme 50

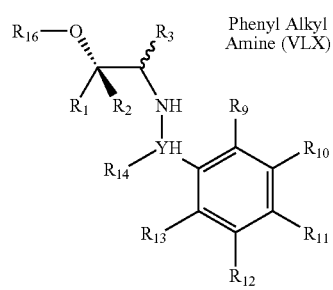

Phenyl Alkyl Amine (VLX)

Pd(dba)$_3$/R-(+)-BINAP
2.5 equiv. Cs$_2$CO$_3$
Toluene
100° C./1–2 Days

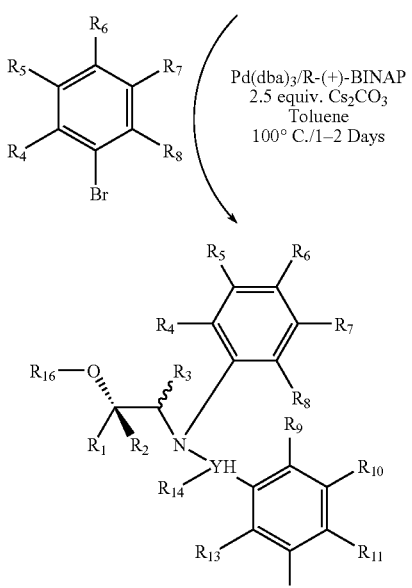

I-CP: (Polycyclic Diphenyl (R)-Chrial Halogenated 1-Substitutedamino-2-Propanols; R$_{16}$ = H)

Scheme 51

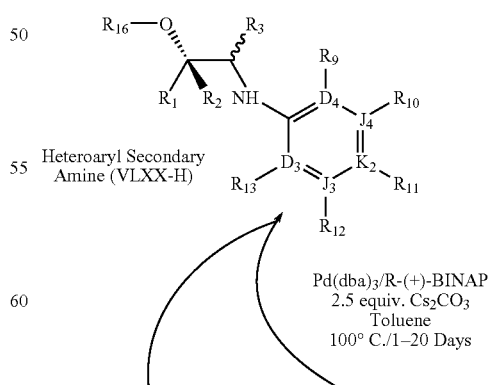

Heteroaryl Secondary Amine (VLXX-H)

Pd(dba)$_3$/R-(+)-BINAP
2.5 equiv. Cs$_2$CO$_3$
Toluene
100° C./1–20 Days

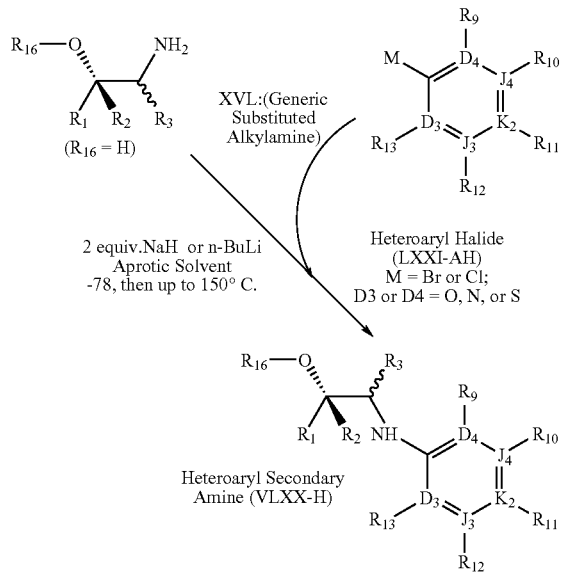
Scheme 52
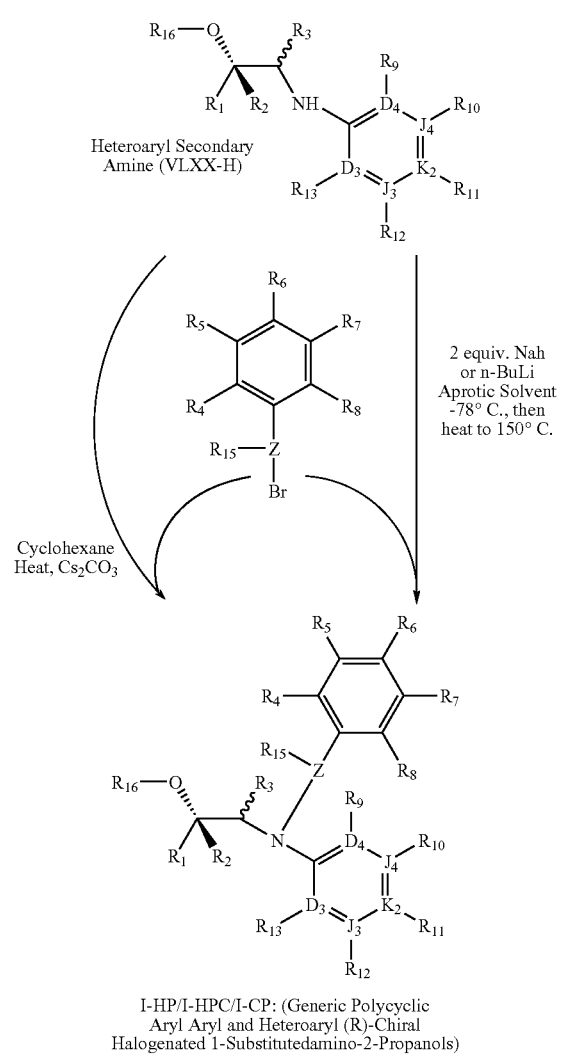
I-HP/I-HPC/I-CP: (Generic Polycyclic Aryl Aryl and Heteroaryl (R)-Chiral Halogenated 1-Substitutedamino-2-Propanols)
Scheme 53
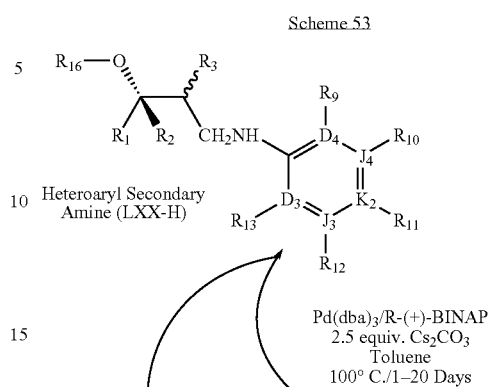
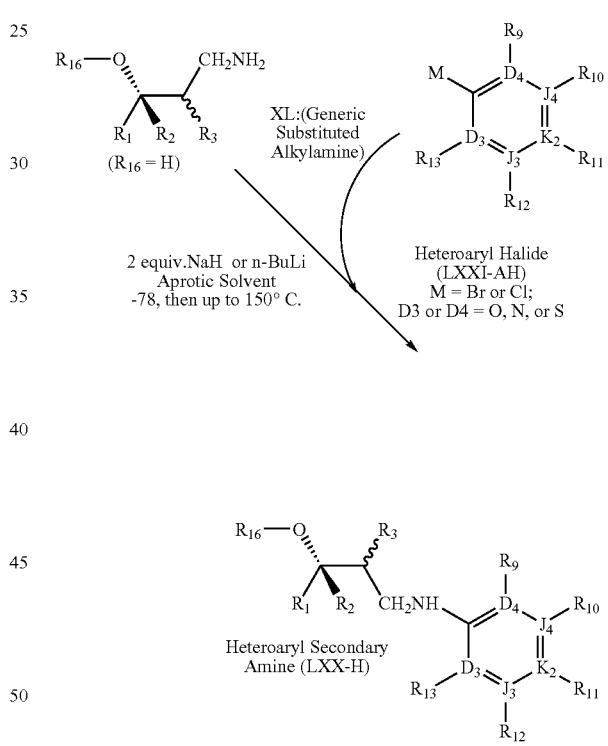
Scheme 54
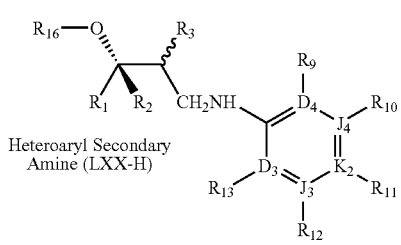
Heteroaryl Secondary Amine (LXX-H)

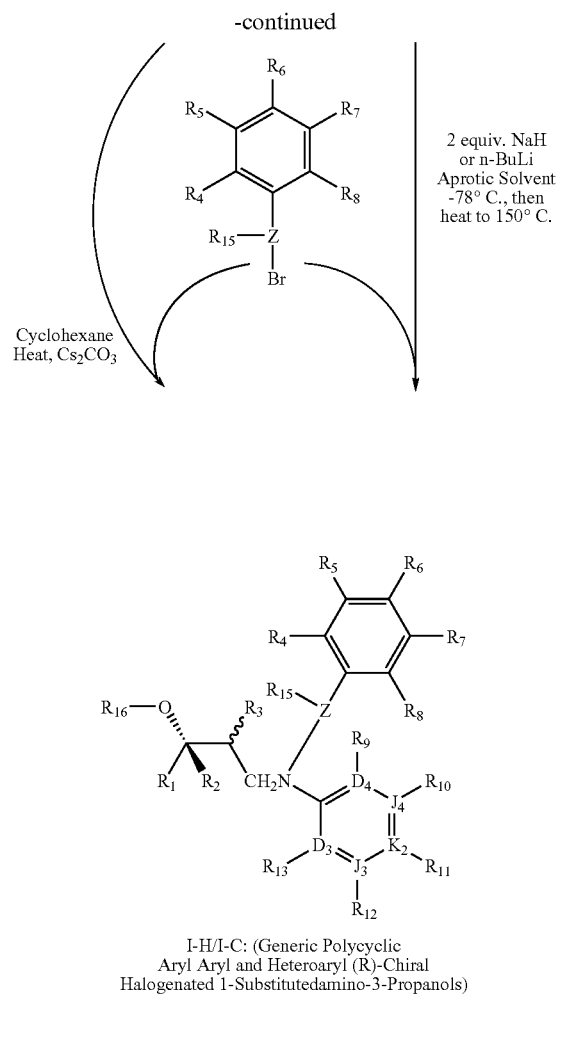

I-H/I-C: (Generic Polycyclic Aryl Aryl and Heteroaryl (R)-Chiral Halogenated 1-Substitutedamino-3-Propanols)

Scheme 55
I-CP: (Polycyclic 3-Carbomethoxyphenyl Phenyl (R)-Chiral Halogenated 1-Substitutedamino-2-Propanols; $R_{16}$ = H)

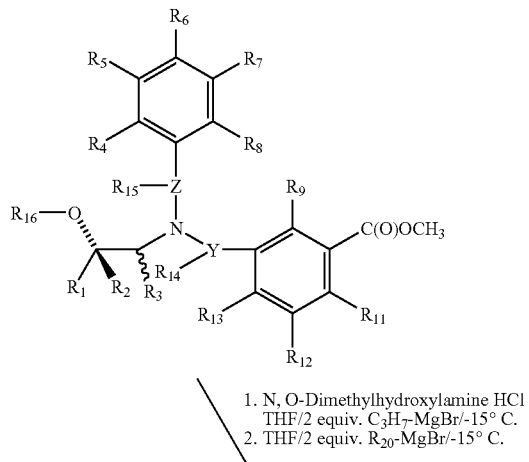

1. N,O-Dimethylhydroxylamine HCl THF/2 equiv. $C_3H_7$-MgBr/-15° C.
2. THF/2 equiv. $R_{20}$-MgBr/-15° C.

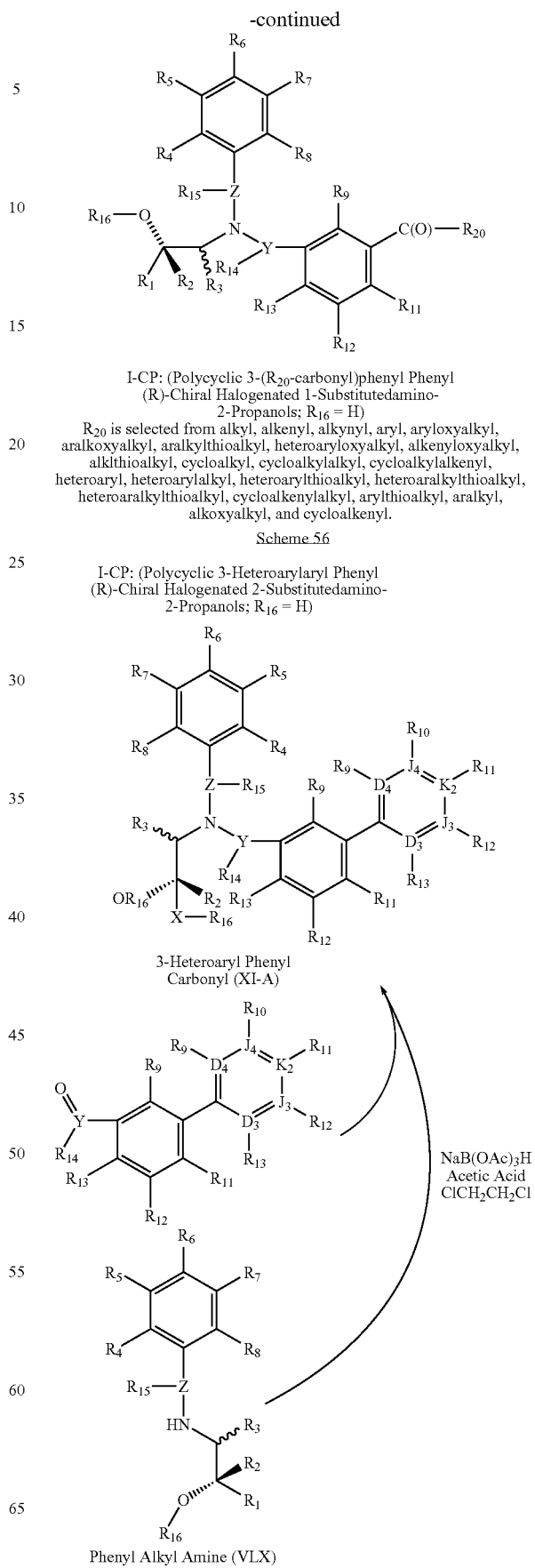

I-CP: (Polycyclic 3-($R_{20}$-carbonyl)phenyl Phenyl (R)-Chiral Halogenated 1-Substitutedamino-2-Propanols; $R_{16}$ = H)
$R_{20}$ is selected from alkyl, alkenyl, alkynyl, aryl, aryloxyalkyl, aralkoxyalkyl, aralkylthioalkyl, heteroaryloxyalkyl, alkenyloxyalkyl, alklthioalkyl, cycloalkyl, cycloalkylalkyl, cycloalkylalkenyl, heteroaryl, heteroarylalkyl, heteroarylthioalkyl, heteroaralkylthioalkyl, heteroaralkylthioalkyl, cycloalkenylalkyl, arylthioalkyl, aralkyl, alkoxyalkyl, and cycloalkenyl.

Scheme 56
I-CP: (Polycyclic 3-Heteroarylaryl Phenyl (R)-Chiral Halogenated 2-Substitutedamino-2-Propanols; $R_{16}$ = H)

3-Heteroaryl Phenyl Carbonyl (XI-A)

Phenyl Alkyl Amine (VLX)

127
-continued

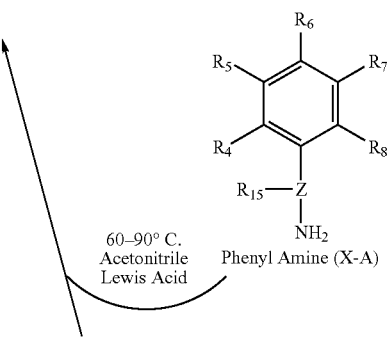

60–90° C.
Acetonitrile
Lewis Acid

Phenyl Amine (X-A)

(XX)

NOTE: HeteroarylAnalogs Can Be Prepared Using
Heteroaryl Analogs of X-A, VLX, and XI-A.

Scheme 57

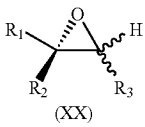

(XX)
60–90° C.
Acetonitrile
Lewis Acid

Phenyl Amines
(XXII-A)

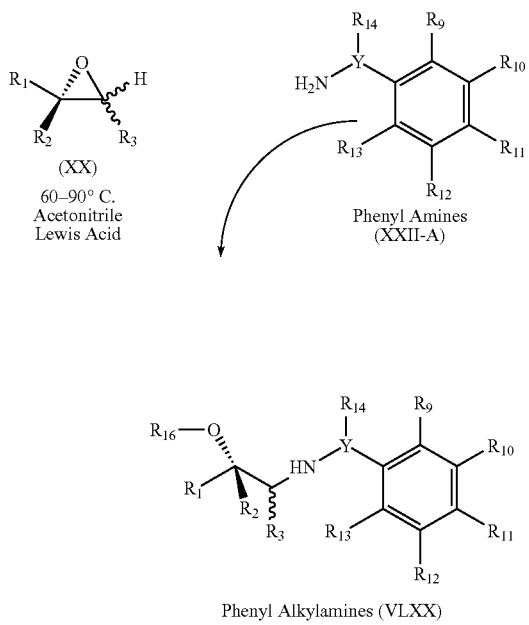

Phenyl Alkylamines (VLXX)

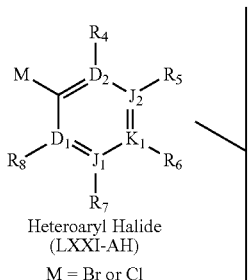

Heteroaryl Halide
(LXXI-AH)
M = Br or Cl

Pd(dba)$_3$/R-(+)-BINAP
2.5 equiv. Cs$_2$CO$_3$
Toluene
100° C./1–20 Days

128
-continued

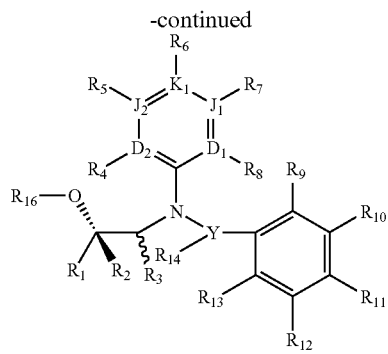

I-HPC: Polycyclic Aryl-Heteroaryl (R)-Chiral
Halogenated 1-Substitutedamino-2-Propanols
when R$_{16}$ equals H) NOTE: Aryl Analogs
(I-CP) of (I-HPC) Can Be Prepared by Starting
With Aryl Bromide Analogs of (LXXI-AH).

Scheme 58

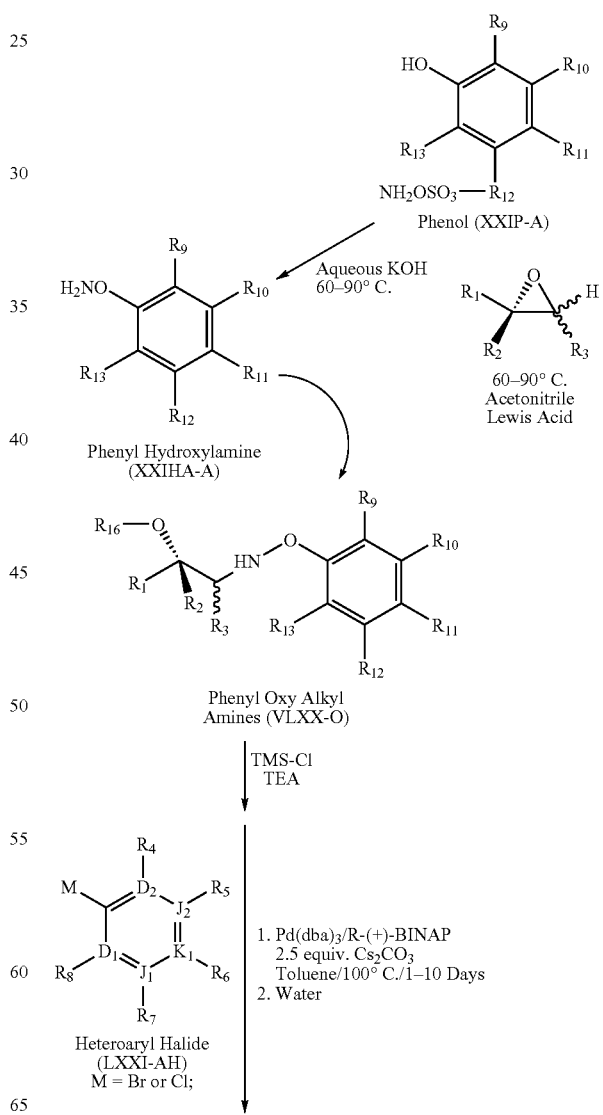

Phenol (XXIP-A)

Aqueous KOH
60–90° C.

Phenyl Hydroxylamine
(XXIHA-A)

60–90° C.
Acetonitrile
Lewis Acid

Phenyl Oxy Alkyl
Amines (VLXX-O)

TMS-Cl
TEA

Heteroaryl Halide
(LXXI-AH)
M = Br or Cl;

1. Pd(dba)$_3$/R-(+)-BINAP
   2.5 equiv. Cs$_2$CO$_3$
   Toluene/100° C./1–10 Days
2. Water -continued

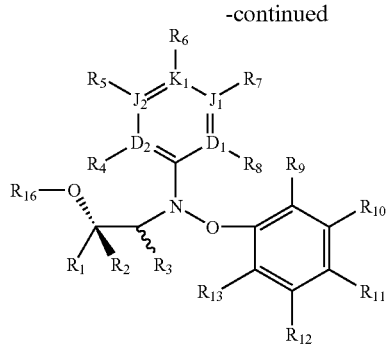

I-HPC: (Polycyclic Heteroaryl-Aryl Phenyl (R)-Chiral Halogenated 1-Substitutedamino-2-Propanols when $R_{16}$ = H and Y = O)
NOTE: Diaryl (I-CP) and Diheteroaryl (I-HP) Analogs Can Be Prepared by Using Aryl Bromide and Heteroaryl-OH, respectively.

The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the preceding schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR and mass spectrometry. These compounds also may be formed in vivo.

The following examples contain detailed descriptions of the methods of preparation of compounds of Formula V-H. These detailed descriptions fall within the scope and are presented for illustrative purposes only and are not intended as a restriction on the scope of the invention. All parts are by weight and temperatures are Degrees centigrade unless otherwise indicated.

EXAMPLE 1

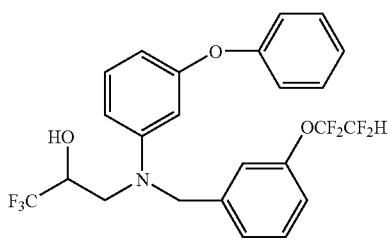

(2R,S)-3-[(3-phenoxyphenyl)[[3-(1,1,2,2-tetrafluoro-ethoxy)phenyl]-methyl]amino]-1,1,1-trifluoro-2-propanol EX-1A) To a solution of 3-(1,1,2,2-tetrafluoroethoxy) toluene (50 g, 0.24 mol) and N-bromosuccinimide (42.75 g, 0.24 mol) in 100 mL of carbon tetrachloride under nitrogen was added 2,2'-azobisisobutyronitrile (0.71 g, 0.004 mol). The resultant mixture was refluxed for 2 h, then cooled to room temperature and quenched with 300 mL of water. The organic layer was collected, washed with water and brine, dried over $MgSO_4$, and concentrated in vacuo to give 66.0 g (96%) of the desired crude 3-(1,1,2,2-tetrafluoroethoxy) bromomethylbenzene product as a yellow oil. $^1$H NMR indicates that this oil is a mixture of products: 7% dibrominated, 67% monobrominated, and 20% starting material. The crude product was used without further purification. ESMS m/z=287 [M+H]$^+$.

EX-1B) The crude product (56 g, 0.14 mol) from EX-1A in 200 mL of cyclohexane was added dropwise under nitrogen to a solution of 3-phenoxyaniline (89 g, 0.480 mol) in 500 mL of cyclohexane. The reaction mixture was refluxed overnight, then cooled to room temperature and diluted with water and diethyl ether. The layers were separated, and the aqueous layer was extracted with diethyl ether. The combined organic layers were dried over $MgSO_4$ and concentrated in vacuo to give a dark oil. The crude product was purified by column chromatography on silica gel eluting with 1:4 ethyl acetate in hexane to afford 44.96 g (83%) of the desired N-(3-phenoxyphenyl)-[[3-(1,1,2,2-tetrafluoroethoxy)phenyl]methyl]amine product as a yellow oil. ESMS m/z=392 [M+H]$^+$.

To a mixture of the amine product (15.0 g, 0.038 mol) from EX-1B and 1,1,1-tri-fluoro-2,3-epoxypropane (8.58 g, 0.077 mol, TCI) was added a suspension of ytterbium (III) trifluoromethanesulfonate (2.37 g, 0.0031 mol) in 15 mL of acetonitrile. The resulting mixture was heated at 50° C. in a sealed glass vial for 1.5 h. The reaction mixture was cooled to room temperature then diluted with water and ethyl acetate and extracted. The organic layers were combined, dried over $MgSO_4$, and concentrated in vacuo. The crude product was purified by column chromatography on silica gel eluting with 1:4 ethyl acetate in hexane to afford 12.03 g (62%) of the desired (2RS)-3-[(3-phenoxyphenyl)[[3-(1, 1,2,2-tetrafluoroethoxy) phenyl]methyl]amino]-1,1,1-trifluoro-2-propanol product as a yellow oil. Anal. calcd. for $C_{24}H_{20}F_7NO_3$: C, 57.26; H, 4.00; N, 2.78. Found: C, 56.96; H, 4.35; N, 2.69. HRMS calcd. 504.1410 [M+H]$^+$. found: 504.1431. $^1$H NMR (CDCl$_3$) δ 7.28 (m, 4H), 7.14 (t, 1H), 7.07, (m, 3H), 7.00 (s, 1H), 6.94 (d, 2H), 6.46 (dd, 1H), 6.38 (dd, 1H), 6.35 (t, 1H), 5.84 (t, 1H), 4.60 (t, 2H), 4.36 (m, 1H), 3.82 (d, 1H), 3.48 (m, 1H), 2.51 (s, 1H). $^{19}$F NMR (CDCl$_3$) δ −79.0 (s, 3F), −88.21 (d, 2F), −137.05 (dd, 2F).

EXAMPLE 2

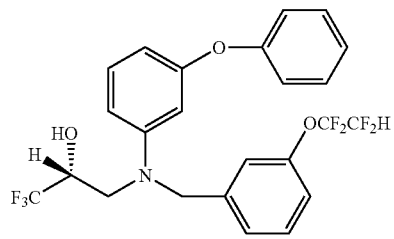

(2R)-3-[(3-phenoxyphenyl)[[3-(1,1,2,2-tetrafluoroet-hoxy)phenyl]methyl]amino]-1,1,1-trifluoro-2-propanol On a Chiralpak AD HPLC column, (2RS)-3-[(3-phenoxyphenyl)[[3-(1,1,2,2-tetrafluoroethoxy)phenyl]methyl]amino]-1,1,1-trifluoro-2-propanol (12.2 g, 0.024 mol) from EX-1 was purified by chiral chromatography to give 1.4 g (0.003 mol, 12%) of (2R)-3-[(3-phenoxyphenyl)[[3-(1,1,2,2-tetrafluoroethoxy)phenyl]methyl]amino]-1,1,1-trifluoro-2-propanol as a light yellow oil. Chiral purification was accomplished by eluting with 1:9 isopropanol in heptane at 1.0 mL/min with 250 nm UV detection. The product eluted at 8.43 min. $[\alpha]_{539}=+16.8.0$ (c 0.125 g/dL, $CH_3CN$), $[\alpha]_{365}=+84.0$ (c 0.125, $CH_3CN$). Anal. calcd. for $C_{24}H_{20}F_7NO_3$: C, 57.26; H, 4.00; N, 2.78. Found: C, 56.96; H, 4.35; N, 2.69. HRMS calcd.: 504.1410 $[M+H]^+$. found: 504.1388. $^1H$ NMR ($CDCl_3$) $\delta$ 7.28 (m, 4H), 7.14 (t, 1H), 7.07, (m, 3H), 7.00 (s, 1H), 6.94 (d, 2H), 6.46 (dd, 1H), 6.38 (dd, 1H), 6.35 (t, 1H), 5.84 (t, 1H), 4.60 (t, 2H), 4.36 (m, 1H), 3.82 (d, 1H), 3.48 (m, 1H), 2.51 (s, 1H). $^{19}F$ NMR ($CDCl_3$) $\delta$ −79.0 (s, 3F), −88.21 (d, 2F), −137.05 (dd, 2F).

EXAMPLE 3

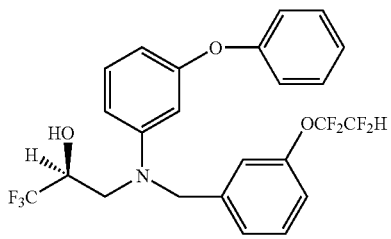

(2S)-3-[(3-phenoxyphenyl)[[3-(1,1,2,2-tetrafluoroethoxy)-phenyl]methyl]amino]-1,1,1-trifluoro-2-propanol On a Chiralpak AD HPLC column, (2RS)-3-[(3-phenoxyphenyl)[[3-(1,1,2,2-tetrafluoroethoxy)phenyl]methyl]amino]-1,1,1-trifluoro-2-propanol (12.2 g, 0.024 mol) from EX-1 was purified by chiral chromatography to give 10.5 g (0.021 mol, 86%) of (2S)-3-[(3-phenoxyphenyl)[[3-(1,1,2,2-tetrafluoroethoxy)phenyl]methyl]amino]-1,1,1-trifluoro-2-propanol as a light yellow oil. Chiral purification was accomplished by eluting with 1:9 isopropanol in heptane at 1.0 mL/min with 250 nm UV detection. The product eluted at 6.36 min. $[\alpha]_{589}=-17.0$ (c 0.265 g/dL, $CH_3CN$), $[\alpha]_{365}=-85.7$ (c 0.265, $CH_3CN$). Anal. calcd. For $C_{24}H_{20}F_7NO_3$: C, 57.26; H, 4.00; N, 2.78. Found: C, 56.96; H, 4.35; N, 2.69. HRMS calcd.: 504.1410 $[M+H]^+$. found: 504.1431. $^1H$ NMR ($CDCl_3$) $\delta$ 7.28 (m, 4H), 7.14 (t, 1H), 7.07, (m, 3H), 7.00 (s, 1H), 6.94 (d, 2H), 6.46 (dd, 1H), 6.38 (dd, 1H), 6.35 (t, 1H), 5.84 (t, 1H), 4.60 (t, 2H), 4.36 (m, 1H), 3.82 (d, 1H), 3.48 (m, 1H), 2.51 (s, 1H). $^{19}F$ NMR ($CDCl_3$) $\delta$ −79.0 (s, 3F), −88.21 (d, 2F), −137.05 (dd, 2F).

EXAMPLE 4

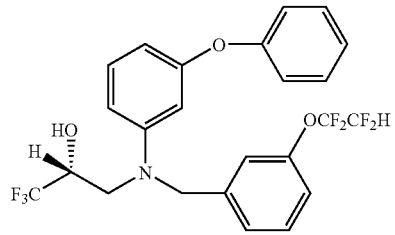

(2R)-3-[(3-phenoxyphenyl)[[3-(1,1,2,2-tetrafluoroethoxy)-phenyl]methyl]amino]-1,1,1-trifluoro-2-propanol Using a procedure adopted from H. C. Brown et al. (*J. Org. Chem.* 60, 41–46, (1995)), R-(+)-1,1,1-trifluoro-2,3-epoxypropane was prepared beginning with the transfer of (+)-B-chlorodiisopinocampheylborane ((+)-DIP-Cl, 1.2 kg, 3.74 mol) to a 5 L three neck flask containing 5 L of ether under nitrogen. Anhydrous ether (5 L) was added, and the mixture was stirred until the solids dissolved and the temperature equilibrated to 0° C. Then 3-bromotrifluoroacetone (326 mL, 3.14 mol) was added, and the reaction was stirred for 72 h while maintaining the temperature between −4 and +5° C. The reaction was followed by $^{19}F$ NMR by removing an aliquot (20 µL), quenching with anhydrous methanol (0.6 mL), and referencing to external $D_2O$. The reduction was 68% complete after 48 h. The ether was removed under vacuum (100 torr to 0.1 torr), leaving a pale, viscous oil. A 5 L 3-neck flask equipped with stirrer, dropping funnel, and short-path distillation head with chilled receiver was charged with 50% (w/w) aqueous NaOH and heated to 40° C. With external heat removed, the quenched reduction mixture was added dropwise to the aqueous NaOH, with the rate controlled to maintain the pot temperature below 65° C. The product epoxide formed immediately, distilling over with a head temperature of 32–42° C. A yellow-orange solid byproduct was broken up by stirring and some foaming was observed. When the distillation was complete, 145 g (43%) of the desired R-(+)-1,1,1-trifluoro-2,3-epoxy-propane product was obtained as a clear, colorless oil. $^1H$ NMR ($C_6D_6$) $\delta$ 2.50 (m, 1H, $CF_3CH$), 2.15 (dd, 1H, J=2.10, 5.01 Hz), 1.75 (m, 1H). $^{19}F$ NMR ($C_6D_6$) $\delta$ −75.4 (d, J=4.7 Hz). Chiral GC/MS analysis was performed on the corresponding diethylamine adduct using a gamma cyclodextrin column (Supelco gammadex120 G-cyclodextrin fused silica): 4 drops of the epoxide, R-(+)-1,1,1-trifluoro-2,3-epoxypropane, and 4 drops of diethylamine were heated briefly in a sealed vial, cooled, diluted with methyl t-butyl ether, and analyzed. Found: two gc peaks: 10.97 min and 11.11 min (ratio 1:230; 99% ee), where the R-product predominated. MS calcd. for $C_7H_{14}F_3NO$: m/z=186 $[M+H]^+$. found: 186, for both gc peaks. In contrast, the diethylamine adduct obtained with the TCI trifluoromethyl-oxirane (lot OGH01) from EX-1, gave 2 peaks with identical MS signals m/z=186, 10.96 min and 11.12 min (ratio 8.5:1; 79% ee), where the S-product predominated.

To a mixture N-(3-phenoxyphenyl)-[[3-(1,1,2,2-tetrafluoroethoxy)phenyl]methyl]-amine from EX-1B (1.48 g, 0.0038 mol) and R-(+)-1,1,1-trifluoro-2,3-epoxypropane (0.64 g, 0.0057 mol) was added a suspension of ytterbium (III) trifluoro-methanesulfonate (0.23 g, 0.0004 mol) in 1.5 mL of acetonitrile. The resulting mixture was heated at 50° C. in a sealed glass tube for 1.5 h. The reaction mixture was cooled to room temperature then diluted with water and ethyl acetate and extracted. The organic layers were combined, dried over MgSO$_4$, and concentrated in vacuo. The crude product was purified by column chromatography on silica gel eluting with 1:4 ethyl acetate in hexane to afford 1.2 g (63%) of the desired (2R)-3-[(3-phenoxyphenyl)-[[3-(1,1,2,2-tetrafluoroethoxy)phenyl]methyl]amino]-1,1,1-trifluoro-2-propanol product as a pure yellow oil (>96% ee by chiral HPLC analysis), which was identical in all respects to EX-2. Anal. calcd. for C$_{24}$H$_{20}$F$_7$NO$_3$: C, 57.26; H, 4.00; N, 2.78. found: C, 56.96; H, 4.35; N, 2.69. HRMS calcd.: 504.1410 [M+H]$^+$. found: 504.1431. $^1$H NMR (CDCl$_3$) δ 7.28 (m, 4H), 7.14 (t, 1H), 7.07, (m, 3H), 7.00 (s, 1H), 6.94 (d, 2H), 6.46 (dd, 1H), 6.38 (dd, 1H), 6.35 (t, 1H), 5.84 (t, 1H), 4.60 (t, 2H), 4.36 (m, 1H), 3.82 (d, 1H), 3.48 (m, 1H), 2.51 (s, 1H). $^{19}$F NMR (CDCl$_3$) δ −79.0 (s, 3F), −88.21 (d, 2F), −137.05 (dd, 2F).

Additional examples can be prepared by one skilled in the art using similiar methods and commercially available epoxides. For example, 3-[(3-phenoxyphenyl)[[3-(trifluoromethoxy)phenyl]methyl]amino]-1-chloro-2-propanols can be prepared from the reaction of N-(3-phenoxyphenyl)-[[3-(trifluoromethoxy)phenyl]methyl]amine with either (R)-epichlorohydrin or (S)-epichlorohydrin, as illustrated in Example Table 1.

EXAMPLE TABLE 1

3-[(3-phenoxyphenyl)[[3-(trifluoromethoxy)phenyl]methyl]amino]-1-chloro-2-propanols.

| Ex. No. | R$_{SUB1}$ | R$_{SUB2}$ | Calculated Mass [M+H]$^+$ | Observed Mass [M+H]$^+$ |
|---|---|---|---|---|
| 5 | OH | H | 452.1240 | 452.1245 |
| 6 | H | OH | 452.1240 | 452.1259 |

EXAMPLE 7

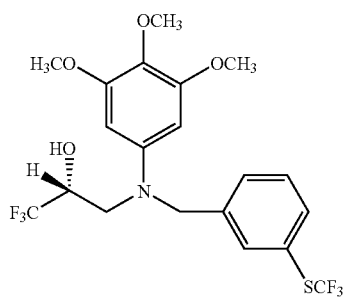

(2R)-3-[(3,4,5-trimethoxyphenyl)[[3-(trifluoromethylthio)phenyl]methyl]-amino]-1,1,1-trifluoro-2-propanol EX-45A) To a 1,2-dichloroethane (12 mL) solution of 3,4,5-trimethoxyaniline (0.80 g, 4.4 mmol) was added (3-trifluoromethylthio)benzaldehyde (0.90 g, 4.4 mmol), NaB(OAc)$_3$H (1.20 g, 5.66 mmol) and acetic acid (0.26 mL, 4.5 mmol). The cloudy solution was stirred at room temperature for 1 h. The reaction mixture was poured into water and extracted with dichloromethane. The organic layer was washed with saturated NaHCO$_3$ and brine, dried (MgSO$_4$) and evaporated to give 1.58 g (96%) of the desired N-(3,4,5-trimethoxyphenyl)[[3-trifluoromethylthiophenyl]methyl]amine product as an off-white solid. MS: m/z=373.8 [M+H]$^+$.

To an acetonitrile (3.2 mL) solution of amine (1.20 g, 3.2 mmol) from EX-45A was added R-(+)-1,1,1-trifluoro-2,3-epoxypropane (0.55 mL, 6.4 mmol) from EX-4 and Yb(OTf)$_3$ (0.40 g, 0.64 mmol). The cloudy solution was stirred in a sealed flask at 50° C. for 18 h. The cooled reaction mixture was diluted with diethyl ether and washed with water and brine. The organic layer was dried (MgSO$_4$) and evaporated to an oil. Purification by flash column chromatography on silica gel eluting with 20% ethyl acetate in hexane gave an oil which was triturated with hexanes to give a white solid. The precipitate was isolated by filtration and dried in vacuo to give 0.82 g (53%) of the desired (2R)-3-[(3,4,5-trimethoxyphenyl)[[3-(trifluoromethylthio)phenyl]methyl]-amino]-1,1,1-trifluoro-2-propanol product as a white solid, m.p. 88.9–89.1° C. (95% ee by chiral HPLC). Anal. calcd. for C$_{20}$H$_{21}$NO$_4$SF$_6$: C, 49.48; H, 4.36; N, 2.89. Found: C, 49.29; H, 4.21; N, 2.81. HRMS calcd.: 486.1174 [M+H]$^+$. found: 486.1158. $^1$H NMR (C$_6$D$_6$) δ 3.10 (d, 1H), 3.18 (dd, 1H), 3.32 (s, 6H), 3.53 (d, 1H), 3.64 (s, 3H), 4.01 (m, 1H), 4.21 (dd, 2H), 5.70 (s, 2H), 6.80 (t, 1H), 6.94 (d, 1H), 7.23 (d, 1H), 7.37 (s, 1H). [α]$_{589}$=+26.8 (c 1.099 g/dL, CHCl$_3$).

EXAMPLE 8

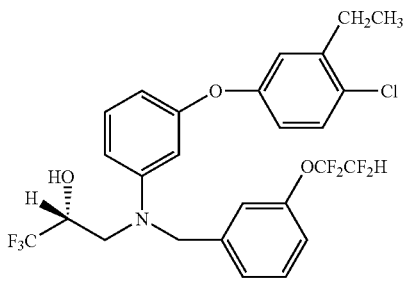

(2R)-3-[[3-(4-chloro-3-ethylphenoxy)phenyl][[3-(1,1,2,2-tetrafluoro-ethoxy)phenyl]methyl]amino]-1,1,1-trifluoro-2-propanol EX-8A) To a solution of 1,3-dinitrobenzene (16.8 g, 0.1 mol) and 4-chloro-3-ethylphenol (15.6 g, 0.1 mol) in 200 mL of dimethylsulfoxide was added cesium carbonate (65 g, 0.2 mol). The reaction mixture was heated at 100° C. under nitrogen overnight then cooled to room temperature. The reaction mixture was filtered through celite then rinsed with diethyl ether and a small amount of water. The filtrate was extracted several times with diethyl ether. The organic layers were combined, washed with water and brine, dried over MgSO$_4$, and concentrated in vacuo to give 21.8 g (78%) of the desired 3-(4-chloro-3-ethylphenoxy)-1-nitrobenzene product as a dark orange oil, which was greater than 90% pure by reverse phase HPLC analysis. HRMS calcd. for C$_{14}$H$_{12}$ClNO$_3$: 295.0849 [M+NH$_4$]$^+$. found 295.0862.

EX-8B) To a solution of 3-(4-chloro-3-ethylphenoxy)-1-nitrobenzene (10 g, 0.036 mol) from EX-8A in 400 mL of glacial acetic acid and 1 mL of water was added zinc metal (20 g, 0.305 mol) at room temperature, and the resultant mixture was stirred for 1 h. The reaction mixture was filtered through celite. The filtrate was neutralized with ammonium hydroxide and extracted with diethyl ether. The organic layer was washed with water and brine, dried over MgSO$_4$, and concentrated in vacuo to give 10 g (100%) of the desired 3-(4-chloro-3-ethylphenoxy)aniline product as a dark orange oil, which was greater than 90% pure by reverse phase HPLC analysis. HRMS calcd. for C$_{14}$H$_{14}$ClNO: 248.0842 [M+H]$^+$. found: 248.0833.

EX-8C) To a solution of 3-(4-chloro-3-ethylphenoxy) aniline (2.0 g, 8.1 mmol) from EX-8B and 3-(1,1,2,2-tetrafluoroethoxy)benzaldehyde (1.6 g, 7.3 mmol) in 30 mL of dichloroethane was added sodium triacetoxyborohydride (2.0 g, 9.7 mmol) and glacial acetic acid (0.51 mL, 8.9 mmol). The reaction mixture was stirred at room temperature for 1 h then quenched with water and extracted with diethyl ether. The organic layer was washed with water and brine, dried over MgSO$_4$, and concentrated in vacuo to give 3.5 g (95%) of the desired N-[(4-chloro-3-ethylphenoxy)phenyl]-3-[[3-(1,1,2,2-tetrafluoroethoxy)phenyl]-methyl] amine product as a brown oil, which was greater than 90% pure by reverse phase HPLC analysis. HRMS calcd. for C$_{23}$H$_{20}$ClF$_4$NO$_2$: 454.1197 [M+H]$^+$. found: 454.1220.

A solution of N-[(4-chloro-3-ethylphenoxy)phenyl]-3-[[3-(1,1,2,2-tetrafluoroethoxy)-phenyl]methyl]amine (1.8 g, 4.0 mmol) from EX-8C, R-(+)-1,1,1-trifluoro-2,3-epoxypropane (0.64 g, 0.0057 mol) from EX-4, and ytterbium (III) trifluoromethanesulfonate (0.25 g, 0.4 mmol) in 1.5 mL of acetonitrile was heated at 40° C. in a sealed glass tube for 1 h. The reaction mixture was cooled to room temperature then diluted with water and diethyl ether and extracted. The ether layer was washed with water and brine, dried over MgSO$_4$, and concentrated in vacuo The crude product was purified by column chromatography on silica gel eluting with 1:7:0.01 of ethyl acetate:hexane:ammonium hydroxide to afford 1.5 g (66%) of the desired (2R)-3-[[3-(4-chloro-3-ethylphenoxy)phenyl][[3-(1,1,2,2-tetrafluoroethoxy)phenyl]methyl]amino]-1,1,1-tri-fluoro-2-propanol product as a yellow oil (96% ee by chiral HPLC analysis). [α]$_{589}^{25}$=+36.9 (c 1.044 g %, CHCl$_3$), [α]$_{365}^{25}$=+189.7 (c 1.044 g %, CHCl$_3$). The refractive index @ 25° C. is 1.5275. Anal. calcd. for C$_{26}$H$_{23}$ClF$_7$NO$_3$: C, 55.18; H, 4.10; N, 2.48. found: C, 54.92; H, 4.05; N, 2.33. HRMS calcd.: 566.1330 [M+H]$^+$. found: 566.1323. $^1$H NMR (CDCl$_3$) δ 7.30 (t, 1H), 7.20 (d, 1H), 7.15 (t, 1H), 7.08 (t, 2H), 7.00 (s, 1H), 6.86 (d, 1H), 6.68 (dd, 1H), 6.48 (dd, 1H), 6.36 (dd, 1H), 6.34 (t, 1H), 5.81 (tt, 1H), 4.62 (s, 2H), 4.32 (m, 1H), 3.84 (dd, 1H), 3.55 (dd, 1H), 2.67 (q, 2H), 2.45 (bs, 1H), 1.17 (t, 3H). $^{19}$F NMR (CDCl$_3$) δ −79.22 (d, 3F), −88.57 (m, 2F), −137.16 (dt, 2F).

Additional examples of (2R)-3-[[3-(substituted-phenoxy)phenyl][[3-(1,1,2,2-tetrafluoroethoxy)phenyl]methyl]amino]-1,1,1-trifluoro-2-propanols and (2R)-3-[[3-(4-chloro-3-ethylphenoxy)phenyl][[3-substituted-phenyl]-methyl]amino]-1,1,1-trifluoro-2-propanols can be prepared by one skilled in the art using similar methods, as shown in Example Tables 2 and 3, respectively.

EXAMPLE TABLE 2

(2R)-3-[[3-(Substituted-phenoxy)phenyl][[3-(1,1,2,2-tetrafluoroethoxy)-phenyl]methyl]amino]-1,1,1-trifluoro-2-propanols.

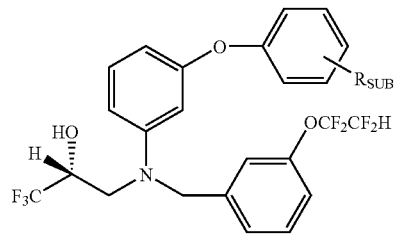

| Ex. No. | R$_{SUB}$ | Calculated Mass [M+H]$^+$ | Observed Mass [M+H]$^+$ |
|---|---|---|---|
| 9 | 4-methyl | 518.1566 | 518.1587 |
| 10 | 3-isopropyl | 546.1879 | 546.1900 |
| 11 | 3-ethyl | 532.1723 | 532.1713 |

EXAMPLE TABLE 3

(2R)-3-[[3-(4-Chloro-3-ethylphenoxy)phenyl][[3-substituted-phenyl]methyl]amino]-1,1,1-trifluoro-2-propanols.

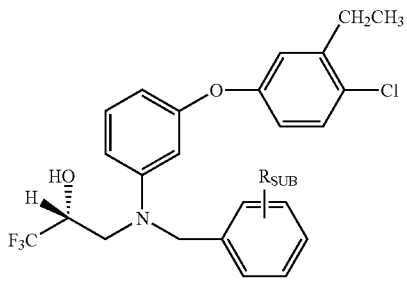

| Ex. No. | R$_{SUB}$ | Calculated Mass [M+H]$^+$ | Observed Mass [M+H]$^+$ |
|---|---|---|---|
| 12 | 3-trifluoromethoxy | 534.1271 | 534.1309 |
| 13 | 3-trifluoromethyl, 4-fluoro | 536.1228 | 536.1265 |
| 14 | 2-fluoro, 4-trifluoromethyl | 536.1228 | 536.1241 |
| 15 | 2-trifluoromethyl, 4-fluoro | 536.1228 | 536.1245 |
| 16 | 2-fluoro, 5-trifluoromethyl | 536.1228 | 536.1252 |
| 17 | 2-fluoro, 6-trifluoromethyl | 536.1228 | 536.1199 |

EXAMPLE 18

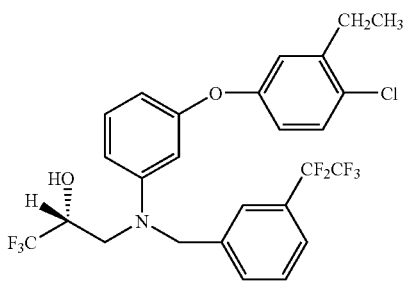

(2R)-3-[[3-(4-chloro-3-ethylphenoxy)phenyl][[3-(1,1,1,2,2-pentafluoroethyl)-phenyl]methyl]amino]-1,1,1-trifluoro-2-propanol EX-18A) Sodium pentafluoroethyl propionate (8.4 g, 50 mmol) and 3-iodotoluene (5.5 g, 25 mmol) were dissolved in anhydrous DMF (300 mL) under nitrogen. CuI (9.5 g, 50 mmol) was added, and the mixture was heated to 160° C. under nitrogen for 4 h, at which time a 15 mL fraction of a mixture of DMF and 3-pentafluoroethyl toluene was collected. The distillate was diluted with Et$_2$O and was washed with brine. The ether layer was dried over MgSO$_4$, filtered and concentrated in vacuo to give 5.25 g (55%) of the desired 3-pentafluoroethyl-toluene product as a colorless oil. $^1$H NMR (CDCl$_3$) δ 7.36 (m, 4H), 2.40 (s, 3H). $^{19}$F NMR (CDCl$_3$) δ −85.2 (s, 3F), −115.2 (s, 2F).

EX-18B) The 3-pentafluoroethyl-toluene (2.9 g, 13.8 mmol) product from EX-18A and N-bromosuccinimide (2.5 g, 13.8 mmol) were dissolved in CCl$_4$ (25 mL). AIBN (50 mg, 0.3 mmol) was added, and the mixture was refluxed for 3.5 h under N$_2$. The reaction mixture was cooled to room temperature and diluted with water. The layers were separated, and the organic layer was washed with brine, dried with anhydrous MgSO$_4$, filtered, and concentrated in vacuo to give 3.4 g (87%) of a colorless oil. The $^1$H NMR spectrum indicated that the crude product contained 3-pentafluoroethyl-benzylbromide (70%), the benzyldibromide (10%) and pentafluoroethyl toluene (20%). $^1$H NMR (CDCl$_3$) δ 7.60 (m, 2H), 7.50 (m, 2H), 4.50 (s, 2H). $^{19}$F NMR (CDCl$_3$) δ −85.1 (s, 3F), −115.4 (s, 2F).

EX-18C) A solution of 3-(4-chloro-3-ethylphenoxy) aniline (1.7 g, 6.9 mmol) was prepared in cyclohexane (13 mL). A solution of crude 3-pentafluoroethyl benzylbromide (1 g, 3.5 mmol) product from EX-18B in cyclohexane (10 mL) was added dropwise under nitrogen over 3 min. The reaction mixture was refluxed under N$_2$ for 24 h and then was cooled to room temperature. The mixture was diluted with Et$_2$O and saturated aqueous NaHCO$_3$. The layers were separated, and the aqueous layer was extracted with Et$_2$O. The organic layer was washed with brine, dried with anhydrous MgSO$_4$, filtered and concentrated in vacuo. The residue was purified by chromatography on silica gel eluting with hexanes in ethyl acetate (95:5) which gave 0.56 g (35%) of the desired N-[3-(4-chloro-3-ethylphenoxy)phenyl][[3-(pentafluoro-ethyl)phenyl]-methyl]amine product as a brown oil. $^1$H NMR (CDCl$_3$) δ 7.53 (m, 4H), 7.27 (d, 1H), 7.15 (t, 1H), 6.93 (d, 1H), 6.77 (dd, 1H), 6.41 (tt, 2H), 6.30 (t, 1H), 4.41 (s, 2H), 2.73 (q, 2H), 1.23 (t, 3H). $^{13}$C NMR (CDCl$_3$) δ 158.6, 156.1, 143.4, 141.3, 140.2, 131.3, 130.7, 130.4, 129.4, 128.1, 120.4, 117.8, 108.8. 103.9, 48.5, 27.5, 14.1. $^{19}$F NMR (CDCl$_3$) δ −85.1 (s, 3F), −115.2 (s, 2F). HRMS calcd. for C$_{23}$H$_{19}$ClF$_5$NO: 456.1154 [M+H]$^+$. found: 456.1164.

The N-[3-(4-chloro-3-ethylphenoxy)phenyl][[3-(pentafluoroethyl)phenyl]-methyl]amine (0.4 g, 0.88 mmol) product of EX-18C was dissolved in anhydrous acetonitrile (1.5 mL). R-(+)-1,1,1-trifluoro-2,3-epoxypropane (0.22 g, 1.94 mmol) and Yb(OTf)$_3$ (22 mg, 0.035 mmol) were added, and the reaction mixture was stirred under N$_2$ at 45° C. in a sealed glass tube for 15 h. The reaction mixture was then cooled to room temperature and diluted with Et$_2$O and saturated aqueous NaHCO$_3$. The layers were separated and the aqueous layer was extracted with Et$_2$O. The ether layers were combined, washed with brine, dried with anhydrous Na$_2$SO$_4$, filtered, and concentrated in vacuo. The viscous oil was adsorbed onto silica gel and purified by column chromatography eluting with hexanes in ethyl acetate (95:5) which gave 0.32 g (64%) of the desired (2R)-3-[(4-chloro-3-ethylphenoxy)phenyl[[3-(pentafluoroethyl)phenyl]methyl]amino]-1,1,1-trifluoro-2-propanol product as a viscous, colorless oil. $^1$H NMR (CDCl$_3$) δ 7.47 (m, 4H), 7.23 (m, 3H), 6.90 (d, 1H), 6.72 (dd, 1H), 6.52 (d, 1H), 6.42 (m, 2H), 4.73 (s, 2H), 4.39 (m, 1H), 3.91 (dd, 1H), 3.58 (m, 2H), 2.73 (q, 2H), 2.57 (s, 1H), 1.22 (t, 3H). $^{19}$F NMR (CDCl$_3$) δ −79.2 (s, 3F), −84.9 (s, 3F), −115.2 (s, 2F). HRMS calcd. for C$_{26}$H$_{22}$ClF$_8$NO$_2$: 568.1290 [M+H]$^+$. found: 568.1296.

EXAMPLE 19

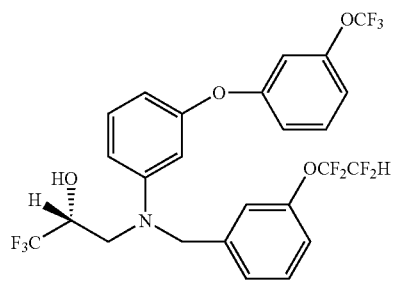

(2R)-3-[[3-(3-trifluoromethoxyphenoxy)phenyl][[3-(1,1,2,2-tetrafluoroethoxy)phenyl]methyl]amino]-1,1,1-trifluoro-2-propanol EX-19A) To a solution of 1,3-dinitrobenzene (4.5 g, 0.03 mol) and 3-trifluoromethoxy-phenol (4.8 g, 0.03 mol) in 54 mL of dimethylsulfoxide was added cesium carbonate (21.8 g, 0.07 mol). The reaction mixture was heated at 100° C. under nitrogen overnight then cooled to room temperature. The reaction mixture was diluted with water and extracted with diethyl ether several times. The organic layers were combined, washed with 1 N HCl and water, dried over MgSO$_4$, and concentrated in vacuo. The crude product was purified by column chromatography on silica gel eluting with 1:9 ethyl acetate in hexane to afford 3.0 g (38%) of the desired 3-(3-trifluoro-methoxyphenoxy)nitrobenzene product as a yellow-orange liquid which was 85% pure by reverse phase HPLC analysis. This material was carried on without further purification.

EX-19B) To a solution of 3-(3-trifluoromethoxyphenoxy) nitrobenzene (3.0 g, 0.01 mol) from EX-19A in 100 mL of glacial acetic acid was added zinc metal (6.6 g, 0.1 mol) at room temperature, and the resultant mixture was stirred for 1 h. The reaction mixture was filtered through celite. The filtrate was neutralized with ammonium hydroxide and extracted with diethyl ether then ethyl acetate. The combined organic layers were dried over MgSO$_4$ and concentrated in vacuo. The crude product was purified by column chromatography on silica gel eluting with 1:9 ethyl acetate in hexane to afford 1.2 g (44%) of the desired 3-(3-trifluoromethoxyphenoxy)aniline product as a yellow oil which was 98% pure by reverse phase HPLC analysis. Anal. calcd. for C$_{13}$H$_{10}$F$_3$NO$_2$: C, 58.00; H, 3.74; N, 5.20. found: C, 57.68; H, 3.57; N, 5.14. HRMS calcd.: 270.0742 [M+H]$^+$. found: 270.0767.

EX-19C) To a solution of 3-(3-trifluoromethoxyphenoxy) aniline (1.0 g, 3.7 mmol) from EX-19B and 3-(1,1,2,2-tetrafluoroethoxy)benzaldehyde (0.83 g, 3.7 mmol) in 18.5 mL of dichloroethane was added sodium triacetoxyborohydride (1.0 g, 4.7 mmol) and glacial acetic acid (0.25 mL, 4.3 mmol). The reaction mixture was stirred at room temperature overnight then quenched with saturated aqueous sodium bicarbonate and extracted with methylene chloride. The organic layer was dried over MgSO₄ and concentrated in vacuo to give 1.8 g (100%) of the desired [3-(3-trifluoromethoxy-phenoxy)phenyl][[3-(1,1,2,2-tetrafluoro-ethoxy)phenyl]methyl]amine product as a yellow oil, which was greater than 90% pure by reverse phase HPLC analysis. HRMS calcd. for $C_{22}H_{16}F_7NO_3$: 476.1097 [M+H]⁺. found: 476.1069. This material was carried on to the next step without further purification.

A solution of [3-(3-trifluoromethoxyphenoxy)phenyl][[3-(1,1,2,2-tetrafluoroethoxy)-phenyl]methyl]amine (1.8 g, 3.7 mmol) from EX-19C, R-(+)-1,1,1-trifluoro-2,3-epoxy-propane (0.57 g, 5.2 mmol), and ytterbium (III) trifluoromethanesulfonate (0.24 g, 0.38 mmol) in 2.0 mL of acetonitrile was heated at 40° C. in a sealed glass tube overnight. At this time reverse phase HPLC analysis indicated that the reaction was only 50% complete. Additional ytterbium (III) trifluoromethanesulfonate and R-(+)-1,1,1-trifluoro-2,3-epoxypropane (0.26 g, 2.3 mmol) were added to the reaction mixture and again heated at 40° C. in a sealed glass tube for 48 h. The reaction mixture was cooled to room temperature then diluted with water and methylene chloride and extracted. The organic layer was washed with brine, dried over MgSO₄, and concentrated in vacuo. The crude product was purified by reverse phase HPLC eluting with 30% to 90% acetonitrile in water to afford 1.25 g (23%) of the desired (2R)-3-[[[3-(3-trifluoromethoxyphenoxy) phenyl][3-(1,1,2,2-tetrafluoroethoxy)phenyl]methyl]amino]-1,1,1-trifluoro-2-propanol product as yellow-brown oil (90% ee by chiral HPLC analysis). HRMS calcd. for $C_{25}H_{19}F_{10}NO_4$: 588.1233 [M+H]⁺. found: 588.1225. ¹H NMR (CDCl₃) δ 7.35–7.18 (m, 3H), 7.12 (t, 2H), 7.01 (s, 1H), 6.93 (d, 1H), 6.85 (d, 1H), 6.82 (s, 1H), 6.56 (dd, 1H), 6.47 (dd, 1H), 6.41 (s, 1H), 5.88 (t, 1H), 4.66 (s, 2H), 4.35 (m, 1H), 3.86 (d, 1H), 3.59 (dd, 1H), 2.02 (s, 1H). ¹⁹F NMR (CDCl₃) δ–58.31 (s, 3F), –79.24 (d, 3F), –88.57 (m, 2F), –137.16 (dt, 2F).

EXAMPLE 20

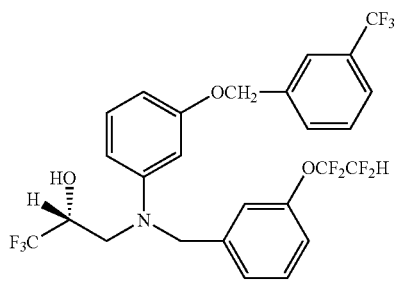

(2R)-3-[[[3-(1,1,2,2-tetrafluoroethoxy)phenyl]methyl][3-[[3-(trifluoromethyl)-phenyl]methoxy]phenyl]amino]-1,1,1-trifluoro-2-propanol EX-20A) To a solution of 3-aminophenol (4.91 g, 45.0 mmol) and 3-(1,1,2,2-tetrafluoroethoxy)benzaldehyde (10.0 g, 45.0 mmol) in 100 mL of 1,2-dichloroethane was added sodium triacetoxyborohydride (14.28 g 67.5 mmol) and glacial acetic acid (2.7 mL, 47.3 mmol). The reaction mixture was stirred at room temperature for 6 h then quenched with water and extracted with dichloromethane. The organic layer was washed with saturated aqueous sodium bicarbonate, dried over MgSO₄, and concentrated in vacuo to give 11.82 g (83%) of the desired 3-[[[3-(1,1,2,2-tetrafluoro-ethoxy)phenyl]methyl]amino]phenol product as a dark orange oil. ¹H NMR (acetone-d₆) δ 7.01–7.38 (m, 5H), 6.26–6.44 (m, 3H), 6.08 (t, 1H), 5.88 (tt, 1H), 4.34 (s, 2H).

EX-20B) A solution of 3-[[[3-(1,1,2,2-tetrafluoroethoxy)phenyl]methyl]amino]phenol (5.1 g, 16.2 mmol) from EX-20A, R-(+)-1,1,1-trifluoro-2,3-epoxypropane (1.5 mL, 17.4 mmol), and ytterbium trifluoromethanesulfonate (1.0 g, 10 mol %) in 10 mL of acetonitrile was heated at 50° C. in a sealed glass tube for 4 h. The reaction mixture was cooled to room temperature, then diluted with water and diethyl ether and extracted. The ether layer was washed with saturated aqueous sodium bicarbonate and brine, dried over MgSO₄, and concentrated in vacuo to give 5.64 g (81%) of the desired (2R)-3-[[[3-(1,1,2,2-tetrafluoroethoxy]phenyl]methyl][3,3,3-trifluoro-2-hydroxy-propyl)amino]-phenol product as a yellow oil. ¹H NMR (acetone-d₆) δ 7.41 (t, 1H), 7.23 (d, 1H), 7.16–7.20 (m, 2H), 6.97 (t, 1H), 6.42 (tt, 1H), 6.18–6.24 (m, 3H), 4.77 (s, 2H), 4.43–4.48 (m, 1H), 3.58 (dd, 1H), 3.39 (dd, 1H).

To a solution of (2R)-3-[[[3-(1,1,2,2-tetrafluoroethoxy) phenyl]methyl][3,3,3-trifluoro-2-hydroxypropyl)amino] phenol (100 mg, 0.23 mmol) from EX-20B and 3-trifluoromethylbenzyl bromide (70.0 mg, 0.27 mmol) in 2.5 mL of acetone was added cesium carbonate (100 mg, 0.31 mmol). The reaction mixture was heated at 60° C. for 18 h then cooled to room temperature. The reaction mixture was filtered through celite, and the filtrate was concentrated. The residue was purified by reverse phase HPLC eluting with 50% to 90% acetonitrile in water to afford 63.3 mg (45%) of the desired (2R)-3-[[[3-(1,1,2,2-tetrafluoroethoxy)phenyl]methyl][3-[[3-(trifluoro-methyl)phenyl]-methoxy]phenyl]amino]-1,1,1-trifluoro-2-propanol product as an orange oil. HRMS calcd. for $C_{26}H_{21}F_{10}NO_3$: 586.1440 [M+H]⁺. found: 586.1419. ¹H NMR (acetone-d₆) δ 7.61–7.82 (m, 4H), 7.41 (t, 1H), 7.25 (d, 1H), 7.10–7.21 (m, 3H), 6.34–6.67 (m, 4H), 5.73 (d, 1H), 5.19 (s, 2H), 4.82 (s, 2H), 4.34–4.48 (m, 1H), 3.99 (dd, 1H), 3.68 (dd, 1H).

Additional examples of (2R)-3-[[[3-(1,1,2,2-tetrafluoroethoxy)phenyl]-methyl]-[3-[[aryl]methoxy]phenyl]amino]-1,1,1-trifluoro-2-propanols are prepared by one skilled in the art using similar methods, as shown in. Example Table 4.

EXAMPLE TABLE 4

(2R)-3 -[[[3-(1,1,2,2-tetrafluoroethoxy)phenyl]methyl][3-[[aryl]methoxy]phenyl]amino]-1,1,1-trifluoro-2-propanols.

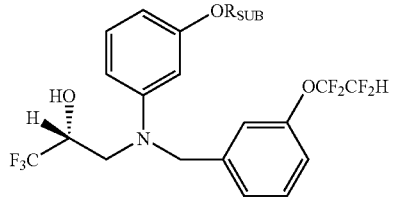

| Ex. No. | R$_{SUB}$ | Calculated Mass [M+H]⁺ | Observed Mass [M+H]⁺ |
|---|---|---|---|
| 21 | 3,5-difluorobenzyl | 554.1378 | 554.1352 |
| 22 | 3-trifluoromethoxybenzyl | 602.1389 | 602.1390 |
| 23 | 3-isopropyl | 470.1566 | 464.1601 |

EXAMPLE 24

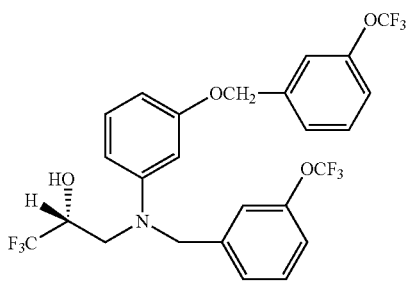

(2R)-3-[[3-[[3-(trifluoromethoxy)phenyl]methoxy]phenyl][[3-(trifluoromethoxy)-phenyl]methyl]amino]-1,1,1-trifluoro-2-propanol (2R)-3-[[3-[[3-(trifluoromethoxy)phenyl]methoxy]phenyl][[3-(trifluoro-methoxy)phenyl]methyl]amino]-1,1,1-trifluoro-2-propanol can be prepared by one skilled in the art using similar methods starting from 3-(trifluoromethoxy)-benzaldehyde. HRMS calcd. for $C_{25}H_{20}F_9NO_4$: 570.1327 [M+H]$^+$. found: 570.1325. $^1$H NMR (acetone-$d_6$) δ 7.43 (t, 1H), 7.32 (d, 1H), 7.18–7.23 (m, 2H), 7.01–7.16 (m, 3H), 6.92–7.00 (m, 1H), 6.38–6.45 (m, 3H), 5.12 (s, 2H), 4.81 (s, 2H), 4.41–4.53 (m, 1H), 3.98 (dd, 1H), 3.63 (dd, 1H).

Additional examples of (2R)-3-[[3-[[aryl]methoxy]phenyl][[3-(trifluoro-methoxy)phenyl]methyl]amino]-1,1,1-trifluoro-2-propanols can be prepared by one skilled in the art using similar methods, as shown in Example Table 5.

EXAMPLE TABLE 5

(2R)-3-[[3-[[aryl]methoxyl]phenyl][[3-(trifluoromethoxy)-phenyl]methyl]amino]-1,1,1-trifluoro-2-propanols.

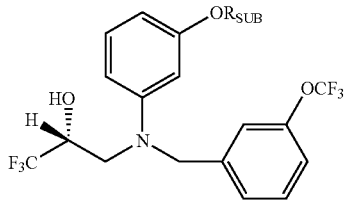

| Ex. No. | $R_{SUB}$ | Calculated Mass [M + H]$^+$ | Observed Mass [M + H]$^+$ |
|---|---|---|---|
| 25 | 4-trifluoromethoxybenzyl | 570.1327 | 570.1299 |
| 26 | 3,5-di(trifluoromethyl)benzyl | 622.1252 | 622.1252 |
| 27 | 3-trifluoromethylbenzyl | 554.1378 | 554.1369 |
| 28 | 3,5-difluorobenzyl | 522.1315 | 522.1259 |
| 29 | benzyl | 486.1504 | 486.1504 |
| 30 | isopropyl | 438.1504 | 438.1509 |
| 31 | cyclohexylmethyl | 492.1973 | 492.1973 |
| 32 | cyclopentyl | 464.1660 | 464.1641 |

EXAMPLE 33

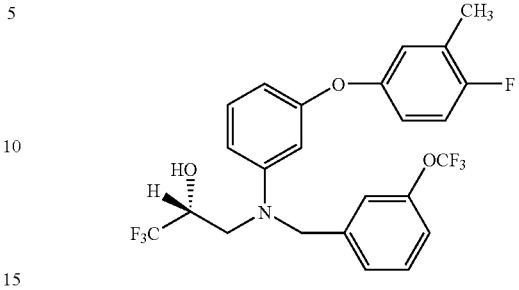

(2R)-3-[[3-(4-fluoro-3-methylphenoxy)phenyl][[3-(trifluoromethoxy)-phenyl]methyl]amino]-1,1,1-trifluoro-2-propanol EX-33A) To a solution of 3-bromoaniline (5.7 mL, 52.6 mmol) and 3-trifluoro-methoxybenzaldehyde (10.0 g, 52.6 mmol) in 135 mL of dichloroethane was added sodium triacetoxyborohydride (14.5 g, 68.4 mmol) and glacial acetic acid (3.1 mL, 54.7 mmol). The reaction was stirred at room temperature for 2 h, then quenched with water and extracted with dichloromethane. The organic layer was washed with saturated aqueous sodium bicarbonate, dried over MgSO$_4$, and concentrated in vacuo. The crude product was purified by column chromatography on silica gel eluting with 1:9 ethyl acetate in hexane to give 14.3 g (78%) of the desired of N-(3-bromophenyl)[[3-(trifluoromethoxy) phenyl]methyl]amine product as a dark brown oil. HRMS calcd. for $C_{14}H_{11}BrF_3NO$: 346.0055 [M+H]$^+$. found: 346.0052.

EX-33B) A solution of of N-(3-bromophenyl)[[3-(trifluoromethoxy)phenyl]methyl]-amine (10.0 g, 28.9 mmol) from EX-33A, R-(+)-1,1,1-trifluoro-2,3-epoxypropane (4.2 g, 37.6 mmol), and ytterbium (III) trifluoromethanesulfonate (1.79 g, 2.89 mmol) in 27 mL of acetonitrile was heated at 50° C. in a sealed glass tube overnight. The reaction mixture was cooled to room temperature and filtered through celite. The crude product was purified by column chromatography on silica gel eluting with 2:3 dichloromethane in hexane to afford 11.9 g (90%) of the desired (2R)-3-[[(3-bromophenyl)][[3-(tri-fluoromethoxy)phenyl]methyl]amino]-1,1,1-trifluoro-2-propanol product as a brown oil (98% ee by chiral HPLC analysis). HRMS calcd. for $C_{17}H_{14}BrF_6NO_2$: 458.0190 [M+H]$^+$. found: 458.0197.

A suspension of 4-fluoro-3-methylphenol (98.0 µL, 0.88 mmol) and cesium carbonate (319.5 mg, 0.98 mmol) in 1 mL of N,N-dimethylacetamide was preheated at 60° C. for 5 minutes. To this solution was added 4 mL of a stock solution containing (2R)-3-[[(3-bromophenyl)][[3-(trifluoromethoxy)phenyl]methyl]amino]-1,1,1-trifluoro-2-propanol (200 mg, 0.437 mmol) from EX-33B, 1-naphthoic acid (164 mg, 0.95 mmol), copper(I) trifluoromethansulfonate benzene complex (21.8 mg, 0.0434 mmol), 4 Å sieves (105 mg), and 4 mL of toluene. The reaction mixture was stirred at 105° C. for 3 weeks and 2 days. During that time, additional cesium carbonate and catalyst were added (a spatula tip of each) to the reaction three different times. The reaction was cooled to room temperature, filtered through celite, and the solvent was evaporated. The residue was purified by reverse phase HPLC eluting with 35% to 90% acetonitrile in water to afford 50.5 mg (23%) of the desired (2R)-3-[[3-(4-fluoro-3-methylphenoxy)phenyl][[3-(trifluoromethoxy)phenyl]methyl]amino]-1,1,1-trifluoro-2-propanol product as an orange oil. HRMS calcd. for $C_{24}H_{20}F_7NO_3$: 504.1410 [M+H]$^+$. found: 504.1389. $^1$H NMR (acetone-d$_6$) δ 7.44 (t, 1H), 7.24 (d, 1H), 7.08–7.21 (m, 3H), 6.98 (t, 1H), 6.75–6.85 (m, 1H), 6.68–6.74 (m, 1H), 6.53 (d, 1H), 6.21–6.34 (m, 2H), 4.79 (t, 2H), 4.46–4.53 (m, 1H), 3.95 (dd, 1H), 2.61–2.72 (m, 1H), 2.20 (s, 3H).

Additional examples (2R)-3-[[(aryloxy)phenyl][[3-(trifluoromethoxy)phenyl]methyl]amino]-1,1,1-trifluoro-2-propanols can be prepared by one skilled in the art using similar methods, as shown in Example Table 6.

EXAMPLE TABLE 6

(2R)-3-[[(aryloxy)phenyl][[3-(trifluoromethoxy)phenyl]-methyl]amino]-1,1,1-trilfluoro-2-propanols.

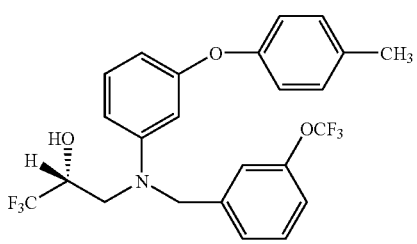

| Ex. No. | R$_{SUB}$ | Calculated Mass [M + H]$^+$ | Observed Mass [M + H]$^+$ |
|---|---|---|---|
| 34 | 3-trilfuoromethoxy | 556.1170 | 556.1180 |
| 35 | 3-isopropyl | 514.1817 | 514.1823 |
| 36 | 3,4-dimethyl | 500.1660 | 500.1654 |
| 37 | 4-chloro-3-methyl | 520.1114 | 520.1129 |
| 38 | 3-tert-butyl | 528.1973 | 528.1942 |
| 39 | 3,4-dichloro | 540.0568 | 540.0567 |
| 40 | 3,4-(CH$_2$CH$_2$CH$_2$CH$_2$)— | 526.1817 | 526.1788 |

EXAMPLE 41

(2R)-3-[[3-(4-methylphenoxy)phenyl][[3-(trifluoromethoxy)phenyl]methyl]amino]-1,1,1-trifluoro-2-propanol EX-41A) To a solution of p-cresol (5.76 g, 0.053 mol) and 1,3-dinitrobenzene (8.97 g, 0.053 mol) in 100 mL of dim ethylsulfoxide was added cesium carbonate (43.4 g, 0.133 mol). The reaction mixture was heated at 100° C. for 18 h, then cooled to room temperature, quenched with water, and extracted with diethyl ether. The organic layers were combined, washed with 0.1 N HCl and water, dried over MgSO$_4$ and concentrated in vacuo. The crude product was purified by column chromatography on silica gel eluting with 1:4 ethyl acetate in hexane to afford 8.0 g (66%) of the desired 3-(4-methylphenoxy)nitrobenzene product as a yellow oil. $^1$H NMR (CDCl$_3$) δ 7.83 (s, 1H), 7.64 (t, 1H), 7.32 (d, 1H), 7.18 (d, 1H), 7.09 (d, 2H), 6.8 (d, 2H), 2.20 (s, 1H).

EX-41B) A solution of 3-(4-methylphenoxy)nitrobenzene (8.0 g, 0.035 mol) from EX-41A in 25 mL of ethanol under nitrogen was charged with 10% palladium on carbon (0.80 g). The resulting mixture was hydrogenated for 4 h at room temperature and 45 psi. The reaction mixture was filtered through celite and concentrated in vacuo to give 6.7 g (96%) of the desired 3-(4-methylphenoxy)aniline product as a yellow oil. ESMS m/z=200 [M+H]$^-$ confirmed the desired $C_{13}H_{13}NO$ product and the complete consumption of starting material.

EX-41C) To a solution of 3-(4-methylphenoxy)aniline (2.91 g, 0.015 mol) from EX-41B, and 3-(trifluoromethoxy) benzaldehyde (3.24 g, 0.015 mol) in 50 mL dichloroethane was added sodium triacetoxyborohydride (4.02 g, 0.019 mol) and glacial acetic acid (0.99 g, 0.017 mol). The reaction mixture was stirred at room temperature for 18 h, then quenched with saturated aqueous sodium bicarbonate and extracted with dichloromethane. The organic layers were combined, dried over MgSO$_4$ and concentrated in vacuo to give 5.38 g (91%) of the desired N-[3-(4-methylphenoxy)-phenyl)]-[[3-(trifluoromethoxy)phenyl]methyl]amine product as an orange oil. ESMS m/z=374 [M+H]$^-$ confirmed the desired $C_{21}H_{18}NO_2F_3$ product and the complete consumption of starting material.

To a mixture of N-[3-(4-methylphenoxy)phenyl)]-[[3-(trifluoromethoxy)-phenyl]-methyl]amine(1.3 g, 0.0035 mol) from EX-41C and R-(+)-1,1,1-trifluoro-2,3-epoxypropane (0.59 g, 0.0053 mol) was added a suspension of ytterbium (III) trifluoromethanesulfonate (0.22 g, 0.0004 mol) in 1.3 mL of acetonitrile. The resulting mixture was heated at 50° C. in a sealed glass tube for 18 h. The reaction mixture was cooled to room temperature, then diluted with water and extracted with ethyl acetate. The crude product was purified by column chromatography on silica gel eluting with 1:4 ethyl acetate in hexane to afford 1.03 g (61%) of the desired (2R)-3-[3-(4-methyl-phenoxy)phenyl][[3-(trifluoromethoxy)phenyl]methyl]amino]-1,1,1-trifluoro-2-propanol product as a pure yellow oil. Anal. calcd. for $C_{24}H_{21}F_6NO_3$: C, 59.38; H, 4.36; N, 2.89. Found: C, 59.17; H, 4.62; N, 2.80. HRMS calcd.: 486.1504 [M+H]$^+$. found: 486.1513. $^1$H NMR (C$_6$D$_6$) δ 6.82 (m, 8H), 6.60 (dd, 1H), 6.42 (dd, 1H), 6.38 (s, 1H), 6.18 (dd, 1H), 4.00 (s, 2H), 3.63 (m, 1H), 3.40 (d, 1H), 3.02 (m, 1H), 2.00 (s, 3H), 1.40 (d, 1H). $^{19}$F NMR (C$_6$D$_6$) δ −57.98 (s, 3F), −78.50 (s, 3F).

Additional examples of (2R)-3-[3-(substituted-phenoxy) phenyl]-[[3-(trifluoro-methoxy)phenyl]methyl]amino]-1,1, 1-trifluoro-2-propanols can prepared by one skilled in the art using similar methods, as shown in Example Table 7.

EXAMPLE TABLE 7

(2R)-3-[3-(substituted-phenoxy)phenyl][[3-(trifluoromethoxy)-phenyl]methyl]amino]-1,1,1-trifluoro-2-propanols.

| Ex. No. | R<sub>SUB</sub> | Calculated Mass [M + H]<sup>+</sup> | Observed Mass [M + H]<sup>+</sup> |
|---|---|---|---|
| 42 | 4-fluoro | 490.1253 | 490.1238 |

EXAMPLE 43

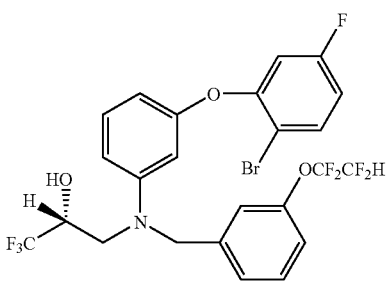

(2R)-3-[[3-(2-bromo-5-fluorophenoxy)phenyl]][3-(1,1,2,2-tetrafluoroethoxy)phenyl]methyl]amino]-1,1,1-trifluoro-2-propanol EX-43A) To a solution of 3-aminophenol (5 g, 46 mmol), 1-bromo-2,4-difluoro-benzene (10 g, 50 mmol) and $Cs_2CO_3$ (16 g, 50 mmol) in 25 mL of dimethyl-formamide was added solid $(CuOTf)_2C_6H_6$ (100 mg), and the mixture was stirred under nitrogen at 85° C. for 22 h, at which time HPLC analysis indicated that the reaction had gone to completion and formed two products. The DMF was removed under reduced pressure. The residue was diluted with ether and filtered through a celite pad. The pad was washed with ether and a small amount of water. The mixture was extracted with ether several times. The combined ether layers were washed with water and brine, then dried over $MgSO_4$. The dried organic layer was evaporated to give 10.2 g (80%) of the desired product, which consisted of a 11:1 ratio of 3-(2-bromo-5-fluoro-phenoxy)aniline and 3-(4-bromo-3-fluorophenoxy)aniline. The crude product was purified by flash column chromatography on silica gel eluting with 1:7:0.01 of ethyl acetate:hexane:ammonium hydroxide to give 8.8 g (68%) of the desired product as a yellow oil, which was a 25:1 ratio of 3-(2-bromo-5-fluorophenoxy)aniline and 3-(4-bromo-3-fluorophenoxy)aniline. HRMS calcd. for $C_{12}H_9NOFBr$: 281.9930 [M+H]<sup>+</sup>. found: 281.9950.

EX-43B) The 3-(2-bromo-5-fluorophenoxy)aniline (1.39 g, 4.95 mmol) product from EX-43A and 3-(1,1,2,2-tetrafluoroethoxy)benzaldehyde (1.0 g, 4.5 mmol) were dissolved in 15 mL of dichloroethane and acetic acid (0.30 mL, 5.4 mmol), then solid $NaBH(OAc)_3$ (1.26 g, 5.9 mmol) was added. The mixture was stirred at room temperature for 1 h, then quenched with water and extracted with ether. The ether layer was washed with water and brine, then dried over $MgSO_4$, and evaporated to give 2.1 g (97%) of crude product, which was purified by flash column chromatography on silica gel eluting with 1:7:0.01 of ethyl acetate: hexane:ammonium hydroxide to give 2.0 g (91%) of the desired 3-[3-(2-bromo-5-fluoro-phenoxy)phenyl][[3-(1,1,2,2-tetrafluoro-ethoxy)phenyl]methyl]amine product, as a light yellow oil, >90% pure by HPLC analysis. HRMS calcd. for $C_{21}H_{15}NO_2BrF_5$: 488.0285 [M+H]<sup>+</sup>. found: 488.0269.

The 3-[3-(2-bromo-5-fluorophenoxy)phenyl][[3-(1,1,2,2-tetrafluoroethoxy)-phenyl]-methyl]amine (0.5 g, 2.0 mmol) product from EX-43B and R-(+)-1,1,1-trifluoro-2,3-epoxypropane (0.17 g, 2.0 mmol) from EX-4 were dissolved in 0.5 mL of acetonitrile. Ytterbium (III) trifluoromethanesulfonate (0.06 g, 0.1 mmol) was added, and the stirred solution was warmed to 40° C. for 1 h, at which time HPLC analysis indicated that no secondary amine starting material remained. The reaction was quenched with water and extracted with ether. The ether layer was washed with water and brine, then dried over $MgSO_4$. The crude product was purified by flash column chromatography on silica gel eluting with 1:7:0.01 of ethyl acetate:hexane:ammonium hydroxide to give 0.4 g (67%) of the desired R-(+)-3-[[3-(2-bromo-5-fluorophenoxy)phenyl][[3-(1,1,2,2-tetrafluoroethoxy)-phenyl]methyl]amino]-1,1,1-trifluoro-2-propanol product as a light yellow oil (>84% ee by chiral HPLC analysis). Anal. calcd. for $C_{24}H_{18}BrF_8NO_3$: C, 48.02; H, 3.02; N, 2.33. found: C, 48.07; H, 3.14; N, 2.31. HRMS calcd.: 600.0420 [M+H]<sup>+</sup>. found: 600.0386. <sup>1</sup>H NMR ($CDCl_3$) δ 7.5 0 (dd, 1H), 7.30 (t, 1H), 7.18 (t, 1H), 7.07 (t, 2H), 6.99 (s, 1H), 6.70 (dt, 1H), 6.56 (dd, 1H), 6.52 (dd, 1H), 6.38 (dd, 1H), 6.32 (m, 1H), 5.87 (tt, 1H,), 4.65 (d, 2H), 4.33 (m, 1H), 3.85 (dd, 1H), 3.56 (dd, 1H), 2.48 (bs, 1H). NOE difference spectra confirmed that the isolated material was the indicated N-[3-(2-bromo-5-fluoro-phenoxy)phenyl]-3-aminopropanol product. <sup>19</sup>F NMR ($CDCl_3$) δ −79.24 (d, 3F), −88.57 (m, 2F), −112.04 (q, 1H), −137.16 (dt, 2F).

EXAMPLE 44

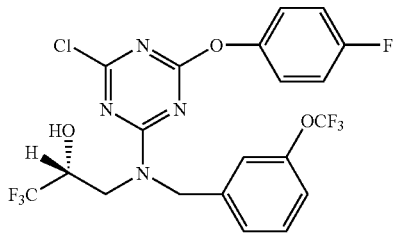

(2R)-N-[2-chloro-6-(p-fluorophenoxy)-1,3,5-triazin-4-yl]-3-[[[3-(trifluoromethoxy)phenyl]methyl] amino]-1,1,1-trifluoro-2-propanol EX-44A) 3-Trifluoromethoxybenzenemethanamine (1.15 g, 6 mmol) and R-(+)-1,1,1-trifluoro-2,3-epoxypropane (0.67 g, 6 mmol) were combined and stirred at 80° C. for 1.5 h. The mixture was cooled to room temperature, and the resulting solid was recrystallized from hot hexanes. The white solid was isolated by vacuum filtration and washed with cold hexanes to give 0.67 g (37%) of pure (2R)-3-[[[3-(trifluoro-methoxy)phenyl]methyl]amino]-1,1,1-trifluoro-2-propanol. $^1$H NMR (CDCl$_3$) δ 7.37 (t, 1H), 7.24 (d, 1H), 7.15 (m, 2H), 3.99 (m, 1H), 3.85 (d, 2H), 2.98 (dd, 1H), 2.88 (dd, 1H), 2.79 (s, 1H). $^{19}$F NMR (CDCl$_3$) δ −58.19 (s, 3F), −78.88 (s, 3F). HRMS calcd. for $C_{11}H_{11}F_6NO_2$: 304.0772 [M+H]$^+$. found: 304.0794.

EX-44B) To a solution of p-fluorophenol 1.00 g (8.92 mmol) in 30 mL of tetrahydrofuran at 0° C. was added a 60% dispersion of sodium hydride in mineral oil (0.36 g, 8.92 mmol). After 30 min, cyanuric chloride (1.64 g, 8.92 mmol) was added as a heterogeneous mixture in tetrahydrofuran at 0° C. The reaction mixture was allowed to slowly warm to room temperature. After 14 h, the mixture was cooled to 0° C., and a saturated aqueous NH$_4$Cl solution was added. The aqueous solution was extracted with diethyl ether (3×50 mL). The combined ether extracts were washed with brine, dried (MgSO$_4$), and concentrated in vacuo to afford 1.34 g (58%) of the desired 2,4-dichloro-6-(4-fluorophenoxy)-1,3,5-triazine product as an off white solid which was taken on to the next step without purification. MS m/z=260 [M+H]$^+$.

To a stirred solution of aminopropanol from EX-44A (0.100 g, 0.330 mmol) in N,N-dimethylformamide at 0° C. was added the 2,4-dichloro-(4-fluorophenoxy)-1,3,5-triazine ether product from EX-44B (0.086 g, 0.330 mmol) as a solution in N,N-di-methylformamide. The reaction mixture was allowed to slowly warm to room temperature. After 14 h, the reaction mixture was cooled to 0° C., and a saturated aq. NaHCO$_3$ solution was added. After stirring the reaction mixture for 30 min at room temperature, the aqueous layer was extracted with ether (3×30 mL). The combined ether extracts were washed with brine, dried (MgSO$_4$), and concentrated in vacuo to give a yellow oil. The crude residue was purified by column chromatography on silica gel eluting with 20% ethyl acetate in hexanes to give 0.075 g (43%) of the desired (2R)-N-[2-chloro-6-(p-fluorophenoxy)-1,3,5-triazin-4-yl]-3-[[[3-(trifluoromethoxy)-phenyl]methyl]amino]-1,1,1-trifluoro-2-propanol product as a pale yellow oil. HRMS calcd. for $C_{20}H_{14}ClF_7N_4O_3$: 526.0643 [M$^+$]. found: 526.0632. $^1$H NMR (C$_6$D$_6$) δ 6.95 (s, 1H), 6.63 (m, 14H), 4.74 (d, 1H), 4.37 (d, 1H), 4.16 (d, 1H), 4.00 (d, 2H), 3.73 (m, 1H), 3.48 (m, 2H), 3.26 (m, 2H), 3.12 (m, 2H).

Based on the preceding procedures, additional substituted (2R)-3-[(N-aryl)-[[aryl]methyl]amino]-1,1,1-trifluoro-2-propanols are prepared by one skilled in the art using similar methods, as shown in Example Table 8. Substituted (3R)-4-[N-(aryl)-[(aryl)methyl]amino]-1,1,1,2,2-pentafluoro-3-butanols are prepared by one skilled in the art using similar methods, as shown in Example Table 9. Substituted (2R)-3-[N-(aryl)[(aryl)oxy]amino]-1,1,1-trifluoro-2-propanols are prepared by one skilled in the art using similar methods, as shown in Example Table 10. Substituted (2R)-3-[N-(aryl)-[(aryl)methyl]amino]-1,1-difluoro-1-chloro-2-propanols are prepared by one skilled in the art using similar methods, as shown in Example Table 11. Substituted (2R)-3-[N,N'-(diaryl)amino]-1,1,1-trifluoro-2-propanols are prepared by one skilled in the art using similar methods, as shown in Example Table 12.

EXAMPLE TABLE 8

Subtituted (2R)-3-[N-(aryl)-[(aryl)methyl]amino]-1,1,1-trifluoro-2-propanols.

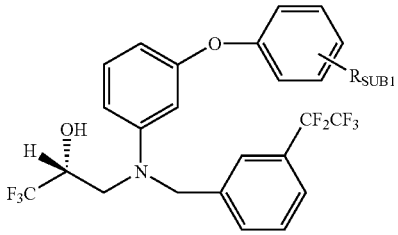

| Ex. No. | R$_{SUB1}$ |
|---|---|
| 45 | 3-isopropyl |
| 46 | 2-Cl, 3-Cl |
| 47 | 3-CF$_3$O |
| 48 | 4-F |
| 49 | 4-CH$_3$ |
| 50 | 2-F, 5-Br |
| 51 | 3-CF$_3$CF$_2$ |
| 52 | 3-CH$_3$CH$_2$ |
| 53 | 3-CH$_3$, 5-CH$_3$ |
| 54 | 3-(CH$_3$)$_3$C |
| 55 | 4-F, 3-CH$_3$ |
| 56 | 3-Cl, 4-Cl |
| 57 | 3,4-(CH$_2$)$_4$ |
| 58 | 3-HCF$_2$CF$_2$O |
| 59 | 3-CHF$_2$O |
| 60 | 3-(CH$_3$)$_2$N |
| 61 | 3-cyclopropyl |
| 62 | 3-(2-furyl) |
| 63 | 3-CF$_3$CF$_2$ |
| 64 | 4-NH$_2$ |
| 65 | 3-CH$_3$, 4-CH$_3$, 5-CH$_3$ |
| 66 | 4-CH$_3$CH$_2$CH$_2$O |
| 67 | 3-CF$_3$ |

EXAMPLE TABLE 8-continued

Substituted (2R)-3-[N-(aryl)-[(aryl)methyl]amino]-1,1,1-trifluoro-2-propanols.

| | |
|---|---|
| 68 | 2-NO$_2$ |

| Ex. No. | R$_{SUB2}$ |
|---|---|
| 69 | 3-CF$_3$O-benzyloxy |
| 70 | 3-CF$_3$-benzyloxy |
| 71 | 3-F, 5-F-benzyloxy |
| 72 | cyclohexylmethyleneoxy |
| 73 | benzyloxy |
| 74 | 3-CF$_3$, 5-CF$_3$-benzyloxy |
| 75 | 4-CF$_3$O-benzyloxy |
| 76 | 4-CH$_3$CH$_2$-benzyloxy |
| 77 | isopropoxy |
| 78 | 3-CF$_3$-benzyl |
| 79 | isopropylthio |
| 80 | cyclopentoxy |
| 81 | 3-Cl-5-pyridinyloxy |
| 82 | 3-CF$_3$S-benzyloxy |
| 83 | 3-CH$_3$, 4-CH$_3$-benzyloxy |
| 84 | 2-F, 3-CF$_3$-benzyloxy |
| 85 | 3-F, 5-CF$_3$-benzyloxy |
| 86 | 4-(CH$_3$)$_2$CH-benzyloxy |
| 87 | 1-phenylethoxy |
| 88 | 4-F, 3-CH$_3$-benzoyl |
| 89 | 3-CF$_3$-phenyl |
| 90 | 4-CH$_3$O-phenylamino |
| 91 | cyclopropoxy |
| 92 | 4-NO$_2$-phenylthio |

| Ex. No. | R$_{SUB1}$ |
|---|---|
| 93 | 3-isopropyl |
| 94 | 2-Cl, 3-Cl |
| 95 | 3-CF$_3$O |
| 96 | 4-F |
| 97 | 4-CH$_3$ |
| 98 | 2-F, 5-Br |
| 99 | 4-Cl, 3-CH$_3$CH$_2$ |
| 100 | 3-CH$_3$CH$_2$ |
| 101 | 3-CH$_3$, 5-CH$_3$ |
| 102 | 3-(CH$_3$)$_3$C |
| 103 | 4-F, 3-CH$_3$ |
| 104 | 3-Cl, 4-Cl |
| 105 | 3,4-(CH$_2$)$_4$ |
| 106 | 3-HCF$_2$CF$_2$O |
| 107 | 3-CHF$_2$O |
| 108 | 3-(CH$_3$)$_2$N |
| 109 | 3-cyclopropyl |
| 110 | 3-(2-furyl) |
| 111 | 3-CF$_3$CF$_2$ |
| 112 | 4-NH$_2$ |
| 113 | 3-CH$_3$, 4-CH$_3$, 5-CH$_3$ |

EXAMPLE TABLE 8-continued

Substituted (2R)-3-[N-(aryl)-[(aryl)methyl]amino]-1,1,1-trifluoro-2-propanols.

| | |
|---|---|
| 114 | 4-CH$_3$CH$_2$CH$_2$O |
| 115 | 3-CF$_3$ |
| 116 | 2-NO$_2$ |

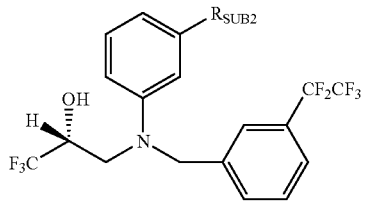

| Ex. No. | R$_{SUB2}$ |
|---|---|
| 117 | 3-CF$_3$O-benzyloxy |
| 118 | 3-CF$_3$-benzyloxy |
| 119 | 3-F, 5-F-benzyloxy |
| 120 | cyclohexylmethyleneoxy |
| 121 | benzyloxy |
| 122 | 3-CF$_3$, 5-CF$_3$-benzyloxy |
| 123 | 4-CF$_3$O-benzyloxy |
| 124 | 4-CH$_3$CH$_2$-benzyloxy |
| 125 | isopropoxy |
| 126 | 3-CF$_3$-benzyl |
| 127 | isopropylthio |
| 128 | cyclopentoxy |
| 129 | 3-Cl-5-pyridinyloxy |
| 130 | 3-CF$_3$S-benzyloxy |
| 131 | 3-CH$_3$, 4-CH$_3$-benzyloxy |
| 132 | 2-F, 3-CF$_3$-benzyloxy |
| 133 | 3-F, 5-CF$_3$-benzyloxy |
| 134 | 4-(CH$_3$)$_2$CH-benzyloxy |
| 135 | 1-phenylethoxy |
| 136 | 4-F, 3-CH$_3$-benzoyl |
| 137 | 3-CF$_3$-phenyl |
| 138 | 4-CH$_3$O-phenylamino |
| 139 | cyclopropoxy |
| 140 | 4-NO$_2$-phenylthio |

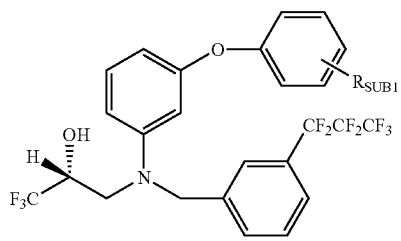

| Ex. No. | R$_{SUB1}$ |
|---|---|
| 141 | 3-isopropyl |
| 142 | 2-Cl, 3-Cl |
| 143 | 3-CF$_3$O |
| 144 | 4-F |
| 145 | 4-CH$_3$ |
| 146 | 2-F, 5-Br |
| 147 | 4-Cl, 3-CH$_3$CH$_2$ |
| 148 | 3-CH$_3$CH$_2$ |
| 149 | 3-CH$_3$, 5-CH$_3$ |
| 150 | 3-(CH$_3$)$_3$C |
| 151 | 4-F, 3-CH$_3$ |
| 152 | 3-Cl, 4-Cl |
| 153 | 3,4-(CH$_2$)$_4$ |
| 154 | 3-HCF$_2$CF$_2$O |
| 155 | 3-CHF$_2$O |
| 156 | 3-(CH$_3$)$_2$N |
| 157 | 3-cyclopropyl |
| 158 | 3-(2-furyl) |
| 159 | 3-CF$_3$CF$_2$ |

EXAMPLE TABLE 8-continued

Substituted (2R)-3-[N-(aryl)-[(aryl)methyl]amino]-1,1,1-trifluoro-2-propanols.

| | |
|---|---|
| 160 | 4-NH$_2$ |
| 161 | 3-CH$_3$, 4-CH$_3$, 5-CH$_3$ |
| 162 | 4-CH$_3$CH$_2$CH$_2$O |
| 163 | 3-CF$_3$ |
| 164 | 2-NO$_2$ |

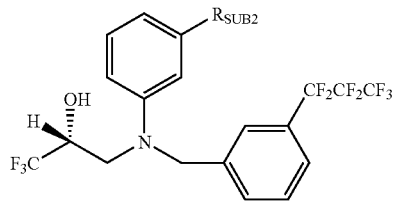

| Ex. No. | R$_{SUB2}$ |
|---|---|
| 165 | 3-CF$_3$O-benzyloxy |
| 166 | 3-CF$_3$-benzyloxy |
| 167 | 3-F, 5-F-benzyloxy |
| 168 | cyclohexylmethyleneoxy |
| 169 | benzyloxy |
| 170 | 3-CF$_3$, 5-CF$_3$-benzyloxy |
| 171 | 4-CF$_3$O-benzyloxy |
| 172 | 4-CH$_3$CH$_2$-benzyloxy |
| 173 | isopropoxy |
| 174 | 3-CF$_3$-benzyl |
| 175 | isopropylthio |
| 176 | cyclopentoxy |
| 177 | 3-Cl-5-pyridinyloxy |
| 178 | 3-CF$_3$S-benzyloxy |
| 179 | 3-CH$_3$, 4-CH$_3$-benzyloxy |
| 180 | 2-F, 3-CF$_3$-benzyloxy |
| 181 | 3-F, 5-CF$_3$-benzyloxy |
| 182 | 4-(CH$_3$)$_2$CH-benzyloxy |
| 183 | 1-phenylethoxy |
| 184 | 4-F, 3-CH$_3$-benzoyl |
| 185 | 3-CF$_3$-phenyl |
| 186 | 4-CH$_3$O-phenylamino |
| 187 | cyclopropoxy |
| 188 | 4-NO$_2$-phenylthio |

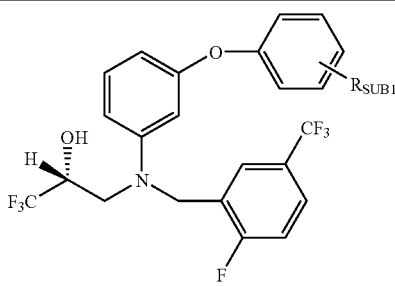

| Ex. No. | R$_{SUB1}$ |
|---|---|
| 189 | 3-isopropyl |
| 190 | 2-Cl, 3-Cl |
| 191 | 3-CF$_3$O |
| 192 | 4-F |
| 193 | 4-CH$_3$ |
| 194 | 2-F, 5-Br |
| 195 | 4-Cl, 3-CH$_3$ |
| 196 | 3-CH$_3$CH$_2$ |
| 197 | 3-CH$_3$, 5-CH$_3$ |
| 198 | 3-(CH$_3$)$_3$C |
| 199 | 4-F, 3-CH$_3$ |
| 200 | 3-Cl, 4-Cl |
| 201 | 3,4-(CH$_2$)$_4$ |
| 202 | 3-HCF$_2$CF$_2$O |
| 203 | 3-CHF$_2$O |

EXAMPLE TABLE 8-continued

Substituted (2R)-3-[N-(aryl)-[(aryl)methyl]amino]-1,1,1-trifluoro-2-propanols.

| | |
|---|---|
| 204 | 3-$(CH_3)_2$N |
| 205 | 3-cyclopropyl |
| 206 | 3-(2-furyl) |
| 207 | 3-$CF_3CF_2$ |
| 208 | 4-$NH_2$ |
| 209 | 3-$CH_3$, 4-$CH_3$, 5-$CH_3$ |
| 210 | 4-$CH_3CH_2CH_2$O |
| 211 | 3-$CF_3$ |
| 212 | 2-$NO_2$ |

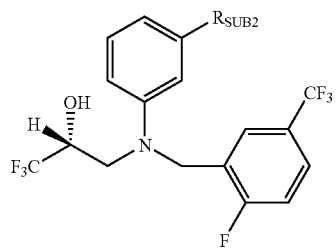

| Ex. No. | $R_{SUB2}$ |
|---|---|
| 213 | 3-$CF_3$O-benzyloxy |
| 214 | 3-$CF_3$-benzyloxy |
| 215 | 3-F, 5-F-benzyloxy |
| 216 | cyclohexylmethyleneoxy |
| 217 | benzyloxy |
| 218 | 3-$CF_3$, 5-$CF_3$-benzyloxy |
| 219 | 4-$CF_3$O-benzyloxy |
| 220 | 4-$CH_3CH_2$-benzyloxy |
| 221 | isopropoxy |
| 222 | 3-$CF_3$-benzyl |
| 223 | isopropylthio |
| 224 | cyclopentoxy |
| 225 | 3-Cl-5-pyridinyloxy |
| 226 | 3-$CF_3$S-benzyloxy |
| 227 | 3-$CH_3$, 4-$CH_3$-benzyloxy |
| 228 | 2-F, 3-$CF_3$-benzyloxy |
| 229 | 3-F, 5-$CF_3$-benzyloxy |
| 230 | 4-$(CH_3)_2$CH-benzyloxy |
| 231 | 1-phenylethoxy |
| 232 | 4-F, 3-$CH_3$-benzoyl |
| 233 | 3-$CF_3$-phenyl |
| 234 | 4-$CH_3$O-phenylamino |
| 235 | cyclopropoxy |
| 236 | 4-$NO_2$-phenylthio |

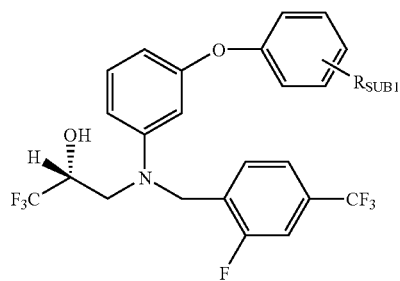

| Ex. No. | $R_{SUB1}$ |
|---|---|
| 237 | 3-isopropyl |
| 238 | 2-Cl, 3-Cl |
| 239 | 3-$CF_3$O |
| 240 | 4-F |
| 241 | 4-$CH_3$ |
| 242 | 2-F, 5-Br |
| 243 | 4-Cl, 3-$CH_3$ |
| 244 | 3-$CH_3CH_2$ |
| 245 | 3-$CH_3$, 5-$CH_3$ |

EXAMPLE TABLE 8-continued

Substituted (2R)-3-[N-(aryl)-[(aryl)methyl]amino]-1,1,1-trifluoro-2-propanols.

| | |
|---|---|
| 246 | 3-$(CH_3)_3$C |
| 247 | 4-F, 3-$CH_3$ |
| 248 | 3-Cl, 4-Cl |
| 249 | 3,4-$(CH_2)_4$ |
| 250 | 3-$HCF_2CF_2$O |
| 251 | 3-$CHF_2$O |
| 252 | 3-$(CH_3)_2$N |
| 253 | 3-cyclopropyl |
| 254 | 3-(2-furyl) |
| 255 | 3-$CF_3CF_2$ |
| 256 | 4-$NH_2$ |
| 257 | 3-$CH_3$, 4-$CH_3$, 5-$CH_3$ |
| 258 | 4-$CH_3CH_2CH_2$O |
| 259 | 3-$CF_3$ |
| 260 | 2-$NO_2$ |

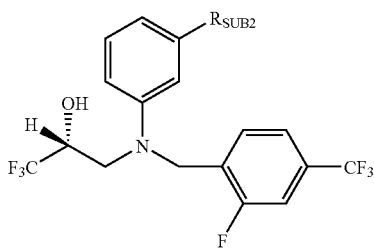

| Ex. No. | $R_{SUB2}$ |
|---|---|
| 261 | 3-$CF_3$O-benzyloxy |
| 262 | 3-$CF_3$-benzyloxy |
| 263 | 3-F, 5-F-benzyloxy |
| 264 | cyclohexylmethyleneoxy |
| 265 | benzyloxy |
| 266 | 3-$CF_3$, 5-$CF_3$-benzyloxy |
| 267 | 4-$CF_3$O-benzyloxy |
| 268 | 4-$CH_3CH_2$-benzyloxy |
| 269 | isopropoxy |
| 270 | 3-$CF_3$-benzyl |
| 271 | isopropylthio |
| 272 | cyclopentoxy |
| 273 | 3-Cl-5-pyridinyloxy |
| 274 | 3-$CF_3$S-benzyloxy |
| 275 | 3-$CH_3$, 4-$CH_3$-benzyloxy |
| 276 | 2-F, 3-$CF_3$-benzyloxy |
| 277 | 3-F, 5-$CF_3$-benzyloxy |
| 278 | 4-$(CH_3)_2$CH-benzyloxy |
| 279 | 1-phenylethoxy |
| 280 | 4-F, 3-$CH_3$-benzoyl |
| 281 | 3-$CF_3$-phenyl |
| 282 | 4-$CH_3$O-phenylamino |
| 283 | cyclopropoxy |
| 284 | 4-$NO_2$-phenylthio |

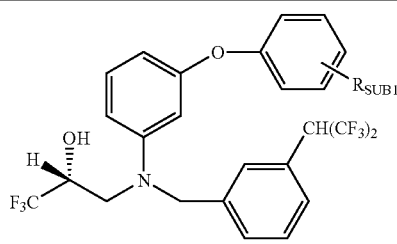

| Ex. No. | $R_{SUB1}$ |
|---|---|
| 285 | 3-isopropyl |
| 286 | 2-Cl, 3-Cl |
| 287 | 3-$CF_3$O |
| 288 | 4-F |
| 289 | 4-$CH_3$ |

EXAMPLE TABLE 8-continued

Substituted (2R)-3-[N-(aryl)-[(aryl)methyl]amino]-1,1,1-trifluoro-2-propanols.

| | |
|---|---|
| 290 | 2-F, 5-Br |
| 291 | 4-Cl, 3-CH$_3$CH$_2$ |
| 292 | 3-CH$_3$CH$_2$ |
| 293 | 3-CH$_3$, 5-CH$_3$ |
| 294 | 3-(CH$_3$)$_3$C |
| 295 | 4-F, 3-CH$_3$ |
| 296 | 3-Cl, 4-Cl |
| 297 | 3,4-(CH$_2$)$_4$ |
| 298 | 3-HCF$_2$CF$_2$O |
| 299 | 3-CHF$_2$O |
| 300 | 3-(CH$_3$)$_2$N |
| 301 | 3-cyclopropyl |
| 302 | 3-(2-furyl) |
| 303 | 3-CF$_3$CF$_2$ |
| 304 | 4-NH$_2$ |
| 305 | 3-CH$_3$, 4-CH$_3$, 5-CH$_3$ |
| 306 | 4-CH$_3$CH$_2$CH$_2$O |
| 307 | 3-CF$_3$ |
| 308 | 2-NO$_2$ |

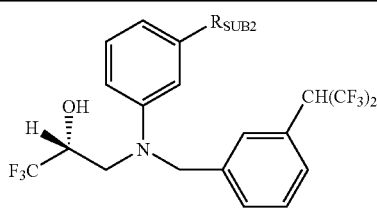

| Ex. No. | R$_{SUB2}$ |
|---|---|
| 309 | 3-CF$_3$O-benzyloxy |
| 310 | 3-CF$_3$-benzyloxy |
| 311 | 3-F, 5-F-benzyloxy |
| 312 | cyclohexylmethyleneoxy |
| 313 | benzyloxy |
| 314 | 3-CF$_3$, 5-CF$_3$-benzyloxy |
| 315 | 4-CF$_3$O-benzyloxy |
| 316 | 4-CH$_3$CH$_2$-benzyloxy |
| 317 | isopropoxy |
| 318 | 3-CF$_3$-benzyl |
| 319 | isopropylthio |
| 320 | cyclopentoxy |
| 321 | 3-Cl-5-pyridinyloxy |
| 322 | 3-CF$_3$S-benzyloxy |
| 323 | 3-CH$_3$, 4-CH$_3$-benzyloxy |
| 324 | 2-F, 3-CF$_3$-benzyloxy |
| 325 | 3-F, 5-CF$_3$-benzyloxy |
| 326 | 4-(CH$_3$)$_2$CH-benzyloxy |
| 327 | 1-phenylethoxy |
| 328 | 4-F, 3-CH$_3$-benzoyl |
| 329 | 3-CF$_3$-phenyl |
| 330 | 4-CH$_3$O-phenylamino |
| 331 | cyclopropoxy |
| 332 | 4-NO$_2$-phenylthio |

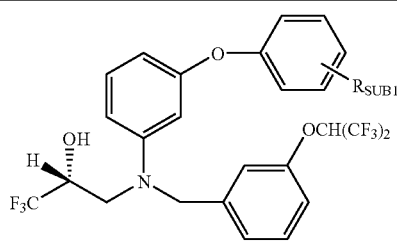

| Ex. No. | R$_{SUB1}$ |
|---|---|
| 333 | 3-isopropyl |
| 334 | 2-Cl, 3-Cl |
| 335 | 3-CF$_3$O |

EXAMPLE TABLE 8-continued

Substituted (2R)-3-[N-(aryl)-[(aryl)methyl]amino]-1,1,1-trifluoro-2-propanols.

| | |
|---|---|
| 336 | 4-F |
| 337 | 4-CH$_3$ |
| 338 | 2-F, 5-Br |
| 339 | 4-Cl, 3-CH$_3$CH$_2$ |
| 340 | 3-CH$_3$CH$_2$ |
| 341 | 3-CH$_3$, 5-CH$_3$ |
| 342 | 3-(CH$_3$)$_3$C |
| 343 | 4-F, 3-CH$_3$ |
| 344 | 3-Cl, 4-Cl |
| 345 | 3,4-(CH$_2$)$_4$ |
| 346 | 3-HCF$_2$CF$_2$O |
| 347 | 3-CHF$_2$O |
| 348 | 3-(CH$_3$)$_2$N |
| 349 | 3-cyclopropyl |
| 350 | 3-(2-furyl) |
| 351 | 3-CF$_3$CF$_2$ |
| 352 | 4-NH$_2$ |
| 353 | 3-CH$_3$, 4-CH$_3$, 5-CH$_3$ |
| 354 | 4-CH$_3$CH$_2$CH$_2$O |
| 355 | 3-CF$_3$ |
| 356 | 2-NO$_2$ |

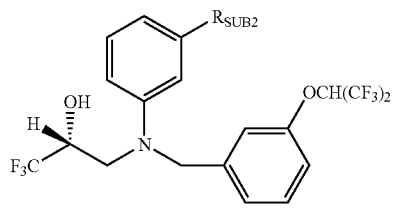

| Ex. No. | R$_{SUB2}$ |
|---|---|
| 357 | 3-CF$_3$O-benzyloxy |
| 358 | 3-CF$_3$-benzyloxy |
| 359 | 3-F, 5-F-benzyloxy |
| 360 | cyclohexylmethyleneoxy |
| 361 | benzyloxy |
| 362 | 3-CF$_3$, 5-CF$_3$-benzyloxy |
| 363 | 4-CF$_3$O-benzyloxy |
| 364 | 4-CH$_3$CH$_2$-benzyloxy |
| 365 | isopropoxy |
| 366 | 3-CF$_3$-benzyl |
| 367 | isopropylthio |
| 368 | cyclopentoxy |
| 369 | 3-Cl-5-pyridinyloxy |
| 370 | 3-CF$_3$S-benzyloxy |
| 371 | 3-CH$_3$, 4-CH$_3$-benzyloxy |
| 372 | 2-F, 3-CF$_3$-benzyloxy |
| 373 | 3-F, 5-CF$_3$-benzyloxy |
| 374 | 4-(CH$_3$)$_2$CH-benzyloxy |
| 375 | 1-phenylethoxy |
| 376 | 4-F, 3-CH$_3$-benzoyl |
| 377 | 3-CF$_3$-phenyl |
| 378 | 4-CH$_3$O-phenylamino |
| 379 | cyclopropoxy |
| 380 | 4-NO$_2$-phenylthio |

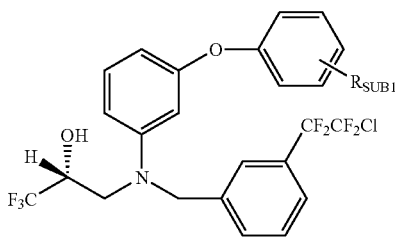

| Ex. No. | R$_{SUB1}$ |
|---|---|
| 381 | 3-isopropyl |

EXAMPLE TABLE 8-continued

Substituted (2R)-3-[N-(aryl)-[(aryl)methyl]amino]-1,1,1-trifluoro-2-propanols.

| | |
|---|---|
| 382 | 2-Cl, 3-Cl |
| 383 | 3-CF$_3$O |
| 384 | 4-F |
| 385 | 4-CH$_3$ |
| 386 | 2-F, 5-Br |
| 387 | 4-Cl, 3-CH$_3$CH$_2$ |
| 388 | 3-CH$_3$CH$_2$ |
| 389 | 3-CH$_3$, 5-CH$_3$ |
| 390 | 3-(CH$_3$)$_3$C |
| 391 | 4-F, 3-CH$_3$ |
| 392 | 3-Cl, 4-Cl |
| 393 | 3,4-(CH$_2$)$_4$ |
| 394 | 3-HCF$_2$CF$_2$O |
| 395 | 3-CHF$_2$O |
| 396 | 3-(CH$_3$)$_2$N |
| 397 | 3-cyclopropyl |
| 398 | 3-(2-furyl) |
| 399 | 3-CF$_3$CF$_2$ |
| 400 | 4-NH$_2$ |
| 401 | 3-CH$_3$, 4-CH$_3$, 5-CH$_3$ |
| 402 | 4-CH$_3$CH$_2$CH$_2$O |
| 403 | 3-CF$_3$ |
| 404 | 2-NO$_2$ |

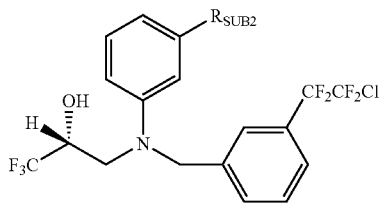

| Ex. No. | R$_{SUB2}$ |
|---|---|
| 405 | 3-CF$_3$O-benzyloxy |
| 406 | 3-CF$_3$-benzyloxy |
| 407 | 3-F, 5-F-benzyloxy |
| 408 | cyclohexylmethyleneoxy |
| 409 | benzyloxy |
| 410 | 3-CF$_3$, 5-CF$_3$-benzyloxy |
| 411 | 4-CF$_3$O-benzyloxy |
| 412 | 4-CH$_3$CH$_2$-benzyloxy |
| 413 | isopropyl |
| 414 | 3-CF$_3$-benzyl |
| 415 | isopropylthio |
| 416 | cyclopentoxy |
| 417 | 3-Cl-5-pyridinyloxy |
| 418 | 3-CF$_3$S-benzyloxy |
| 419 | 3-CH$_3$, 4-CH$_3$-benzyloxy |
| 420 | 2-F, 3-CF$_3$-benzyloxy |
| 421 | 3-F, 5-CF$_3$-benzyloxy |
| 422 | 4-(CH$_3$)$_2$CH-benzyloxy |
| 423 | 1-phenylethoxy |
| 424 | 4-F, 3-CH$_3$-benzoyl |
| 425 | 3-CF$_3$-phenyl |

EXAMPLE TABLE 8-continued

Substituted (2R)-3-[N-(aryl)-[(aryl)methyl]amino]-1,1,1-trifluoro-2-propanols.

| | |
|---|---|
| 426 | 4-CH$_3$O-phenylamino |
| 427 | cyclopropoxy |
| 428 | 4-NO$_2$-phenylthio |

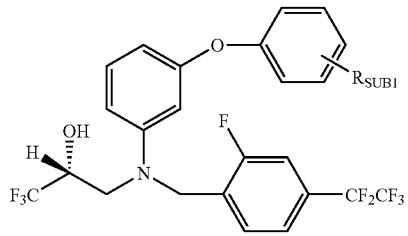

| Ex. No. | R$_{SUB1}$ |
|---|---|
| 429 | 3-isopropyl |
| 430 | 2-Cl, 3-Cl |
| 431 | 3-CF$_3$O |
| 432 | 4-F |
| 433 | 4-CH$_3$ |
| 434 | 2-F, 5-Br |
| 435 | 4-Cl, 3-CH$_3$CH$_2$ |
| 436 | 3-CH$_3$CH$_2$ |
| 437 | 3-CH$_3$, 5-CH$_3$ |
| 438 | 3-(CH$_3$)$_3$C |
| 439 | 4-F, 3-CH$_3$ |
| 440 | 3-Cl, 4-Cl |
| 441 | 3,4-(CH$_2$)$_4$ |
| 442 | 3-HCF$_2$CF$_2$O |
| 443 | 3-CHF$_2$O |
| 444 | 3-(CH$_3$)$_2$N |
| 445 | 3-cyclopropyl |
| 446 | 3-(2-furyl) |
| 447 | 3-CF$_3$CF$_2$ |
| 448 | 4-NH$_2$ |
| 449 | 3-CH$_3$, 4-CH$_3$, 5-CH$_3$ |
| 450 | 4-CH$_3$CH$_2$CH$_2$O |
| 451 | 3-CF$_3$ |
| 452 | 2-NO$_2$ |

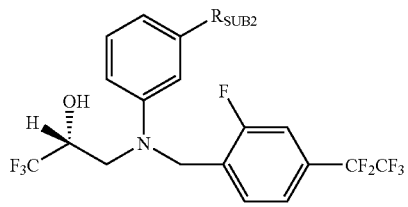

| Ex. No. | R$_{SUB2}$ |
|---|---|
| 453 | 3-CF$_3$O-benzyloxy |
| 454 | 3-CF$_3$-benzyloxy |
| 455 | 3-F, 5-F-benzyloxy |
| 456 | cyclohexylmethyleneoxy |
| 457 | benzyloxy |
| 458 | 3-CF$_3$, 5-CF$_3$-benzyloxy |
| 459 | 4-CF$_3$O-benzyloxy |
| 460 | 4-CH$_3$CH$_2$-benzyloxy |
| 461 | isopropoxy |
| 462 | 3-CF$_3$-benzyl |
| 463 | isopropylthio |
| 464 | cyclopentoxy |
| 465 | 3-Cl-5-pyridinyloxy |
| 466 | 3-CF$_3$S-benzyloxy |
| 467 | 3-CH$_3$, 4-CH$_3$-benzyloxy |
| 468 | 2-F, 3-CF$_3$-benzyloxy |
| 469 | 3-F, 5-CF$_3$-benzyloxy |
| 470 | 4-(CH$_3$)$_2$CH-benzyloxy |
| 471 | 1-phenylethoxy |

EXAMPLE TABLE 8-continued

Substituted (2R)-3-[N-(aryl)-[(aryl)methyl]amino]-1,1,1-trifluoro-2-propanols.

| Ex. No. | |
|---|---|
| 472 | 4-F, 3-CH$_3$-benzoyl |
| 473 | 3-CF$_3$-phenyl |
| 474 | 4-CH$_3$O-phenylamino |
| 475 | cyclopropoxy |
| 476 | 4-NO$_2$-phenylthio |

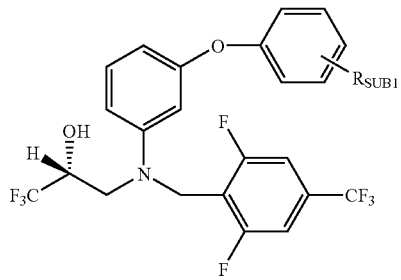

| Ex. No. | R$_{SUB1}$ |
|---|---|
| 477 | 3-isopropyl |
| 478 | 2-Cl, 3-Cl |
| 479 | 3-CF$_3$O |
| 480 | 4-F |
| 481 | 4-CH$_3$ |
| 482 | 2-F, 5-Br |
| 483 | 4-Cl, 3-CH$_3$CH$_2$ |
| 484 | 3-CH$_3$CH$_2$ |
| 485 | 3-CH$_3$, 5-CH$_3$ |
| 486 | 3-(CH$_3$)$_3$C |
| 487 | 4-F, 3-CH$_3$ |
| 488 | 3-Cl, 4-Cl |
| 489 | 3,4-(CH$_2$)$_4$ |
| 490 | 3-HCF$_2$CF$_2$O |
| 491 | 3-CHF$_2$O |
| 492 | 3-(CH$_3$)$_2$N |
| 493 | 3-cyclopropyl |
| 494 | 3-(2-furyl) |
| 495 | 3-CF$_3$CF$_2$ |
| 496 | 4-NH$_2$ |
| 497 | 3-CH$_3$, 4-CH$_3$, 5-CH$_3$ |
| 498 | 4-CH$_3$CH$_2$CH$_2$O |
| 499 | 3-CF$_3$ |
| 500 | 2-NO$_2$ |

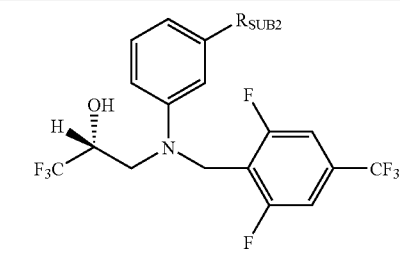

| Ex. No. | R$_{SUB2}$ |
|---|---|
| 501 | 3-CF$_3$O-benzyloxy |
| 502 | 3-CF$_3$-benzyloxy |
| 503 | 3-F, 5-F-benzyloxy |
| 504 | cyclohexylmethyleneoxy |
| 505 | benzyloxy |
| 506 | 3-CF$_3$, 5-CF$_3$-benzyloxy |
| 507 | 4-CF$_3$O-benzyloxy |
| 508 | 4-CH$_3$CH$_2$-benzyloxy |
| 509 | isopropoxy |
| 510 | 3-CF$_3$-benzyl |
| 511 | isopropylthio |
| 512 | cyclopentoxy |
| 513 | 3-Cl-5-pyridinyloxy |

EXAMPLE TABLE 8-continued

Substituted (2R)-3-[N-(aryl)-[(aryl)methyl]amino]-1,1,1-trifluoro-2-propanols.

| | |
|---|---|
| 514 | 3-CF$_3$S-benzyloxy |
| 515 | 3-CH$_3$, 4-CH$_3$-benzyloxy |
| 516 | 2-F, 3-CF$_3$-benzyloxy |
| 517 | 3-F, 5-CF$_3$-benzyloxy |
| 518 | 4-(CH$_3$)$_2$CH-benzyloxy |
| 519 | 1-phenylethoxy |
| 520 | 4-F, 3-CH$_3$-benzoyl |
| 521 | 3-CF$_3$-phenyl |
| 522 | 4-CH$_3$O-phenylamino |
| 523 | cyclopropoxy |
| 524 | 4-NO$_2$-phenylthio |

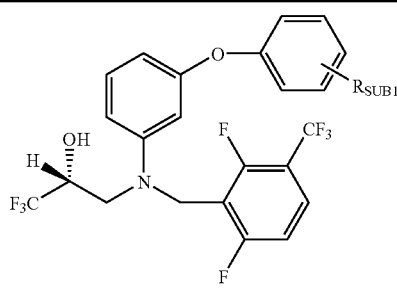

| Ex. No. | R$_{SUB1}$ |
|---|---|
| 525 | 3-isopropyl |
| 526 | 2-Cl, 3-Cl |
| 527 | 3-CF$_3$O |
| 528 | 4-F |
| 529 | 4-CH$_3$ |
| 530 | 2-F, 5-Br |
| 531 | 4-Cl, 3-CH$_3$CH$_2$ |
| 532 | 3-CH$_3$CH$_2$ |
| 533 | 3-CH$_3$, 5-CH$_3$ |
| 534 | 3-(CH$_3$)$_3$C |
| 535 | 4-F, 3-CH$_3$ |
| 536 | 3-Cl, 4-Cl |
| 537 | 3,4-(CH$_2$)$_4$ |
| 538 | 3-HCF$_2$CF$_2$O |
| 539 | 3-CHF$_2$O |
| 540 | 3-(CH$_3$)$_2$N |
| 541 | 3-cyclopropyl |
| 542 | 3-(2-furyl) |
| 543 | 3-CF$_3$CF$_2$ |
| 544 | 4-NH$_2$ |
| 545 | 3-CH$_3$, 4-CH$_3$, 5-CH$_3$ |
| 546 | 4-CH$_3$CH$_2$CH$_2$O |
| 547 | 3-CF$_3$ |
| 548 | 2-NO$_2$ |

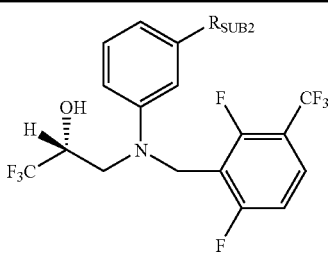

| Ex. No. | R$_{SUB2}$ |
|---|---|
| 549 | 3-CF$_3$O-benzyloxy |
| 550 | 3-CF$_3$-benzyloxy |
| 551 | 3-F, 5-F-benzyloxy |
| 552 | cyclohexylmethyleneoxy |
| 553 | benzyloxy |
| 554 | 3-CF$_3$, 5-CF$_3$-benzyloxy |
| 555 | 4-CF$_3$O-benzyloxy |

EXAMPLE TABLE 8-continued

Substituted (2R)-3-[N-(aryl)-[(aryl)methyl]amino]-1,1,1-trifluoro-2-propanols.

| | |
|---|---|
| 556 | 4-CH$_3$CH$_2$-benzyloxy |
| 557 | isopropoxy |
| 558 | 3-CF$_3$-benzyl |
| 559 | isopropylthio |
| 560 | cyclopentoxy |
| 561 | 3-Cl-5-pyridinyloxy |
| 562 | 3-CF$_3$S-benzyloxy |
| 563 | 3-CH$_3$, 4-CH$_3$-benzyloxy |
| 564 | 2-F, 3-CF$_3$-benzyloxy |
| 565 | 3-F, 5-CF$_3$-benzyloxy |
| 566 | 4-(CH$_3$)$_2$CH-benzyloxy |
| 567 | 1-phenylethoxy |
| 568 | 4-F, 3-CH$_3$-benzoyl |
| 569 | 3-CF$_3$-phenyl |
| 570 | 4-CH$_3$O-phenylamino |
| 571 | cyclopropoxy |
| 572 | 4-NO$_2$-phenylthio |

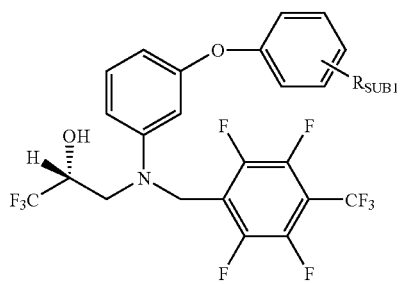

| Ex. No. | R$_{SUB1}$ |
|---|---|
| 573 | 3-isopropyl |
| 574 | 2-Cl, 3-Cl |
| 575 | 3-CF$_3$O |
| 576 | 4-F |
| 577 | 4-CH$_3$ |
| 578 | 2-F, 5-Br |
| 579 | 4-Cl, 3-CH$_3$CH$_2$ |
| 580 | 3-CH$_3$CH$_2$ |
| 581 | 3-CH$_3$, 5-CH$_3$ |
| 582 | 3-(CH$_3$)$_3$C |
| 583 | 4-F, 3-CH$_3$ |
| 584 | 3-Cl, 4-Cl |
| 585 | 3,4-(CH$_2$)$_4$ |
| 586 | 3-HCF$_2$CF$_2$O |
| 587 | 3-CHF$_2$O |
| 588 | 3-(CH$_3$)$_2$N |
| 589 | 3-cyclopropyl |
| 590 | 3-(2-furyl) |
| 591 | 3-CF$_3$CF$_2$ |
| 592 | 4-NH$_2$ |
| 593 | 3-CH$_3$, 4-CH$_3$, 5-CH$_3$ |

EXAMPLE TABLE 8-continued

Substituted (2R)-3-[N-(aryl)-[(aryl)methyl]amino]-1,1,1-trifluoro-2-propanols.

| | |
|---|---|
| 594 | 4-CH$_3$CH$_2$CH$_2$O |
| 595 | 3-CF$_3$ |
| 596 | 2-NO$_2$ |

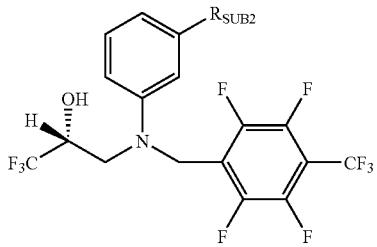

| Ex. No. | R$_{SUB2}$ |
|---|---|
| 597 | 3-CF$_3$O-benzyloxy |
| 598 | 3-CF$_3$-benzyloxy |
| 599 | 3-F, 5-F-benzyloxy |
| 600 | cyclohexylmethyleneoxy |
| 601 | benzyloxy |
| 602 | 3-CF$_3$, 5-CF$_3$-benzyloxy |
| 603 | 4-CF$_3$O-benzyloxy |
| 604 | 4-CH$_3$CH$_2$-benzyloxy |
| 605 | isopropoxy |
| 606 | 3-CF$_3$-benzyl |
| 607 | isopropylthio |
| 608 | cyclopentoxy |
| 609 | 3-Cl-5-pyridinyloxy |
| 610 | 3-CF$_3$S-benzyloxy |
| 611 | 3-CH$_3$, 4-CH$_3$-benzyloxy |
| 612 | 2-F, 3-CF$_3$-benzyloxy |
| 613 | 3-F, 5-CF$_3$-benzyloxy |
| 614 | 4-(CH$_3$)$_2$CH-benzyloxy |
| 615 | 1-phenylethoxy |
| 616 | 4-F, 3-CH$_3$-benzoyl |
| 617 | 3-CF$_3$-phenyl |
| 618 | 4-CH$_3$O-phenylamino |
| 619 | cyclopropoxy |
| 620 | 4-NO$_2$-phenylthio |

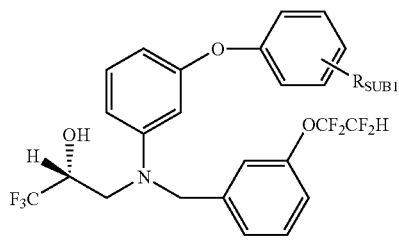

| Ex. No. | R$_{SUB1}$ | Calculated Mass [M + H]$^+$ | Observed Mass [M + H]$^+$ |
|---|---|---|---|
| 621 | 4-F | 522.1315 | 522.1297 |
| 622 | 2-Cl, 3-Cl | 572.0630 | 572.0653 |
| 623 | 2-F, 5-Br | 600.0420 | 600.0404 |
| 624 | 4-Cl, 3-CH$_3$ | 551.1098 | 551.1101 |
| 625 | 3-CH$_3$, 5-CH$_3$ | 532.1722 | 532.1705 |
| 626 | 3-(CH$_3$)$_3$C | 560.2035 | 560.2055 |
| 627 | 4-F, 3-CH$_3$ | 536.1471 | 536.1480 |
| 628 | 3-Cl, 4-Cl | 572.0630 | 572.0630 |
| 629 | 3,4-(CH$_2$)$_4$ | 558.1879 | 558.1881 |
| 630 | 3-HCF$_2$CF$_2$O | | |
| 631 | 3-CHF$_2$O | | |
| 632 | 3-(CH$_3$)$_2$N | 547.1831 | 547.1844 |
| 633 | 3-cyclopropyl | | |
| 634 | 3-(2-furyl) | | |
| 635 | 3-CF$_3$CF$_2$ | | |
| 636 | 3-cyclopentyl | | |

EXAMPLE TABLE 8-continued

Substituted (2R)-3-[N-(aryl)-[(aryl)methyl]amino]-1,1,1-trifluoro-2-propanols.

| | | | |
|---|---|---|---|
| 637 | 4-$NH_2$ | 519.1519 | 519.1529 |
| 638 | 3-$CH_3$, 4-$CH_3$, 5-$CH_3$ | 546.1879 | 546.1901 |
| 639 | 4-$CH_3CH_2O$ | 547.1594 | 547.1594 |
| 640 | 3-$CF_3$ | | |
| 641 | 2-$NO_2$ | 549.1260 | 549.1235 |
| 642 | 3,4-dimethyl | 531.1644 | 531.1649 |
| 643 | 3-methyl, 5-ethyl | 546.1879 | 546.1899 |
| 644 | 3-methyl | 517.1488 | 517.1493 |
| 645 | 2,3-difluoro | 540.1221 | 540.1182 |
| 646 | 4-$CF_3$ | 572.1282 | 572.1268 |
| 647 | 2-fluoro, 3-$CF_3$ | 590.1189 | 590.1184 |
| 648 | 2-fluoro, 4-$CF_3$ | 590.1189 | 590.1155 |
| 649 | 2-chloro, 4-fluoro | 556.0925 | 556.0891 |
| 650 | 4-n-propyl | 546.1879 | 546.1878 |
| 651 | 3-chloro, 4-fluoro | 556.0925 | 556.0932 |
| 652 | 2,4-difluoro | 540.1221 | 540.1194 |
| 653 | 3,5-difluoro | 540.1221 | 540.1217 |
| 654 | 3,4-difluoro | 540.1221 | 540.1248 |
| 655 | 3-fluoro | 522.1315 | 522.1337 |
| 656 | 2-chloro | 538.1019 | 538.1021 |
| 657 | 2-fluoro | 522.1315 | 522.1310 |
| 658 | 2,5-difluoro | 540.1221 | 540.1255 |
| 659 | 4-chloro, 2-fluoro | 556.0926 | 556.0954 |
| 660 | 2,4-dichloro | 572.0630 | 572.0667 |
| 661 | 2-fluoro, 3-$CH_3$ | | |
| 662 | 4-chloro | 537.0942 | 537.0944 |
| 663 | 4-isopropyl, 3-methyl | 560.2035 | 560.2035 |
| 664 | 2,3,4-trifluoro | 558.1127 | 558.1161 |
| 665 | 2,3,5-trifluoro | 558.1127 | 558.1109 |
| 666 | 4-propoxy | 562.1828 | 562.1803 |
| 667 | 4-isopropyl | 546.1879 | 546.1899 |
| 668 | 4-$CF_3O$— | 588.1233 | 588.1241 |
| 669 | 4-butoxy | 576.1958 | 576.1969 |
| 670 | 3-methyl, 4-$CH_3S$— | 564.1443 | 564.1476 |
| 671 | 4-nitro | 549.1260 | 549.1306 |
| 672 | 3-$CF_3S$— | | |
| 673 | 4-chloro, 3-fluoro | 556.0925 | 556.0933 |
| 674 | 3,5-dimethoxy | 564.1623 | 564.1617 |
| 675 | 4-bromo | 582.0716 | 582.0473 |
| 676 | 4-sec-butyl | 560.2035 | 560.2051 |
| 677 | 3-fluoro-2-nitro | 567.1166 | 567.1135 |
| 678 | 3-methoxy | 533.1437 | 533.1450 |
| 679 | 4-bromo-2-nitro | 627.0366 | 627.0375 |
| 680 | 4-cyano | 529.1362 | 529.1364 |
| 681 | 4-$CH_3S$— | 550.1209 | 550.1251 |
| 682 | 3,4-(CH=CH)$_2$ | 554.1566 | 554.1578 |
| 683 | 4-$CH_3CH_2NH$— | 547.1832 | 547.1819 |
| 684 | 4-propionyl | 560.1672 | 560.1694 |
| 685 | 3-phenyl | 580.1723 | 580.1772 |
| 686 | 4-cyclopentyl | 572.2035 | 572.2029 |

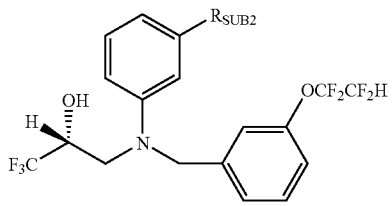

| Ex. No. | $R_{SUB2}$ | Calculated Mass $[M + H]^+$ | Observed Mass $[M + H]^+$ |
|---|---|---|---|
| 687 | 6-methyl-3-pridinyloxy | 518.1440 | 518.1452 |
| 688 | 5-chloro-3-pyridinyloxy | 539.0972 | 539.1002 |
| 689 | 3-pyridinyloxy | 505.1362 | 505.1369 |
| 690 | 2-methyl-3-pyridinyloxy | 519.1518 | 519.1517 |
| 691 | 5-indolinyloxy | 543.1519 | 543.1630 |
| 692 | 4-fluoro-2-pyridinyloxy | 523.1268 | 523.1243 |
| 693 | 2-cyano-3-pyridinyloxy | 530.1315 | 530.1300 |
| 694 | 5-bromo-2-pyridinyloxy | 583.0667 | 583.0405 |
| 695 | 3-$CF_3$-2-pyridinyloxy | 573.1236 | 573.1205 |
| 696 | 2-pyridinylmethyleneoxy | 519.1519 | 519.1522 |
| 697 | cyclohexylmethyleneoxy | 524.2036 | 524.2028 |

EXAMPLE TABLE 8-continued

Substituted (2R)-3-[N-(aryl)-[(aryl)methyl]amino]-1,1,1-trifluoro-2-propanols.

| | | | |
|---|---|---|---|
| 698 | isopropoxy | 470.1488 | 470.1565 |
| 699 | cyclopentyloxy | 496.1723 | 496.1719 |
| 700 | neo-pentoxy | 498.1879 | 498.1845 |
| 701 | 4-(methoxycarbonyl)-butoxy | 542.1777 | 542.1827 |
| 702 | trifluoromethoxy | 496.0971 | 496.0959 |
| 703 | 2-methylpropoxy | 484.1723 | 484.1718 |
| 704 | 2-methoxyethoxy | 486.1515 | 486.1537 |
| 705 | 2-oxobutoxy | 498.1515 | 498.1529 |
| 706 | cyclohexyloxy | 510.1880 | 510.1910 |
| 707 | (methoxycarbonyl)methoxy | 500.1308 | 500.1297 |
| 708 | 4-tetrahydropyranyloxy | 512.1672 | 512.1631 |
| 709 | 1-phenylethoxy | 532.1723 | 532.1711 |
| 710 | 3-$CF_3$O-benzyloxy | 602.1389 | 602.1380 |
| 711 | 3-trifluoromethyl-benzyloxy | 586.1440 | 586.1419 |
| 712 | 3,5-dimethyl-benzyloxy | 546.1879 | 546.1890 |
| 713 | 3-bromo-benzyloxy | 596.0671 | 596.0641 |
| 714 | 3-$CF_3$S-benzyloxy | 618.1161 | 618.1151 |
| 715 | 3,4-dimethyl-benzyloxy | 546.1879 | 546.1881 |
| 716 | 3,5-difluoro-benzyloxy | 554.1378 | 554.1390 |
| 717 | 2-fluoro-3-$CF_3$-benzyloxy | 604.1346 | 604.1329 |
| 718 | benzyloxy | 518.1566 | 518.1578 |
| 719 | 3,5-($CF_3$)$_2$-benzyloxy | 654.1314 | 654.1308 |
| 720 | 3-fluoro-5-$CF_3$-benzyloxy | 604.1346 | 604.1309 |
| 721 | 4-$CF_3$O-benzyloxy | 602.1389 | 602.1383 |
| 722 | 3-chloro-benzyloxy | 552.1176 | 552.1157 |
| 723 | 4-ethyl-benzyloxy | 546.1879 | 546.1862 |
| 724 | 3-methyl-benzyloxy | 532.1723 | 532.1692 |
| 725 | 2-fluoro-benzyloxy | 536.1472 | 536.1465 |
| 726 | 2,3-difluoro-benzyloxy | 554.1378 | 554.1364 |
| 727 | 4-isopropyl-benzyloxy | 560.2036 | 560.2020 |
| 728 | 4-methyl-benzyloxy | 532.1723 | 532.1729 |
| 729 | 4-bromo-benzyloxy | 596.0671 | 596.0669 |
| 730 | 4-$CF_3$-benzyloxy | 586.1440 | 586.1400 |
| 731 | 4-fluoro-benzyloxy | 536.1472 | 536.1454 |
| 732 | 3-iodo-benzyloxy | 644.0533 | 644.0517 |
| 733 | 4-$CF_3$S-benzyloxy | 618.1161 | 618.1165 |
| 734 | 4-$CF_2$HO-benzyloxy | 584.1483 | 584.1480 |
| 735 | 4-fluoro-3-$CF_3$-benzyloxy | 604.1346 | 604.1336 |
| 736 | 2,3,5-trifluoro-benzyloxy | 572.1284 | 572.1276 |
| 737 | 4-chloro-benzyloxy | 552.1176 | 552.1188 |
| 738 | 2,5-difluoro-benzyloxy | 554.1378 | 554.1350 |
| 739 | 3-chloro-2-fluoro-benzyloxy | 570.1082 | 570.1069 |
| 740 | 2,4-($CF_3$)$_2$-benzyloxy | 654.1314 | 654.1321 |
| 741 | 3,5-dichloro-benzyloxy | 586.1787 | 586.1378 |
| 742 | 3-methoxy-benzyloxy | 548.1672 | 548.1676 |
| 743 | 4-cyano-benzyloxy | 543.1519 | 543.1517 |
| 744 | 4-tert-butyl-benzyloxy | 574.2192 | 574.2163 |
| 745 | isopropylthio | 486.1338 | 486.1351 |
| 746 | 4-nitrophenylthio | 565.1032 | 565.1034 |
| 747 | 4-acetylphenylthio | 562.1287 | 562.1261 |
| 748 | (4-chloro-thien-2-yl)-methylthio | 574.0512 | 574.0523 |
| 749 | 4-methoxy-phenylamino | 532.1597 | 532.1592 |
| 750 | 3-methoxy-phenylamino | 532.1597 | 532.1593 |
| 751 | 4-chloro-phenylamino | 536.1102 | 536.1125 |
| 752 | 4-n-propyl-phenylamino | 544.1961 | 544.1959 |
| 753 | 3-cyano-phenylamino | 527.1444 | 527.1448 |
| 754 | 3-$CF_3$-benzyl | 570.1413 | 570.1480 |
| 755 | 3-methyl-4-fluoro-benzyl | 534.1679 | 534.1688 |
| 756 | 3-$CF_3$-phenyl | 556.1334 | 556.1339 |
| 757 | 2,4-dichloro-phenyl | 556.0681 | 556.0651 |
| 758 | 3-methoxybenzyl | 532.1723 | 532.1705 |
| 759 | 4-methoxyphenyl | 518.1566 | 518.1533 |
| 760 | 3-chloro-4-fluoro-phenyl | 540.0976 | 540.0957 |
| 761 | 4-fluoro-3-methyl-benzoyl | 548.1410 | 548.1441 |
| 762 | 3-chlorobenzyl | 536.1227 | 536.1218 |
| 763 | 3,4-dimethylbenzyl | 530.1930 | 530.1887 |
| 764 | 3,5-dichlorobenzyl | 570.0838 | 570.0801 |
| 765 | 2,3,4-trifluorophenyl | 542.1177 | 542.1152 |
| 766 | 3-chloro-4-fluoro-benzyl | 554.1133 | 554.1108 |
| 767 | 4-fluoro-3-methyl-phenyl | 520.1523 | 520.1494 |
| 768 | 3-methyl-4-chloro-benzyl | 550.1384 | 550.1380 |
| 769 | 2-methylpropanoyl | 482.1566 | 482.1576 |
| 770 | 4-methylthiobenzyl | 548.1494 | 548.1503 |
| 771 | 4-fluorophenyl | 506.1366 | 506.1336 |
| 772 | 4-chlorophenyl | 522.1071 | 522.1049 |
| 773 | 3-methoxyphenyl | 518.1566 | 518.1544 |

EXAMPLE TABLE 8-continued

Substituted (2R)-3-[N-(aryl)-[(aryl)methyl]amino]-1,1,1-trifluoro-2-propanols.

| 774 | 4-methylbenyzl | 516.1774 | 516.1769 |
| 775 | 1-hydroxy-2-methyl-propyl | 484.1723 | 484.1725 |
| 776 | benzyl | 502.1617 | 502.1609 |
| 777 | 2-$CF_3$-phenyl | 556.1334 | 556.1286 |
| 778 | 3,4-dichlorophenyl | 556.0681 | 556.0698 |
| 779 | benzoyl | 516.1410 | 516.1383 |
| 780 | 4-fluorobenzoyl | 534.1315 | 534.1273 |
| 781 | N-piperidinyl | 494.1804 | 494.1804 |
| 782 | phenyl | 488.1460 | 488.1457 |
| 783 | thien-2-yl | 494.1024 | 494.0987 |

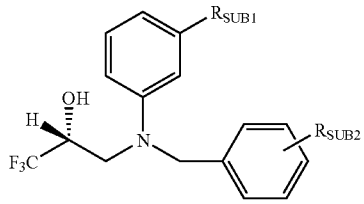

| Ex. No. | $R_{SUB1}$ | $R_{SUB2}$ | Calculated Mass $[M + H]^+$ | Observed Mass $[M + H]^+$ |
| --- | --- | --- | --- | --- |
| 784 | phenoxy | 3-cyclopentyl | 456.2150 | 456.2143 |
| 785 | phenoxy | 3-isopropoxy | 446.1943 | 446.1936 |
| 786 | phenoxy | 3-$CF_3$S | 488.1119 | 488.1116 |
| 787 | 4-F-phenoxy | 3-$CF_3$S | 505.0946 | 505.0927 |
| 788 | 4-F-phenoxy | 3-sec-butoxy | 478.2005 | 478.1880 |
| 789 | phenoxy | 3-$(CF_3)_2$COH— | 554.1378 | 554.1385 |
| 790 | 4-$CH_3$-phenoxy | 3-$CF_3$S | 502.1275 | 502.1261 |
| 791 | phenoxy | 3-(2-furyl) | 454.1630 | 454.1635 |
| 792 | 4-F-phenoxy | 3-isopropoxy | 464.1849 | 464.1867 |
| 793 | phenoxy | 3-isobutyl | 444.2150 | 444.2157 |
| 794 | phenoxy | 3-tert-butoxy | 460.2100 | 460.2103 |
| 795 | 4-F-phenoxy | 3-$CH_3CH_2O$— | 450.1692 | 450.1682 |
| 796 | 4-F-phenoxy | 3-$CF_3O$— | 490.1253 | 490.1211 |
| 797 | phenoxy | 4-F-3-(2-furyl)- | 472.1536 | 472.1530 |
| 798 | 4-F-phenoxy | 3-n-propoxy- | 464.1849 | 464.1820 |
| 799 | 4-F-phenoxy | 3-cyclopentyloxy- | 490.2005 | 490.1998 |
| 800 | phenoxy | 3-(3-furyl)- | 454.1630 | 454.1646 |
| 801 | 4-F-phenoxy | 3-cyclopropyl-methyleneoxy | 476.1849 | 476.1857 |
| 802 | phenoxy | 3-$CF_3CH_2O$— | 486.1504 | 486.1498 |

EXAMPLE TABLE 9

(3R)-4-[N-(aryl)-[(aryl)methyl]amino]-1,1,1,2,2-pentafluoro-3-butanols.

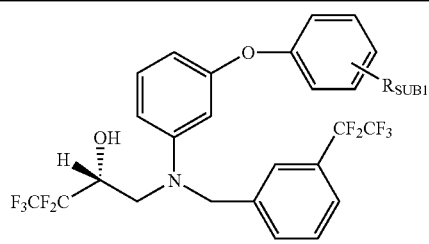

| Ex. No. | $R_{SUB1}$ |
| --- | --- |
| 803 | 3-isopropyl |
| 804 | 2-Cl, 3-Cl |
| 805 | 3-$CF_3O$ |
| 806 | 4-F |
| 807 | 4-$CH_3$ |
| 808 | 2-F, 5-Br |
| 809 | 4-Cl, 3-$CH_3CH_2$ |
| 810 | 3-$CH_3CH_2$ |
| 811 | 3-$CH_3$, 5-$CH_3$ |
| 812 | 3-$(CH_3)_3$C |
| 813 | 4-F, 3-$CH_3$ |
| 814 | 3-Cl, 4-Cl |
| 815 | 3,4-$(CH_2)_4$ |
| 816 | 3-$HCF_2CF_2O$ |
| 817 | 3-$CHF_2O$ |
| 818 | 3-$(CH_3)_2$N |
| 819 | 3-cyclopropyl |
| 820 | 3-(2-furyl) |
| 821 | 3-$CF_3CF_2$ |
| 822 | 4-$NH_2$ |
| 823 | 3-$CH_3$, 4-$CH_3$, 5-$CH_3$ |
| 824 | 4-$CH_3CH_2CH_2O$ |
| 825 | 3-$CF_3$ |
| 826 | 2-$NO_2$ |

EXAMPLE TABLE 9-continued (3R)-4-[N-(aryl)-[(aryl)methyl]amino]-1,1,1,2,2-pentafluoro-3-butanols.

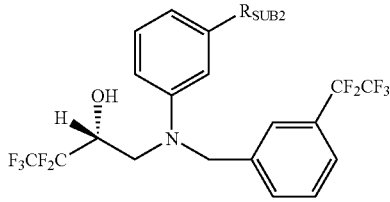

| Ex. No. | $R_{SUB2}$ |
|---|---|
| 827 | 3-$CF_3$O-benzyloxy |
| 828 | 3-$CF_3$-benzyloxy |
| 829 | 3-F, 5-F-benzyloxy |
| 830 | cyclohexylmethyleneoxy |
| 831 | benzyloxy |
| 832 | 3-$CF_3$, 5-$CF_3$-benzyloxy |
| 833 | 4-$CF_3$O-benzyloxy |
| 834 | 4-$CH_3CH_2$-benzyloxy |
| 835 | isopropoxy |
| 836 | 3-$CF_3$-benzyl |
| 837 | isopropylthio |
| 838 | cyclopentoxy |
| 839 | 3-Cl-5-pyridinyloxy |
| 840 | 3-$CF_3$S-benzyloxy |
| 841 | 3-$CH_3$, 4-$CH_3$-benzyloxy |
| 842 | 2-F, 3-$CF_3$-benzyloxy |
| 843 | 3-F, 5-$CF_3$-benzyloxy |
| 844 | 4-$(CH_3)_2$CH-benzyloxy |
| 845 | 1-phenylethoxy |
| 846 | 4-F, 3-$CH_3$-benzoyl |
| 847 | 3-$CF_3$-phenyl |
| 848 | 4-$CH_3$O-phenylamino |
| 849 | cyclopropoxy |
| 850 | 4-$NO_2$-phenylthio |

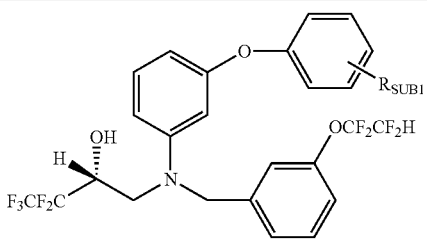

| Ex. No. | $R_{SUB1}$ |
|---|---|
| 851 | 3-isopropyl |
| 852 | 2-Cl, 3-Cl |
| 853 | 3-$CF_3$O |
| 854 | 4-F |
| 855 | 4-$CH_3$ |
| 856 | 2-F, 5-Br |
| 857 | 4-Cl, 3-$CH_3CH_2$ |
| 858 | 3-$CH_3CH_2$ |
| 859 | 3-$CH_3$, 5-$CH_3$ |
| 860 | 3-$(CH_3)_3$C |
| 861 | 4-F, 3-$CH_3$ |
| 862 | 3-Cl, 4-Cl |
| 863 | 3,4-$(CH_2)_4$ |
| 864 | 3-$HCF_2CF_2$O |
| 865 | 3-$CHF_2$O |
| 866 | 3-$(CH_3)_2$N |
| 867 | 3-cyclopropyl |
| 868 | 3-(2-furyl) |
| 869 | 3-$CF_3CF_2$ |
| 870 | 4-$NH_2$ |
| 871 | 3-$CH_3$, 4-$CH_3$, 5-$CH_3$ |
| 872 | 4-$CH_3CH_2CH_2$O |
| 873 | 3-$CF_3$ |
| 874 | 2-$NO_2$ |

EXAMPLE TABLE 9-continued (3R)-4-[N-(aryl)-[(aryl)methyl]amino]-1,1,1,2,2-pentafluoro-3-butanols.

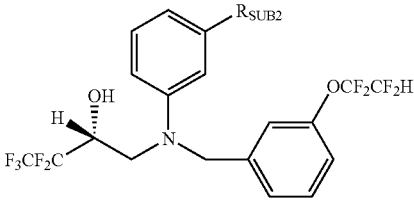

| Ex. No. | $R_{SUB2}$ |
|---|---|
| 875 | 3-$CF_3$O-benzyloxy |
| 876 | 3-$CF_3$-benzyloxy |
| 877 | 3-F, 5-F-benzyloxy |
| 878 | cyclohexylmethyleneoxy |
| 879 | benzyloxy |
| 880 | 3-$CF_3$, 5-$CF_3$-benzyloxy |
| 881 | 4-$CF_3$O-benzyloxy |
| 882 | 4-$CH_3CH_2$-benzyloxy |
| 883 | isopropoxy |
| 884 | 3-$CF_3$-benzyl |
| 885 | isopropylthio |
| 886 | cyclopentoxy |
| 887 | 3-Cl-5-pyridinyloxy |
| 888 | 3-$CF_3$S-benzyloxy |
| 889 | 3-$CH_3$, 4-$CH_3$-benzyloxy |
| 890 | 2-F, 3-$CF_3$-benzyloxy |
| 891 | 3-F, 5-$CF_3$-benzyloxy |
| 892 | 4-$(CH_3)_2$CH-benzyloxy |
| 893 | 1-phenylethoxy |
| 894 | 4-F, 3-$CH_3$-benzoyl |
| 895 | 3-$CF_3$-phenyl |
| 896 | 4-$CH_3$O-phenylamino |
| 897 | cyclopropoxy |
| 898 | 4-$NO_2$-phenylthio |

EXAMPLE TABLE 10

Substituted (2R)-3-[N-(aryl)-[(aryl)oxy]amino]-1,1,1-trifluoro-2-propanols.

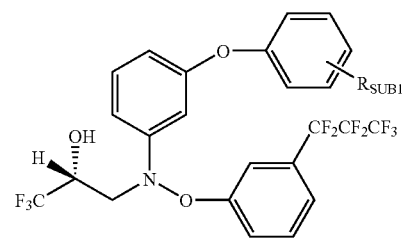

| Ex. No. | $R_{SUB1}$ |
|---|---|
| 899 | 3-isopropyl |
| 900 | 2-Cl, 3-Cl |
| 901 | 3-$CF_3$O |
| 902 | 4-F |
| 903 | 4-$CH_3$ |
| 904 | 2-F, 5-Br |
| 905 | 4-Cl, 3-$CH_3CH_2$ |
| 906 | 3-$CH_3CH_2$ |
| 907 | 3-$CH_3$, 5-$CH_3$ |
| 908 | 3-$(CH_3)_3$C |
| 909 | 4-F, 3-$CH_3$ |
| 910 | 3-Cl, 4-Cl |
| 911 | 3,4-$(CH_2)_4$ |
| 912 | 3-$HCF_2CF_2$O |
| 913 | 3-$CHF_2$O |
| 914 | 3-$(CH_3)_2$N |
| 915 | 3-cyclopropyl |
| 916 | 3-(2-furyl) |
| 917 | 3-$CF_3CF_2$ |

EXAMPLE TABLE 10-continued

Substituted (2R)-3-[N-(aryl)-[(aryl)oxy]amino]-1,1,1-trifluoro-2-propanols.

| | |
|---|---|
| 918 | 4-NH$_2$ |
| 919 | 3-CH$_3$, 4-CH$_3$, 5-CH$_3$ |
| 920 | 4-CH$_3$CH$_2$CH$_2$O |
| 921 | 3-CF$_3$ |
| 922 | 2-NO$_2$ |

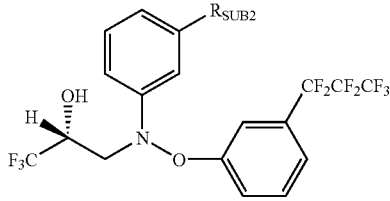

| Ex. No. | R$_{SUB2}$ |
|---|---|
| 923 | 3-CF$_3$O-benzyloxy |
| 924 | 3-CF$_3$-benzyloxy |
| 925 | 3-F, 5-F-benzyloxy |
| 926 | cyclohexylmethyleneoxy |
| 927 | benzyloxy |
| 928 | 3-CF$_3$, 5-CF$_3$-benzyloxy |
| 929 | 4-CF$_3$O-benzyloxy |
| 930 | 4-CH$_3$CH$_2$-benzyloxy |
| 931 | isopropoxy |
| 932 | 3-CF$_3$-benzyl |
| 933 | isopropylthio |
| 934 | cyclopentoxy |
| 935 | 3-Cl-5-pyridinyloxy |
| 936 | 3-CF$_3$S-benzyloxy |
| 937 | 3-CH$_3$, 4-CH$_3$-benzyloxy |
| 938 | 2-F, 3-CF$_3$-benzyloxy |
| 939 | 3-F, 5-CF$_3$-benzyloxy |
| 940 | 4-(CH$_3$)$_2$CH-benzyloxy |
| 941 | 1-phenylethoxy |
| 942 | 4-F, 3-CH$_3$-benzoyl |
| 943 | 3-CF$_3$-phenyl |
| 944 | 4-CH$_3$O-phenylamino |
| 945 | cyclopropoxy |
| 946 | 4-NO$_2$-phenylthio |

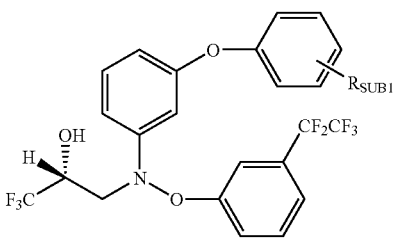

| Ex. No. | R$_{SUB1}$ |
|---|---|
| 947 | 3-isopropyl |
| 948 | 2-Cl, 3-Cl |
| 949 | 3-CF$_3$O |
| 950 | 4-F |
| 951 | 4-CH$_3$ |
| 952 | 2-F, 5-Br |
| 953 | 4-Cl, 3-CH$_3$CH$_2$ |
| 954 | 3-CH$_3$CH$_2$ |
| 955 | 3-CH$_3$, 5-CH$_3$ |
| 956 | 3-(CH$_3$)$_3$C |
| 957 | 4-F, 3-CH$_3$ |
| 958 | 3-Cl, 4-Cl |
| 959 | 3,4-(CH$_2$)$_4$ |
| 960 | 3-HCF$_2$CF$_2$O |
| 961 | 3-CHF$_2$O |
| 962 | 3-(CH$_3$)$_2$N |
| 963 | 3-cyclopropyl |
| 964 | 3-(2-furyl) |
| 965 | 3-CF$_3$CF$_2$ |

EXAMPLE TABLE 10-continued

Substituted (2R)-3-[N-(aryl)-[(aryl)oxy]amino]-1,1,1-trifluoro-2-propanols.

| | |
|---|---|
| 966 | 4-NH$_2$ |
| 967 | 3-CH$_3$, 4-CH$_3$, 5-CH$_3$ |
| 968 | 4-CH$_3$CH$_2$CH$_2$O |
| 969 | 3-CF$_3$ |
| 970 | 2-NO$_2$ |

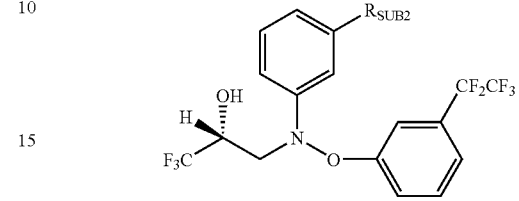

| Ex. No. | R$_{SUB2}$ |
|---|---|
| 971 | 3-CF$_3$O-benzyloxy |
| 972 | 3-CF$_3$-benzyloxy |
| 973 | 3-F, 5-F-benzyloxy |
| 974 | cyclohexylmethyleneoxy |
| 975 | benzyloxy |
| 976 | 3-CF$_3$, 5-CF$_3$-benzyloxy |
| 977 | 4-CF$_3$O-benzyloxy |
| 978 | 4-CH$_3$CH$_2$-benzyloxy |
| 979 | isopropoxy |
| 980 | 3-CF$_3$-benzyl |
| 981 | isopropylthio |
| 982 | cyclopentoxy |
| 983 | 3-Cl-5-pyridinyloxy |
| 984 | 3-CF$_3$S-benzyloxy |
| 985 | 3-CH$_3$, 4-CH$_3$-benzyloxy |
| 986 | 2-F, 3-CF$_3$-benzyloxy |
| 987 | 3-F, 5-CF$_3$-benzyloxy |
| 988 | 4-(CH$_3$)$_2$CH-benzyloxy |
| 989 | 1-phenylethoxy |
| 990 | 4-F, 3-CH$_3$-benzoyl |
| 991 | 3-CF$_3$-phenyl |
| 992 | 4-CH$_3$O-phenylamino |
| 993 | cyclopropoxy |
| 994 | 4-NO$_2$-phenylthio |

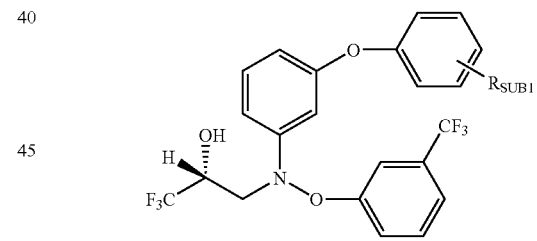

| Ex. No. | R$_{SUB1}$ |
|---|---|
| 995 | 3-isopropyl |
| 996 | 2-Cl, 3-Cl |
| 997 | 3-CF$_3$O |
| 998 | 4-F |
| 999 | 4-CH$_3$ |
| 1000 | 2-F, 5-Br |
| 1001 | 4-Cl, 3-CH$_3$CH$_2$ |
| 1002 | 3-CH$_3$CH$_2$ |
| 1003 | 3-CH$_3$, 5-CH$_3$ |
| 1004 | 3-(CH$_3$)$_3$C |
| 1005 | 4-F, 3-CH$_3$ |
| 1006 | 3-Cl, 4-Cl |
| 1007 | 3,4-(CH$_2$)$_4$ |
| 1008 | 3-HCF$_2$CF$_2$O |
| 1009 | 3-CHF$_2$O |
| 1010 | 3-(CH$_3$)$_2$N |
| 1011 | 3-cyclopropyl |
| 1012 | 3-(2-furyl) |
| 1013 | 3-CF$_3$CF$_2$ |

EXAMPLE TABLE 10-continued

Substituted (2R)-3-[N-(aryl)-[(aryl)oxy]amino]-1,1,1-trifluoro-2-propanols.

| | |
|---|---|
| 1014 | 4-NH$_2$ |
| 1015 | 3-CH$_3$, 4-CH$_3$, 5-CH$_3$ |
| 1016 | 4-CH$_3$CH$_2$CH$_2$O |
| 1017 | 3-CF$_3$ |
| 1018 | 2-NO$_2$ |

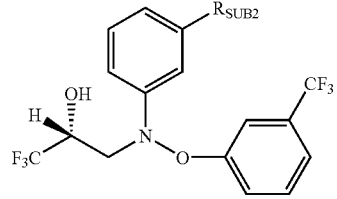

| Ex. No. | R$_{SUB2}$ |
|---|---|
| 1019 | 3-CF$_3$O-benzyloxy |
| 1020 | 3-CF$_3$-benzyloxy |
| 1021 | 3-F, 5-F-benzyloxy |
| 1022 | cyclohexylmethyleneoxy |
| 1023 | benzyloxy |
| 1024 | 3-CF$_3$, 5-CF$_3$-benzyloxy |
| 1025 | 4-CF$_3$O-benzyloxy |
| 1026 | 4-CH$_3$CH$_2$-benzyloxy |
| 1027 | isopropoxy |
| 1028 | 3-CF$_3$-benzyl |
| 1029 | isopropylthio |
| 1030 | cyclopentoxy |
| 1031 | 3-Cl-5-pyridinyloxy |
| 1032 | 3-CF$_3$S-benzyloxy |
| 1033 | 3-CH$_3$, 4-CH$_3$-benzyloxy |
| 1034 | 2-F, 3-CF$_3$-benzyloxy |
| 1035 | 3-F, 5-CF$_3$-benzyloxy |
| 1036 | 4-(CH$_3$)$_2$CH-benzyloxy |
| 1037 | 1-phenylethoxy |
| 1038 | 4-F, 3-CH$_3$-benzoyl |
| 1039 | 3-CF$_3$-phenyl |
| 1040 | 4-CH$_3$O-phenylamino |
| 1041 | cyclopropoxy |
| 1042 | 4-NO$_2$-phenylthio |

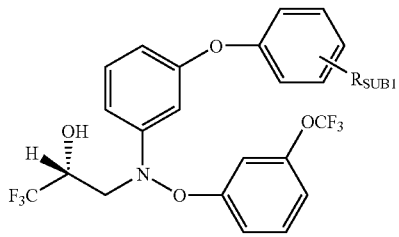

| Ex. No. | R$_{SUB1}$ |
|---|---|
| 1043 | 3-isopropyl |
| 1044 | 2-Cl, 3-Cl |
| 1045 | 3-CF$_3$O |
| 1046 | 4-F |
| 1047 | 4-CH$_3$ |
| 1048 | 2-F, 5-Br |
| 1049 | 4-Cl, 3-CH$_3$CH$_2$ |
| 1050 | 3-CH$_3$CH$_2$ |
| 1051 | 3-CH$_3$, 5-CH$_3$ |
| 1052 | 3-(CH$_3$)$_3$C |
| 1053 | 4-F, 3-CH$_3$ |
| 1054 | 3-Cl, 4-Cl |
| 1055 | 3,4-(CH$_2$)$_4$ |
| 1056 | 3-HCF$_2$CF$_2$O |
| 1057 | 3-CHF$_2$O |
| 1058 | 3-(CH$_3$)$_2$N |
| 1059 | 3-cyclopropyl |
| 1060 | 3-(2-furyl) |
| 1061 | 3-CF$_3$CF$_2$ |

EXAMPLE TABLE 10-continued

Substituted (2R)-3-[N-(aryl)-[(aryl)oxy]amino]-1,1,1-trifluoro-2-propanols.

| | |
|---|---|
| 1062 | 4-NH$_2$ |
| 1063 | 3-CH$_3$, 4-CH$_3$, 5-CH$_3$ |
| 1064 | 4-CH$_3$CH$_2$CH$_2$O |
| 1065 | 3-CF$_3$ |
| 1066 | 2-NO$_2$ |

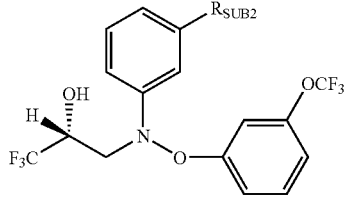

| Ex. No. | R$_{SUB2}$ |
|---|---|
| 1067 | 3-CF$_3$O-benzyloxy |
| 1068 | 3-CF$_3$-benzyloxy |
| 1069 | 3-F, 5-F-benzyloxy |
| 1070 | cyclohexylmethyleneoxy |
| 1071 | benzyloxy |
| 1072 | 3-CF$_3$, 5-CF$_3$-benzyloxy |
| 1073 | 4-CF$_3$O-benzyloxy |
| 1074 | 4-CH$_3$CH$_2$-benzyloxy |
| 1075 | isopropoxy |
| 1076 | 3-CF$_3$-benzyl |
| 1077 | isopropylthio |
| 1078 | cyclopentoxy |
| 1079 | 3-Cl-5-pyridinyloxy |
| 1080 | 3-CF$_3$S-benzyloxy |
| 1081 | 3-CH$_3$, 4-CH$_3$-benzyloxy |
| 1082 | 2-F, 3-CF$_3$-benzyloxy |
| 1083 | 3-F, 5-CF$_3$-benzyloxy |
| 1084 | 4-(CH$_3$)$_2$CH-benzyloxy |
| 1085 | 1-phenylethoxy |
| 1086 | 4-F, 3-CH$_3$-benzoyl |
| 1087 | 3-CF$_3$-phenyl |
| 1088 | 4-CH$_3$O-phenylamino |
| 1089 | cyclopropoxy |
| 1090 | 4-NO$_2$-phenylthio |

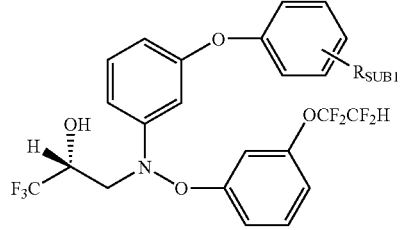

| Ex. No. | R$_{SUB1}$ |
|---|---|
| 1091 | 3-isopropyl |
| 1092 | 2-Cl, 3-Cl |
| 1093 | 3-CF$_3$O |
| 1094 | 4-F |
| 1095 | 4-CH$_3$ |
| 1096 | 2-F, 5-Br |
| 1097 | 4-Cl, 3-CH$_3$CH$_2$ |
| 1098 | 3-CH$_3$CH$_2$ |
| 1099 | 3-CH$_3$, 5-CH$_3$ |
| 1100 | 3-(CH$_3$)$_3$C |
| 1101 | 4-F, 3-CH$_3$ |
| 1102 | 3-Cl, 4-Cl |
| 1103 | 3,4-(CH$_2$)$_4$ |
| 1104 | 3-HCF$_2$CF$_2$O |
| 1105 | 3-CHF$_2$O |
| 1106 | 3-(CH$_3$)$_2$N |
| 1107 | 3-cyclopropyl |
| 1108 | 3-(2-furyl) |
| 1109 | 3-CF$_3$CF$_2$ |

EXAMPLE TABLE 10-continued

Substituted (2R)-3-[N-(aryl)-[(aryl)oxy]amino]-1,1,1-trifluoro-2-propanols.

| | |
|---|---|
| 1110 | 4-NH$_2$ |
| 1111 | 3-CH$_3$, 4-CH$_3$, 5-CH$_3$ |
| 1112 | 4-CH$_3$CH$_2$CH$_2$O |
| 1113 | 3-CF$_3$ |
| 1114 | 2-NO$_2$ |

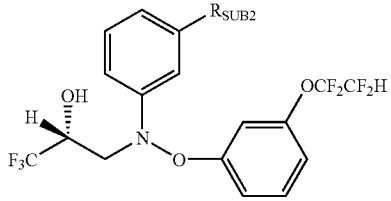

| Ex. No. | R$_{SUB2}$ |
|---|---|
| 1115 | 3-CF$_3$O-benzyloxy |
| 1116 | 3-CF$_3$-benzyloxy |
| 1117 | 3-F, 5-F-benzyloxy |
| 1118 | cyclohexylmethyleneoxy |
| 1119 | benzyloxy |
| 1120 | 3-CF$_3$, 5-CF$_3$-benzyloxy |
| 1121 | 4-CF$_3$O-benzyloxy |
| 1122 | 4-CH$_3$CH$_2$-benzyloxy |
| 1123 | isopropoxy |
| 1124 | 3-CF$_3$-benzyl |
| 1125 | isopropylthio |
| 1126 | cyclopentoxy |
| 1127 | 3-Cl-5-pyridinyloxy |
| 1128 | 3-CF$_3$S-benzyloxy |
| 1129 | 3-CH$_3$, 4-CH$_3$-benzyloxy |
| 1130 | 2-F, 3-CF$_3$-benzyloxy |
| 1131 | 3-F, 5-CF$_3$-benzyloxy |
| 1132 | 4-(CH$_3$)$_2$CH-benzyloxy |
| 1133 | 1-phenylethoxy |
| 1134 | 4-F, 3-CH$_3$-benzoyl |
| 1135 | 3-CF$_3$-phenyl |
| 1136 | 4-CH$_3$O-phenylamino |
| 1137 | cyclopropoxy |
| 1138 | 4-NO$_2$-phenylthio |

EXAMPLE TABLE 11

(2R)-3-[N-(aryl)-[(aryl)methyl]amino]-1,1-difluoro-1-chloro-2-propanols.

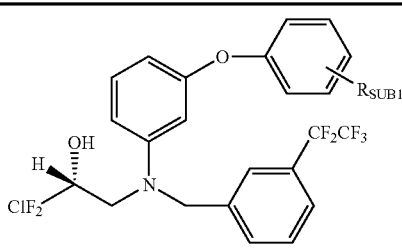

| Ex. No. | R$_{SUB1}$ |
|---|---|
| 1139 | 3-isopropyl |
| 1140 | 2-Cl, 3-Cl |
| 1141 | 3-CF$_3$O |
| 1142 | 4-F |
| 1143 | 4-CH$_3$ |
| 1144 | 2-F, 5-Br |
| 1145 | 4-Cl, 3-CH$_3$CH$_2$ |
| 1146 | 3-CH$_3$CH$_2$ |
| 1147 | 3-CH$_3$, 5-CH$_3$ |
| 1148 | 3-(CH$_3$)$_3$C |
| 1149 | 4-F, 3-CH$_3$ |
| 1150 | 3-Cl, 4-Cl |
| 1151 | 3,4-(CH$_2$)$_4$ |

EXAMPLE TABLE 11-continued (2R)-3-[N-(aryl)-[(aryl)methyl]amino]-1,1-difluoro-1-chloro-2-propanols.

| | |
|---|---|
| 1152 | 3-HCF$_2$CF$_2$O |
| 1153 | 3-CHF$_2$O |
| 1154 | 3-(CH$_3$)$_2$N |
| 1155 | 3-cyclopropyl |
| 1156 | 3-(2-furyl) |
| 1157 | 3-CF$_3$CF$_2$ |
| 1158 | 4-NH$_2$ |
| 1159 | 3-CH$_3$, 4-CH$_3$, 5-CH$_3$ |
| 1160 | 4-CH$_3$CH$_2$CH$_2$O |
| 1161 | 3-CF$_3$ |
| 1162 | 2-NO$_2$ |

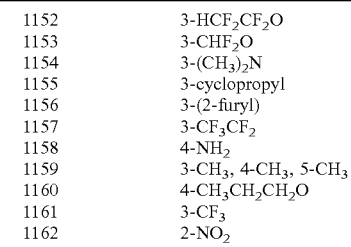

| Ex. No. | R$_{SUB2}$ |
|---|---|
| 1163 | 3-CF$_3$O-benzyloxy |
| 1164 | 3-CF$_3$-benzyloxy |
| 1165 | 3-F, 5-F-benzyloxy |
| 1166 | cyclohexylmethyleneoxy |
| 1167 | benzyloxy |
| 1168 | 3-CF$_3$, 5-CF$_3$-benzyloxy |
| 1169 | 4-CF$_3$O-benzyloxy |
| 1170 | 4-CH$_3$CH$_2$-benzyloxy |
| 1171 | isopropoxy |
| 1172 | 3-CF$_3$-benzyl |
| 1173 | isopropylthio |
| 1174 | cyclopentoxy |
| 1175 | 3-Cl-5-pyridinyloxy |
| 1176 | 3-CF$_3$S-benzyloxy |
| 1177 | 3-CH$_3$, 4-CH$_3$-benzyloxy |
| 1178 | 2-F, 3-CF$_3$-benzyloxy |
| 1179 | 3-F, 5-CF$_3$-benzyloxy |
| 1180 | 4-(CH$_3$)$_2$CH-benzyloxy |
| 1181 | 1-phenylethoxy |
| 1182 | 4-F, 3-CH$_3$-benzoyl |
| 1183 | 3-CF$_3$-phenyl |
| 1184 | 4-CH$_3$O-phenylamino |
| 1185 | cyclopropoxy |
| 1186 | 4-NO$_2$-phenylthio |

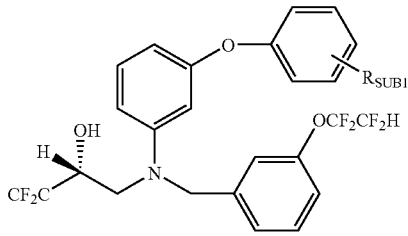

| Ex. No. | R$_{SUB1}$ |
|---|---|
| 1187 | 3-isopropyl |
| 1188 | 2-Cl, 3-Cl |
| 1189 | 3-CF$_3$O |
| 1190 | 4-F |
| 1191 | 4-CH$_3$ |
| 1192 | 2-F, 5-Br |
| 1193 | 4-Cl, 3-CH$_3$CH$_2$ |
| 1194 | 3-CH$_3$CH$_2$ |
| 1195 | 3-CH$_3$, 5-CH$_3$ |
| 1196 | 3-(CH$_3$)$_3$C |
| 1197 | 4-F, 3-CH$_3$ |
| 1198 | 3-Cl, 4-Cl |
| 1199 | 3,4-(CH$_2$)$_4$ |

EXAMPLE TABLE 11-continued (2R)-3-[N-(aryl)-[(aryl)methyl]amino]-1,1-difluoro-1-chloro-2-propanols.

| | |
|---|---|
| 1200 | 3-HCF$_2$CF$_2$O |
| 1201 | 3-CHF$_2$O |
| 1202 | 3-(CH$_3$)$_2$N |
| 1203 | 3-cyclopropyl |
| 1204 | 3-(2-furyl) |
| 1205 | 3-CF$_3$CF$_2$ |
| 1206 | 4-NH$_2$ |
| 1207 | 3-CH$_3$, 4-CH$_3$, 5-CH$_3$ |
| 1208 | 4-CH$_3$CH$_2$CH$_2$O |
| 1209 | 3-CF$_3$ |
| 1210 | 2-NO$_2$ |

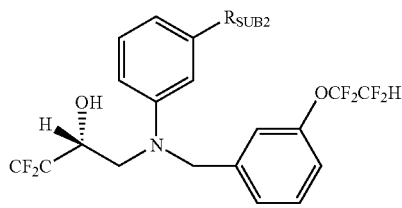

| Ex. No. | R$_{SUB2}$ |
|---|---|
| 1211 | 3-CF$_3$O-benzyloxy |
| 1212 | 3-CF$_3$-benzyloxy |
| 1213 | 3-F, 5-F-benzyloxy |
| 1214 | cyclohexylmethyleneoxy |
| 1215 | benzyloxy |
| 1216 | 3-CF$_3$, 5-CF$_3$-benzyloxy |
| 1217 | 4-CF$_3$O-benzyloxy |
| 1218 | 4-CH$_3$CH$_2$-benzyloxy |
| 1219 | isopropoxy |
| 1220 | 3-CF$_3$-benzyl |
| 1221 | isopropylthio |
| 1222 | cyclopentoxy |
| 1223 | 3-Cl-5-pyridinyloxy |
| 1224 | 3-CF$_3$S-benzyloxy |
| 1225 | 3-CH$_3$, 4-CH$_3$-benzyloxy |
| 1226 | 2-F, 3-CF$_3$-benzyloxy |
| 1227 | 3-F, 5-CF$_3$-benzyloxy |
| 1228 | 4-(CH$_3$)$_2$CH-benzyloxy |
| 1229 | 1-phenylethoxy |
| 1230 | 4-F, 3-CH$_3$-benzoyl |
| 1231 | 3-CF$_3$-phenyl |
| 1232 | 4-CH$_3$O-phenylamino |
| 1233 | cyclopropoxy |
| 1234 | 4-NO$_2$-phenylthio |

EXAMPLE TABLE 12

(2R)-3-[N,N'-(diaryl)amino]-1,1,1-trifluoro-2-propanols.

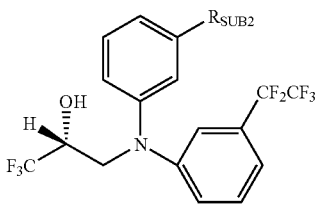

| Ex. No. | R$_{SUB1}$ |
|---|---|
| 1235 | 3-isopropyl |
| 1236 | 2-Cl, 3-Cl |
| 1237 | 3-CF$_3$O |
| 1238 | 4-F |
| 1239 | 4-CH$_3$ |
| 1240 | 2-F, 5-Br |
| 1241 | 4-Cl, 3-CH$_3$CH$_2$ |

EXAMPLE TABLE 12-continued (2R)-3-[N,N'-(diaryl)amino]-1,1,1-trifluoro-2-propanols.

| | |
|---|---|
| 1242 | 3-CH$_3$CH$_2$ |
| 1243 | 3-CH$_3$, 5-CH$_3$ |
| 1244 | 3-(CH$_3$)$_3$C |
| 1245 | 4-F, 3-CH$_3$ |
| 1246 | 3-Cl, 4-Cl |
| 1247 | 3,4-(CH$_2$)$_4$ |
| 1248 | 3-HCF$_2$CF$_2$O |
| 1249 | 3-CHF$_2$O |
| 1250 | 3-(CH$_3$)$_2$N |
| 1251 | 3-cyclopropyl |
| 1252 | 3-(2-furyl) |
| 1253 | 3-CF$_3$CF$_2$ |
| 1254 | 4-NH$_2$ |
| 1255 | 3-CH$_3$, 4-CH$_3$, 5-CH$_3$ |
| 1256 | 4-CH$_3$CH$_2$CH$_2$O |
| 1257 | 3-CF$_3$ |
| 1258 | 2-NO$_2$ |

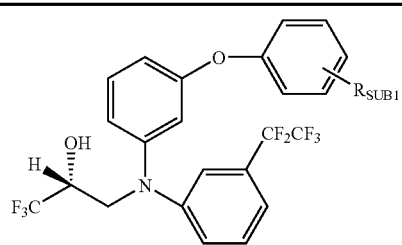

| Ex. No. | R$_{SUB2}$ |
|---|---|
| 1259 | 3-CF$_3$O-benzyloxy |
| 1260 | 3-CF$_3$-benzyloxy |
| 1261 | 3-F, 5-F-benzyloxy |
| 1262 | cyclohexylmethyleneoxy |
| 1263 | benzyloxy |
| 1264 | 3-CF$_3$, 5-CF$_3$-benzyloxy |
| 1265 | 4-CF$_3$O-benzyloxy |
| 1266 | 4-CH$_3$CH$_2$-benzyloxy |
| 1267 | isopropoxy |
| 1268 | 3-CF$_3$-benzyl |
| 1269 | isopropylthio |
| 1270 | cyclopentoxy |
| 1271 | 3-Cl-5-pyridinyloxy |
| 1272 | 3-CF$_3$S-benzyloxy |
| 1273 | 3-CH$_3$, 4-CH$_3$-benzyloxy |
| 1274 | 2-F, 3-CF$_3$-benzyloxy |
| 1275 | 3-F, 5-CF$_3$-benzyloxy |
| 1276 | 4-(CH$_3$)$_2$CH-benzyloxy |
| 1277 | 1-phenylethoxy |
| 1278 | 4-F, 3-CH$_3$-benzoyl |
| 1279 | 3-CF$_3$-phenyl |
| 1280 | 4-CH$_3$O-phenylamino |
| 1281 | cyclopropoxy |
| 1282 | 4-NO$_2$-phenylthio |

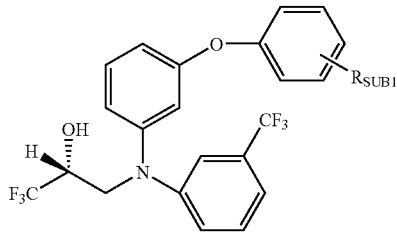

| Ex. No. | R$_{SUB1}$ |
|---|---|
| 1283 | 3-isopropyl |
| 1284 | 2-Cl, 3-Cl |
| 1285 | 3-CF$_3$O |
| 1286 | 4-F |
| 1287 | 4-CH$_3$ |
| 1288 | 2-F, 5-Br |
| 1289 | 4-Cl, 3-CH$_3$CH$_2$ |

EXAMPLE TABLE 12-continued (2R)-3-[N,N'-(diaryl)amino]-1,1,1-trifluoro-2-propanols.

| | |
|---|---|
| 1290 | 3-$CH_3CH_2$ |
| 1291 | 3-$CH_3$, 5-$CH_3$ |
| 1292 | 3-$(CH_3)_3C$ |
| 1293 | 4-F, 3-$CH_3$ |
| 1294 | 3-Cl, 4-Cl |
| 1295 | 3,4-$(CH_2)_4$ |
| 1296 | 3-$HCF_2CF_2O$ |
| 1297 | 3-$CHF_2O$ |
| 1298 | 3-$(CH_3)_2N$ |
| 1299 | 3-cyclopropyl |
| 1300 | 3-(2-furyl) |
| 1301 | 3-$CF_3CF_2$ |
| 1302 | 4-$NH_2$ |
| 1303 | 3-$CH_3$, 4-$CH_3$, 5-$CH_3$ |
| 1304 | 4-$CH_3CH_2CH_2O$ |
| 1305 | 3-$CF_3$ |
| 1306 | 2-$NO_2$ |

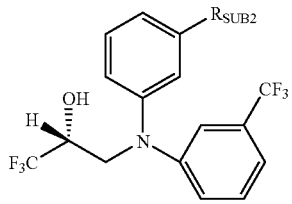

| Ex. No. | $R_{SUB2}$ |
|---|---|
| 1307 | 3-$CF_3$O-benzyloxy |
| 1308 | 3-$CF_3$-benzyloxy |
| 1309 | 3-F, 5-F-benzyloxy |
| 1310 | cyclohexylmethyleneoxy |
| 1311 | benzyloxy |
| 1312 | 3-$CF_3$, 5-$CF_3$-benzyloxy |
| 1313 | 4-$CF_3$O-benzyloxy |
| 1314 | 4-$CH_3CH_2$-benzyloxy |
| 1315 | isopropoxy |
| 1316 | 3-$CF_3$-benzyl |
| 1317 | isopropylthio |
| 1318 | cyclopentoxy |
| 1319 | 3-Cl-5-pyridinyloxy |
| 1320 | 3-$CF_3$S-benzyloxy |
| 1321 | 3-$CH_3$, 4-$CH_3$-benzyloxy |
| 1322 | 2-F, 3-$CF_3$-benzyloxy |
| 1323 | 3-F, 5-$CF_3$-benzyloxy |
| 1324 | 4-$(CH_3)_2CH$-benzyloxy |
| 1325 | 1-phenylethoxy |
| 1326 | 4-F, 3-$CH_3$-benzoyl |
| 1327 | 3-$CF_3$-phenyl |
| 1328 | 4-$CH_3$O-phenylamino |
| 1329 | cyclopropoxy |
| 1330 | 4-$NO_2$-phenylthio |

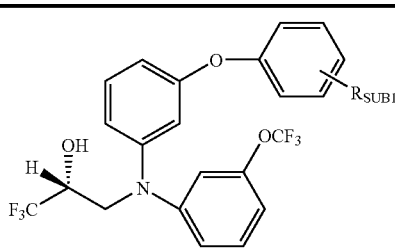

| Ex. No. | $R_{SUB1}$ |
|---|---|
| 1331 | 3-isopropyl |
| 1332 | 2-Cl, 3-Cl |
| 1333 | 3-$CF_3$O |
| 1334 | 4-F |
| 1335 | 4-$CH_3$ |
| 1336 | 2-F, 5-Br |
| 1337 | 4-Cl, 3-$CH_3CH_2$ |

EXAMPLE TABLE 12-continued (2R)-3-[N,N'-(diaryl)amino]-1,1,1-trifluoro-2-propanols.

| | |
|---|---|
| 1338 | 3-$CH_3CH_2$ |
| 1339 | 3-$CH_3$, 5-$CH_3$ |
| 1340 | 3-$(CH_3)_3C$ |
| 1341 | 4-F, 3-$CH_3$ |
| 1342 | 3-Cl, 4-Cl |
| 1343 | 3,4-$(CH_2)_4$ |
| 1344 | 3-$HCF_2CF_2O$ |
| 1345 | 3-$CHF_2O$ |
| 1346 | 3-$(CH_3)_2N$ |
| 1347 | 3-cyclopropyl |
| 1348 | 3-(2-furyl) |
| 1349 | 3-$CF_3CF_2$ |
| 1350 | 4-$NH_2$ |
| 1351 | 3-$CH_3$, 4-$CH_3$, 5-$CH_3$ |
| 1352 | 4-$CH_3CH_2CH_2O$ |
| 1353 | 3-$CF_3$ |
| 1354 | 2-$NO_2$ |

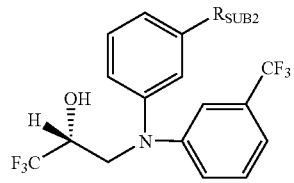

| Ex. No. | $R_{SUB2}$ |
|---|---|
| 1355 | 3-$CF_3$O-benzyloxy |
| 1356 | 3-$CF_3$-benzyloxy |
| 1357 | 3-F, 5-F-benzyloxy |
| 1358 | cyclohexylmethyleneoxy |
| 1359 | benzyloxy |
| 1360 | 3-$CF_3$, 5-$CF_3$-benzyloxy |
| 1361 | 4-$CF_3$O-benzyloxy |
| 1362 | 4-$CH_3CH_2$-benzyloxy |
| 1363 | isopropoxy |
| 1364 | 3-$CF_3$-benzyl |
| 1365 | isopropylthio |
| 1366 | cyclopentoxy |
| 1367 | 3-Cl-5-pyridinyloxy |
| 1368 | 3-$CF_3$S-benzyloxy |
| 1369 | 3-$CH_3$, 4-$CH_3$-benzyloxy |
| 1370 | 2-F, 3-$CF_3$-benzyloxy |
| 1371 | 3-F, 5-$CF_3$-benzyloxy |
| 1372 | 4-$(CH_3)_2CH$-benzyloxy |
| 1373 | 1-phenylethoxy |
| 1374 | 4-F, 3-$CH_3$-benzoyl |
| 1375 | 3-$CF_3$-phenyl |
| 1376 | 4-$CH_3$O-phenylamino |
| 1377 | cyclopropoxy |
| 1378 | 4-$NO_2$-phenylthio |

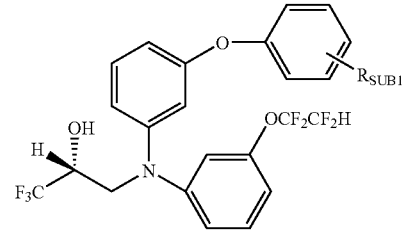

| Ex. No. | $R_{SUB1}$ |
|---|---|
| 1379 | 3-isopropyl |
| 1380 | 2-Cl, 3-Cl |
| 1381 | 3-$CF_3$O |
| 1382 | 4-F |
| 1383 | 4-$CH_3$ |
| 1384 | 2-F, 5-Br |
| 1385 | 4-Cl, 3-$CH_3CH_2$ |
| 1386 | 3-$CH_3CH_2$ |

EXAMPLE TABLE 12-continued (2R)-3-[N,N'-(diaryl)amino]-1,1,1-trifluoro-2-propanols.

| | |
|---|---|
| 1387 | 3-$CH_3$, 5-$CH_3$ |
| 1388 | 3-$(CH_3)_3$C |
| 1389 | 4-F, 3-$CH_3$ |
| 1390 | 3-Cl, 4-Cl |
| 1391 | 3,4-$(CH_2)_4$ |
| 1392 | 3-$HCF_2CF_2O$ |
| 1393 | 3-$CHF_2O$ |
| 1394 | 3-$(CH_3)_2N$ |
| 1395 | 3-cyclopropyl |
| 1396 | 3-(2-furyl) |
| 1397 | 3-$CF_3CF_2$ |
| 1398 | 4-$NH_2$ |
| 1399 | 3-$CH_3$, 4-$CH_3$, 5-$CH_3$ |
| 1400 | 4-$CH_3CH_2CH_2O$ |
| 1401 | 3-$CF_3$ |
| 1402 | 2-$NO_2$ |

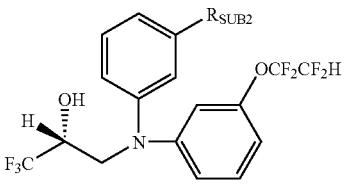

| Ex. No. | $R_{SUB2}$ |
|---|---|
| 1403 | 3-$CF_3$O-benzyloxy |
| 1404 | 3-$CF_3$-benzyloxy |
| 1405 | 3-F, 5-F-benzyloxy |
| 1406 | cyclohexylmethyleneoxy |
| 1407 | benzyloxy |
| 1408 | 3-$CF_3$, 5-$CF_3$-benzyloxy |
| 1409 | 4-$CF_3$O-benzyloxy |
| 1410 | 4-$CH_3CH_2$-benzyloxy |
| 1411 | isopropoxy |
| 1412 | 3-$CF_3$-benzyl |
| 1413 | isopropylthio |
| 1414 | cyclopentoxy |
| 1415 | 3-Cl-5-pyridinyloxy |
| 1416 | 3-$CF_3$S-benzyloxy |
| 1417 | 3-$CH_3$, 4-$CH_3$-benzyloxy |
| 1418 | 2-F, 3-$CF_3$-benzyloxy |
| 1419 | 3-F, 5-$CF_3$-benzyloxy |
| 1420 | 4-$(CH_3)_2$CH-benzyloxy |
| 1421 | 1-phenylethoxy |
| 1422 | 4-F, 3-$CH_3$-benzoyl |
| 1423 | 3-$CF_3$-phenyl |
| 1424 | 4-$CH_3$O-phenylamino |
| 1425 | cyclopropoxy |
| 1426 | 4-$NO_2$-phenylthio |

Bioassays

CETP Activity In Vitro

Assay of CETP Inhibition Using Purified Components (Reconstituted Buffer Assay)

The ability of compounds to inhibit CETP activity was assessed using an in vitro assay that measured the rate of transfer of radiolabeled cholesteryl ester ([$^3$H]CE) from HDL donor particles to LDL acceptor particles. Details of the assay are provided by Glenn, K. C. et al. (Glenn and Melton, "Quantification of Cholesteryl Ester Transfer Protein (CETP): A) CETP Activity and B) Immunochemical Assay of CETP Protein," Meth. Enzymol., 263, 339–351 (1996)). Human recombinant CETP can be obtained from the serum-free conditioned medium of CHO cells transfected with a cDNA for CETP and purified as described by Wang, S. et al. (*J. Biol. Chem.* 267, 17487–17490 (1992)). To measure CETP activity, [$^3$H]CE-labeled-HDL, LDL, CETP and assay buffer (50 mM tris(hydroxymethyl)aminomethane, pH 7.4; 150 mM sodium chloride; 2 mM ethylenediamine-tetraacetic acid (EDTA); 1% bovine serum albumin) were incubated in a final volume of 200 μL, for 2 hours at 37° C. in 96 well plates. Inhibitors were included in the assay by diluting from a 10 mM DMSO stock solution into 16% (v/v) aqueous DMSO so that the final concentration of inhibitor was 800 μM. The inhibitors were then diluted 1:1 with CETP in assay buffer, and then 25 μL of that solution was mixed with 175 μL of lipoprotein pool for assay. Following incubation, LDL was differentially precipitated by the addition of 50 μL of 1% (w/v) dextran sulfate/0.5 M magnesium chloride, mixed by vortex, and incubated at room temperature for 10 minutes. A potion of the solution (200 μL) was transferred to a filter plate (Millipore). After filtration, the radioactivity present in the precipitated LDL was measured by liquid scintillation counting. Correction for non-specific transfer or precipitation was made by including samples that do not contain CETP. The rate of [$^3$H]CE transfer using this assay was linear with respect to time and CETP concentration, up to 25–30% of [$^3$H]CE transferred.

The potency of test compounds was determined by performing the above described assay in the presence of varying concentrations of the test compounds and determining the concentration required for 50% inhibition of transfer of [$^3$H]CE from HDL to LDL. This value was defined as the $IC_{50}$. The $IC_{50}$ values determined from this assay are accurate when the $IC_{50}$ is greater than 10 nM. In the case where compounds have greater inhibitory potency, accurate measurements of $IC_{50}$ may be determined using longer incubation times (up to 18 hours) and lower final concentrations of CETP (<50 nM).

Examples of $IC_{50}$ values determined by these methods are summarized in Table 9.

Assay of CETP Inhibition in Human Plasma

Blood was obtained from healthy volunteers, recruited from the personnel of Monsanto Company, Saint Louis, Mo. Blood was collected in tubes containing EDTA (EDTA plasma pool). The EDTA human plasma pool, previously stored at −20° C., was thawed at room temperature and centrifuged for 5 minutes to remove any particulate matter. Tritiated HDL, radiolabeled in the cholesteryl ester moiety ([$^3$H]CE-HDL) as described by Morton and Zilversmit (J. Biol. Chem., 256, 11992–95 (1981)), was added to the plasma to a final concentration of 25 μg/mL cholesterol. Equal volumes (396 μL) of the plasma containing the [$^3$H]CE-HDL were added by pipette into micro tubes (Titertube®, Bio-Rad laboratories, Hercules, Calif.). Inhibitor compounds, dissolved as 20–50 mM stock solutions in DMSO, were serially diluted in DMSO (or an alternative solvent in some cases, such as dimethylformamide or ethanol). Four μL of each of the serial dilutions of inhibitor compounds or DMSO alone were then added to each of the tubes containing plasma (396 μL). After mixing, triplicate aliquots (100 μL) from each plasma tube were then transferred to wells of 96-well round-bottomed polystyrene microtiter plates (Corning, Corning, N.Y.). Plates were sealed with plastic film and incubated at 37° C. for 4 hours. "Test" samples contained plasma with dilutions of inhibitor compounds. "Control" samples contained plasma with DMSO diluted to the same concentration as the test samples, but without inhibitor. "Blank" samples were prepared as "control" samples, but were left in the micro tubes at 4° C. for the 4 hour incubation and were then added to the microtiter wells at the end of the incubation period. VLDL and LDL were precipitated by the addition of 10 μL of precipitating reagent (1% (w/v) dextran sulfate (Dextralip50)/0.5 M magnesium chloride, pH 7.4) to all wells. The wells were mixed on a plate mixer and then incubated at ambient temperature for 10 min. The plates were then centrifuged at 1000×g for 30 min at 10° C. The supernatants (50 µL) from each well were then transferred to Picoplate™ 96 plate wells (Packard, Meriden, Conn.) containing Microscint™-40 (Packard, Meriden, Conn.). The plates were heat-sealed (TopSeal™-P, Packard, Meriden, Conn.) according to the manufacturer's directions and mixed for 30 min. Radioactivity was measured on a microplate scintillation counter (TopCount, Packard, Meriden, Conn.). The maximum percentage transfer in the control wells (% transfer) was determined using the following equation:

$$\% \text{ Transfer} = \frac{[dpm_{blank} - dpm_{control}] \times 100}{dpm_{blank}}$$

The percentage of transfer relative to the control (% control) was determined in the wells containing inhibitor compounds was determined as follows:

$$\% \text{ Control} = \frac{[dpm_{blank} - dpm_{test}] \times 100}{dpm_{blank} - dpm_{control}}$$

$IC_{50}$ values were then calculated from plots of % control versus concentration of inhibitor compound. $IC_{50}$ values were determined as the concentration of inhibitor compound inhibiting transfer of [$^3$H]CE from the supernatant [$^3$H]CE-HDL to the precipitated VLDL and LDL by 50% compared to the transfer obtained in the control wells.

Examples of plasma $IC_{50}$ values determined by these methods are summarized in Table 10.

Assay of CETP Inhibition In Vivo.

Inhibition of CETP activity by a test compound can be determined by administering the compound to an animal by intravenous injection or oral gavage, measuring the amount of transfer of tritium-labeled cholesteryl ester ([$^3$H]CE) from HDL to VLDL and LDL particles, and comparing this amount of transfer with the amount of transfer observed in control animals.

Male golden Syrian hamsters were maintained on a diet of chow containing 0.24% cholesterol for at least two weeks prior to the study. For animals receiving intravenous dosing immediately before the experiment, animals were anesthetized with pentobarbital. Anesthesia was maintained throughout the experiment. In-dwelling catheters were inserted into the jugular vein and carotid artery. At the start of the experiment all animals received 0.2 mL of a solution containing [$^3$H]CE-HDL into the jugular vein. [$^3$H]CE-HDL is a preparation of human HDL containing tritium-labeled cholesteryl ester, and was prepared according to the method of Glenn et al. (Meth. Enzymol., 263, 339–351 (1996)). Test compound was dissolved as a 80 mM stock solution in vehicle (2% ethanol: 98% PEG 400, Sigma Chemical Company, St. Louis, Mo., USA) and administered either by bolus injection or by continuous infusion. Two minutes after the [$^3$H]CE-HDL dose was administered, animals received 0.1 mL of the test solution injected into the jugular vein. Control animals received 0.1 mL of the intravenous vehicle solution without test compound. After 5 minutes, the first blood samples (0.5 mL) were taken from the carotid artery and collected in standard microtainer tubes containing ethylenediamine tetraacetic acid. Saline (0.5 mL) was injected to flush the catheter and replace blood volume. Subsequent blood samples were taken at two hours and four hours by the same method. Blood samples were mixed well and kept on ice until the completion of the experiment. Plasma was obtained by centrifugation of the blood samples at 4° C. The plasma (50 µL) was treated with 5 µL of precipitating reagent (dextran sulfate, 10 g/L; 0.5 M magnesium chloride) to remove VLDL/LDL. After centrifugation, the resulting supernatant (25 µL) containing the HDL was analyzed for radioactivity using a liquid scintillation counter.

The percentage [$^3$H]CE transferred from HDL to LDL and VLDL (% transfer) was calculated based on the total radioactivity in equivalent plasma samples before precipitation. Typically, the amount of transfer from HDL to LDL and VLDL in control animals was 20% to 35% after 4 hours. The polyethylene glycol vehicle was determined to have no effect on CETP activity in this model.

Alternatively, conscious, non-anesthetized animals received an oral gavage dose of test compound as a suspension in 0.1% methyl cellulose in water. At a time determined for each compound at which plasma levels of the test substance reached their peak ($C_{max}$) after oral dosing, the animals were anesthetized with pentobarbital and then dosed with 0.2 mL of a solution containing [$^3$H]CE-HDL into the jugular vein as described above. Control animals received 0.25 mL of the vehicle solution without test compound by oral gavage. After 4 hours, the animals were sacrificed, blood samples were collected, and the percentage [$^3$H]CE transferred from HDL to LDL and VLDL (% transfer) assayed, as described above. The aqueous methyl cellulose vehicle was determined to have no effect on CETP activity in this model. Results from testing in this model are summarized in Table 11.

Alternatively, inhibition of CETP activity by a test compound was determined by administering the compound to mice which have been selected for expression of human CETP (hCETP) by transgenic manipulation (hCETP mice). Test compounds were administered by intravenous injection, or oral gavage and the amount of transfer of tritium-labeled cholesteryl ester ([$^3$H]CE) from HDL to VLDL and LDL particles was determined, and compared to the amount of transfer observed in control animals. C57B1/6 mice that were homozygous for the HCETP gene were maintained on a high fat chow diet, such as TD 88051, as described by Nishina et al. (J Lipid Res., 31, 859–869 (1990)) for at least two weeks prior to the study. Mice received an oral gavage dose of test compound as a suspension in 0.1% methyl cellulose in water or an intravenous bolus injection of test compound in 10% ethanol and 90% polyethylene glycol. Control animals received the vehicle solution without test compound by oral gavage or by an intravenous bolus injection. At the start of the experiment all animals received 0.05 mL of a solution containing [$^3$H]CE-HDL into the tail vein. [$^3$H]CE-HDL is a preparation of human HDL containing tritium-labeled cholesteryl ester, and was prepared according to the method of Glenn et al. (Meth. Enzymol., 263, 339–351 (1996)). After 30 minutes, the animals were exsanguinated and blood collected in standard microtainer tubes containing ethylenediamine tetraacetic acid. Blood samples were mixed well and kept on ice until the completion of the experiment. Plasma was obtained by centrifugation of the blood samples at 4° C. The plasma was separated and analyzed by gel filtration chromatography and the relative proportion of [$^3$H]CE in the VLDL, LDL and HDL regions was determined.

The percentage [$^3$H]CE transferred from HDL to LDL and VLDL (% transfer) was calculated based on the total radioactivity in equivalent plasma samples before precipitation. Typically, the amount of transfer from HDL to LDL and VLDL in control animals was 20% to 35% after 30 min. The polyethylene glycol and the aqueous methyl cellulose vehicles were determined to have no effect on CETP activity in this model. Results from testing in this model are summarized in Table 12.

Assay of Plasma HDL Elevation In Vivo.

Syrian Golden hamsters were made hypercholesterolemic by feeding cholesterol supplemented chow for a minimum of two weeks, as described above. Test compounds were administered orally in selected aqueous or oil based vehicles for up to 1 week. Serum was obtained and analyzed by precipitation or size exclusion chromatography for the relative abundance of VLDL, LDL and HDL. Results from testing in this model are summarized in Table 13.

Alternatively, a strain of C57b1 mouse was made to transgenicaly express human CETP. Plasma concentrations of hCETP ranged from 2–20 μg/ml. The hCETP mice were made hypercholesterolemic by feeding cholesterol and fat supplemented chow for a minimum of two weeks, as described above. Test compounds were administered orally in selected aqueous or oil based vehicles for up to 1 week. Serum was obtained and analyzed by size exclusion chromatography for the relative abundance of VLDL, LDL and HDL. Results from testing in this model are summarized in Table 14.

Alternatively, cynomologous monkeys were maintained on a normal chow diet. The compound corresponding to example 8 was dissolved in a corn oil based vehicle and administered by oral gavage at 10 mpk q.d. for up to 11 days. Plasma levels of drug were detected throughout the experiment in treated animals at ranges of 0.1–1.5 μg/mL. Periodically, plasma samples were taken and analyzed for total cholesterol and HDL. After seven days, the treated animals exhibited a 2% increase in HDL and a 5% increase in total cholesterol, relative to vehicle-treated controls.

Alternatively, rabbits were maintained on a normal chow diet. The compound corresponding to example 8 was dissolved in a vehicle of ethanol:propylene glycol (1.5:18) and administered by Alzet pump at 30 mg/day/animal for up to 14 days. Plasma concentrations of drug were detected throughout the duration of the pump infusion in treated animals and averaged 1.2 μg/mL. Periodically, plasma samples were taken and analyzed for triglycerides, total cholesterol, and HDL. After fourteen days, the treated animals exhibited a 12% decrease in HDL, a 19% decrease in total cholesterol, as well as a 17% increase in triglycerides, compared to pre-dose levels.

TABLE 9

Inhibition of CETP Activity by Examples in Reconstituted Buffer Assay.

| Ex. No. | IC$_{50}$ (μM) |
| --- | --- |
| 8 | 0.0008 |
| 11 | 0.001 |
| 19 | 0.004 |
| 9 | 0.008 |
| 10 | 0.012 |
| 2 | 0.014 |
| 4 | 0.014 |
| 20 | 0.027 |
| 22 | 0.027 |
| 12 | 0.034 |
| 14 | 0.04 |
| 18 | 0.044 |
| 16 | 0.049 |
| 43 | 0.058 |
| 23 | 0.066 |
| 34 | 0.076 |
| 41 | 0.086 |
| 21 | 0.11 |
| 13 | 0.13 |
| 1 | 0.14 |
| 33 | 0.15 |
| 38 | 0.18 |
| 36 | 0.20 |
| 37 | 0.21 |
| 40 | 0.23 |
| 35 | 0.28 |
| 24 | 0.33 |
| 42 | 0.38 |
| 27 | 0.44 |
| 26 | 0.53 |
| 29 | 0.72 |
| 3 | 0.76 |
| 28 | 0.86 |
| 32 | 1.2 |
| 25 | 1.4 |
| 39 | 1.6 |
| 15 | 1.6 |
| 30 | 2.7 |
| 33B | 3.2 |
| 5 | 3.4 |
| 31 | 3.5 |
| 7 | 4.9 |
| 44 | 6.8 |
| 17 | 18 |
| 6 | 68 |
| 44A | >50 |

TABLE 10

Inhibition of CETP Activity by Examples in Human Plasma Assay.

| Ex. No. | IC$_{50}$ (μM) |
| --- | --- |
| 8 | 0.049 |
| 11 | 0.072 |
| 10 | 0.11 |
| 22 | 0.14 |
| 19 | 0.19 |
| 20 | 0.3 |
| 18 | 0.44 |
| 14 | 0.59 |
| 9 | 0.62 |
| 2 | 0.65 |
| 4 | 0.65 |
| 16 | 0.77 |
| 12 | 0.79 |
| 34 | 1.4 |
| 43 | 1.5 |
| 23 | 2.0 |
| 1 | 5.6 |
| 41 | 7.2 |
| 42 | 11 |
| 3 | 20 |

TABLE 11

Inhibition of CETP-mediated Transfer in Hamster

| Ex. No. | Single Oral Dose | % Inhibition of Transfer |
|---|---|---|
| 8 | 10 mpk | 35 |

TABLE 12

Inhibition of CETP-mediated Transfer in hCETP Mice.

| Ex. No. | Single Oral Dose | % Inhibition of Transfer |
|---|---|---|
| 8 | 60 mpk | 40 |

TABLE 13

Change in Lipoprotein Profile in Hamster.

| Ex. No. | Oral Dose qd, 5 days | % Change in Lipoprotein Profile | | |
|---|---|---|---|---|
| | | HDL | LDL | VLDL |
| 8 | 30 mpk | 12 | −12 | −22 |

TABLE 14

Change in Lipoprotein Profile in hCETP Mice.

| Ex. No. | Oral Dose qd, 5 days | % Change in Lipoprotein Profile | | |
|---|---|---|---|---|
| | | HDL | LDL | VLDL |
| 8 | 30 mpk | 12 | 20 | — |

We claim:

1. A compound of Formula I:

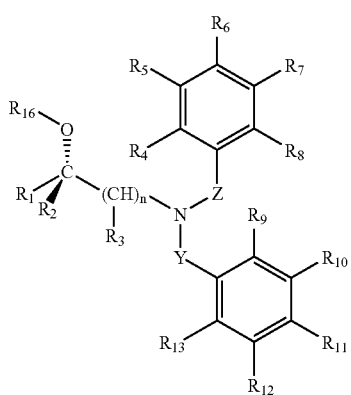

(I)

or a pharmaceutically acceptable salt thereof, wherein;
$R_{16}$ is bonded together with a substituent selected from the group consisting of $R_4$, $R_8$, $R_9$, and $R_{13}$ to form a heterocyclyl ring having from 6 through 10 members;
n is 1 or 2;
$R_1$ is haloalkyl or haloalkoxyalkyl with the proviso that $R_1$ is selected to have the highest Cahn-Ingold-Prelog stereochemical system ranking of three groups bonded to the hydroxy-substituted carbon to which $R_1$ and $R_2$ are attached in radical Ia

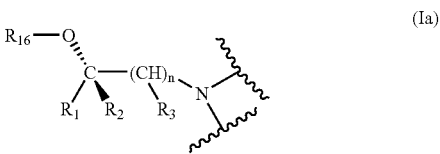

(Ia)

which radical Ia is a fragment of Formula I;
$R_2$ is selected from the group consisting of hydrido, aryl, aralkyl, elkyl, alkenyl, alkenyloxyalkyl, haloalkyl, haloalkenyl, halocycloalkyl, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl;
$R_3$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamido, and carboxamidoalkyl;
Y is a bond or $(C(R_{14})_2)_q$ wherein q is 1 or 2;
Z is a bond or $(C(R_{15})_2)_q$ wherein q is 1 or 2;
$R_{14}$ and $R_{15}$ are independently hydrido or alkyl;
$R_4$, $R_8$, $R_9$, and $R_{13}$ are independently selected from the group consisting of hydrido, halo, haloalkyl, and alkyl unless $R_4$ is bonded together with $R_{16}$ or $R_8$ is bonded together with $R_{16}$ or $R_9$ is bonded together with $R_{16}$ or $R_{13}$ is bonded together with $R_{16}$;
$R_5$, $R_6$, $R_7$, $R_{10}$, $R_{11}$, and $R_{12}$ are independently selected from the group consisting of hydrido, perhaloaryloxy, alkanoylalkyl, alkanoylalkoxy, alkanoyloxy, N-aryl-N-alkylamino, heterocyclylalkoxy, heterocyclylthio, hydroxyalkoxy, carboxaridoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, alkylamino, alkylthio, arylamino, aralkylamino, arylthio, arylthioalkyl, alkylsulfonyl, alkylsulfonamido, monoarylamidosulfonyl, arylsulfonyl, heteroarylthio, heteroarylsulfonyl, heterocyclylsulfonyl, heterocyclylthio, alkenoyl, alkenoyl, aroyl, heteroaroyl, aralkanoyl, heteroaralkanoyl, haloalkanoyl, alkyl, alkynyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;
with the proviso that at least one of $R_4$, $R_5$, $R_6$, $R_7$, and $R_8$ is not hydrido or with the proviso that at least one of $R_9$, $R_{10}$, $R_{11}$, $R_{12}$, and $R_{13}$ is not hydrido.

2. Compound of claim 1 or a pharmaceutically acceptable saltthereof, wherein at least one of $R_4$, $R_5$, $R_6$, $R_7$, and $R_8$ is not hydrido and at least one of $R_9$, $R_{14}$, $R_{11}$, $R_{12}$, and $R_{13}$ is not hydrido.

3. Compound of claim 2 or a pharmaceutically acceptable salt thereof, wherein;

$R_{16}$ is bonded together with $R_4$ or $R_9$ to form a heterocyclyl ring having from 6 through 8 members;

n is 1 or 2;

$R_1$ is haloalkyl or haloalkoxyalkyl with the proviso that $R_1$ is selected to have the highest Cahn-Ingold-Prelog stereochemical system ranking of said three groups bonded to the hydroxy-substituted carbon to which $R_1$ and $R_2$ are attached in said fragment of the Formula I and with the further proviso that said haloalkyl has two or more halo substituents;

$R_2$ is hydrido;

$R_3$ is hydrido;

Y is selected from the group consisting of a bond, $CH_2$, and $CH_2CH_2$;

Z is selected from the group consisting of a bond, $CH_2$, and $CH_2CH_2$;

$R_4$ is hydrido or halo unless $R_4$ is bonded together with $R_{16}$;

$R_9$ is hydrido or halo unless $R_9$ is bonded together with $R_{16}$;

$R_8$ and $R_{13}$ are independently hydrido or halo;

$R_5$, $R_6$, $R_7$, $R_{14}$, $R_{11}$, and $R_{12}$ are independently selected from the group consisting of hydrido, perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-arylcarboxamidoalkoxy, cycloalkylcarbonyl, cyanoalkoxy, heterocyclylcarbonyl, heteroaralkoxy, heterocyclyloxy, aralkylaryl, aralkyl, haloalkylthio, alkoxy, cycloalkoxy, cycloalkylalkoxy, alkylamino, alkylthio, arylamino, arylthio, arylsulfonyl, heteroarylthio, heteroarylsulfonyl, aroyl, alkyl, cycloalkyl, cycloalkylalkanoyl, halo, haloalkyl, haloalkoxy, hydroxyaloalkyl, hydroxyhaloalkoxy, aryl, arylaxy, aralkoxy, saturated heterocyclyl, heteroaaryl, heteroaryloxyalkyl, and heteroaryloxy;

with the proviso that at least one of $R_4$, $R_5$, $R_6$, $R_7$, and $R_8$ is not hydrido and with the further proviso that at least one of $R_9$, $R_{10}$, $R_{11}$, $R_{12}$, and $R_{13}$ is not hydrido.

4. Compound of claim 3 or pharmaceutically acceptable salts thereof, wherein;

$R_{16}$ is bonded together with $R_4$ or $R_9$ to form a heterocyclyl ring having 6 or 7 members;

n is 1;

$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;

$R_2$ is hydrido;

$R_3$ is hydrido;

Y is $CH_2$ or $CH_2CH_2$;

Z is a bond;

$R_4$ is hydrido or fluoro unless $R_4$ is bonded together with $R_{16}$;

$R_9$ is hydrido or fluoro unless $R_9$ is bonded together with $R_{16}$;

$R_8$ and $R_{13}$ are independently hydrido or fluoro;

$R_7$ and $R_{12}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, difluoromethoxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2.5-difluorophenoxv. 3,5-dimethoxvphenoxv, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-triuluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$, are independently selected from the group consisting of chloro, fluoro, hydrido, pentafluoroethyl, 1,1,2,2-tetrafluoroethoxy, trifluoromethyl, and trifluoromethoxy;

$R_5$ and $R_{10}$ are independently selected from the group consisting of hydrido, fluoro, and trifluoromethyl.

5. Compound of claim 4 or a pharmaceutically acceptable salt thereof, wherein;

$R_{16}$ is bonded together with $R_4$ or $R_9$ to form a 6-membered heterocyclyl ring;

n is 1;

$R_1$ is selected from the group consisting of trifluoromethyl, difluoromethyl, chlorodifluoromethyl, and pentafluoroethyl;

$R_2$ is hydrido;

$R_3$ is hydrido;

Y is $CH_2$;

Z is a bond;

$R_4$ is hydrido or fluoro unless $R_4$ is bonded together with $R_{16}$;

$R_9$ is hydrido or fluoro unless $R_9$ is bonded together with $R_{16}$;

$R_8$ and $R_{13}$ are independently hydrido or fluoro;

$R_7$ and $R_{12}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-difluorophenoxy, 2,4-dichorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 4-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 4-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methyl benxyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-triluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrido, pentafluoroethyl, 1,1,2,2-tetrafluoroethoxy, and trifluoromethyl;

$R_5$ and $R_{10}$ are independently selected from the group consisting of hydrido, fluoro, and trifluoromethyl.

6. Compound of claim 1 of Formula II:

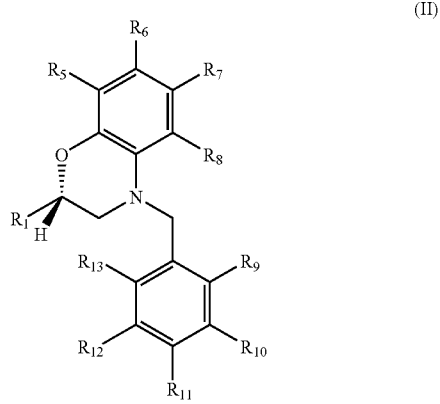

(II)

pharmaceutically acceptable salt thereof, wherein;

$R_1$ is haloalkoxyalkyl or haloalkyl with the proviso that said haloalkyl has two or more halo substituents;

$R_8$, $R_9$, and $R_{13}$ are independently hydrido or halo;

R$_5$, R$_6$, R$_7$, R$_{10}$, R$_{11}$, and R$_{12}$ are independently selected from the group consisting of hydrido, perhaloaryloxy, N-aryll-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, heteroaralkoxy, aralkyl, haloalkylthio, alkoxy, cycloalkoxy, cycloalkylalkoxy, alkylthio, arylamino, arylthio, arylsulfonyl, aroyl, alkyl, cycloalkyl, cycloalkylalkanoyl, halo, haloalkyl, haloalkoxy, hydroxyhaloalkyl, hydroxyhaloalkoxy, aryl, aryloxy, aralkoxy, heteroaryl, heteroaryloxyalkyl, and heteroaryloxy;

with the proviso that at least one of R$_9$, R$_{10}$, R$_{11}$, R$_{12}$, and R$_{13}$ is not hydrido.

7. Compound of claim 6 or a pharmaceutically acceptable salt thereof, wherein;

R$_1$ is trifluoromethyl;

R$_8$, R$_9$, and R$_{13}$ are independently hydrido or fluoro;

R$_7$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoroethoxybenzyl oxy, 3-trifluoromethoxyphenoxy, 3-trifluoromethylbenzyloxy, and 3-trifluoromethylthiophenoxy;

R$_{12}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

R$_5$, R$_6$, R$_{10}$, and R$_{11}$, are independently hydrido or fluoro.

8. Compound of claim 7 or a pharmaceutically acceptable salt thereof, wherein;

R$_1$ is trifluoromethyl;

R$_8$, R$_9$, and R$_{13}$ are independently hydrido or fluoro;

R$_7$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

R$_{12}$ is selected from the group consisting of 1,1,2,2-tetrafluoroethoxy, pentafluoroethyl, and trifluoromethyl;

R$_5$, R$_6$, R$_{10}$, and R$_{11}$, are independently hydrido or fluoro.

9. Compound of claim 1 or a pharmaceutically acceptable salt thereof, wherein said compound is a compound of Formula III:

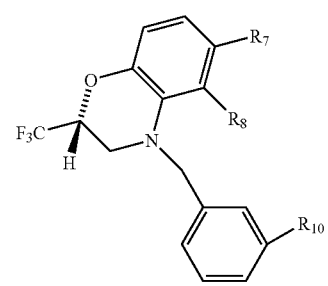

(III)

wherein R$_7$, R$_8$, and R$_{10}$ are selected to form a compound selected from the group consisting of;

R$_7$ is 4-chloro-3-ethylphenoxy, R$_8$ is hydrido, and R$_{10}$ is 1,1,2,2-tetrafluoroethoxy;

R$_7$ is phenoxy, R$_8$ is hydrido, and R$_{10}$ is 1,1,2,2-tetrafluoroethoxy;

R$_7$ is 4-chloro-3-ethylphenoxy, R$_8$ is hydrido, and R$_{10}$ is pentafluoroethyl;

R$_7$ is phenoxy, R$_8$ is hydrido, and R$_{10}$ is pentafluoroethyl;

R$_7$ is 4-chloro-3-ethylphenoxy, R$_8$ is hydrido, and R$_{10}$ is trifluoromethyl;

R$_7$ is phenoxy, R$_8$ is hydrido, and R$_{10}$ is trifluoromethyl;

R$_7$ is 4-chloro-3-ethylphenoxy, R$_8$ is fluoro, and R$_{10}$ is 1,1,2,2-tetrafluoroethoxy;

R$_7$ is 4-chloro-3-ethylphenoxy, R$_8$ is hydrido, and R$_{10}$ is 2-furyl; and R$_7$ is 4-chloro-3-ethylphenoxy, R$_8$ is hydrido, and R$_{10}$ is trifluoromethylthio.

10. A compound of claim 1 or a pharmaceutically acceptable salt thereof, wherein said compound is a compound of Formula IV:

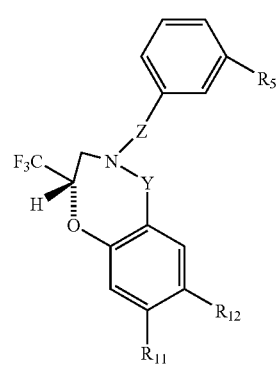

(IV)

wherein R$_5$, R$_{11}$, R$_{12}$, Y, and Z are selected to form a compound selected from the group consisting of;

R$_5$ is 4-chloro-3-ethylphenoxy, R$_{11}$ is trifluoromethyl, R$_{12}$ is hydrido, Y is methylene, and Z is a bond;

R$_5$ is 4-chloro-3-ethylphenoxy, R$_{11}$ is hydrido, R$_{12}$ is trifluoromethyl, Y is methylene, and Z is a bond;

R$_5$ is 4-chloro-3-ethylphenoxy, R$_{11}$ is trifluoromethyl, R$_{12}$ is hydrido, Y is a bond, and Z is a bond; and R$_5$ is 4-chloro-3-ethylphenoxy, R$_{11}$ is hydrido, R$_{12}$ is trifluoromethyl, Y is a bond, and Z is a bond.

11. A pharmaceutical composition comprising a therapeutically effective amount of a compound or a pharmaceutically acceptable salt thereof, together with a pharmaceutically acceptable carrier, said compound being of Formula I:

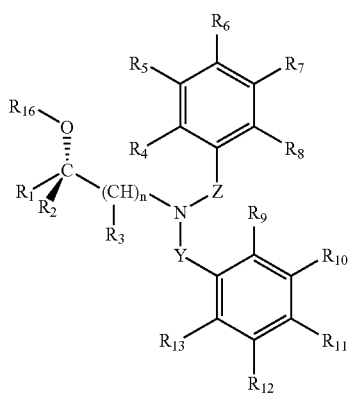

wherein:
R$_{16}$ is bonded together with a substituent selected from the group consisting of R$_4$, R$_8$, R$_9$, and R$_{13}$ to form a heterocyclyl ring having from 6 through 10 members;
n is 1 or 2;
R$_1$ is haloalkyl or haloalkoxyalkyl with the proviso that R1 is selected to have the highest Cahn-ingold-Prelog stereochemical system ranking of three groups bonded to the hydroxy-substituted carbon to which R$_1$ and R$_2$ are attached in radical Ia:

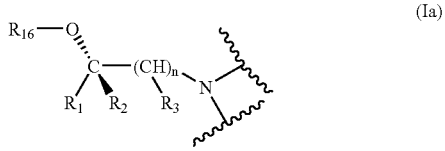

which radical Ia is a fragment of Formula I;
R$_2$ is selected from the group consisting of hydrido, aryl, aralkyl, alkyl, alkenyl, alkenyloxyalkyl, haloalkyl, haloalkenyl, halocycloalkyl, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl;
R$_3$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamido, and carboxamidoalkyl;
Y is a bond or (C(R$_{14}$)$_2$)$_q$ wherein q is 1 or 2;
Z is a bond or (C(R$_{15}$)$_2$)$_q$ wherein q is 1 or 2;
R$_{14}$ and R$_{15}$ are independently hydride: or alkyl;
R$_4$, R$_8$, R$_9$, and R$_{13}$ are independently selected from the group consisting of hydrido, halo, haloalkyl, and alkyl unless R$_4$ is bonded together with R$_{16}$ or R$_8$ is bonded together with R$_{16}$ or R$_9$ is bonded together with R$_{15}$ or R$_{13}$ is bonded together with R$_{16}$;
R$_5$, R$_6$, R$_7$, R$_{10}$, R$_{11}$, and R$_{12}$ are independently selected from the group consisting of hydrido, perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocylylcarbonyl, carboxy, heteroaralkylthio, heteroaralkoxy, cycioalkylamino, acylalkyl, acyla-lkoxy, aroylalkoxy, heterocyclyloxy, aralkylaryl, aralkyl, aralkenyl, aralkynyl, heterocyclyl, haloalky-lthio, alkanoyloxy, alkoxy, alkoxyalkyl, cycloalkoxy, cycloalkylalkoxy, hydroxy, amino, thio, nitro, alkylamino, alkylthio, arylamino, aralkylamino, arylthio, aryithioalkyl, alkylsulfonyl, alkylsulfonamido, monoarylamidosulfonyl, arylsulfonyl, heteroarylthio, heteroarylsulfonyl, heterocyclylsulfonyl, heterocyclylthio, alkanoyl, alkanoyl, aroyl, heteroaroyl, aralkanoyl, heteroaralkanoyl, haloalkanoyl, alkyl, alkynyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;
with the proviso that at least one of R$_4$, R$_5$, R$_6$, R$_7$, and R$_8$ is not hydrido or with the proviso that at least one of R$_9$, R$_{10}$, R$_{11}$, R$_{12}$, and R$_{13}$ is not hydrido.

12. The pharmaceutical composition of claim 11, wherein said compound is of Formula I, wherein at least one of R$_4$, R$_5$, R$_6$, R$_7$, and R$_8$ is not hydrido and at least one of R$_9$, R$_{10}$, R$_{11}$, R$_{12}$, and R$_{13}$ is not hydrido.

13. The pharmaceutical composition of claim 12, wherein said compound is of Formula 1, wherein;
R$_{16}$ is bonded together with R$_4$ or R$_9$ to form a heterocyclyl ring having from 6 through 8 members;
n is 1 or 2;
R$_1$ is haloalkyl or haloalkoxyalkyl with the proviso that R$_1$ is selected to have the highest Cahn-Ingold-Prelog stereochemical system ranking of said three groups bonded to the hydroxy-substituted carbon to which R$_1$ and R$_2$ are attached in said fragment of the Formula I and with the further proviso that said haloalkyl has two or more halo substituents;
R$_2$ is hydrido;
R$_3$ is hydrido;
Y is selected from the group consisting of a bond, CH$_2$, and CH$_2$CH$_2$;
Z is selected from the group consisting of a bond, CH$_2$, and CH$_2$CH$_2$;
R$_4$ is hydrido or halo unless R$_4$ is bonded together with R$_{16}$;
R$_9$ is hydrido or halo unless R$_9$ is bonded together with R$_{16}$;
R$_8$ and R$_{13}$ are independently hydrido or halo;
R$_5$, R$_6$, R$_7$, R$_{10}$, R$_{11}$, and R$_{12}$ are independently selected from the group consisting of hydrido, perhaloaryloxy, N-aryl-N-alkylamino, heterocyclylalkoxy, heterocyclylthio, hydroxyalkoxy, carboxamidoalkoxy, alkokycarbonylalkoxy, alkoxycarbonylalkenyloxy, araloylalkoxy, aralkenoyl, N-arylcarboxamidoalkoxy, cycloalkylcarbonyl, cyanoalkoxy, heterocyclylcarbonyl, heteroaralkoxy, heterocyclyloxy, aralkylaryl, aralkyl, haloalkylthio, alkoxy, cycloalkoxy, cycloalkylalkoxy, alkylamino, alkylthio, arylamino, arylthio, arylsulfonyl, beteroarylthio, heteroarylsulfonyl, aroyl, alkyl, cycloalkyl, cycloalkylalkanoyl, halo, haloalkyl, haloalkoxy, hydroxyhaloalkyl, hydroxyhaloalkoxy, aryl, aryloxy, aralkoxy, saturated heterocyclyl, heteroaryl, heteroaryloxyalkyl, and heteroaryloxy;

with the proviso that at least one of $R_4$, $R_5$, $R_6$, $R_7$, and $R_8$ is not hydrido and with the further proviso that at least one of $R_9$, $R_{10}$, $R_{11}$, $R_{12}$, and $R_{13}$ is not hydrido.

14. The pharmaceutical composition of claim 13, wherein said compound is of Formula I, wherein;
$R_{16}$ is bonded together with $R_4$ or $R_9$ to form a heterocyclyl ring having 6 or 7 members;
n is 1;
$R_1$ is selected from the group consisting of trifluoromethyl, 1,1,2,2-tetrafluoroethoxymethyl, trifluoromethoxymethyl, difluoromethyl, chlorodifluoromethhyl, and pentafluoroethyl;
$R_2$ is hydrido;
$R_3$ is hydrido;
Y is $CH_2$ or $CH_2CH_2$;
Z is a bond;
$R_4$ is hydrido or fluoro unless $R_4$ is bonded together with $R_{16}$;
$R_9$ is hydrido or fluoro unless $R_9$ is bonded together with $R_{16}$;
$R_8$ and $R_{13}$ are independently hydrido or fluoro;
$R_7$ and $R_{12}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-difluorophenoxy, 3,4-difluorophenoxy, 2,3-difluorobenzyloxy, 2,4-difluorobenzyloxy, 3,4-difluorobenzyloxy, 2,5-difluorobenzyloxy, difluoromethoxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorophenoxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and triluoromethylthio;
$R_6$ and $R_{11}$ are independently selected from the group consisting of chloro, fluoro, hydrido, pentafluoroethyl, 1,1,2,2-tetrafluoroethoxy, trifluoromethyl, and trifluoromethoxy;
$R_5$ and $R_{10}$ are independently selected from the group consisting of hydrido, fluoro, and trifluoromethyl.

15. The pharmaceutical composition of claim 14, wherein said compound is of Formula I, wherein;
$R_{16}$ is bonded together with $R_4$ or $R_9$ to form a 6-membered heterocyclyl ring;
n is 1;
$R_1$ is selected from the group consisting of trifluoromethyl, difluoromethyl, chlorodifluoromethyl, and pentafluoroethyl;
$R_2$ is hydrido;
$R_3$ is hydrido;
Y is $CH_2$;
Z is a bond;
$R_4$ is hydrido or fluoro unless $R_4$ is bonded together with $R_{16}$;
$R_9$ is hydrido or fluoro unless $R_9$ is bonded together with $R_{16}$;
$R_8$ and $R_{13}$ are independently hydrido or fluoro;
$R_7$ and $R_{12}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyelopentoxy, cyclopentyl, cyclopentylcarbonyl, cyclopropylmethoxy, 2,3-dichlorophenoxy, 2,4-dichlorophenaxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 4-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 4-isopropylbenzyloxy, 3-isopropyiphenoxy, isopropylthio, 4-isopropyl-3-methylphenoxy, 3-isothiazolyl, 4-isothiazolyl, 5-isothiazolyl, 3-methoxvbenzyl; 4-methoxyphenylamino, 3-methyl benzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-truoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethyl phenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrido, pentafluoroethyl, 1,1,2,2-tetrafluoroethoxy, and trifluoromethyl;

$R_5$ and $R_{10}$ are independently selected from the group consisting of hydrido, fluoro, and trifluoromethyl.

16. The pharmaceutical composition of claim 13, wherein said compound is of Formula II:

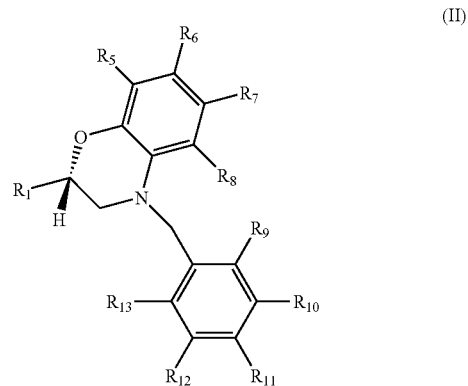

(II)

or a pharmaceutically acceptable salt thereof, wherein;

$R_1$ is haloalkoxyalkyl or haloalkyl with the proviso that said haloalkyl has two or more halo substituents;

$R_8$, $R_9$, and $R_{13}$ are independently hydrido or halo;

$R_5$, $R_6$, $R_7$, $R_{10}$, $R_{11}$, and $R_{12}$ are independently selected from the group consisting of hydrido, perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, heteroaralkoxy, aralkyl, haloalkylthio, alkoxy, cycloalkoxy, cycloalkylalkoxy, alkylthio, arylamino, arylthio, arylsulfonyl, aroyl, alkyl, cycloalkyl, cycloalkylalkanoyl, halo, haloalkyl, haloalkoxy, hydroxyhaloalkyl, hydroxyhaloalkoxy, aryl, aryloxy, aralkoxy, heteroaryl, heteroaryloxyalkyl, and heteroaryloxy;

with the proviso that at least one of $R_9$, $R_{10}$, $R_{11}$, $R_{12}$, and $R_{13}$ is not hydrido.

17. The pharmaceutical composition of claim 16, wherein said compound is of Formula II, wherein;

$R_1$ is trifluoromethyl;

$R_8$, $R_9$, and $R_{13}$ are independently hydrido or fluoro;

$R_7$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{12}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_5$, $R_6$, $R_{10}$ and $R_{11}$ are independently hydrido or fluoro.

18. The pharmaceutical composition of claim 17, wherein said compound is of Formula II, wherein;

$R_1$ is trifluoromethyl;

$R_8$, $R_9$, and $R_{13}$ are independently hydrido or fluoro;

$R_7$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4- dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxynhenoxy, 3-trifluoromethylbenzyloxy, and 3-trifluoromethylthiophenoxy;

$R_{12}$ is selected from the group consisting of 1,1,2,2-tetrafluoroethoxy, pentafluoroethyl, and trifluoromethyl;

$R_5$, $R_6$, $R_{10}$, and $R_{11}$ are independently hydrido or fluoro.

19. The pharmaceutical composition of claim 11, wherein said compound is a compound of Formula III:

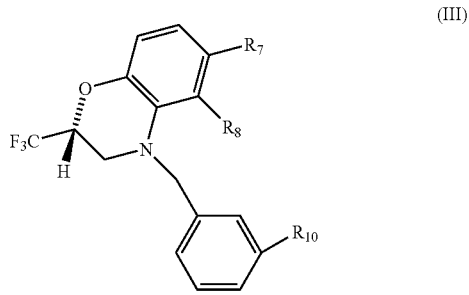

wherein $R_7$, $R_8$, and $R_{10}$ are selected to form a compound selected from the group consisting of;
$R_7$ is 4-chloro-3-ethylphenoxy, $R_8$ is hydrido, and $R_{10}$ is 1,1,2,2-tetrafluoroethoxy;
$R_7$ is phenoxy, $R_8$ is hydrido, and $R_{10}$ is 1,1,2,2-tetrafluoroethoxy;
$R_7$ is 4-chloro-3-ethylphenoxy, $R_8$ is hydrido, and $R_{10}$ is pentafluoroethyl;
$R_7$ is phenoxy, $R_8$ is hydrido, and $R_{10}$ is pentafluoroethyl;
$R_7$ is 4-chloro-3-ethylphenoxy, $R_8$ is hydrido, and $R_{10}$ is trifluoromethyl;
$R_7$ is phenoxy, $R_8$ is hydrido, and $R_{14}$ is trifluoromethyl;
$R_7$ is 4-chloro-3-ethylphenoxy, $R_8$ is fluoro and $R_{10}$ is 1,1,2,2-tetrafluoroethoxy;
$R_7$ is 4-chloro-3-ethylphenoxy, $R_8$ is hydrido, and $R_{10}$ is 2-furyl; and
$R_7$ is 4-chloro-3-ethylphenoxy, $R_8$ is hydrido, and $R_{10}$ is trifluoromethylthio.

20. The pharmaceutical composition of claim 11, wherein said compound is a compound of Formula IV:

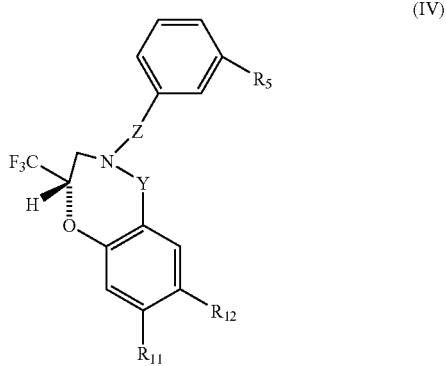

wherein $R_5$, $R_{11}$, $R_{12}$, Y, and Z are selected to form a compound selected from the group consisting of;
$R_5$ is 4-chloro-3-ethylphenoxy, $R_{11}$ is trifluoromethyl, $R_{12}$ is hydrido, Y is methylene, and Z is a bond;
$R_5$ is 4-chloro-3-ethylphenoxy, $R_{11}$ is hydrido, $R_{12}$ is trifluoromethyl, Y is methylene, and Z is a bond;
$R_5$ is 4-chloro-3-ethylphenoxy, $R_{11}$ is trifluoromethyl, $R_{12}$ is hydrido, Y is a bond, and Z is a bond; and
$R_5$ is 4-chloro-3-ethylphenoxy, $R_{11}$ is hydrido, $R_{12}$ is trifluoromethyl, Y is a bond, and Z is a bond.

21. A method of treating or preventing a CETP-mediated disorder in a subject by administering a therapeutically effective amount of a compound or a pharmaceutically acceptable salt thereof, said compound being of Formula I:

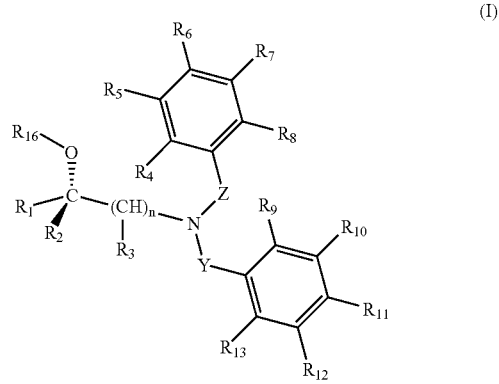

$R_{16}$ is bonded together with a substituent selected from the group consisting of $R_4$, $R_8$, $R_9$, and $R_{13}$ to form a heterocyclyl ring having from 6 through 10 members;
n is 1 or 2;
$R_1$ is haloalkyl or haloalkoxyalkyl with the proviso that $R_1$ is selected to have the highest Cahn-Ingold-Prelog stereochemical system ranking of three groups bonded to the hydroxy-substituted carbon to which $R_1$ and $R_2$ are attached in radical Ia:

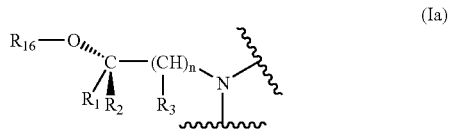

which radical Ia is a fragment of Formula I;
$R_2$ is selected from the group consisting of hydrido, aryl, aralkyl, alkyl, alkenyl, alkenyloxyalkyl, haloalkyl, haloalkenyl, halocycloalkyl, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl;
$R_3$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkeny, haloalkoxyalkyl, haloalkenyloxyalkyl, monocyanoalkyl, dicyanoalkyl, carboxamido, and carboxamidoalkyl;
Y is a bond or $(C(R_{14})_2)_q$ wherein q is 1 or 2;
Z is a bond or $(C(R_{15})_2)q$ wherein q is 1 or 2;
$R_{14}$ and $R_{15}$ are independently hydrido or alkyl;

$R_4$, $R_8$, $R_9$, and $R_{13}$ are independently selected from the group consisting of hydrido, halo, haloalkyl, and alkyl unless $R_4$ is bonded together with $R_{16}$ or $R_8$ is bonded together with $R_{16}$ or $R_9$ is bonded together with $R_{16}$ or $R_{13}$ is bonded together with $R_{16}$;

$R_5$, $R_6$, $R_7$, $R_{10}$, $R_{11}$, and $R_{12}$ are independently selected from the group consisting of hydrido, perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxy, amino, thio, nitro, alkylamino, alkylthio, arylamino, aralkylamino, arylthio, arylthioalkyl, alkylsulfonyl, alkyl sulfonamido, monoarylamidosulfonyl, arylsulfonyl, heteroarylthio, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarbonylamido, arylamidocarbonylamido, carboalkoxyalkyl, carboalkoxyalkenyl, carboxamido, carboxamidoalkyl, and cyano;

with the proviso that at least one of $R_4$, $R_5$, $R_6$, $R_7$, and $R_8$ is not hydrido or with the proviso that at least one of $R_9$, $R_{10}$, $R_{11}$, $R_{12}$, and $R_{13}$ is not hydrido.

22. The method of claim 21, wherein said compound is of Formula I, wherein at least one of $R_4$, $R_5$, $R_6$, $R_7$, and $R_8$ that is not hydrido and at least one of $R_9$, $R_{10}$, $R1_1$, $R_{12}$, and $R_{13}$ that is not hydrido.

23. The method of claim 22, wherein said compound is of Formula I, wherein;
$R_{16}$ is bonded together with $R_4$ or $R_9$ to form a heterocyclyl ring having from 6 through 8 members;
n is 1 or 2;
$R_1$ is haloalkyl or haloalkoxyalkyl with the proviso that $R_1$ is selected to have the highest Cahn-Ingold-Prelog stereochemical system ranking of said three groups bonded to the hydroxy-substituted carbon to which $R_1$ and $R_2$ are attached in said fragment of the Formula I and with the further proviso that said haloalkyl has two or more halo substituents;
$R_2$ is hydrido;
$R_3$ is hydrido;
Y is selected from the group consisting of a bond, $CH_2$, and $CH_2CH_2$;
Z is selected from the group consisting of a bond, $CH_2$, and $CH_2CH_2$;
$R_4$ is hydrido or halo unless $R_4$ is bonded together with $R_{16}$;
$R_9$ is hydrido or halo unless $R_9$ is bonded together with $R_{16}$;
$R_8$ and $R_{13}$ are independently hydrido or halo;
$R_5$, $R_6$, $R_7$, $R_{10}$, $R_{11}$, and $R_{12}$ are independently selected from the group consisting of hydrido, perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, arallanoylalkoxy, aralkenoyl, N-arylcarboxamidoalkoxy, cycloalkylcarbonyl, cyanoalkoxy, heterocyclylcarbonyl, heteroaralkoxy, heterocyclyloxy, aralkylaryl, aralkyl, haloalkylthio, alkoxy, cycloalkoxy, cycloalkylalkoxy, alkylamino, alkylthio, arylamino, arylthio, arylsulfonyl, heteroarylthio, heteroarylsulfonyl, amyl, alkyl, cycloalkyl, cycloalkylalkanoyl, halo, haloalkyl, haloalkoxy, hydroxyhaloalkyl, hydroxyhaloalkoxy, aryl, aryloxy, aralkoxy, saturated heterocyclyl, heteroaryl, heteroaryloxyalkyl, and heteroaryloxy;

with the proviso that at least one of $R_4$, $R_5$, $R_6$, $R_7$, and $R_8$ is not hydrido and with the further proviso that at least one of $R_9$, $R_{10}$, $R_{11}$, $R_{12}$, and $R_{13}$ is not hydrido.

24. The method of claim 23, wherein said compound is of Formula I, wherein;
$R_{16}$ is bonded together with $R_4$ or $R_9$ to form a heterocyclyl ring having 6 or 7 members;
n is 1;
$R_1$ is selected from the group consisting of trifluoromethyl, 1,1,2,2-tetrafluoroethoxymethyl, trifluoromethoxymethyl, difluoromethyl, chlorodifluoromethyl, and pentafluoroethyl;
$R_2$ hydrido;
$R_3$ is hydrido;
Y is $CH_2$ or $CH_2CH_2$;
Z is a bond;
$R_4$ is hydrido or fluoro unless $R_4$ is bonded together with $R_{16}$;
$R_9$ is hydrido or fluoro unless $R_9$ is bonded together with $R_{16}$;
$R_8$ and $R_{13}$ are independently hydrido or fluoro;
$R_7$ and $R_{12}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, -chlorophenoxy, 3-chloro4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3 5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, difluoromethoxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy; 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3 3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-znethoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methyipropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4y1, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-I-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,35-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrido, pentafluoroethyl, 1,1,2,2-tetrafluoroethoxy, trifluoromethyl, and trifluoromethoxy;

$R_5$ and $R_{10}$ are independently selected from the group consisting of hydrido, fluoro, and, trifluoromethyl.

25. The method of claim 24 wherein said compound is of Formula I, wherein;

$R_{16}$ is bonded together with $R_4$ or $R_9$ to form a 6-membered heterocyclyl ring;

N is 1;

$R_1$ is selected from the group consisting of trifluoromethyl, difluoromethyl, chlorodifluoromethyl, and pentafluoroethyl;

$R_2$ is hydrido;

$R_3$ is hydrido;

Y is $CH_2$;

Z is a bond;

$R_4$ is hydrido or fluoro unless R4 is bonded together with $R_{16}$;

$R_9$ is hydrido or fluoro unless $R_9$ is bonded together with $R_{16}$;

$R_8$ and $R_{13}$ are independently hydrido or fluoro;

$R_7$ and $R_{12}$ are independently selected from the group consisting of benzyloxy, 5-bromo-2-fluorophenoxy, 4-bromo-3-fluorophenoxy, 3-bromobenzyloxy, 4-bromophenoxy4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro--3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 4-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro 4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 4-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl; 4-methoxyphenylamino, 3-methylbenzyloxy, 4-methylbenxyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4 trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromnethylthiobenzyloxy, and trifluoromethylthio;

$R_6$ and $R_{11}$ are independently selected from the group consisting of chloro, fluoro, hydrido, pentafluoroethyl, 1,1,2,2-tetrafluoroethoxy, and trifluoromethyl;

$R_5$ and $R_{10}$ are independently selected from the group consisting of hydrido, fluoro, and trifluoromethyl.

26. The method of claim 23, wherein said compound is of Formula II:

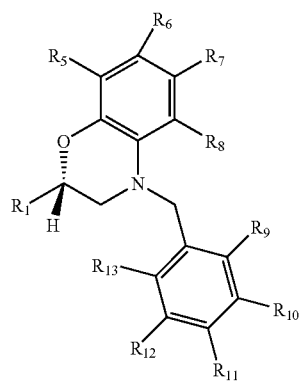

(II)

wherein;

$R_1$ is haloalkoxyalkyl or haloalkyl with the proviso that said haloalkyl has two or more halo substituents;

$R_8$, $R_9$, and $R_13$ are independently hydrido or halo;

$R_5$, $R_6$, $R_7$, $R_{10}$, $R_{11}$, and $R_{12}$ are independently selected from the group consisting of hydrido, perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, heteroaralkoxy, aralkyl, haloalkylthio, alkoxy, cycloalkoxy, cycloalkylalkoxy, alkylthio, arylamino, arylthio, arylsulfonyl, aroyl, alkyl, cycloalkyl, cycloalkylalkanoyl, halo, haloalkyl, haloalkoxy, hydroxyhaloalkyl, hydroxyhaloalkoxy, aryl, aryloxy, aralkoxy, heteroaryl, heteroaryloxyalkyl, and heteroaryloxy;

with the proviso that at least one of $R_9$, $R_{10}$, $R_{11}$, $R_{12}$, and $R_{13}$ is not hydrido.

27. The method of claim 26, wherein said compound is of Formula II, wherein;

$R_1$ is trifluoromethyl;

$R_8$, $R_9$, and $R_{13}$ are independently hydrido or fluoro;

$R_7$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,5-tetrahydronaphthyloxy), 3-trifluoromethoxybenzyl oxy, 3-trifluoromethoxyphenoxy, 3-trifluoromethylben7yloxy, and 3-trifluoromethylthiophenoxy;

$R_{12}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_5$, $R_6$, $R_{10}$, and $R_{11}$ are independently hydrido or fluoro.

28. The method of claim 27, wherein said compound is of Formula II, wherein;

$R_1$ is trifluoromethyl;

$R_8$, $R_9$, and $R_{13}$ are independently hydrido or fluoro;

$R_7$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyoxy-3-trifluoromethoxyphenoxy; 3-trifluoromethylbenzyloxy, and 3-trifluoromethylthiophenoxy;

$R_{12}$ is selected from the group consisting of 1,1,2,2-tetrafluoroethoxy, pentafluoroethyl, and trifluoromethyl;

$R_5$, $R_6$, $R_{10}$, and $R_{11}$ are independently hydrido or fluoro.

29. The method of claim 21, wherein said compound is a compound of Formula III:

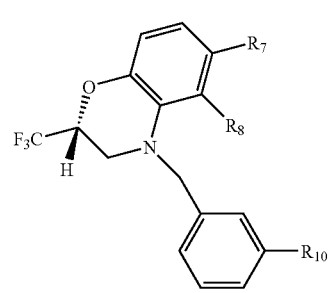

(III)

wherein $R_7$, $R_8$, and $R_{10}$ are selected to form a compound selected from the group consisting of;

$R_7$ is 4-chloro-3-ethylphenoxy, $R_8$ is hydrido, and $R_{10}$ is 1,1,2,2-tetrafluoroethoxy;

$R_7$ is phenoxy, $R_8$ is hydrido, and $R_{10}$ is 1,1,2,2-tetrafluoroethoxy;

$R_7$ is 4-chloro-3-ethylphenoxy, $R_8$ is hydrido, and $R_{10}$ is pentafluoroethyl;

$R_7$ is phenoxy, $R_8$ is hydrido, and $R_{10}$ is pentafluoroethyl;

$R_7$ is 4-chloro-3-ethylphenoxy, $R_8$ is hydrido, and $R_{10}$ is trifluoromethyl;

$R_7$ is phenoxy, $R_8$ is hydrido, and $R_{10}$ is trifluoromethyl;

$R_7$ is 4-chloro-3-ethylphenoxy, $R_8$ is fluoro, and $R_{10}$ is 1,1,2,2-tetrafluoroethoxy;

$R_7$ is 4-chloro-3-ethylphenoxy, $R_8$ is hydrido, and $R_{10}$ is 2-furyl; and $R_7$ is 4-chloro-3-ethylphenoxy, $R_8$ is hydrido, and $R_{10}$ is trifluoromethylthio.

30. The method of claim 21, wherein said compound is a compound of Formula IV:

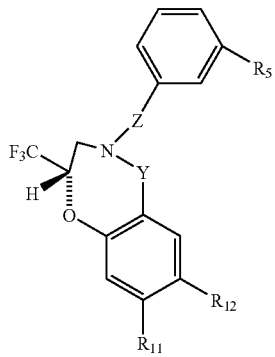

(IV)

wherein $R_5$, $R_{11}$, $R_{12}$, Y, and Z are selected to form a compound selected from the group consisting of;
$R_5$ is 4-chloro-3-ethylphenoxy, $R_{11}$ is trifluoromethyl, $R_{12}$ is hydrido, Y is methylene, and Z is a bond;
$R_5$ is 4-chloro-3-ethylphenoxy, $R_{11}$ is hydrido, $R_{12}$ is trifluoromethyl, Y is methylene, and Z is a bond;
$R_5$ is 4-chloro-3-ethylphenoxy, $R_{11}$ is trifluoromethyl, $R_{12}$ is hydrido, Y is a bond, and Z is a bond; and
$R_5$ is 4-chloro-3-ethylphenoxy, $R_{11}$ is hydrido, $R_{12}$ is trifluoromethyl, Y is a bond, and Z is a bond.

31. The method of claim 21 further characterized by treating coronary artery disease in a subject by administering a therapeutically effective amount of a compound of claim 21 or a pharmaceutically acceptable salt thereof.

32. The method of claim 21 further characterized by preventing coronary artery disease in a subject by administering a therapeutically effective amount of a compound of claim 21 or a pharmaceutically acceptable salt thereof.

33. The method of claim 21 further characterized by preventing cerebral vascular accident (CVA) in a subject by administering a therapeutically effective amount of a compound of claim 21 or a pharmaceutically acceptable salt thereof.

34. The method of claim 21 further characterized by treating or preventing dyslipidemia in a subject by administering a therapeutically effective amount of a compound of claim 21 or a pharmaceutically acceptable salt thereof.

* * * * *